(12) United States Patent
Jung et al.

(10) Patent No.: US 11,691,957 B2
(45) Date of Patent: Jul. 4, 2023

(54) CONDENSED CYCLIC COMPOUND AND ORGANIC LIGHT-EMITTING DEVICE INCLUDING THE SAME

(71) Applicant: Samsung Electronics Co., Ltd., Suwon-si (KR)

(72) Inventors: Yongsik Jung, Seoul (KR); Wataru Sotoyama, Kanagawa (JP); Hosuk Kang, Suwon-si (KR); Sungjun Kim, Seongnam-si (KR); Joonghyuk Kim, Seoul (KR); Youngmok Son, Hwaseong-si (KR); Won-Joon Son, Yongin-si (KR); Yeonsook Chung, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 302 days.

(21) Appl. No.: 16/897,189

(22) Filed: Jun. 9, 2020

(65) Prior Publication Data

US 2021/0198222 A1 Jul. 1, 2021

(30) Foreign Application Priority Data

Dec. 27, 2019 (KR) .......................... 10-2019-0176733

(51) Int. Cl.
| | |
|---|---|
| *C07D 307/79* | (2006.01) |
| *C07D 407/04* | (2006.01) |
| *C07D 409/04* | (2006.01) |
| *C07D 407/10* | (2006.01) |
| *C07D 333/54* | (2006.01) |
| *C07D 409/14* | (2006.01) |
| *C07D 409/10* | (2006.01) |
| *C07D 405/04* | (2006.01) |
| *C07D 413/10* | (2006.01) |
| *C07D 471/04* | (2006.01) |
| *C07F 7/08* | (2006.01) |
| *H10K 85/40* | (2023.01) |
| *H10K 85/60* | (2023.01) |
| *H10K 50/17* | (2023.01) |
| *H10K 50/12* | (2023.01) |

(Continued)

(52) U.S. Cl.
CPC ......... *C07D 307/79* (2013.01); *C07D 307/87* (2013.01); *C07D 333/54* (2013.01); *C07D 333/72* (2013.01); *C07D 405/04* (2013.01); *C07D 405/10* (2013.01); *C07D 407/04* (2013.01); *C07D 407/10* (2013.01); *C07D 407/14* (2013.01); *C07D 409/04* (2013.01); *C07D 409/10* (2013.01); *C07D 409/14* (2013.01); *C07D 413/04* (2013.01); *C07D 413/10* (2013.01); *C07D 419/04* (2013.01); *C07D 471/04* (2013.01); *C07F 7/0816* (2013.01); *H01L 51/0065* (2013.01); *H01L 51/0068* (2013.01); *H01L 51/0069* (2013.01); *H01L 51/0072* (2013.01); *H01L 51/0073* (2013.01); *H01L 51/0074* (2013.01); *H01L 51/0094* (2013.01); *H01L 51/5024* (2013.01); *H01L 51/5092* (2013.01); *H01L 51/4273* (2013.01); *H01L 51/5056* (2013.01); *H01L 51/5072* (2013.01)

(58) Field of Classification Search
CPC .. C07D 307/87; C07D 307/79; C07D 333/54; C07D 333/72; C07D 405/04; C07D 405/10; C07D 407/04; C07D 407/10; C07D 407/14; C07D 409/04; C07D 409/10; C07D 413/04; C07D 413/10; C07D 419/04; C07D 471/04; C07F 7/0816; H01L 51/0065; H01L 51/0068; H01L 51/0069; H01L 51/0072; H01L 51/0073; H01L 51/0074; H01L 51/0094; H01L 51/5024; H01L 51/5092; H01L 51/4273; H01L 51/5056; H01L 51/5072
See application file for complete search history.

(56) References Cited

U.S. PATENT DOCUMENTS

2020/0006674 A1 1/2020 Lin et al.

FOREIGN PATENT DOCUMENTS

| JP | H11354281 A | 12/1999 | | |
|---|---|---|---|---|
| JP | 2014-82405 | * | 5/2014 | ............. C07C 13/62 |

(Continued)

OTHER PUBLICATIONS

English Abstract of JPH11354281.

*Primary Examiner* — Alicia L Otton
(74) *Attorney, Agent, or Firm* — Cantor Colburn LLP

(57) ABSTRACT

Provided are a condensed cyclic compound represented by Formula 1 and an organic light-emitting device including the same:

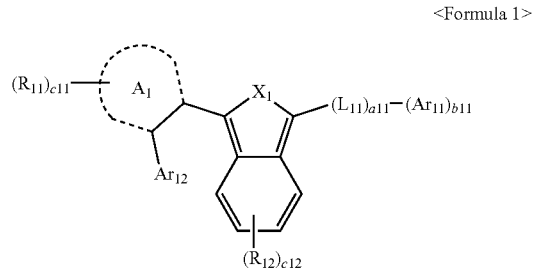

<Formula 1> wherein, in Formula 1, $X_1$, $A_1$, $L_{11}$, a11, $Ar_{11}$, $Ar_{12}$, b11, $R_{11}$, $R_{12}$, c11, and c12 are the same as defined in the specification.

19 Claims, 1 Drawing Sheet

(51) Int. Cl.
*C07D 405/10* (2006.01)
*C07D 413/04* (2006.01)
*C07D 419/04* (2006.01)
*C07D 407/14* (2006.01)
*C07D 333/72* (2006.01)
*H01L 51/00* (2006.01)
*H01L 51/50* (2006.01)
*C07D 307/87* (2006.01)
*H01L 51/42* (2006.01)

(56) References Cited

FOREIGN PATENT DOCUMENTS

WO      2009021126 A9    2/2009
WO      2014204464 A1    12/2014

* cited by examiner

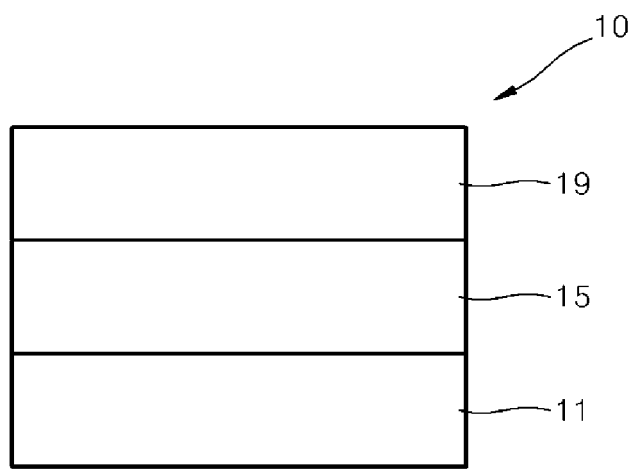

CONDENSED CYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2019-0176733, filed on Dec. 27, 2019, in the Korean Intellectual Property Office, the disclosure of which is incorporated herein in its entirety by reference.

BACKGROUND

1. Field

The present disclosure relates to a condensed cyclic compound and an organic light-emitting device including the same.

2. Description of the Related Art

Organic light-emitting devices are self-emission devices, which have a wide viewing angle, excellent contrast, rapid response time, and excellent characteristics in terms of luminance, driving voltage, and response speed, and produce full-color images.

In an example, an organic light-emitting device includes an anode, a cathode, and an organic layer between the anode and the cathode, wherein the organic layer includes an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transit from an excited state to a ground state, thereby generating light.

SUMMARY

Provided are a novel condensed cyclic compound and an organic light-emitting device using the same.

Additional aspects will be set forth in part in the description which follows and, in part, will be apparent from the description, or may be learned by practice of the presented embodiments.

According to an aspect of an embodiment, provided is a condensed cyclic compound represented by Formula 1:

<Formula 1>

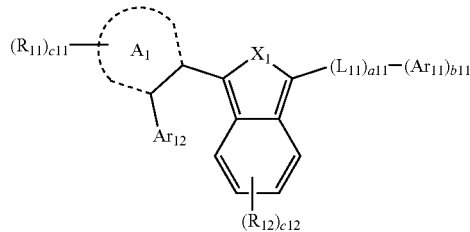

wherein, in Formula 1, $X_1$ is O or S, $A_1$ is a $C_5$-$C_{60}$ carbocyclic group or a $C_1$-$C_{60}$ heterocyclic group, $L_{11}$ is a substituted or unsubstituted $C_5$-$C_{60}$ carbocyclic group or a substituted or unsubstituted $C_1$-$C_{60}$ heterocyclic group, a11 is an integer of 0 to 3, $Ar_{11}$ and $Ar_{12}$ are each independently a $C_6$-$C_{60}$ aryl group, a $C_1$-$C_{60}$ heteroaryl group, a monovalent non-aromatic condensed polycyclic group, or a monovalent non-aromatic condensed heteropolycyclic group, each unsubstituted or substituted with at least one $R_a$, b11 is an integer of 1 to 5, $L_{12}$ is *—$Ar_{31}$—*', *—O—*', *—S—*', —[C($R_{31}$)($R_{32}$)]$_{k11}$—*', *—C($R_{31}$)=*', *=C($R_{31}$)—*', *—C($R_{31}$)=C($R_{32}$)—*', *—C(=O)—*', *—C(=S)—*', *—C≡C—*', *—N($R_{31}$)—*', *—P($R_{31}$)—*', *—[Si($R_{31}$)($R_{32}$)]$_{k11}$—*', or *—P($R_{31}$)($R_{32}$)—*', wherein $L_{12}$ is optionally linked to $A_1$ and $A_{12}$ to form a substituted or unsubstituted $C_5$-$C_{30}$ carbocyclic group or a substituted or unsubstituted $C_1$-$C_{30}$ heterocyclic group, a12 is an integer of 0 or 1, $R_{11}$, $R_{12}$, and $R_a$ are each independently hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), or —B($Q_6$)($Q_7$), c11 is an integer of 1 to 20, c12 is an integer of 1 to 4, when c11 is 2 or greater, two adjacent $R_{11}$(s) are optionally linked to each other to form a substituted or unsubstituted $C_5$-$C_{30}$ carbocyclic group or a substituted or unsubstituted $C_1$-$C_{30}$ heterocyclic group, when c12 is 2 or greater, two adjacent $R_{12}$(s) are optionally linked to each other to form a substituted or unsubstituted $C_5$-$C_{30}$ carbocyclic group or a substituted or unsubstituted $C_1$-$C_{30}$ heterocyclic group, $A_1$ and $Ar_{12}$ are optionally condensed with each other via a first linking group of a single bond, *—$Ar_{31}$—*', *—O—*', *—S—*', *—[C($R_{31}$)($R_{32}$)]$_{k11}$—*', *—C($R_{31}$)=*', *=C($R_{31}$)—*', *—C($R_{31}$)=C($R_{32}$)—*', *—C(=O)—*', *—C(=S)—*', *—C≡C—*', *—N($R_{31}$)—*', *—P($R_{31}$)—*', *—[Si($R_{31}$)($R_{32}$)]$_{k11}$—*', or *—P($R_{31}$)($R_{32}$)—*' to form a substituted or unsubstituted $C_5$-$C_{30}$ carbocyclic group or a substituted or unsubstituted $C_1$-$C_{30}$ heterocyclic group, Ar$_{31}$ is a C$_5$-C$_{30}$ carbocyclic group, R$_{31}$ and R$_{32}$ are each independently the same as defined in connection with R$_{11}$, k11 is 1, 2, 3, or 4, at least one of substituents of the substituted C$_5$-C$_{60}$ carbocyclic group, the substituted C$_1$-C$_{60}$ heterocyclic group, the substituted C$_1$-C$_{60}$ alkyl group, the substituted C$_2$-C$_{60}$ alkenyl group, the substituted C$_2$-C$_{60}$ alkynyl group, the substituted C$_1$-C$_{60}$ alkoxy group, the substituted C$_3$-C$_{10}$ cycloalkyl group, the substituted C$_1$-C$_{10}$ heterocycloalkyl group, the substituted C$_3$-C$_{10}$ cycloalkenyl group, the substituted C$_2$-C$_{10}$ heterocycloalkenyl group, the substituted C$_6$-C$_{60}$ aryl group, the substituted C$_6$-C$_{60}$ aryloxy group, the substituted C$_6$-C$_{60}$ arylthio group, the substituted C$_1$-C$_{60}$ heteroaryl group, the substituted monovalent non-aromatic condensed polycyclic group, and the substituted monovalent non-aromatic condensed heteropolycyclic group is:

deuterium, —CD$_3$, —CD$_2$H, —CDH$_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, or a C$_1$-C$_{60}$ alkoxy group;

a C$_1$-C$_{60}$ alkyl group, a C$_2$-C$_{60}$ alkenyl group, a C$_2$-C$_{60}$ alkynyl group, or a C$_1$-C$_{60}$ alkoxy group, each substituted with at least one deuterium, —CD$_3$, —CD$_2$H, —CDH$_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_3$-C$_{10}$ cycloalkyl group, a C$_1$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{11}$)(Q$_{12}$)(Q$_{13}$), —N(Q$_{14}$)(Q$_{15}$), —B(Q$_{16}$)(Q$_{17}$), or any combination thereof;

a C$_3$-C$_{10}$ cycloalkyl group, a C$_1$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, or a monovalent non-aromatic condensed heteropolycyclic group;

a C$_3$-C$_{10}$ cycloalkyl group, a C$_1$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, or a monovalent non-aromatic condensed heteropolycyclic group, each substituted with at least one deuterium, —CD$_3$, —CD$_2$H, —CDH$_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{21}$)(Q$_{22}$)(Q$_{23}$), —N(Q$_{24}$)(Q$_{25}$), —B(Q$_{26}$)(Q$_{27}$), or any combination thereof; or —Si(Q$_{31}$)(Q$_{32}$)(Q$_{33}$), —N(Q$_{34}$)(Q$_{35}$), or —B(Q$_{36}$)(Q$_{37}$), and Q$_1$ to Q$_7$, Q$_{11}$ to Q$_{17}$, Q$_{21}$ to Q$_{27}$, and Q$_{31}$ to Q$_{37}$ are each independently hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_1$-C$_{60}$ heteroaryl group, a monovalent non-aromatic condensed polycyclic group, or a monovalent non-aromatic condensed heteropolycyclic group, provided that the condensed cyclic compound represented by Formula 1 is not Compound A:

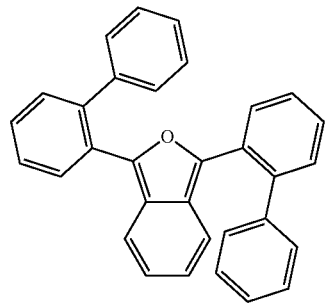

<Compound A>

According to an aspect of another embodiment, an organic light-emitting device includes: a first electrode; a second electrode; and an organic layer disposed between the first electrode and the second electrode and including an emission layer; wherein the organic layer including at least one of the above-described condensed cyclic compounds.

According to an aspect of another embodiment, an organic light-emitting device includes: a first electrode; a second electrode; and an organic layer disposed between the first electrode and the second electrode and including an emission layer, wherein the emission layer includes a host and a dopant, the host includes a condensed cyclic compound represented by Formula 1, and an amount of the host in the emission layer is larger than that of the dopant in the emission layer:

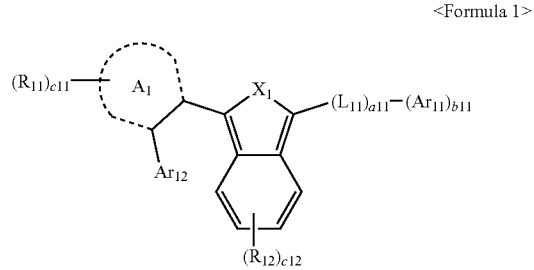

<Formula 1> wherein, in Formula 1, X$_1$, A$_1$, L$_{11}$, a11, Ar$_{11}$, Ar$_{12}$, b11, R$_{11}$, R$_{12}$, c11, and c12 are the same as defined above.

BRIEF DESCRIPTION OF THE DRAWING

These and/or other aspects will become apparent and more readily appreciated from the following description of the embodiments, taken in conjunction with the accompanying drawings in which:

FIGURE is a schematic cross-sectional view of an organic light-emitting device according to an exemplary embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween In contrast, when an element is referred to as being "directly on" another element, there are no intervening elements present It will be understood that, although the terms "first," "second," "third" etc. may be used herein to describe various elements, components, regions, layers and/or sections, these elements, components, regions, layers and/or sections should not be limited by these terms These terms are only used to distinguish one element, component, region, layer or section from another element, component, region, layer or section Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise.

"Or" means "and/or." As used herein, the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the FIGURES It will be understood that relative terms are intended to encompass different orientations of the device in addition to the orientation depicted in the FIGURES For example, if the device in one of the FIGURES is turned over, elements described as being on the "lower" side of other elements would then be oriented on "upper" sides of the other elements The exemplary term "lower," can therefore, encompasses both an orientation of "lower" and "upper," depending on the particular orientation of the FIGURE Similarly, if the device in one of the FIGURES is turned over, elements described as "below" or "beneath" other elements would then be oriented "above" the other elements The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments As such, variations from the shapes of the illustrations as a result, for example, of manufacturing techniques and/or tolerances, are to be expected Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features Moreover, sharp angles that are illustrated may be rounded Thus, the regions illustrated in the figures are schematic in nature and their shapes are not intended to illustrate the precise shape of a region and are not intended to limit the scope of the present claims.

An aspect of the present disclosure provides a condensed cyclic compound represented by Formula 1.

<Formula 1>

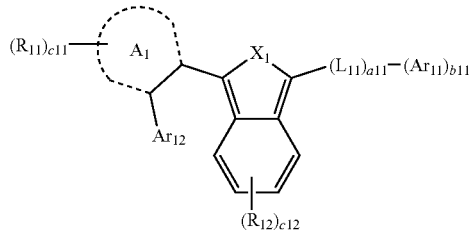

In Formula 1, $X_1$ may be O or S.

In Formula 1, $A_1$ may be a $C_5$-$C_{60}$ carbocyclic group or a $C_1$-$C_{60}$ heterocyclic group.

For example, $A_1$ may be a benzene group, a naphthalene group, an anthracene group, a phenanthrene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, an imidazopyridine group, an indolizine group, a pyrazolopyridine group, an indole group, a benzofuran group, a benzothiophene group, an isobenzothiophene group, a benzoxazole group, an isobenzoxazole group, a triazole group, a tetrazole group, an oxadiazole group, a thiadiazole group, a triazine group, a dibenzofuran group, a dibenzothiophene group, or a dibenzosilole group.

In one or more embodiments, $A_1$ may be a benzene group, a naphthalene group, a phenanthrene group, a fluorene group, a spiro-fluorene group, a pyrrole group, a thiophene group, a furan group, an imidazole group, a pyrazole group, a thiazole group, an isothiazole group, an oxazole group, an isoxazole group, a pyridine group, a pyrimidine group, a quinoline group, a carbazole group, an imidazopyridine group, an indolizine group, a pyrazolopyridine group, an indole group, a benzofuran group, a benzothiophene group, an indole group, a triazole group, a dibenzofuran group, or a dibenzosilole group.

In one or more embodiments, $A_1$ may be a group represented by one of Formulae 2-1 to 2-52:

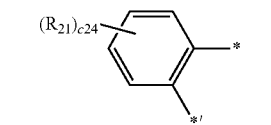

2-1

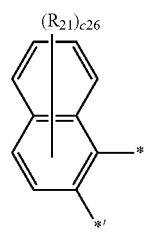

2-2

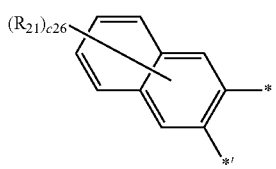

2-3

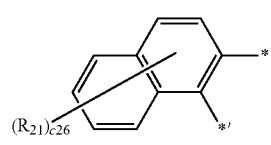

2-4

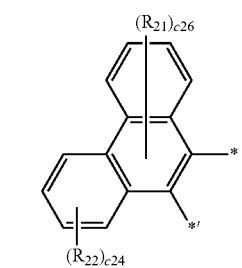

2-5

-continued

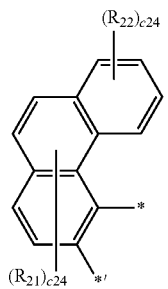

2-6

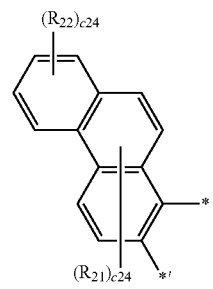

2-7

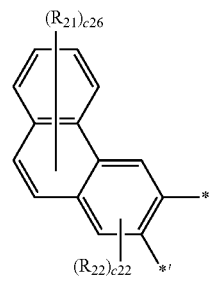

2-8

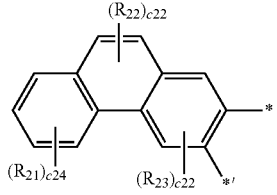

2-9

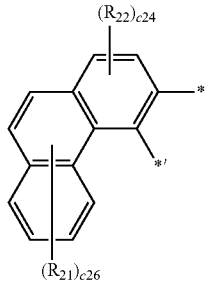

2-10

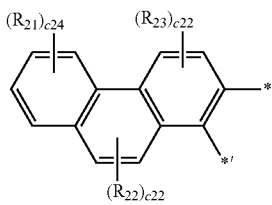

2-11

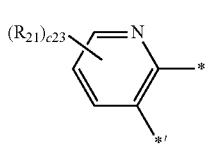 2-12
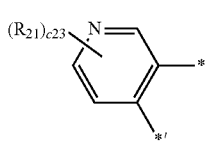 2-13
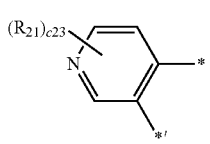 2-14
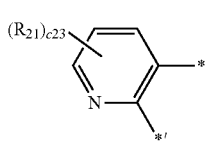 2-15
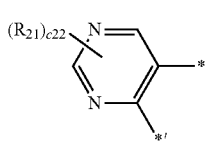 2-16
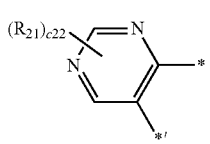 2-17
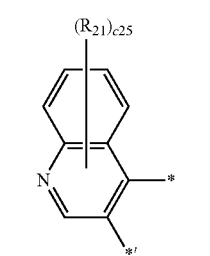 2-18
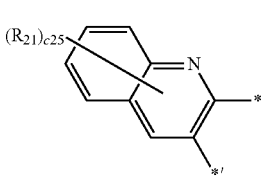 2-19
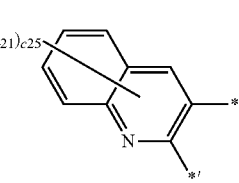 2-20
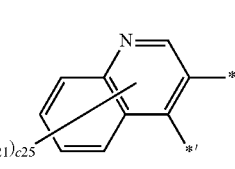 2-21
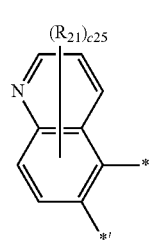 2-22
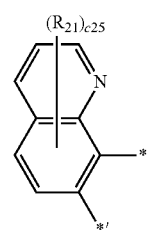 2-23
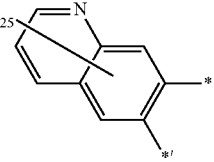 2-24
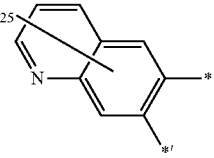 2-25
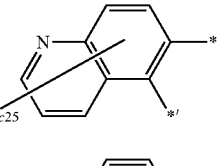 2-26
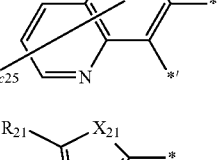 2-27
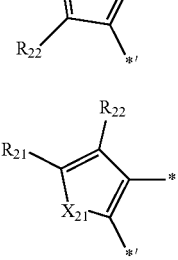 2-28
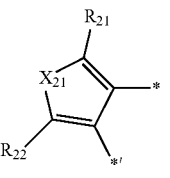 2-29
2-30

-continued 2-46
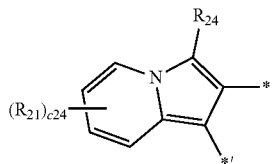

2-47
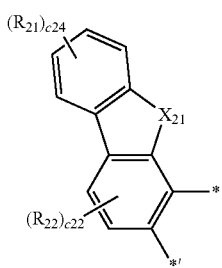

2-48
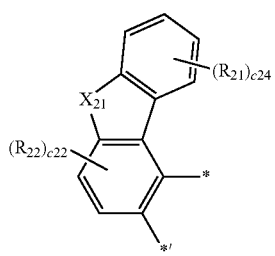

2-49
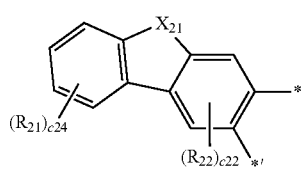

2-50
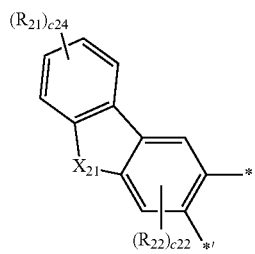

2-51
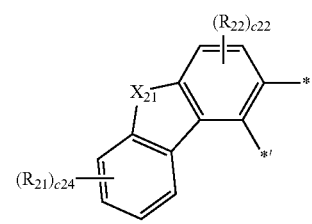

2-52
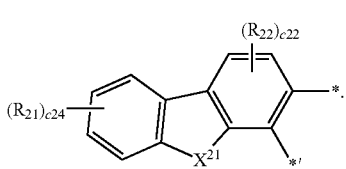

In Formulae 2-1 to 2-52, $X_{21}$ may be O, S, N($R_{24}$), C($R_{24}$)($R_{25}$), or Si($R_{24}$)($R_{25}$), $R_{21}$ to $R_{25}$ may each independently be understood with reference to the description of $R_{11}$ in the specification, c22 may be 1 or 2, c23 may be an integer of 1 to 3, c24 may be an integer of 1 to 4, c25 may be an integer of 1 to 5, c26 may be an integer of 1 to 6, and

* and *' may be binding sites to adjacent atoms.

For example, in Formulae 2-28 to 2-41 and Formulae 2-47 to 2-52, $X_{21}$ may be O, S, or N($R_{24}$). However, embodiments are not limited thereto.

In one or more embodiments, the group represented by Formula 2-1 may be a group represented by Formulae 2-1(1) to 2-1(10).

2-1(1)
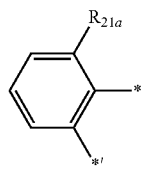

2-1(2)
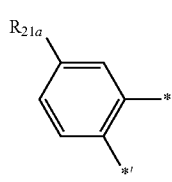

2-1(3)
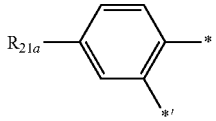

2-1(4)
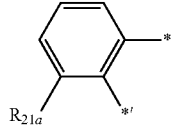

2-1(5)
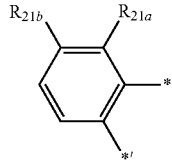

2-1(6)
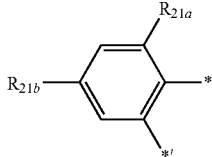

2-1(7)
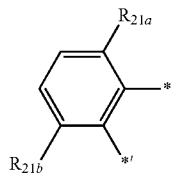

-continued

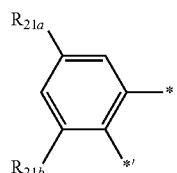
2-1(8)

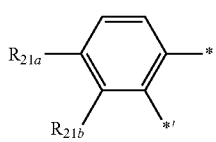
2-1(9)

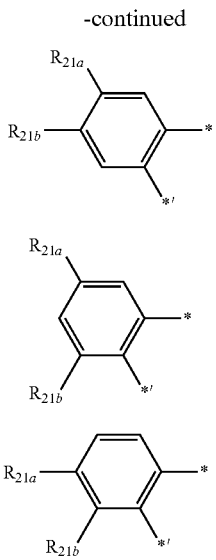
2-1(10)

In Formulae 2-1(1) to 2-1(10), $R_{21a}$ and $R_{21b}$ may each independently be understood with reference to the description of $R_{21}$ in the specification, and

* and *' may be binding sites to adjacent atoms.

In Formula 1, $L_{11}$ may be a substituted or unsubstituted $C_5$-$C_{60}$ carbocyclic group or a substituted or unsubstituted $C_1$-$C_{60}$ heterocyclic group.

$L_{11}$ may be a divalent, tervalent, tetravalent, pentavalent, or hexavalent group according to the number b11 of $Ar_{11}$(s) substituted to $L_{11}$. For example, when b11 is 1, $L_{11}$ may be a divalent group. For example, when b11 is 2, $L_{11}$ may be a tervalent group.

For example, $L_{11}$ may be a cyclopentylene group, a cyclohexylene group, a cyclopentenylene group, a cyclohexenylene group, a cycloheptenylene group, a phenylene group, a biphenylene group, a terphenylene group, a pentalenylene group, an indenylene group, a naphthylene group, an azulenylene group, a heptalenylene group, an indacenylene group, an acenaphthylene group, a fluorenylene group, a spiro-bifluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoxazolylene group, a benzimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, an imidazopyrimidinylene group, an imidazopyridinylene group, a pyridoindolylene group, a benzofuropyridinylene group, a benzothienopyridinylene group, a pyrimidoindolylene group, a benzofuropyrimidinylene group, a benzothienopyrimidinylene group, a phenoxazinylene group, a pyridobenzoxazinylene group, or a pyridobenzothiazinylene group, each unsubstituted or substituted with at least one deuterium, —F, —Cl, —Br, —I, a hydroxyl group, a cyano group, a nitro group, an amino group, a $C_1$-$C_{60}$ alkyl group, a $C_1$-$C_{60}$ alkoxy group, a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzoxazinyl group, a pyridobenzothiazinyl group, or any combination thereof.

In one or more embodiments, $L_{11}$ may be a group represented by Formulae 4-1 to 4-36.

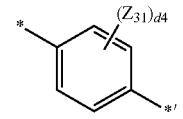
4-1

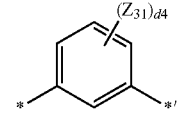
4-2

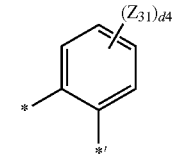
4-3

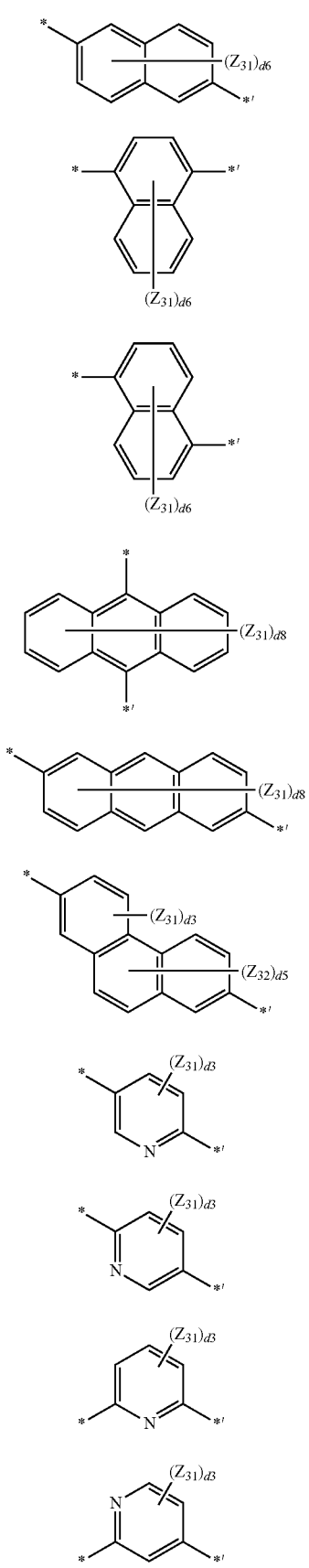

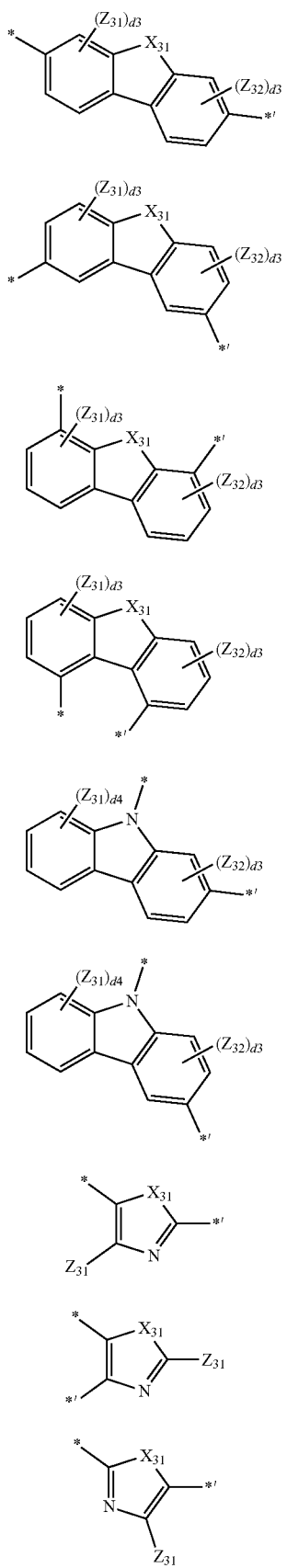

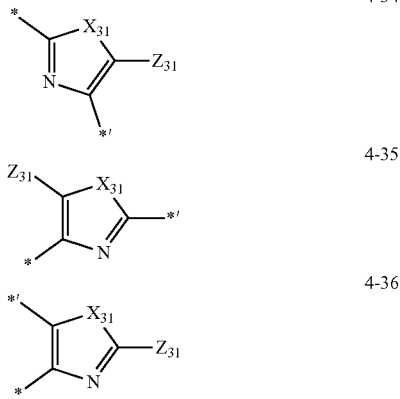

In Formulae 4-1 to 4-36, $X_{31}$ may be O, S, $N(Z_{33})$, $C(Z_{33})(Z_{34})$, or $Si(Z_{33})(Z_{34})$, $Z_{31}$ to $Z_{34}$ may each independently be hydrogen, deuterium, —F, —Cl, —Br, —I, a hydroxyl group, a cyano group, a nitro group, an amino group, a $C_1$-$C_{20}$ alkyl group, a $C_1$-$C_{20}$ alkoxy group, a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a spiro-bifluorenyl group, an anthracenyl group, a fluoranthenyl group, a triphenylenyl group, a pyrenyl group, a chrysenyl group, a pyrrolyl group, an imidazolyl group, a pyrazolyl group, a pyridinyl group, a pyrazinyl group, a pyrimidinyl group, a pyridazinyl group, an indolyl group, a carbazolyl group, a phenanthridinyl group, an acridinyl group, a phenanthrolinyl group, an oxazolyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, a triazinyl group, a dibenzofuranyl group, or a dibenzothiophenyl group, d2 may be an integer of 1 to 2,
d3 may be an integer of 1 to 3,
d4 may be an integer of 1 to 4,
d5 may be an integer of 1 to 5,
d6 may be an integer of 1 to 6,
d8 may be an integer of 1 to 8, and
\* and \*' may be binding sites to adjacent atoms.

In Formula 1, a11, which indicates the number of $L_{11}(s)$, may be an integer of 0 to 3. When a11 is 0, -$(L_{11})_{a11}$- may be a single bond. When a11 is 2 or greater, two or more $L_{11}(s)$ may be identical to or different from each other.

In one or more embodiments, a11 may be 0 or 1. However, embodiments are not limited thereto.

In Formula 1, $Ar_{11}$ and $Ar_{12}$ may each independently be a $C_6$-$C_{60}$ aryl group, a $C_1$-$C_{60}$ heteroaryl group, a monovalent non-aromatic condensed polycyclic group, or a monovalent non-aromatic condensed heteropolycyclic group, each unsubstituted or substituted with at least one $R_a$.

In one or more embodiments, $Ar_{11}$ and $Ar_{12}$ may each independently a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a benzofluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a naphthobenzofuranyl group, a naphthobenzothiophenyl group, a benzocarbazolyl group, a dibenzocarbazolyl group, an imidazopyridinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzoxazinyl group, or a pyridobenzothiazinyl group, each unsubstituted or substituted with at least one $R_a$.

In one or more embodiments, $Ar_{11}$ and $Ar_{12}$ may each independently be a group represented by Formulae 5-1 to 5-48.

5-1
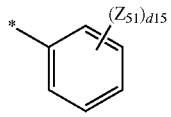

5-2
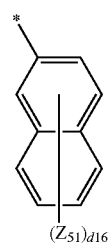

5-3
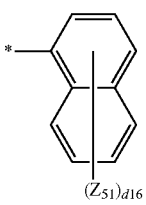

5-4
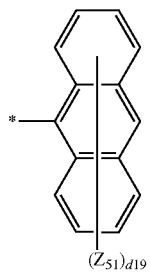

-continued 5-5
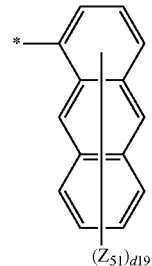

5-6
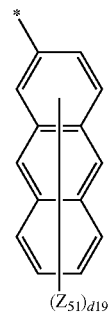

5-7
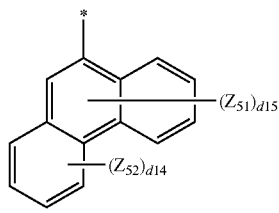

5-8
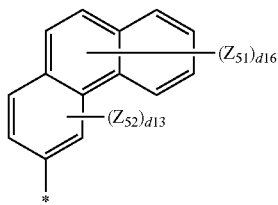

5-9
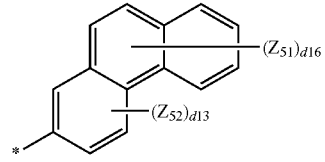

5-10
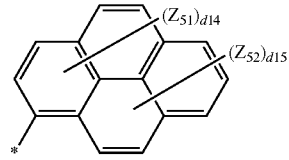

5-11
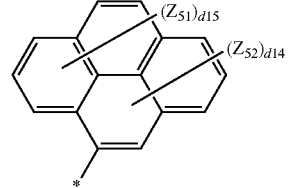

-continued
5-12
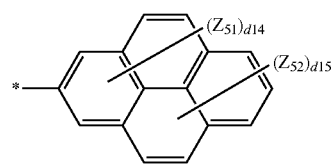
5-13
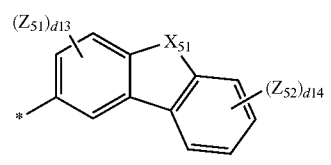
5-14
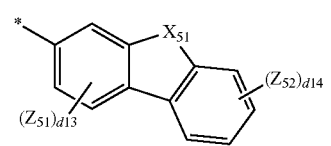
5-15
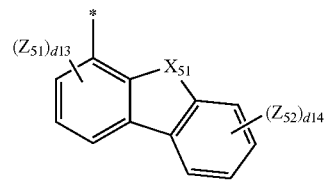
5-16
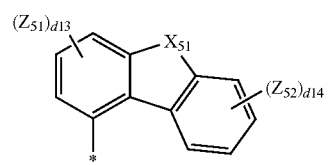
5-17
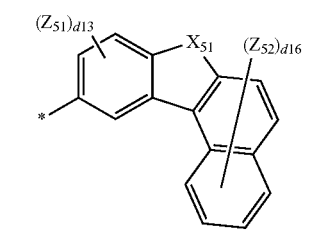
5-18
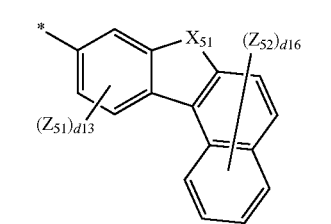
5-19
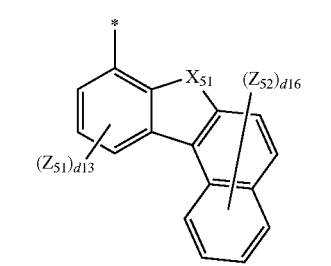
-continued
5-20
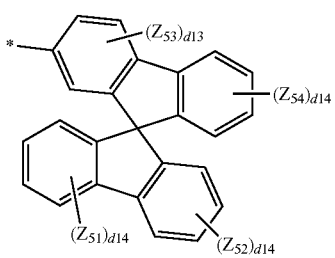
5-21
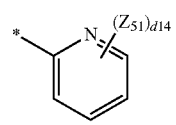
5-22
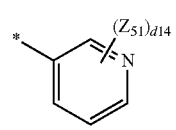
5-23
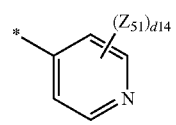
5-24
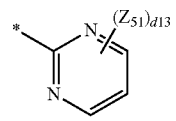
5-25
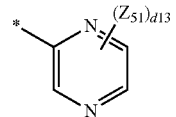
5-26
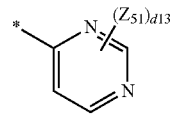
5-27
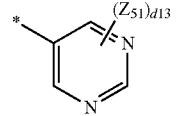
5-28
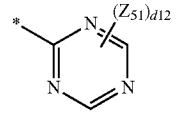
5-29
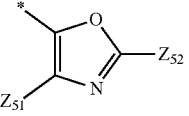
5-30
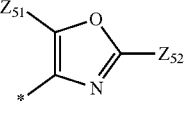

In Formulae 5-1 to 5-48,
$X_{51}$ may be O, S, $N(Z_{53})$, $C(Z_{53})(Z_{54})$, or $Si(Z_{53})(Z_{54})$,
$Z_{51}$ to $Z_{54}$ may each independently be understood with reference to the description of $R_a$ of Formula 1,
d12 may be an integer of 1 to 2,
d13 may be an integer of 1 to 3,
d14 may be an integer of 1 to 4,
d15 may be an integer of 1 to 5,
d16 may be an integer of 1 to 6,
d19 may be an integer of 1 to 9, and
* may be a binding site to an adjacent atom.
In one or more embodiments, in Formulae 5-1 to 5-48, $Z_{51}$ to $Z_{54}$ may each independently be hydrogen, deuterium, —F, —Cl, —Br, —I, a hydroxyl group, a cyano group, a nitro group, an amino group, a $C_1$-$C_{20}$ alkyl group, a $C_1$-$C_{20}$ alkoxy group, a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a spiro-bifluorenyl group, an anthracenyl group, a fluoranthenyl group, a triphenylenyl group, a pyrenyl group, a chrysenyl group, a pyrrolyl group, an imidazolyl group, a pyrazolyl group, a pyridinyl group, a pyrazinyl group, a pyrimidinyl group, a pyridazinyl group, an indolyl group, a carbazolyl group, a phenanthridinyl group, an acridinyl group, a phenanthrolinyl group, an oxazolyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, a triazinyl group, a dibenzofuranyl group, or a dibenzothiophenyl group.

In one or more embodiments, $Ar_{12}$ may be groups represented by Formulae 5-1 to 5-3, Formulae 5-13 to 5-16, and Formulae 5-21 to 5-48.

In Formula 1, b11, which indicates the number of $Ar_{11}(s)$, may be an integer 1 to 5. When b11 is 2 or greater, two or more $Ar_{11}(s)$ may be identical to or different from each other.

In Formula 1, $R_{11}$, $R_{12}$ and $R_a$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted heteroaryl group, a substituted or unsubstituted monovalent non-aromatic condensed polycyclic group, a substituted or unsubstituted monovalent non-aromatic condensed heteropolycyclic group, —Si(Q$_1$)(Q$_2$)(Q$_3$), —N(Q$_4$)(Q$_5$), or —B(Q$_6$)(Q$_7$). Here, $Q_1$ to $Q_7$ may be the same as defined in the specification.

In one or more embodiments, $R_{11}$, $R_{12}$, and $R_a$ may each independently be:

hydrogen, deuterium, —F, —Cl, —Br, —I, a hydroxyl group, a cyano group, a nitro group, an amino group, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one deuterium, —F, —Cl, —Br, —I, a hydroxyl group, a cyano group, a nitro group, an amino group, or any combination thereof;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzoxazinyl group, or a pyridobenzothiazinyl group, each unsubstituted or substituted with at least one deuterium, —F, —Cl, —Br, —I, a hydroxyl group, a cyano group, a nitro group, an amino group, a $C_1$-$C_{20}$ alkyl group, a $C_1$-$C_{20}$ alkoxy group, a phenyl group, a biphenyl group, a terphenyl group, or any combination thereof; or —Si(Q$_1$)(Q$_2$)(Q$_3$), —N(Q$_4$)(Q$_5$), or —B(Q$_6$)(Q$_7$), and $Q_1$ to $Q_7$ may each independently be hydrogen, deuterium, a $C_1$-$C_{10}$ alkyl group, a phenyl group, a naphthyl group, a fluorenyl group, a carbazolyl group, a dibenzofuranyl group, a dibenzothiophenyl group, or a biphenyl group.

In one or more embodiments, $R_{11}$, $R_{12}$ and $R_a$ may each independently be:

hydrogen, deuterium, —F, a cyano group, or a nitro group;

a $C_1$-$C_{10}$ alkyl group or a $C_1$-$C_{10}$ alkoxy group, each unsubstituted or substituted with at least one deuterium, —F, a cyano group, a nitro group, or any combination thereof;

a phenyl group, a biphenyl group, a terphenyl group, a naphthyl group, a fluorenyl group, a pyridinyl group, a pyrimidinyl group, a triazinyl group, an imidazolyl group, an oxazolyl group, a thiazolyl group, a carbazolyl group, a dibenzofuranyl group, or a dibenzothiophenyl group, each unsubstituted or substituted with at least one deuterium, —F, a cyano group, a nitro group, a $C_1$-$C_{20}$ alkyl group, a $C_1$-$C_{10}$ alkoxy group, a phenyl group, a biphenyl group, a terphenyl group, or any combination thereof; or —N(Q$_4$)(Q$_5$), and $Q_4$ and $Q_5$ may each independently hydrogen, deuterium, a $C_1$-$C_{10}$ alkyl group, a phenyl group, a naphthyl group, a fluorenyl group, a carbazolyl group, a dibenzofuranyl group, a dibenzothiophenyl group, or a biphenyl group. However, embodiments are not limited thereto.

In Formula 1, c11 and c12 indicate the number of $R_{11}(s)$ and the number of $R_{12}(s)$, respectively. For example, c11 may be an integer of 1 to 20, and c12 may be an integer of 1 to 4.

When c11 is 2 or greater, two or more $R_{11}(s)$ may be identical to or different from each other. When c12 is 2 or greater, two or more $R_{12}(s)$ may be identical to or different from each other.

When c11 is 2 or greater, two adjacent $R_{11}(s)$ may optionally be linked to one another to form a substituted or unsubstituted $C_5$-$C_{30}$ carbocyclic group or a substituted or unsubstituted $C_1$-$C_{30}$ heterocyclic group. When c12 is 2 or greater, two adjacent $R_{12}(s)$ may optionally be linked to one another to form a substituted or unsubstituted $C_5$-$C_{30}$ carbocyclic group, or a substituted or unsubstituted $C_1$-$C_{30}$ heterocyclic group.

In Formula 1, $A_1$ and $Ar_{12}$ may optionally be condensed with each other via a first linking group of a single bond, *—$Ar_{31}$—*', *—O—*', *—$[C(R_{31})(R_{32})]_{k11}$—*', *—$C(R_{31})$=*', *=$C(R_{31})$—*', *—$C(R_{31})$=$C(R_{32})$—', *—C(=O)—*', *—C(=S)—*', *—C≡C—*', *—$N(R_{31})$—*', *—$P(R_{31})$—*', *—$[Si(R_{31})(R_{32})]_{k11}$—*', or *—$P(R_{31})(R_{32})$—*', to form a substituted or unsubstituted $C_5$-$C_{30}$ carbocyclic group or a substituted or unsubstituted $C_1$-$C_{30}$ heterocyclic group, $Ar_{31}$ may be a $C_5$-$C_{30}$ carbocyclic group, $R_{31}$ and $R_{32}$ may each independently be understood with reference to the above description of $R_{11}$, and k11 may be 1, 2, 3 or 4.

In Formula 1, when a12 is zero, then $A_1$ and $Ar_{12}$ are linked to each other via a first linking group, a moiety represented by

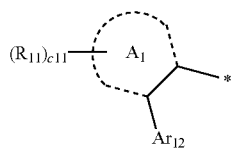

in Formula 1 may be represented by one of Formulae 1-1 to 1-12.

1-1
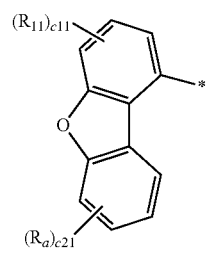

1-2
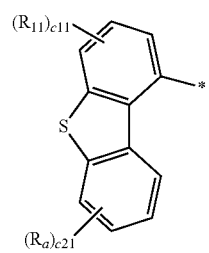

1-3
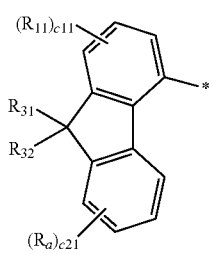

-continued 1-4
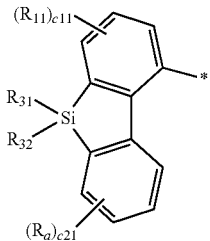

1-5
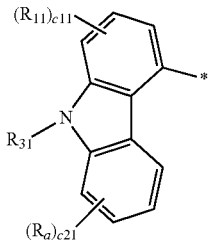

1-6
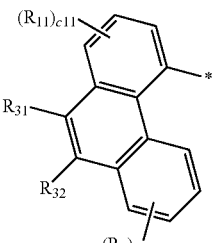

1-7
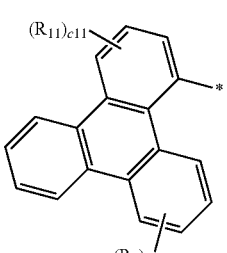

1-8
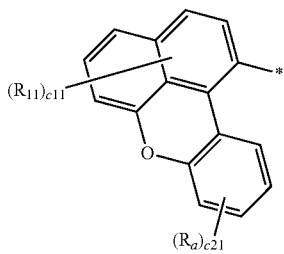

1-9
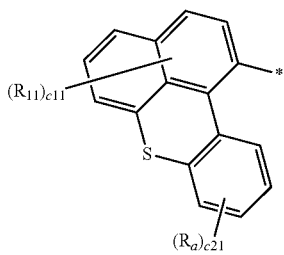

-continued 1-10
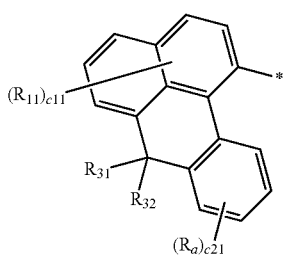

1-11
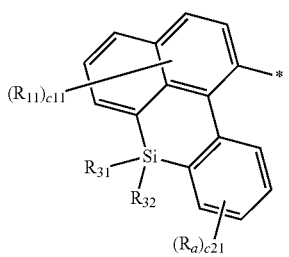

1-12
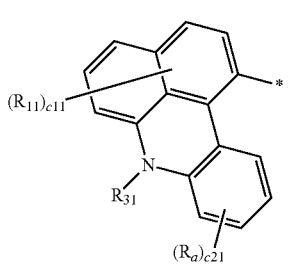

In Formulae 1-1 to 1-12,
c21 may be an integer 1 to 4,
$R_{11}$, $R_a$, c11, $R_{31}$, and $R_{32}$ may each independently be understood with reference to the descriptions thereof provided in the specification, and
* may be a binding site to an adjacent atom.

The condensed cyclic compound represented by Formula 1 may satisfy Inequality 1 and Inequality 2.

$E(T_1) < E(S_1) < 2E(T_1)$  <Inequality 1>

$2E(T_1) - E(S_1) < 0.5$ eV  <Inequality 2>

In Inequalities 1 and 2,
$E(T_1)$ is the lowest excitation triplet energy level (eV) of the condensed cyclic compound, and
$E(S_1)$ is the lowest excitation singlet energy level (eV) of the condensed cyclic compound,
wherein $E(T_1)$ and $E(S_1)$ are the energy levels evaluated using a density functional theory (DFT) method of Gaussian program structurally optimized at a level of B3LYP/6-31G*(d,p).

The condensed cyclic compound represented by Formula 1 may be one of Compounds 1 to 120 and Compounds 122 to 800. However, embodiments are not limited thereto:

1
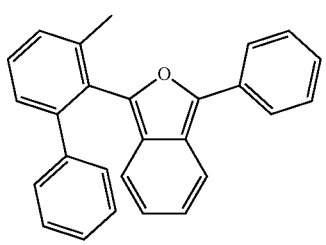

2
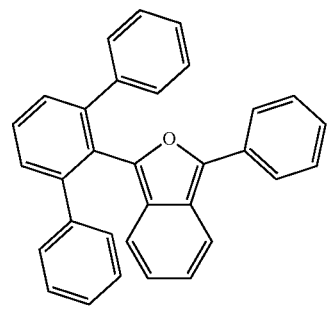

3
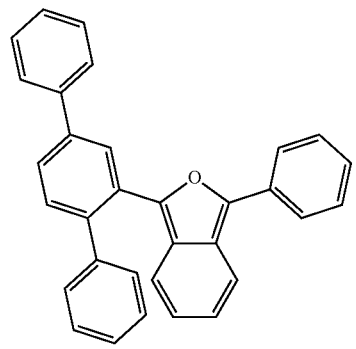

4
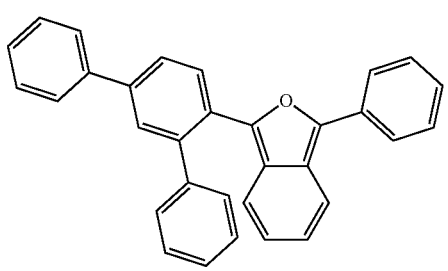

5
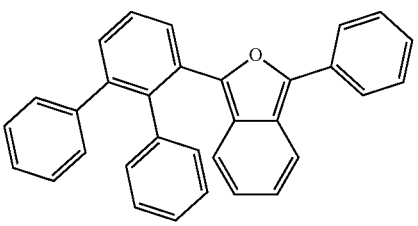

6
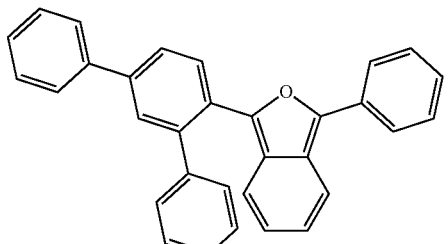

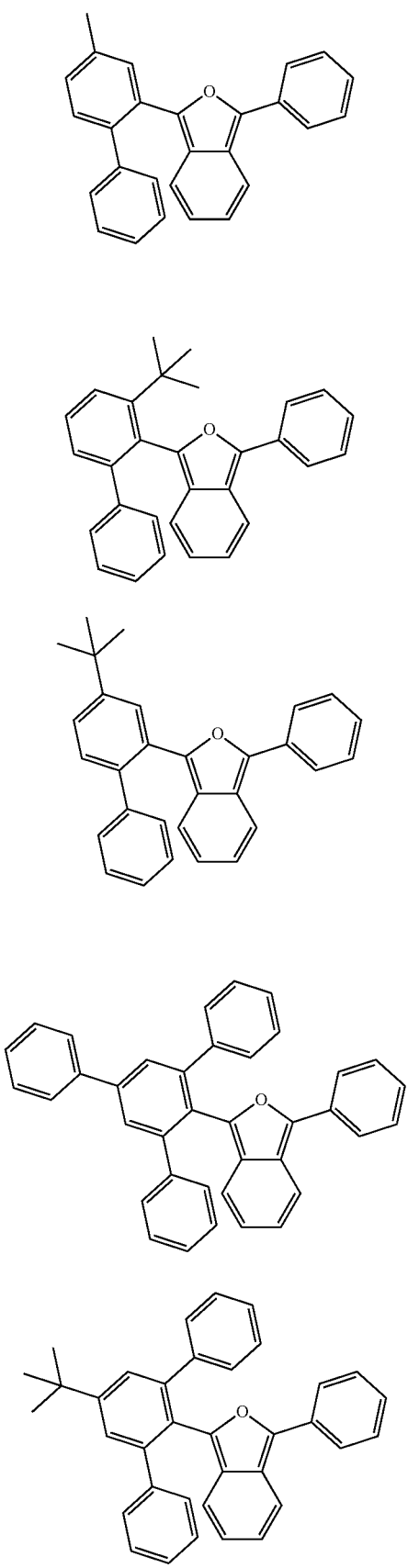
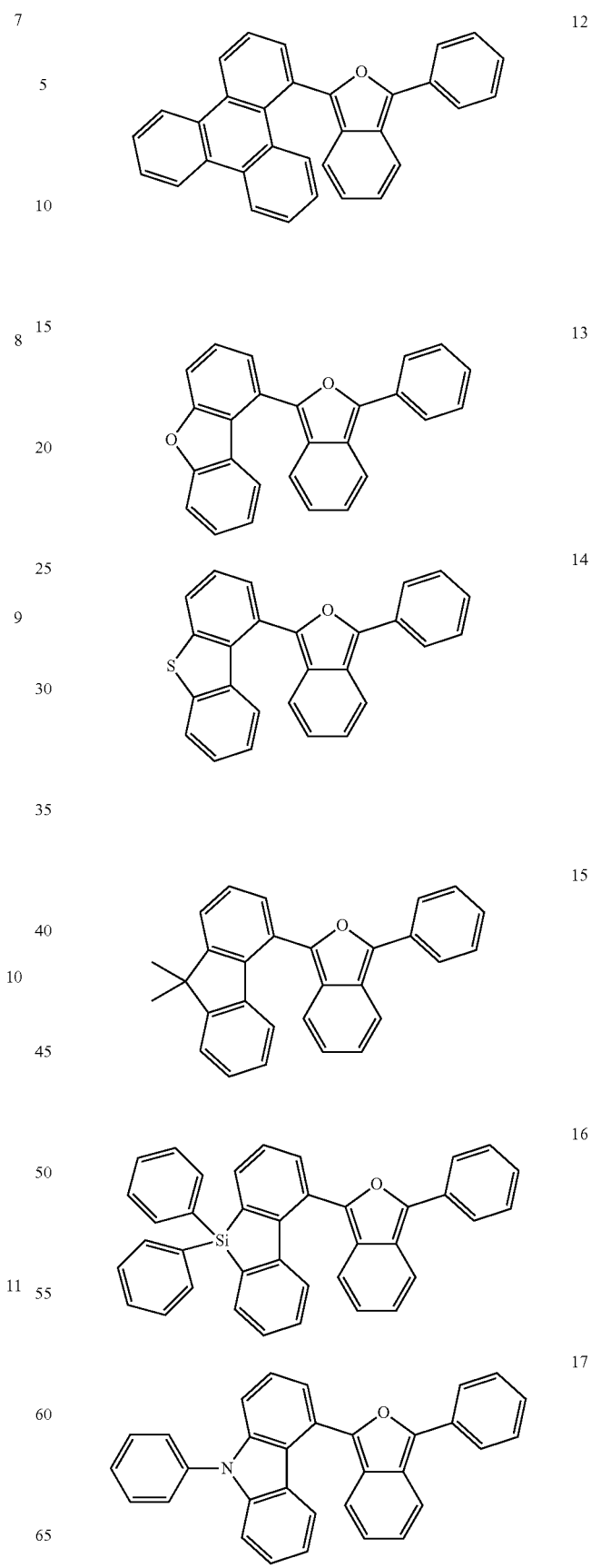

18
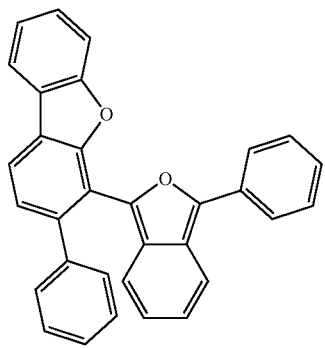
19
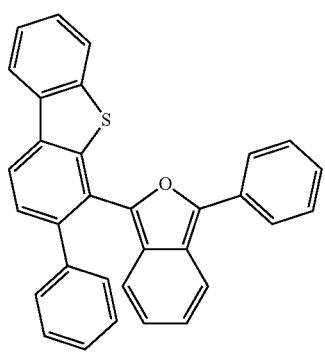
20
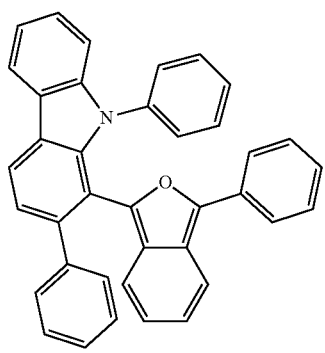
21
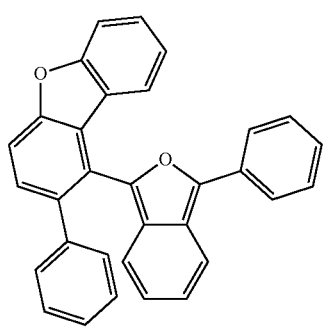
22
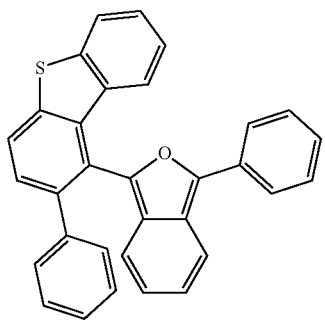
23
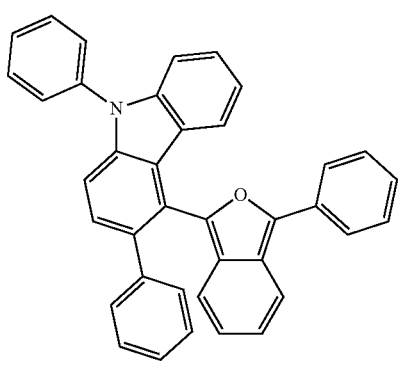
24
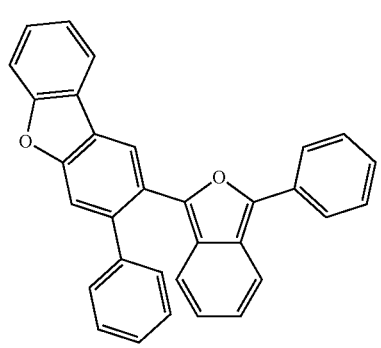
25
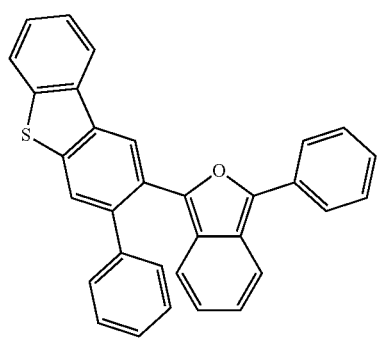

26
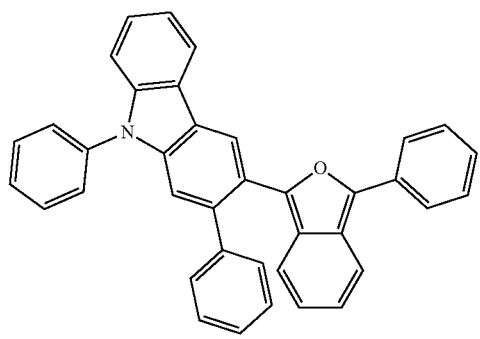
27
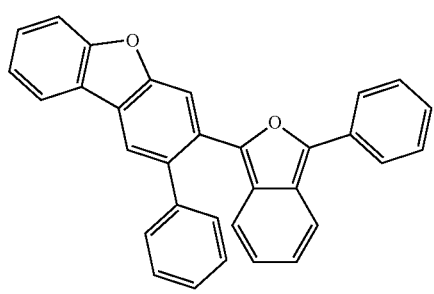
28
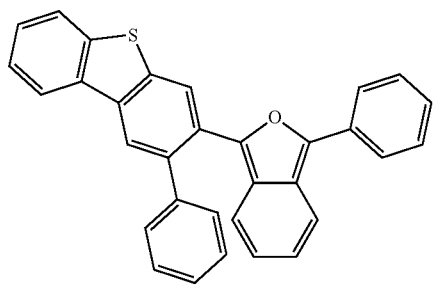
29
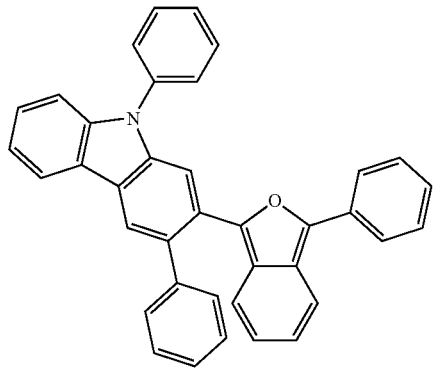
30
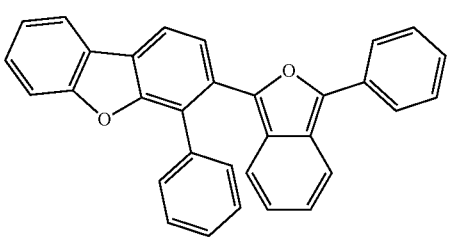
31
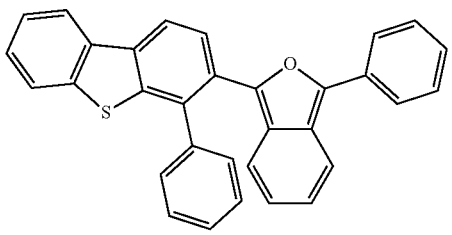
32
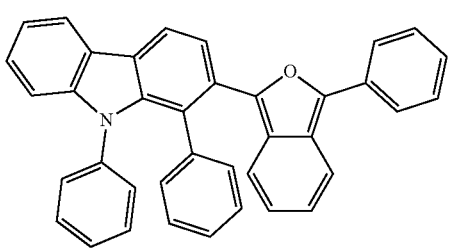
33
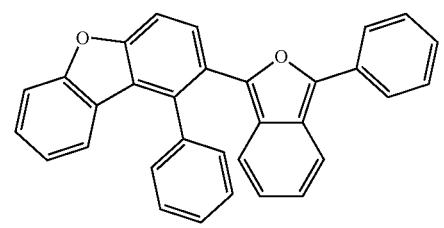
34
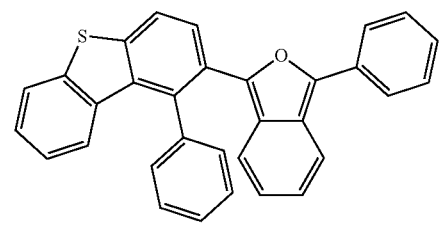
35
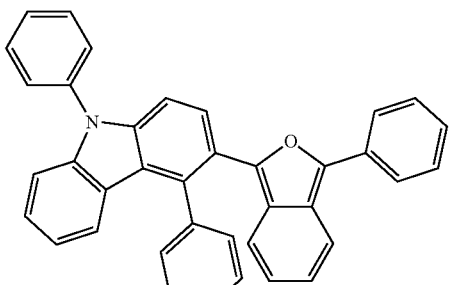
36
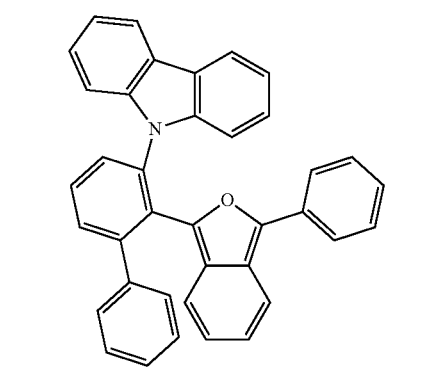

37
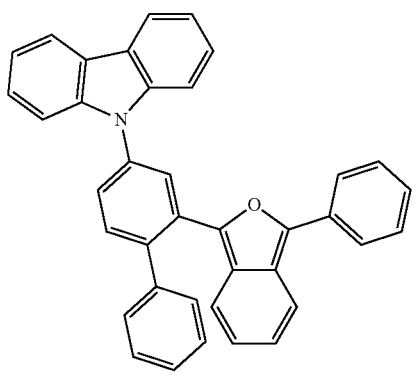
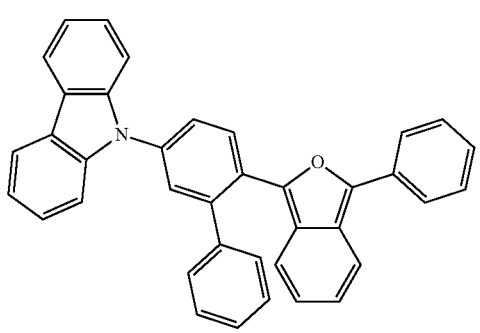
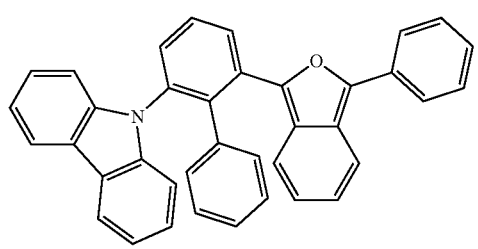
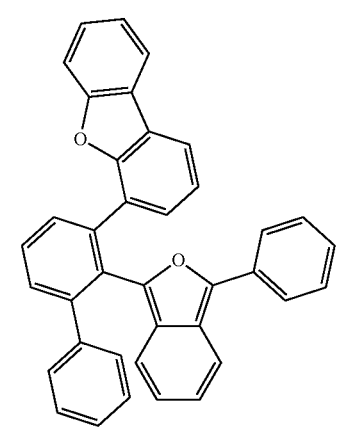
38
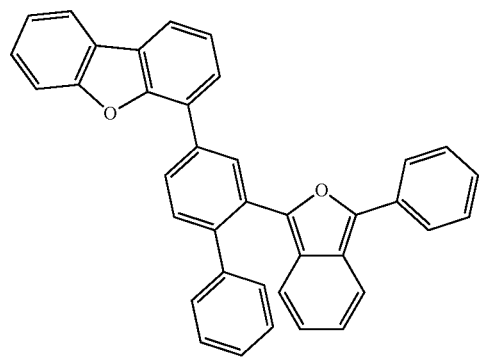
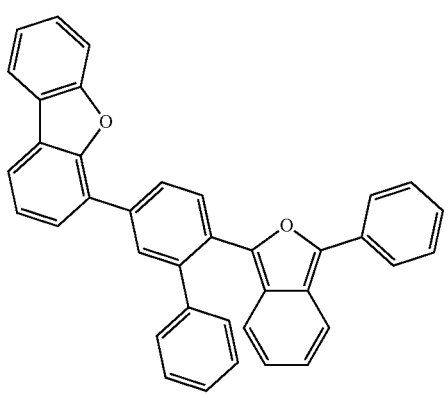
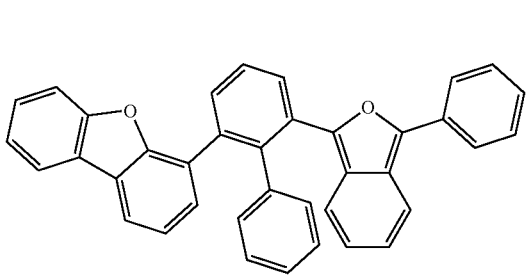

45
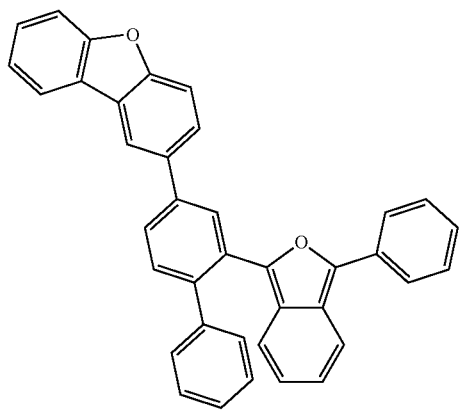
46
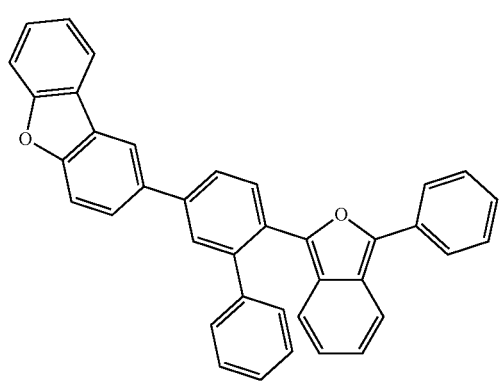
47
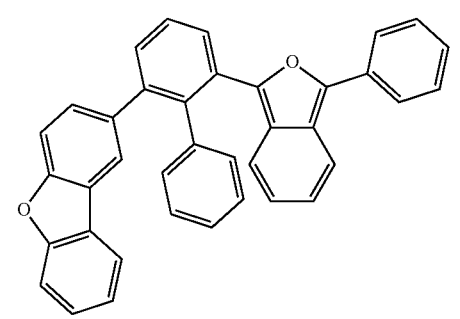
48
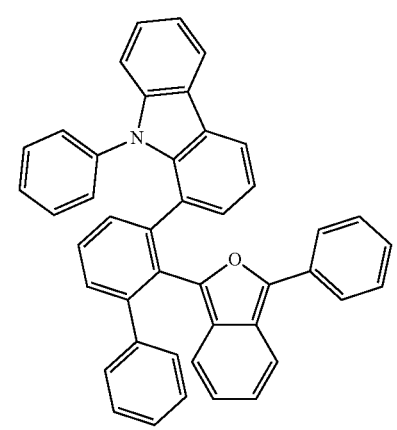
49
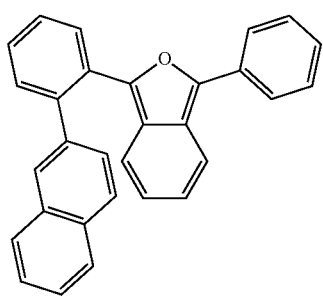
50
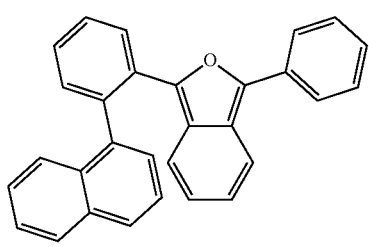
51
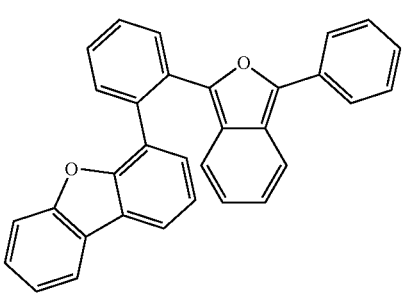
52
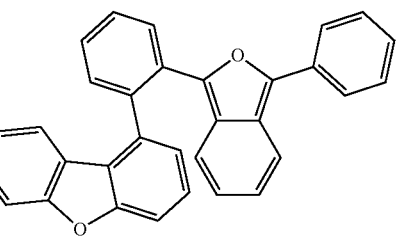
53
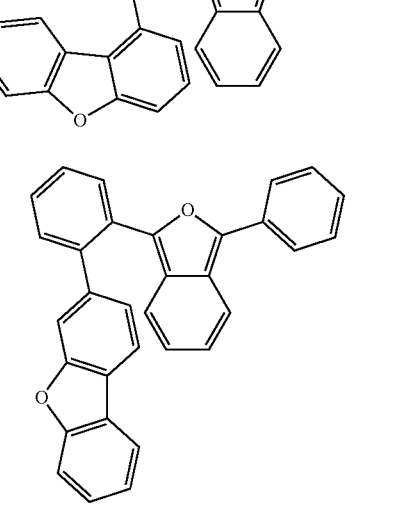

54
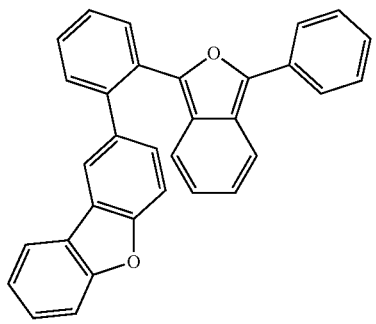
55
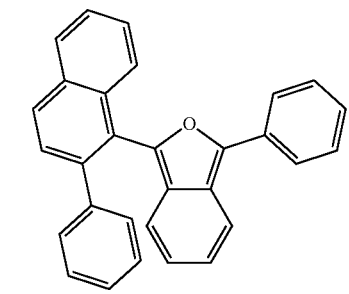
56
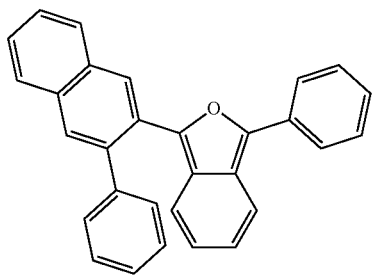
57
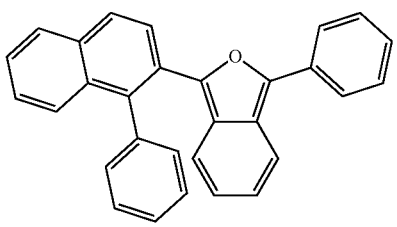
58
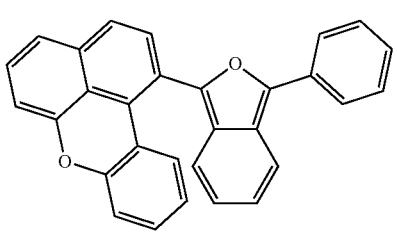
59
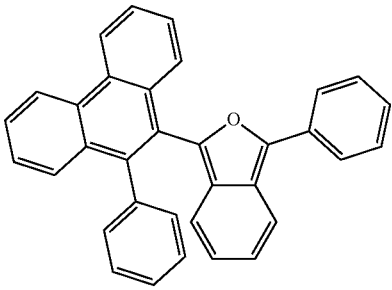
60
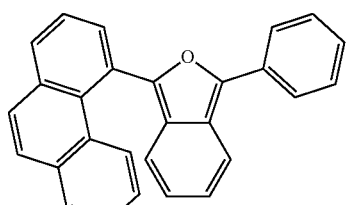
61
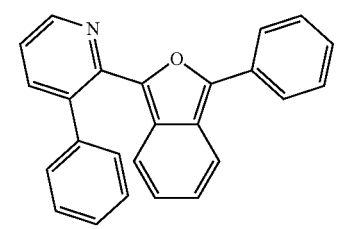
62
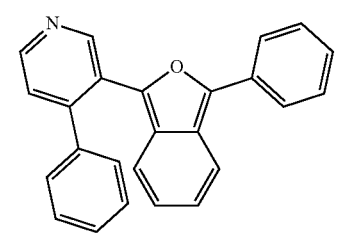
63
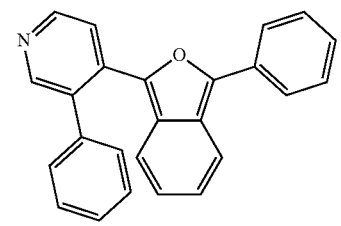
64
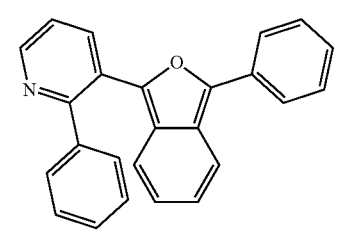

65
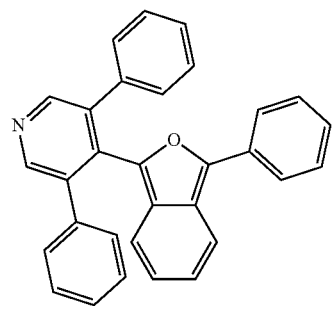
66
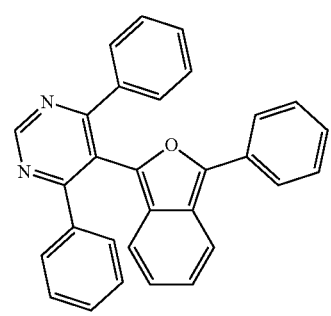
67
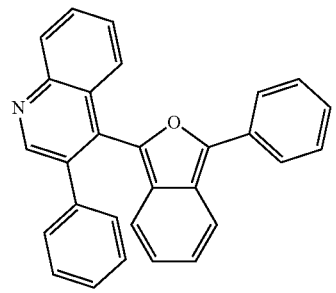
68
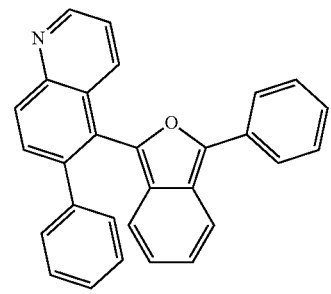
69
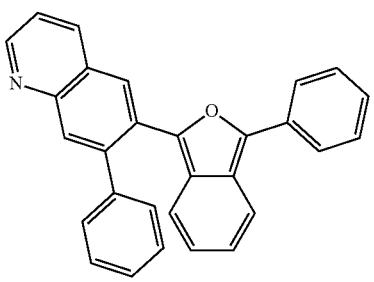
70
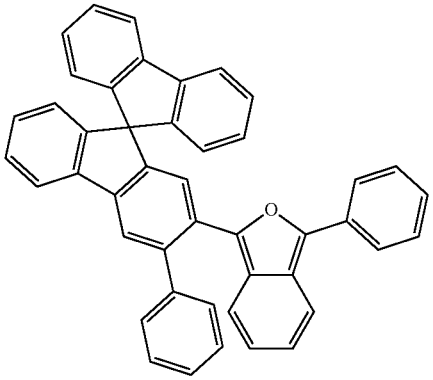
71
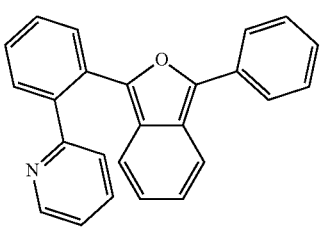
72
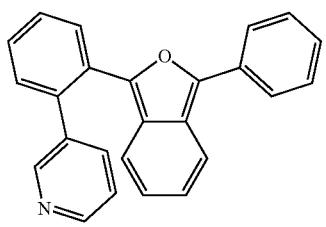
73
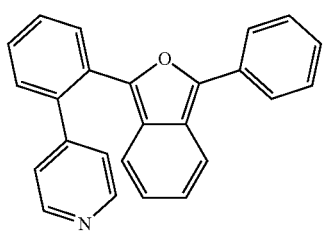
74
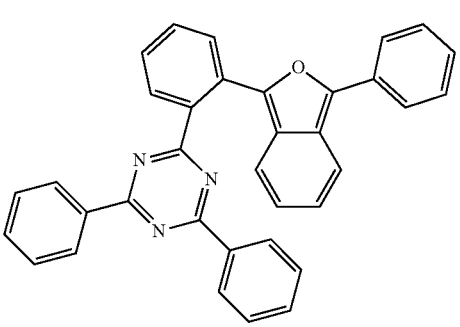

75
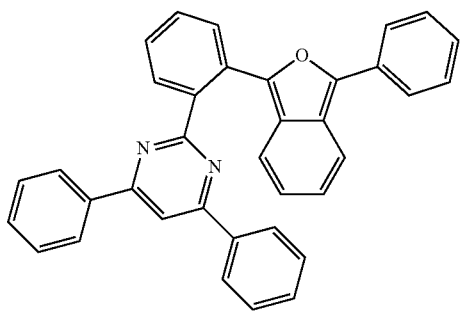
76
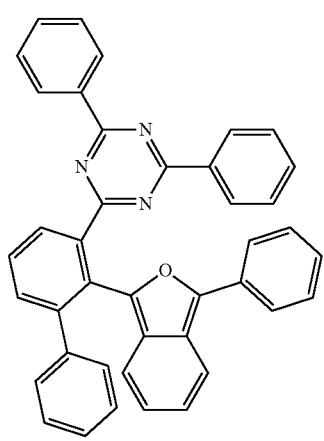
77
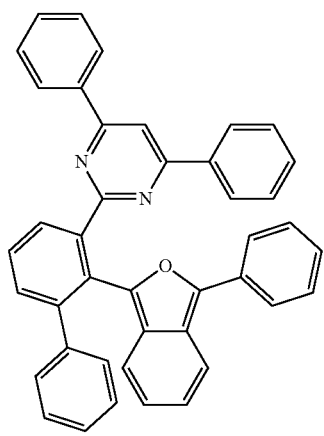
78
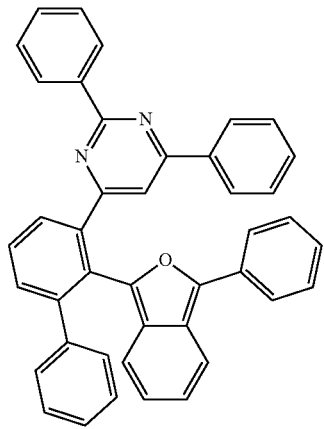
79
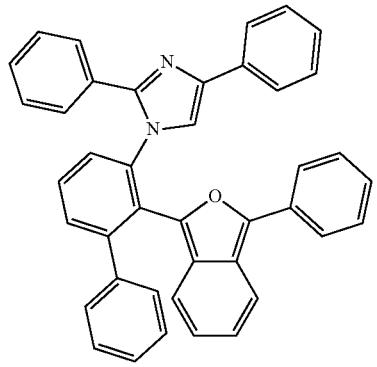
80
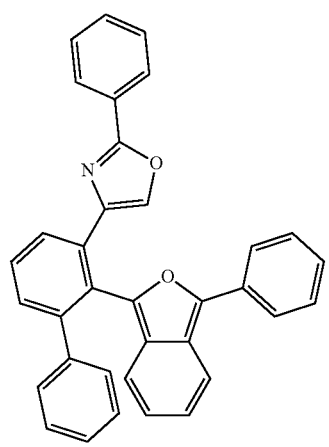
81
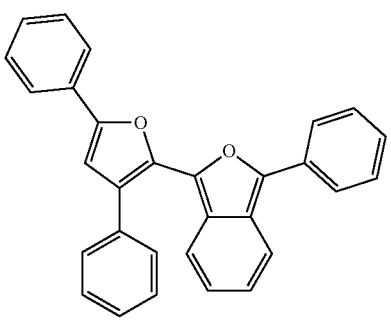
82
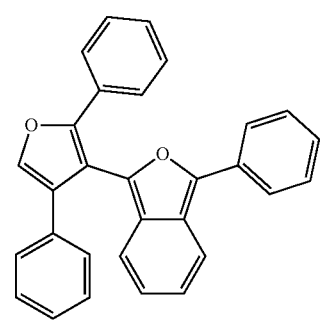

83
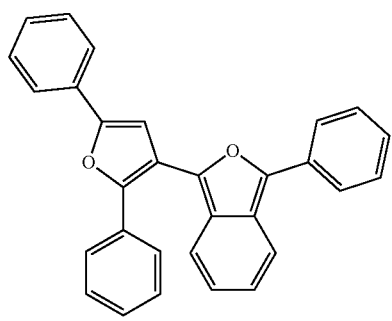
84
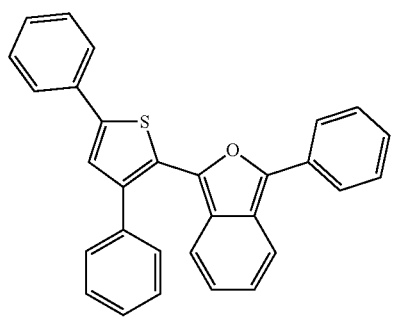
85
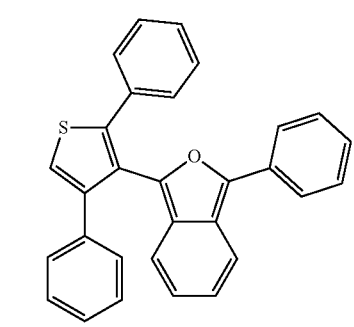
86
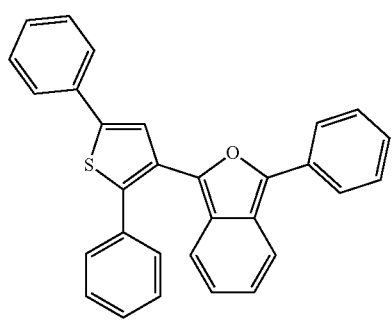
87
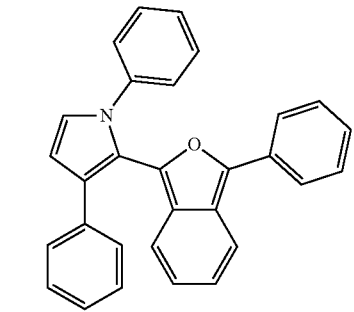
88
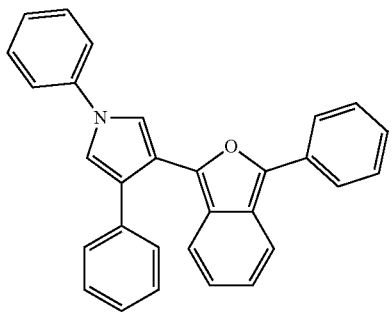
89
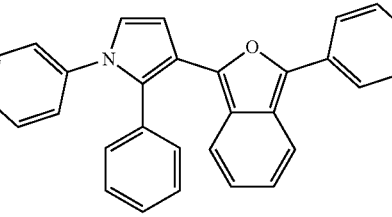
90
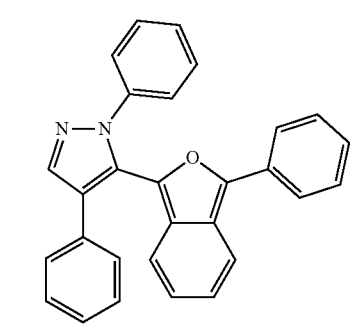
91
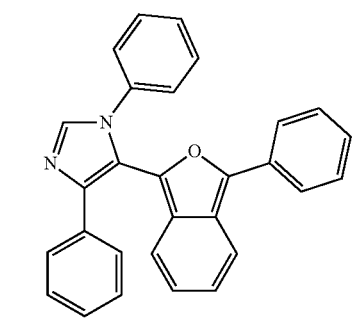
92
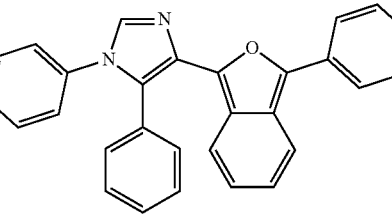
93
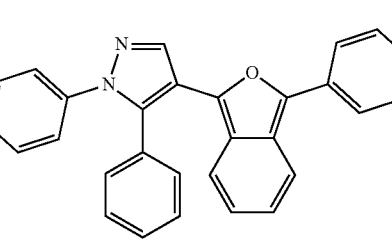

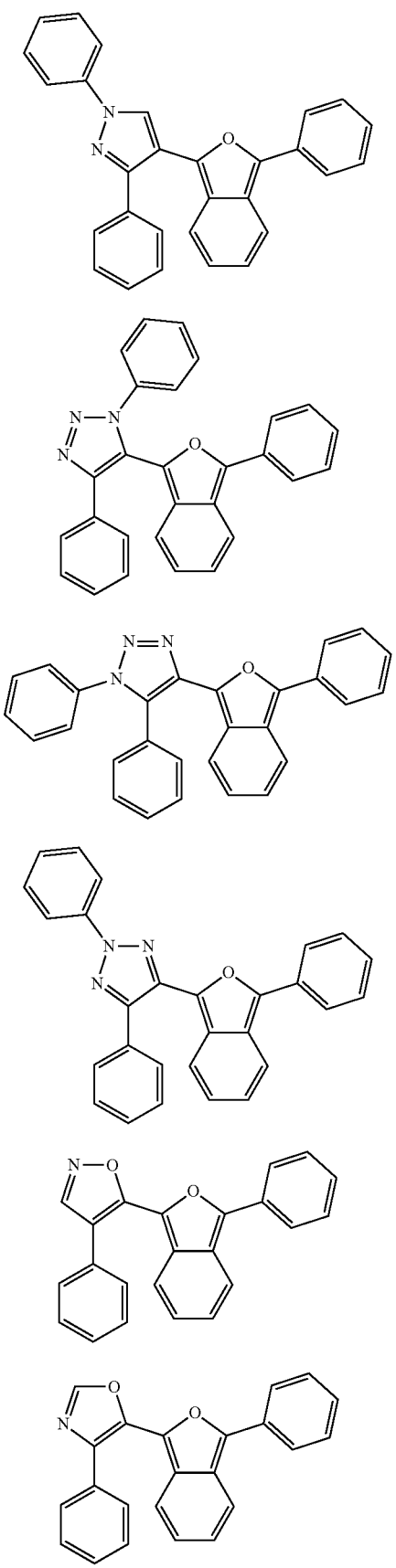
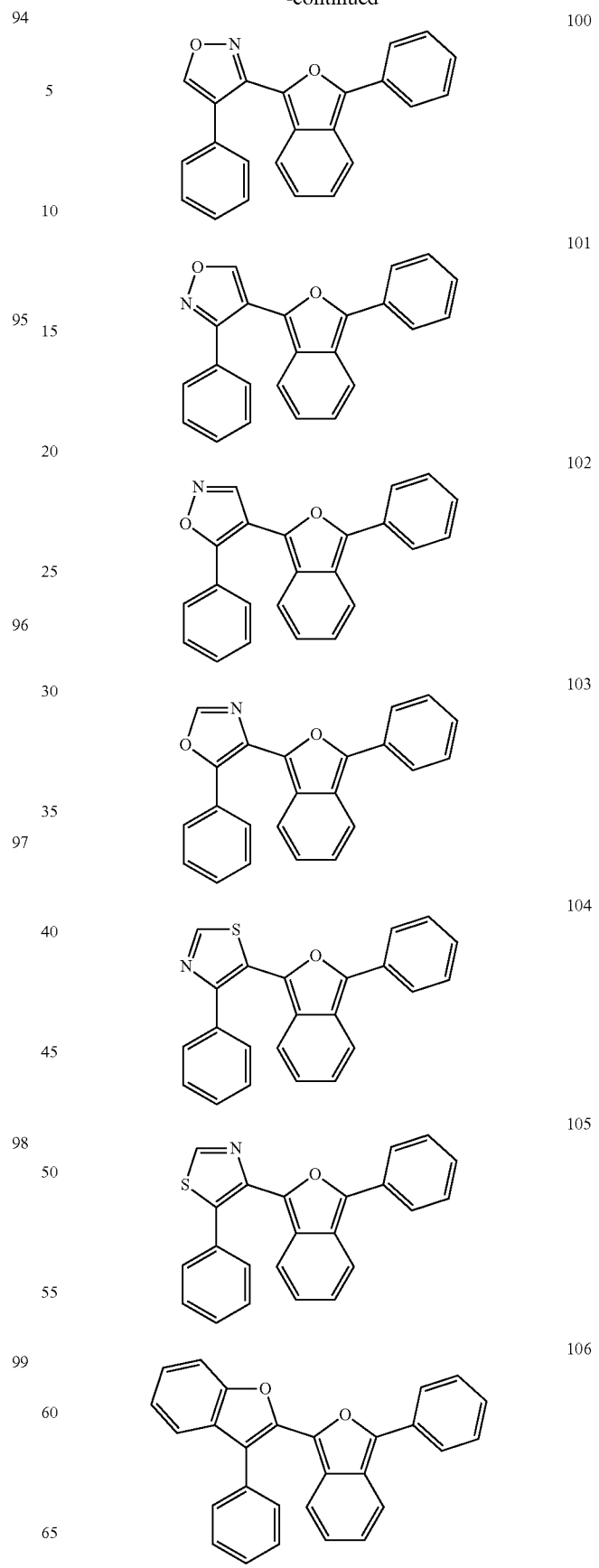

107 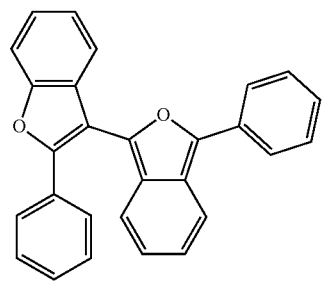
108 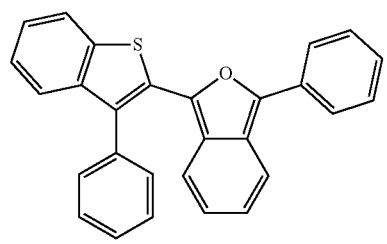
109 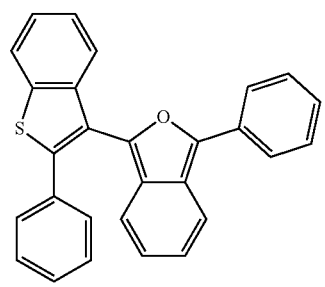
110 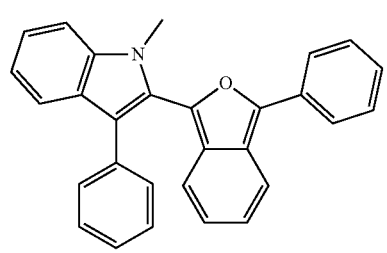
111 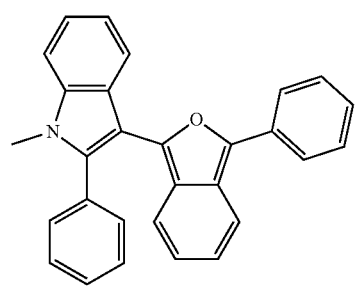
112 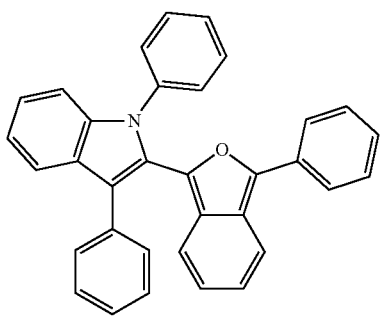
113 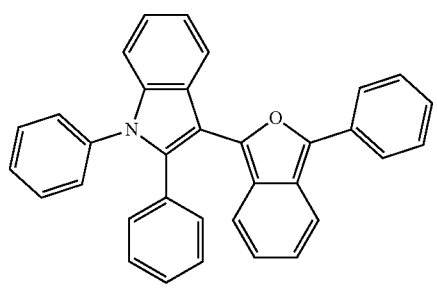
114 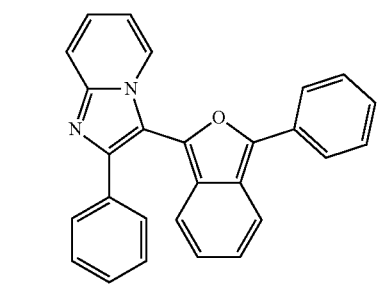
115 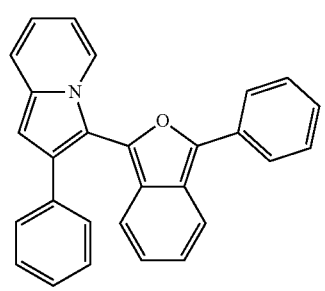
116 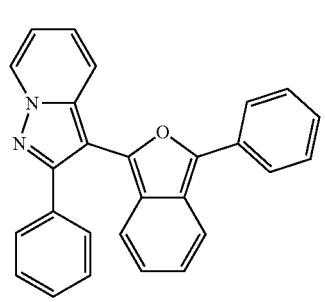

117
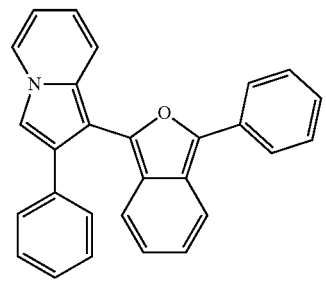
118
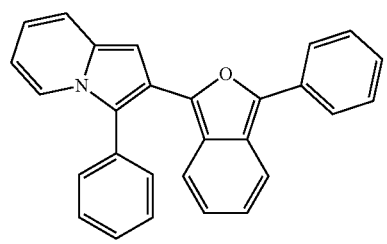
119
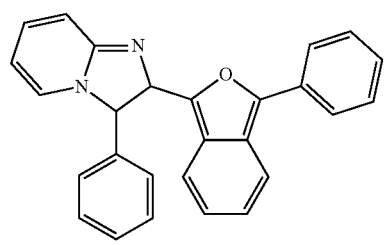
120
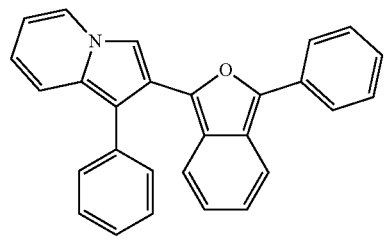
122
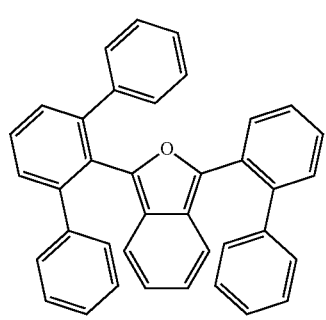
123
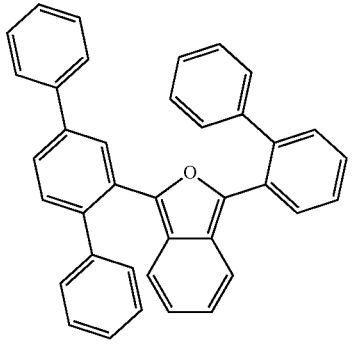
124
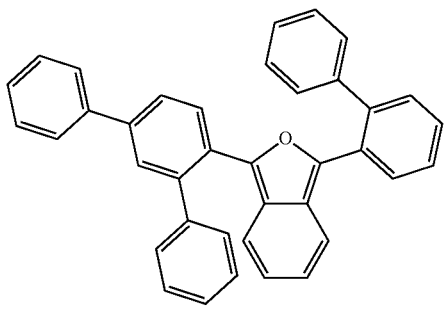
125
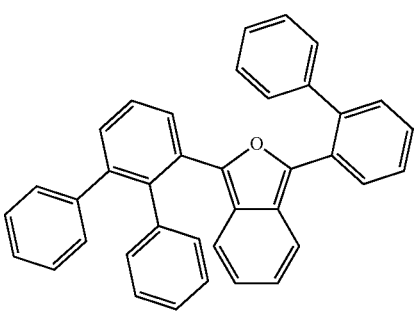
126
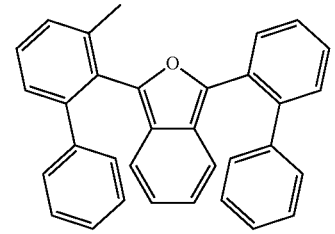
127
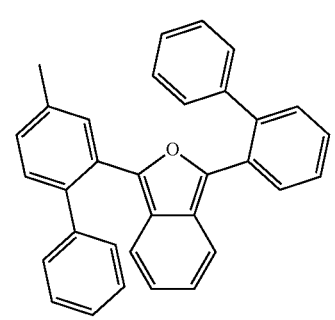

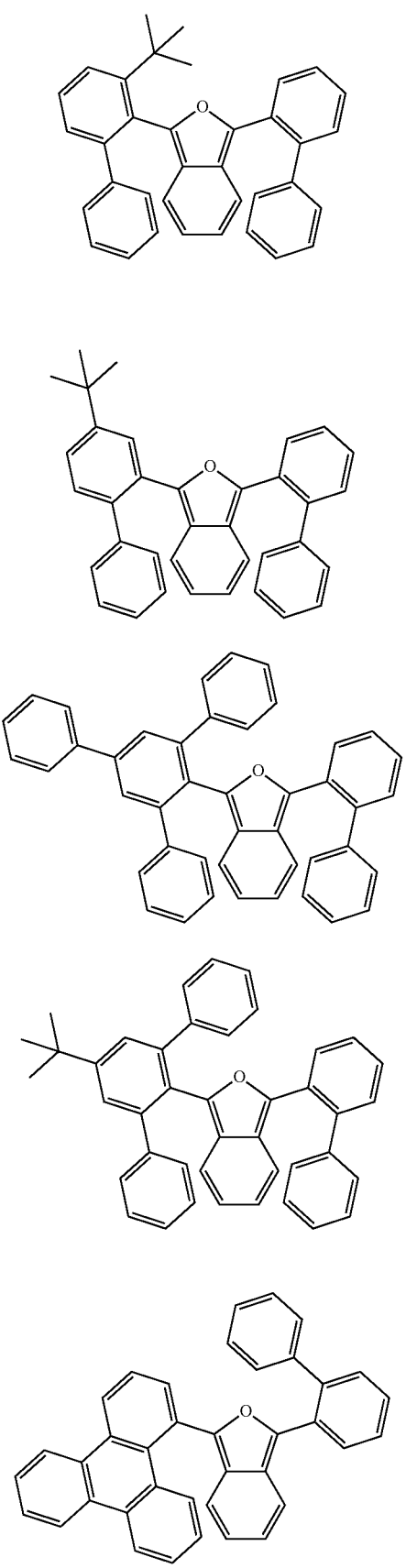
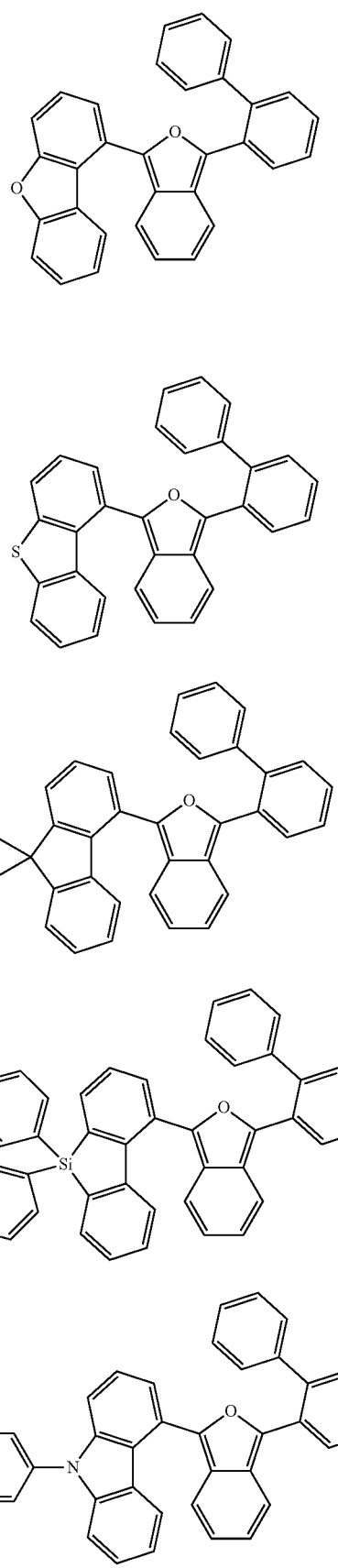

138 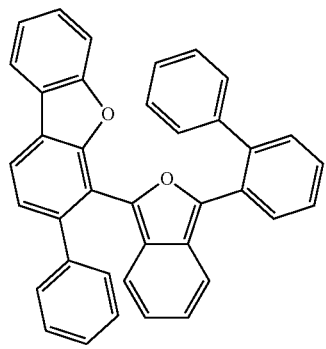
139 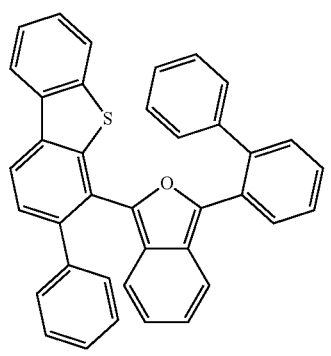
140 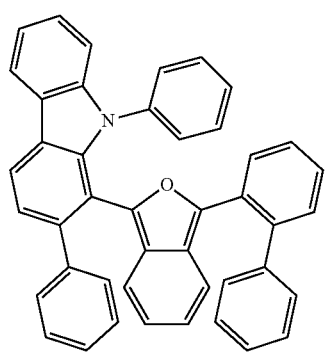
141 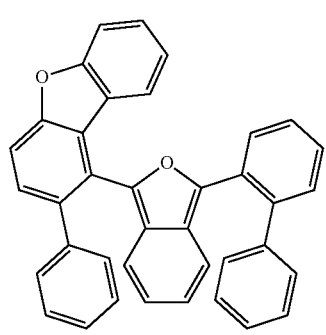
142 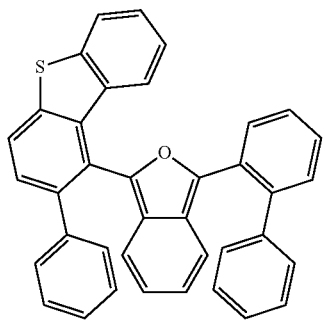
143 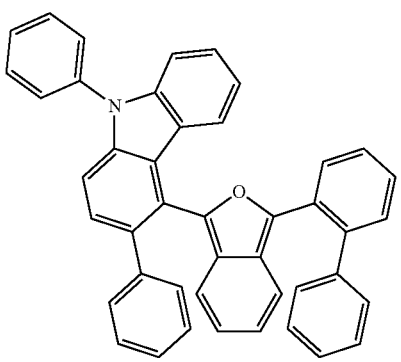
144 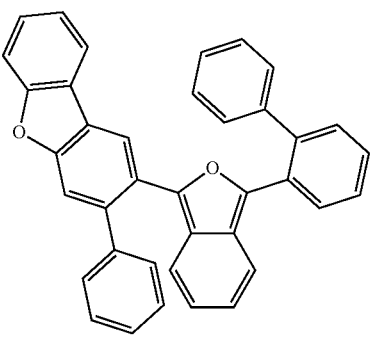
145 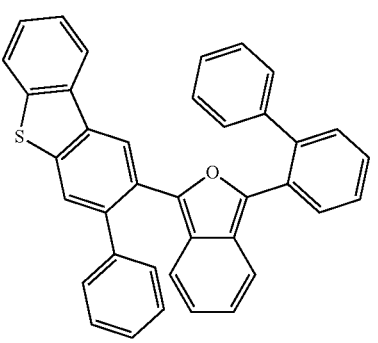

146
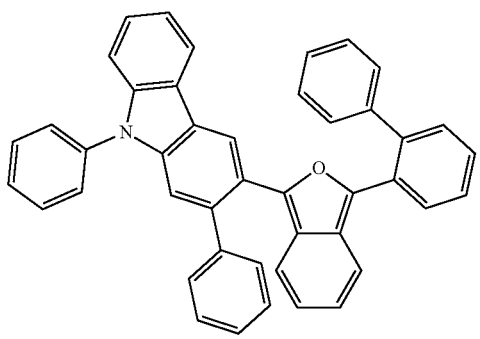
147
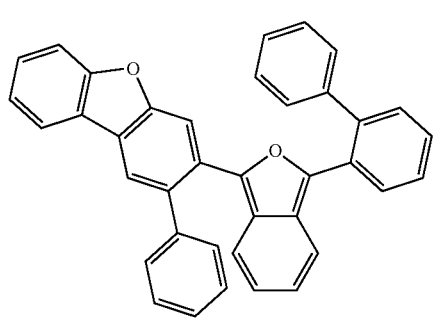
148
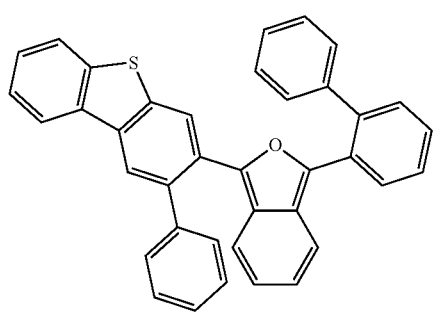
149
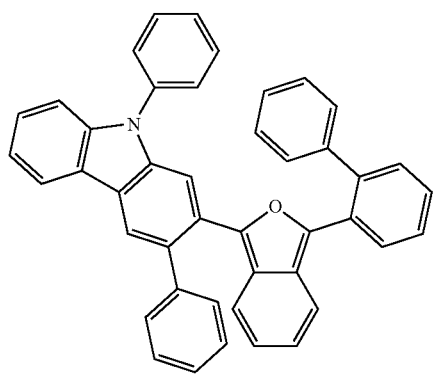
150
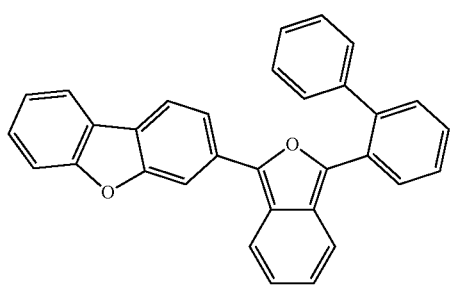
151
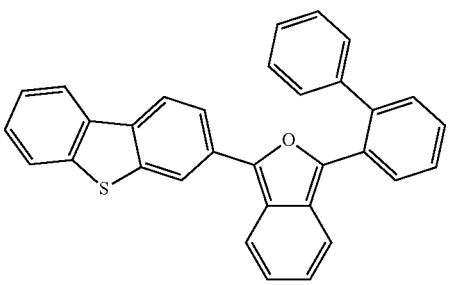
152
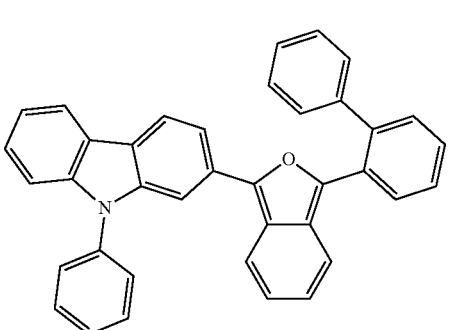
153
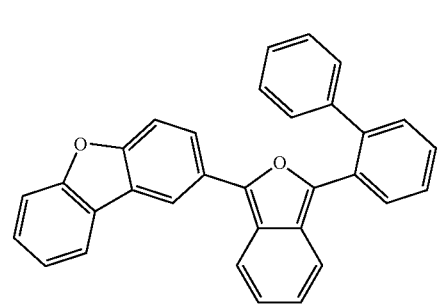
154
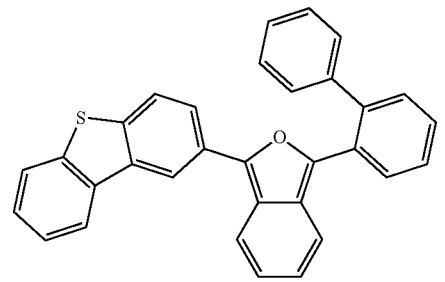
155
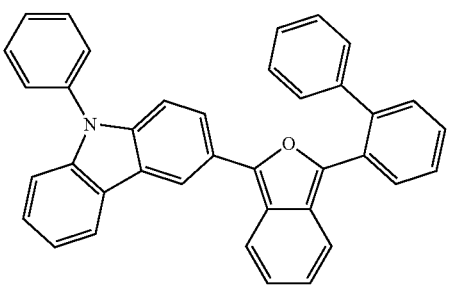

156
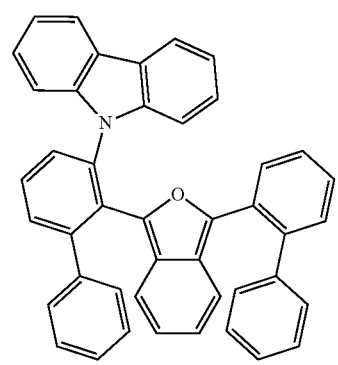
157
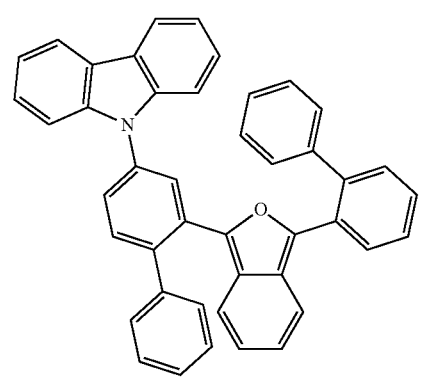
158
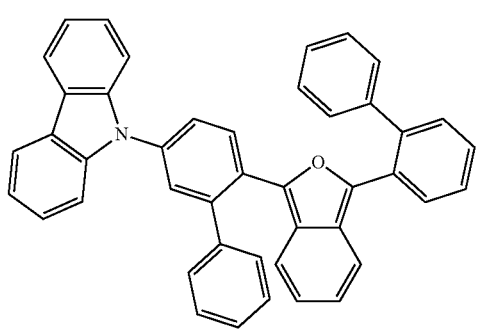
159
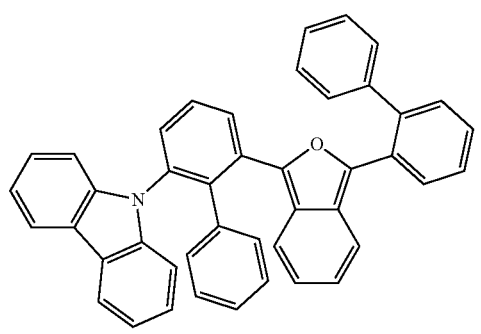
160
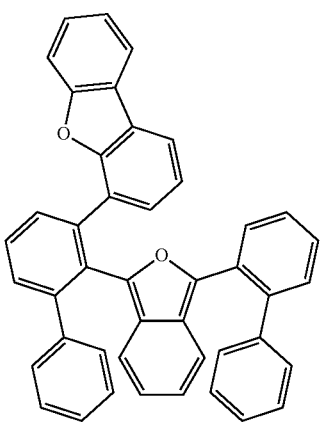
161
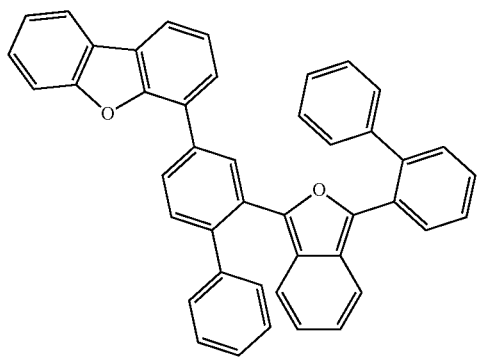
162
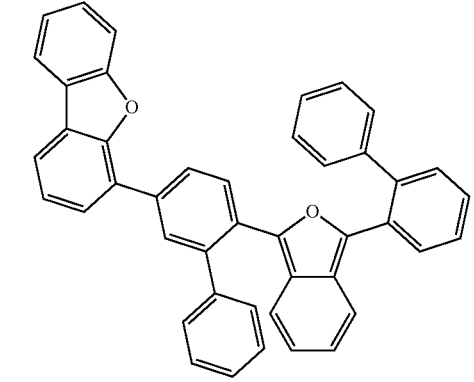
163
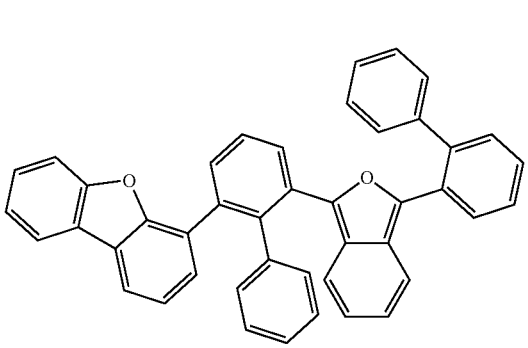

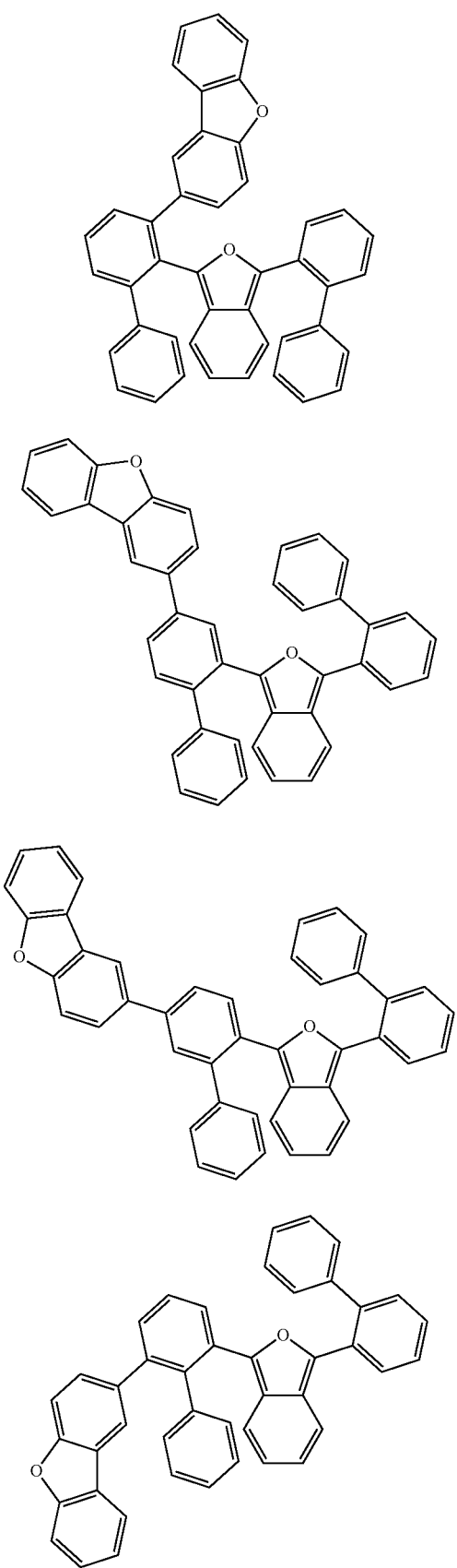
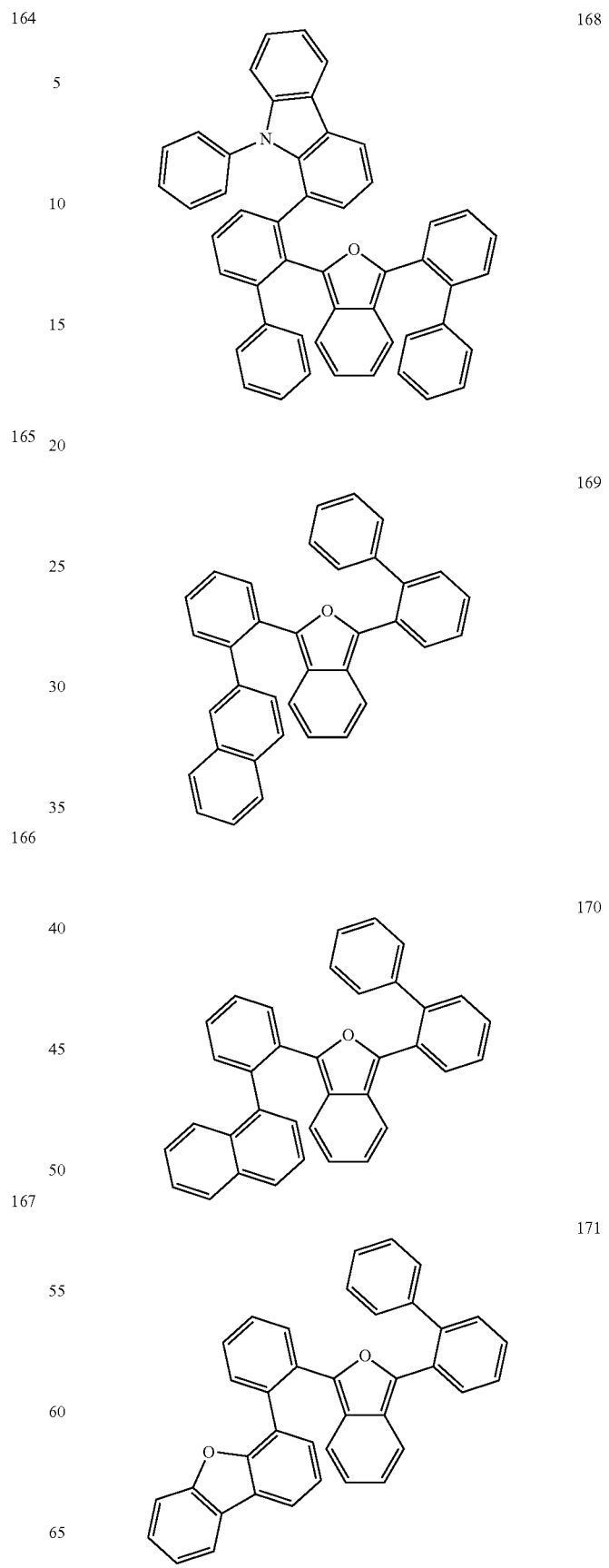

172 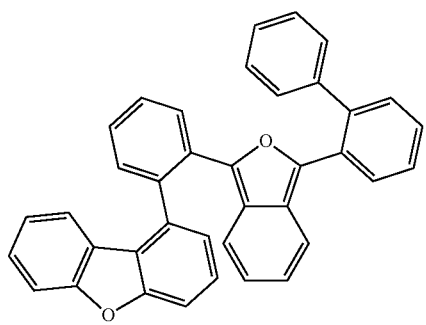
173 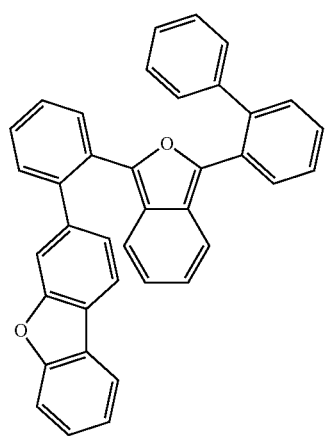
174 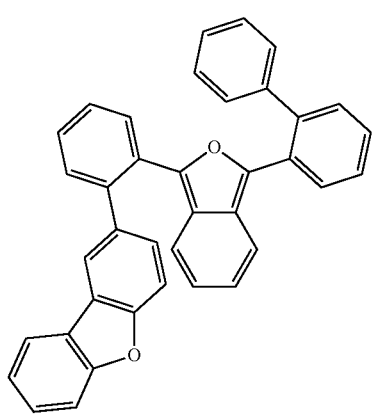
175 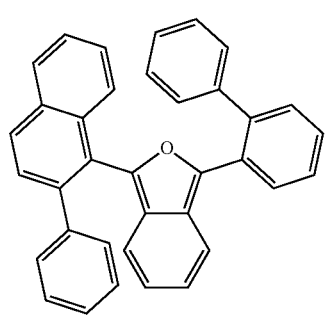
176 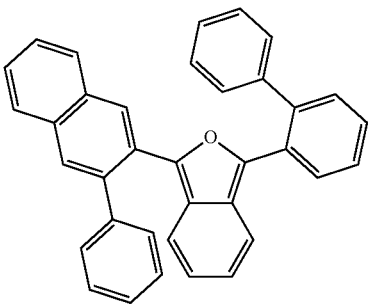
177 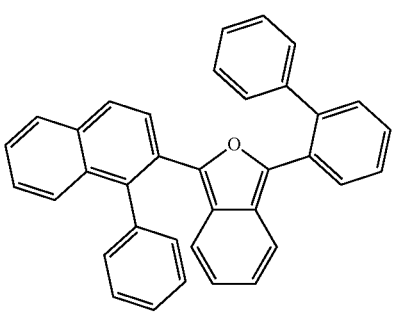
178 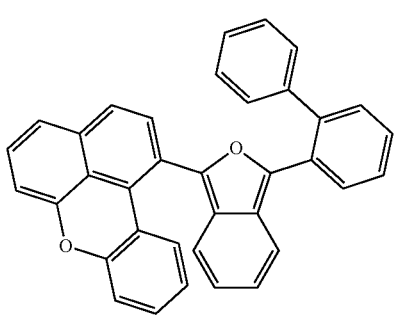
179 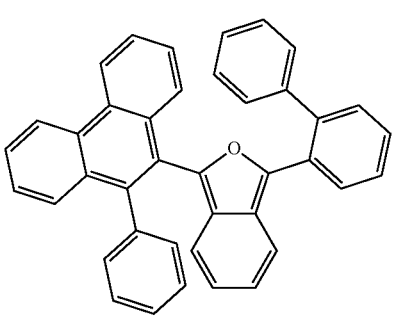
180 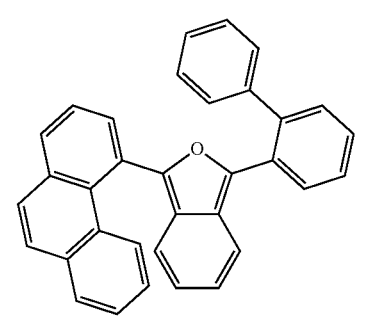

181
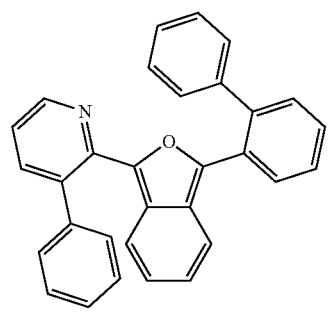
182
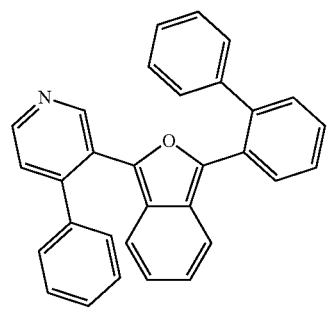
183
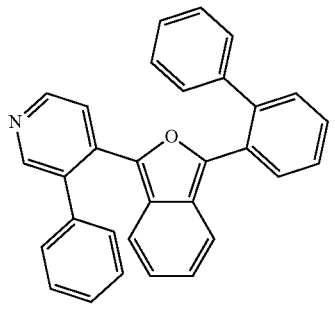
184
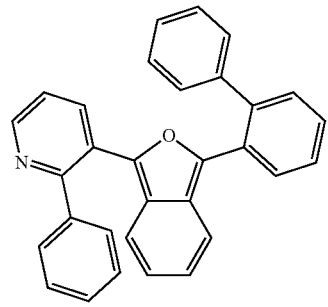
185
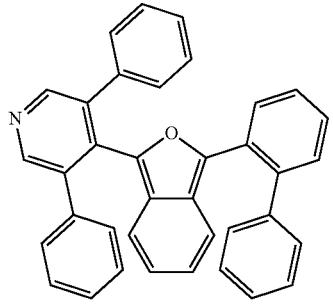
186
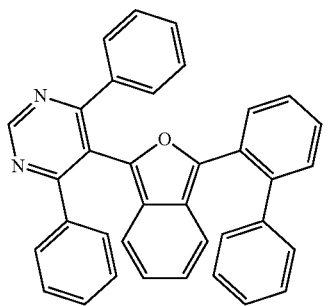
187
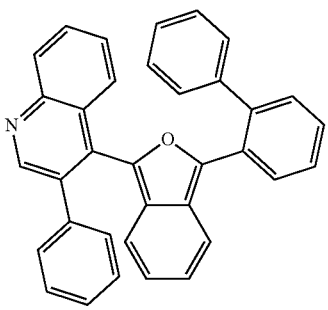
188
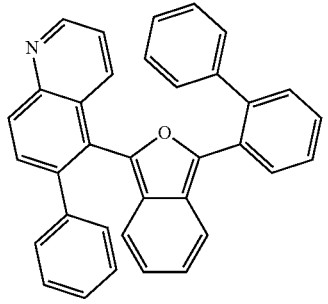
189
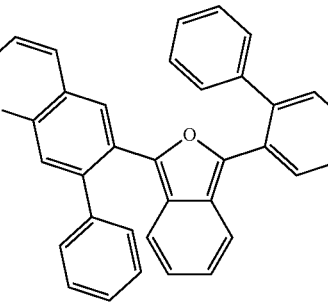
190
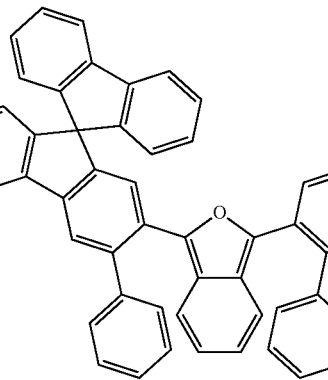

191 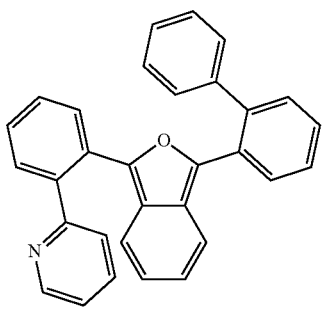
192 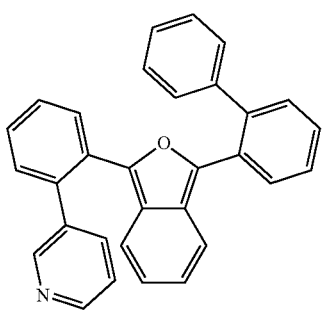
193 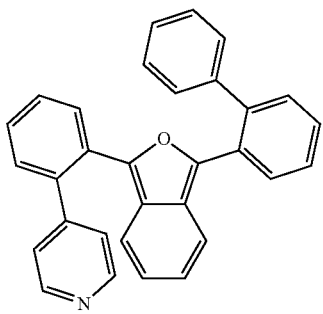
194 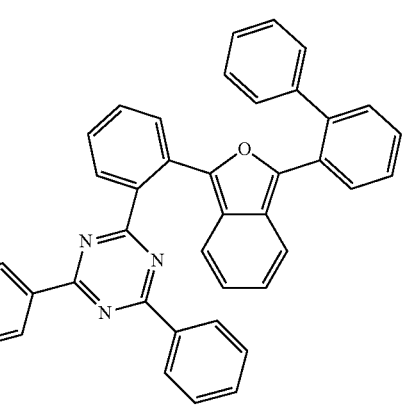
195 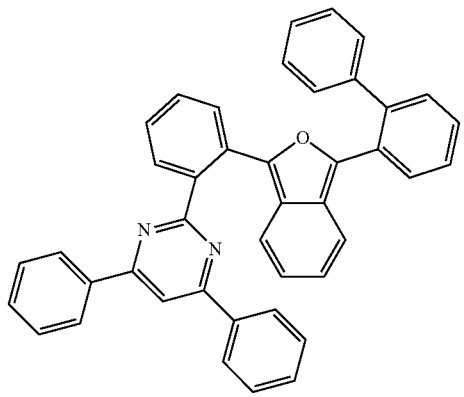
196 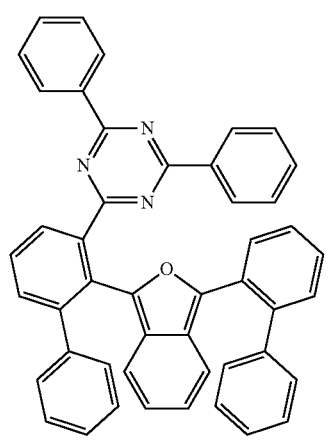
197 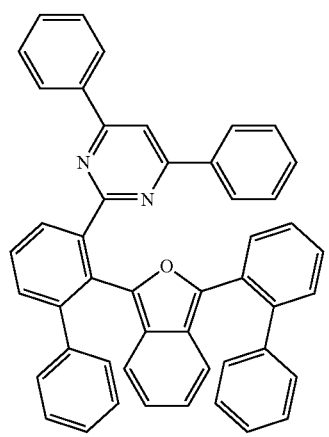

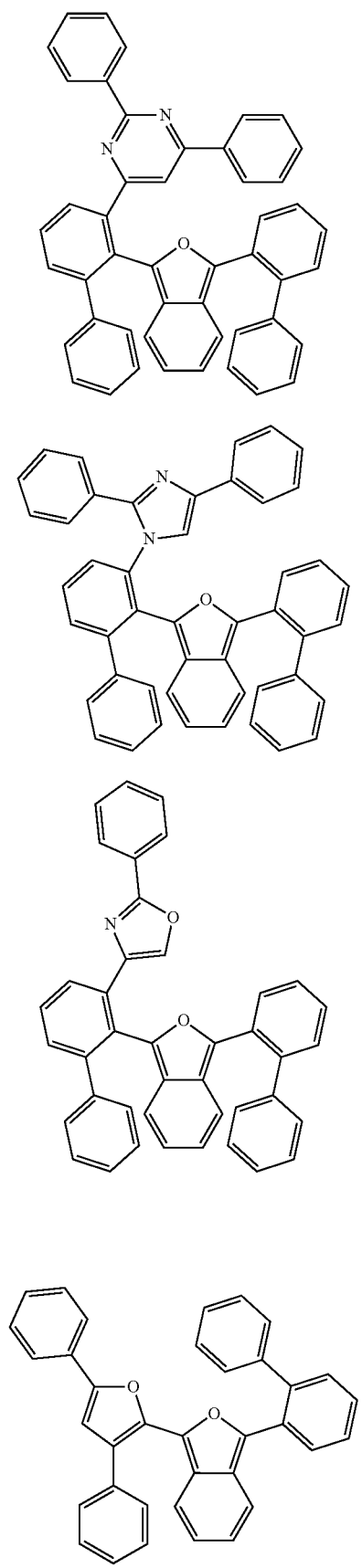
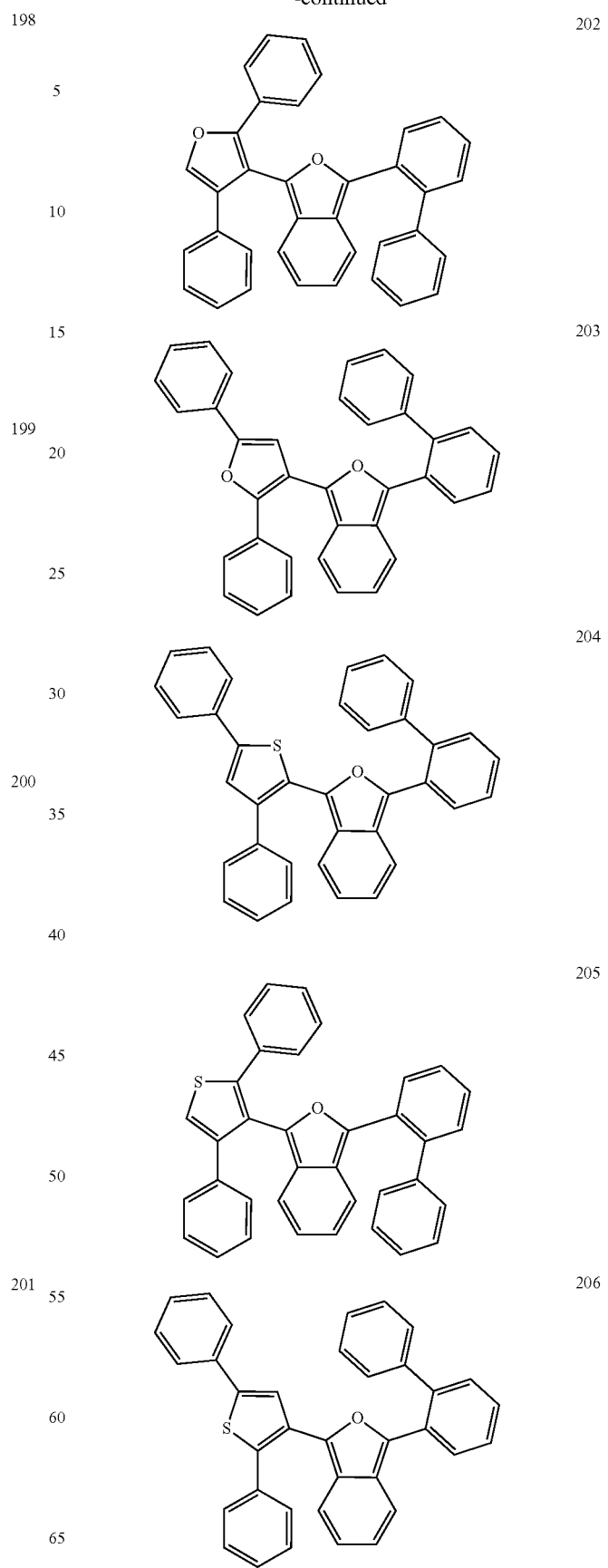

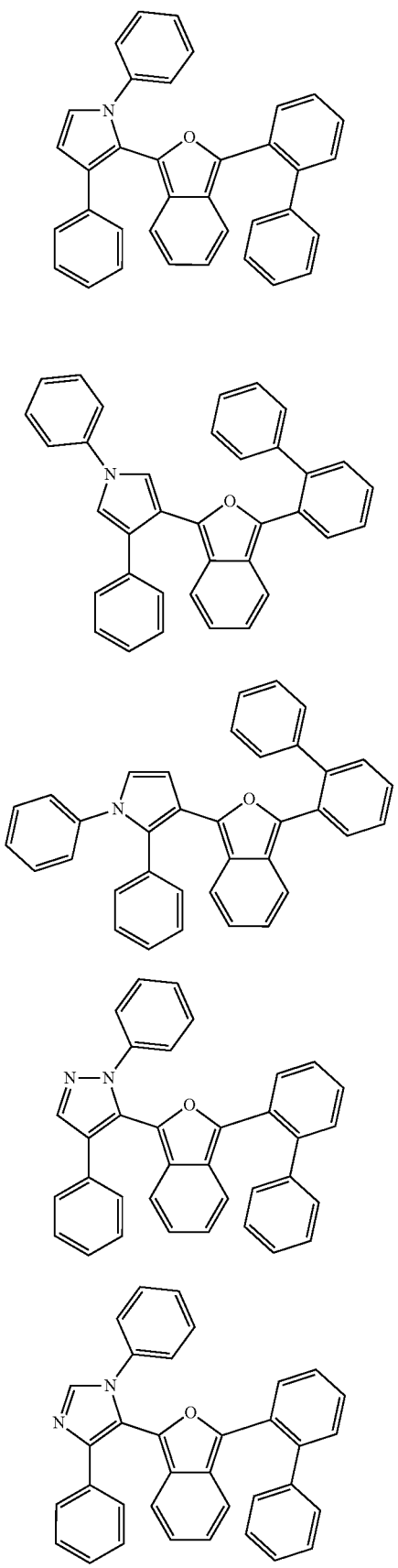
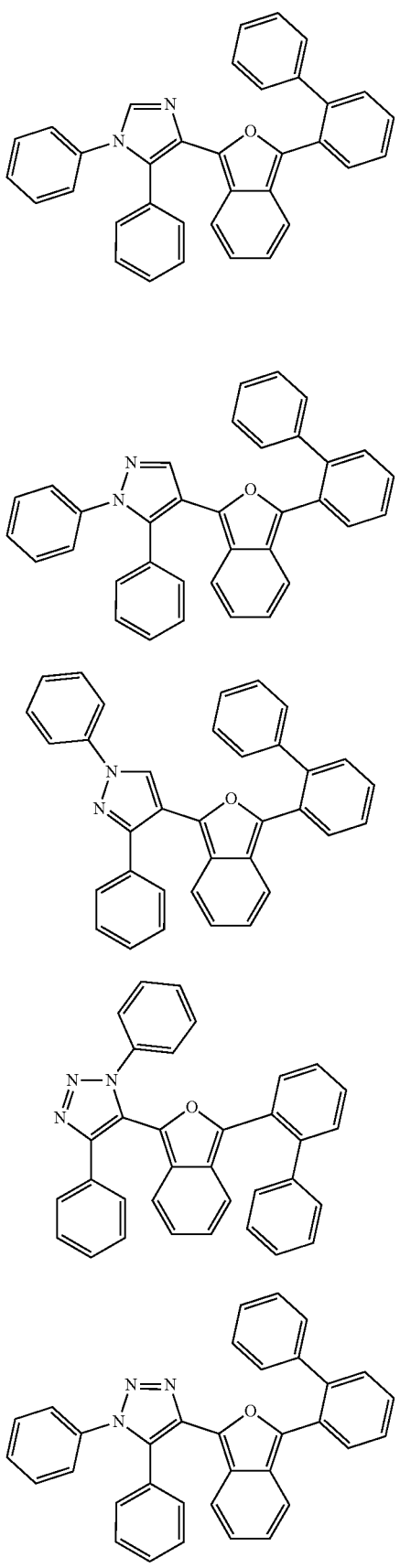

217
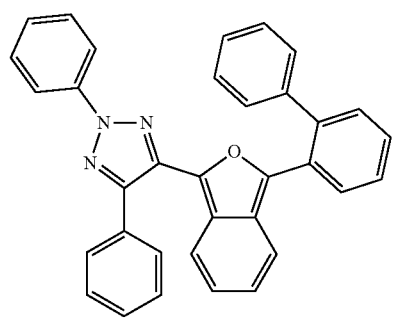
218
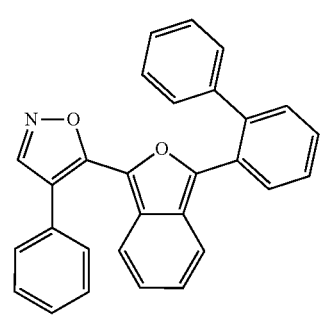
219
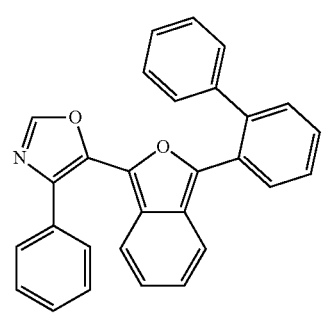
220
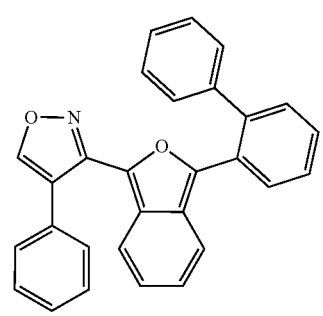
221
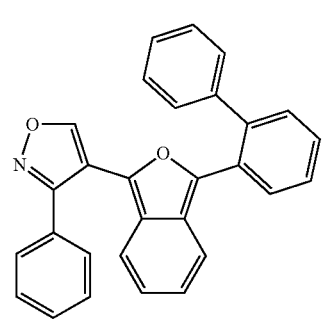
222
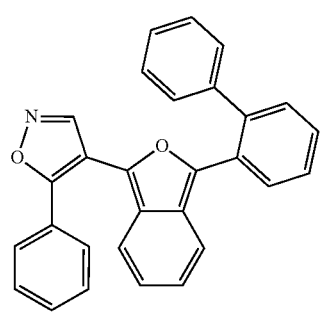
223
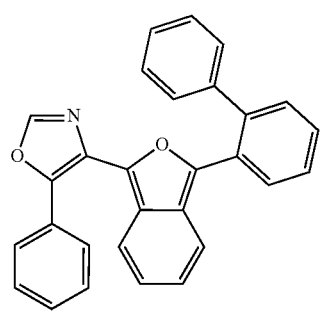
224
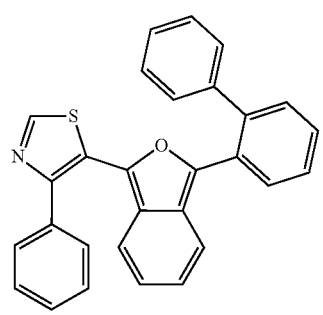
225
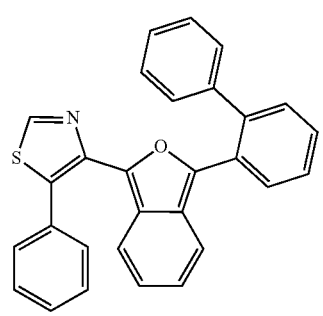
226
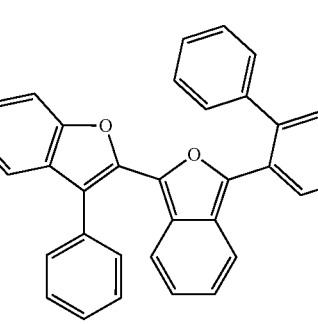

227 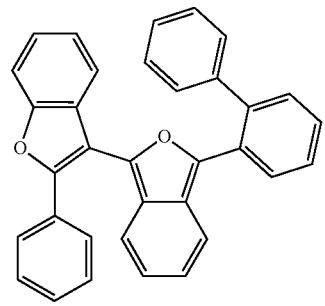
228 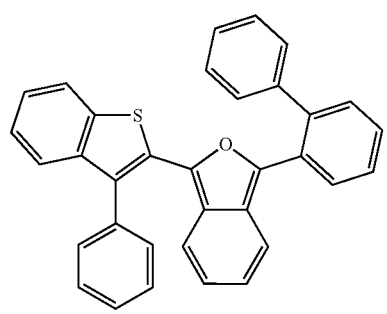
229 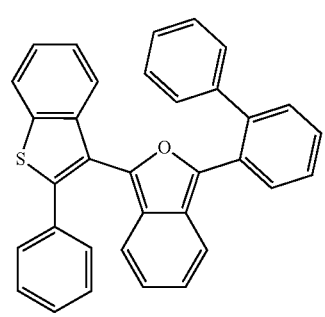
230 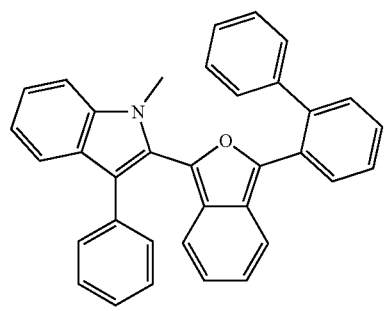
231 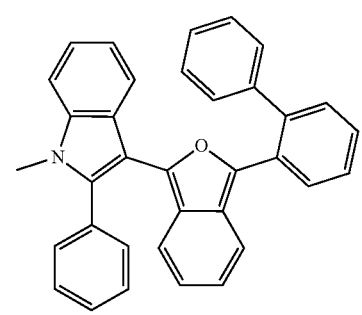
232 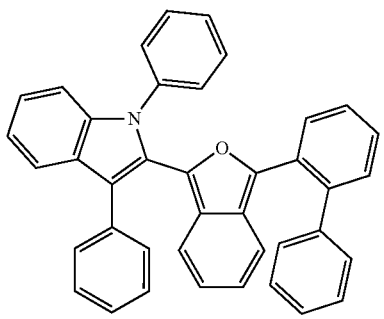
233 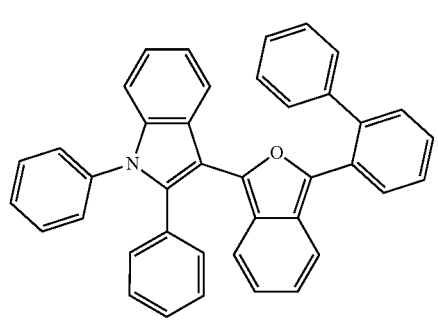
234 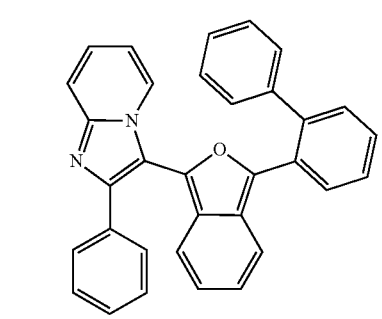
235 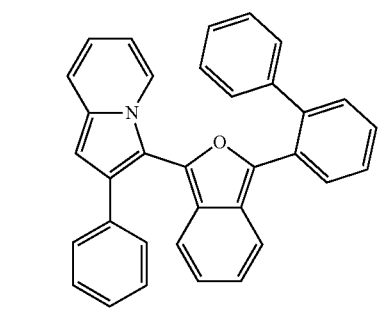
236 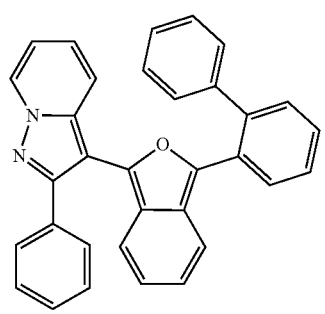

237 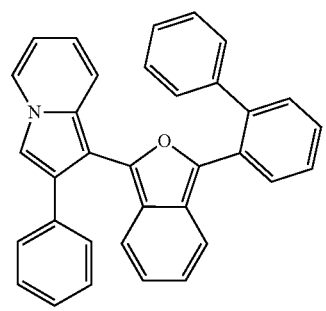
238 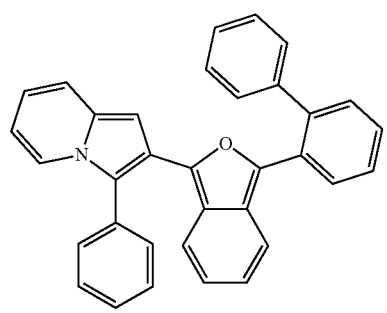
239 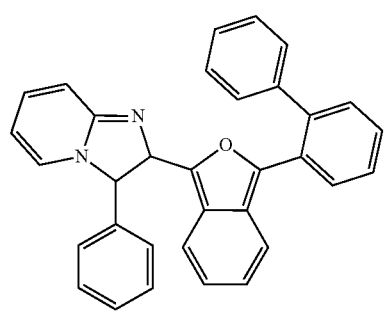
240 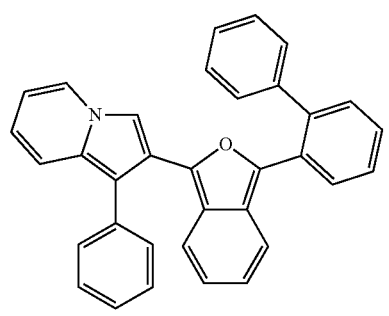
241 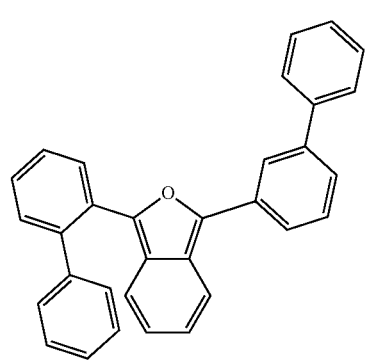
242 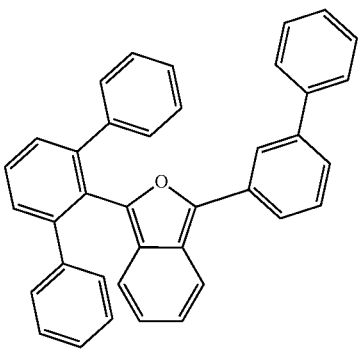
243 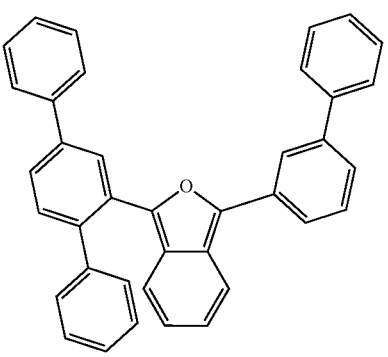
244 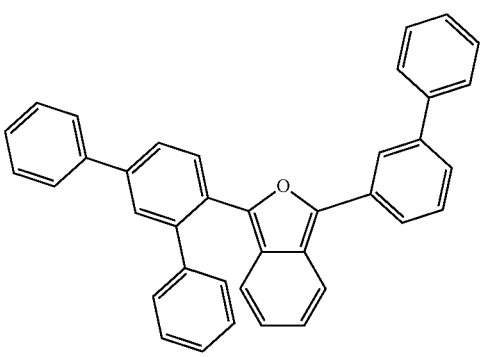
245 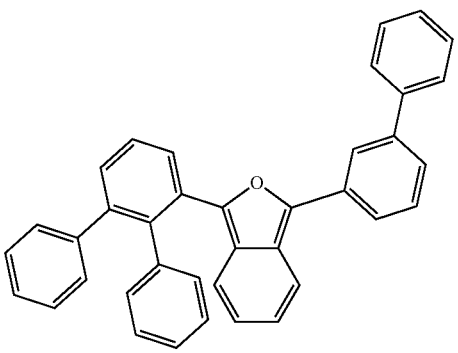

246 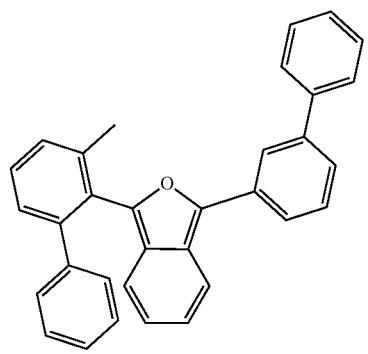
247 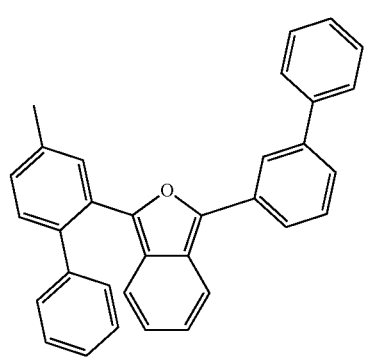
248 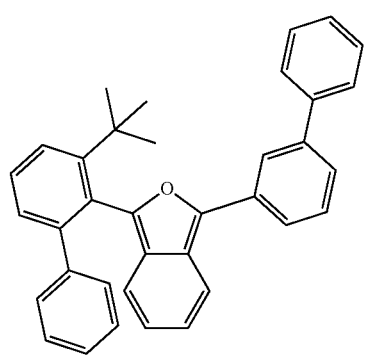
249 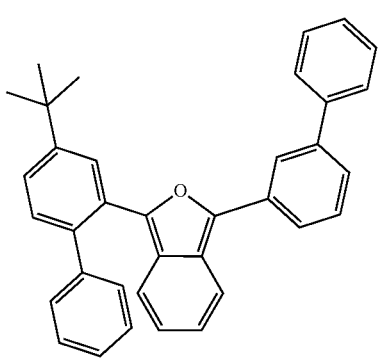
250 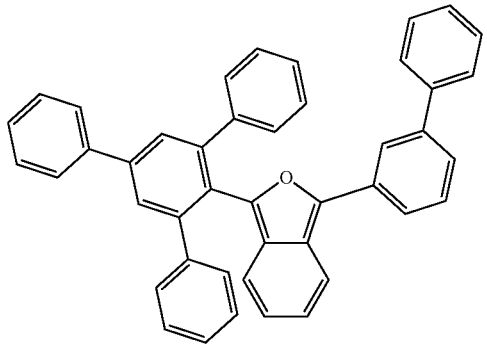
251 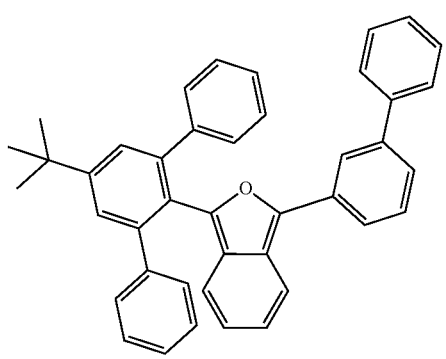
252 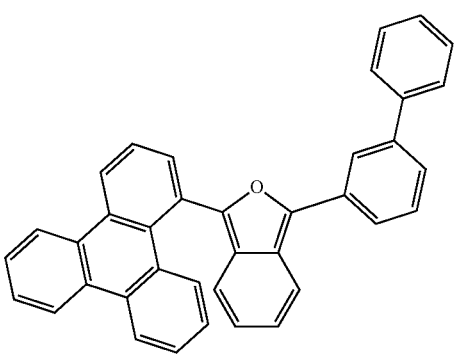
253 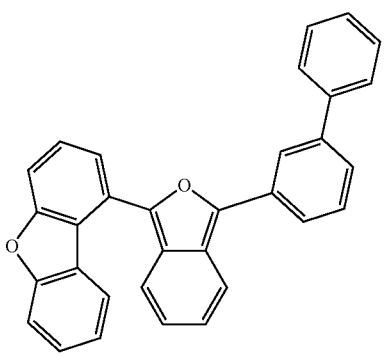

254
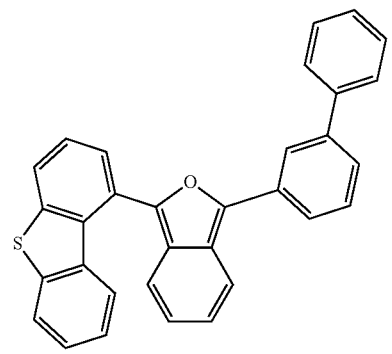
255
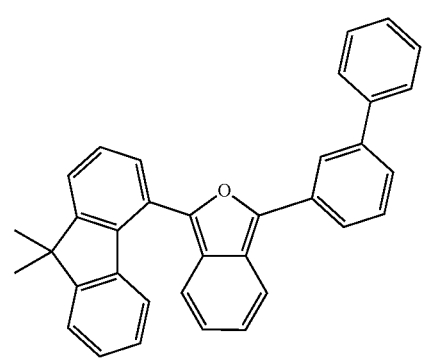
256
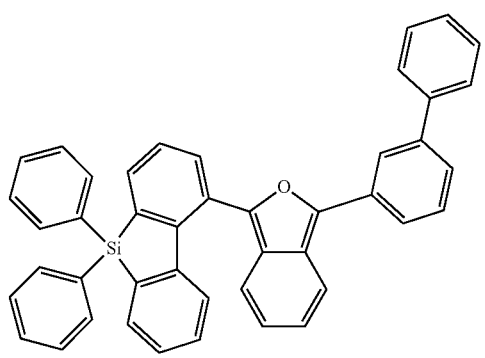
257
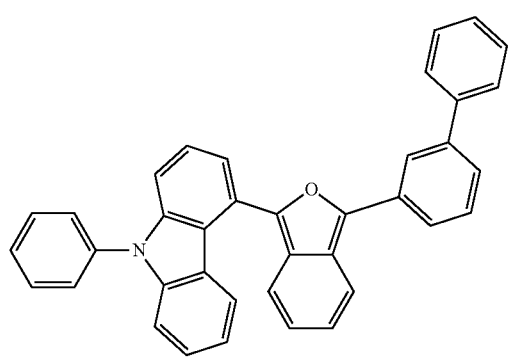
258
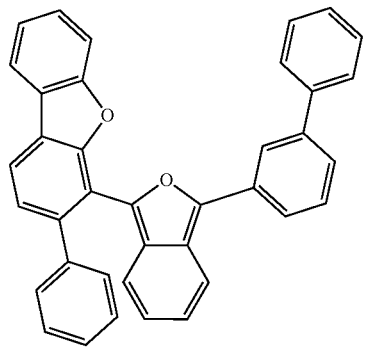
259
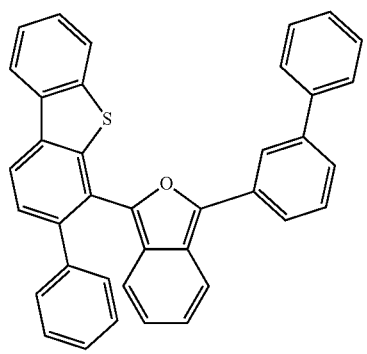
260
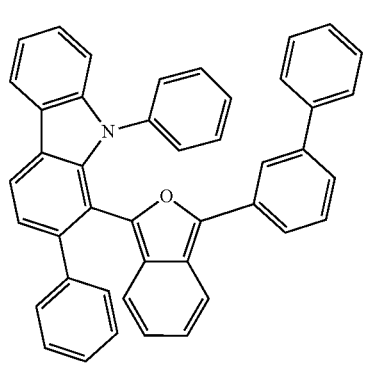
261
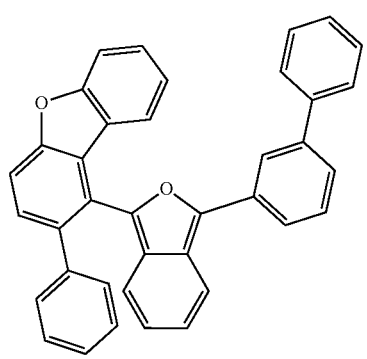

262
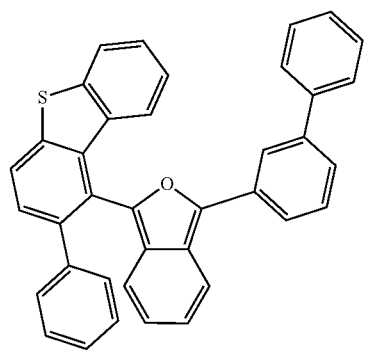
266
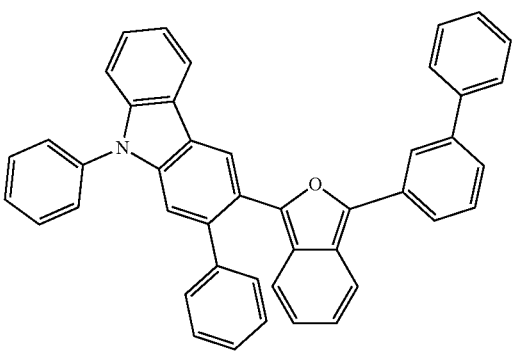
263
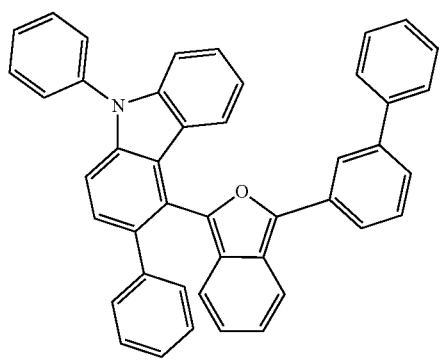
267
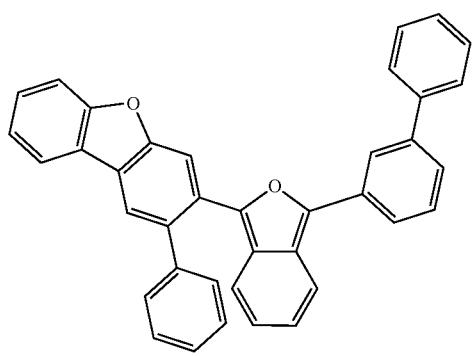
264
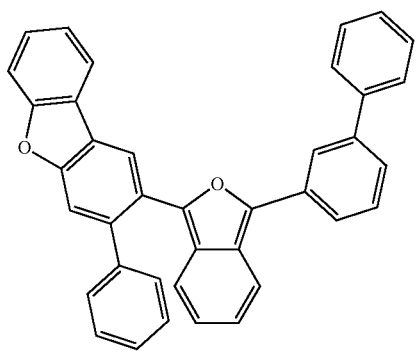
268
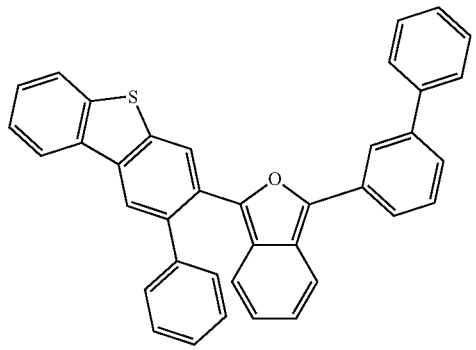
265
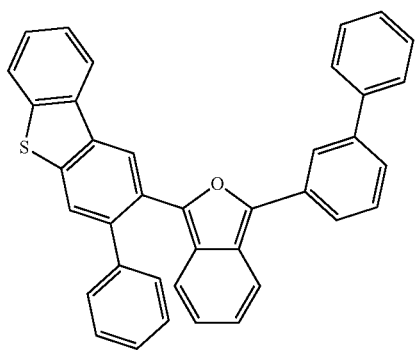
269
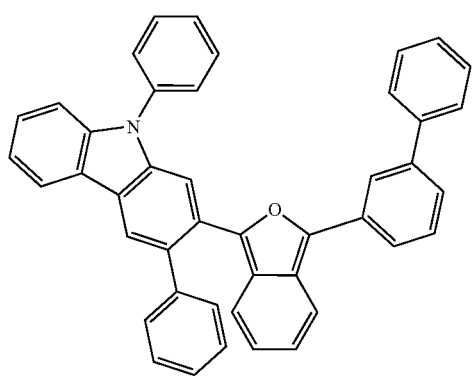

87
-continued
270
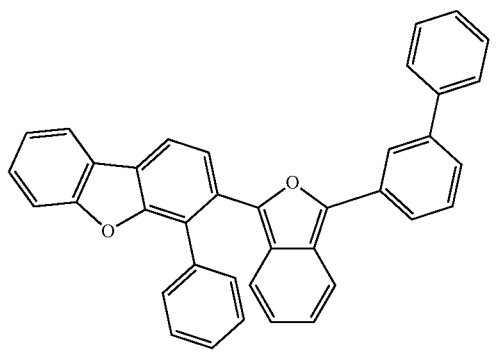
271
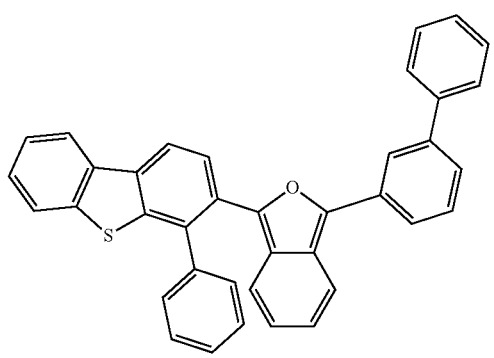
272
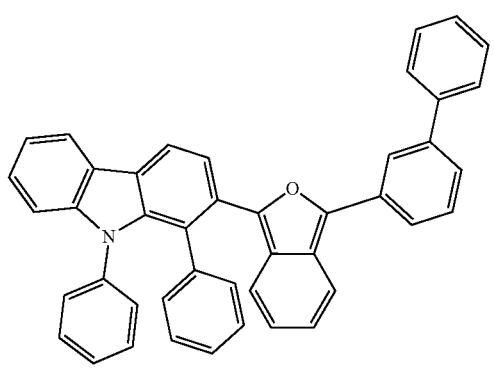
273
88
-continued
274
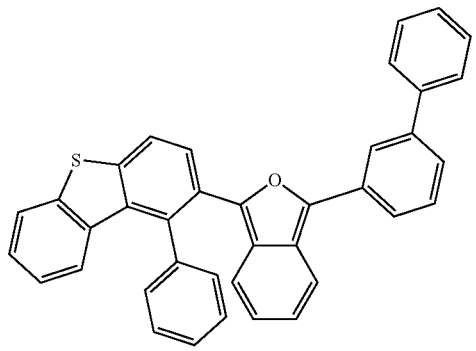
275
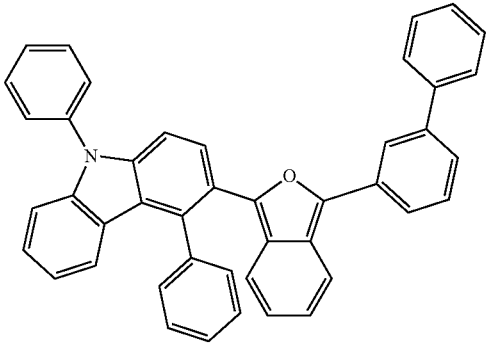
276
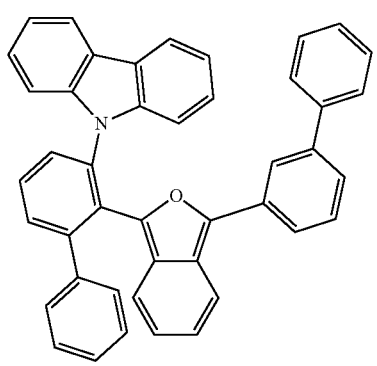
277
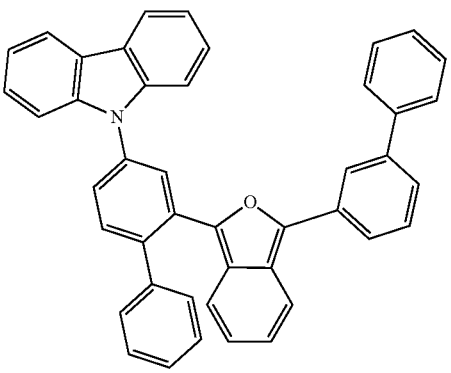

278
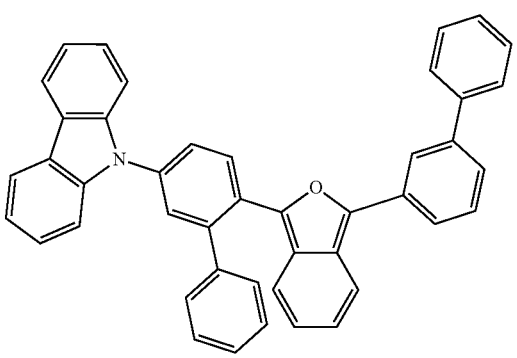
279
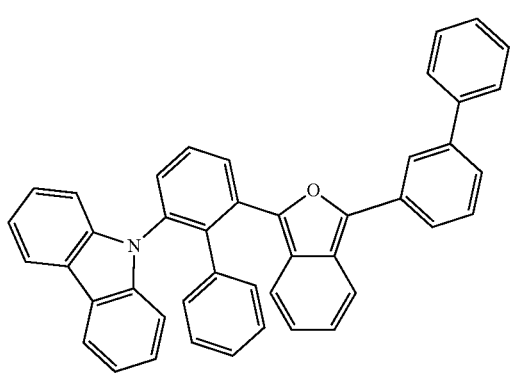
280
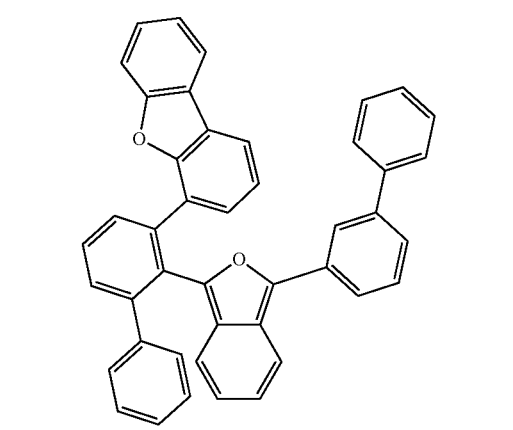
281
282
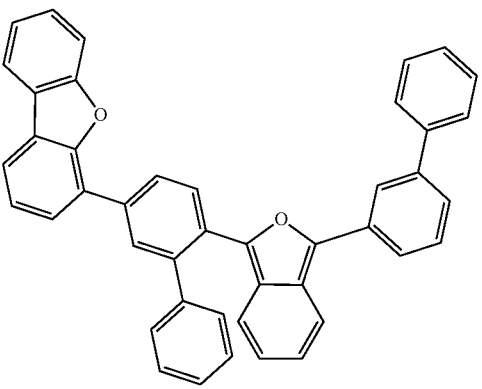
283
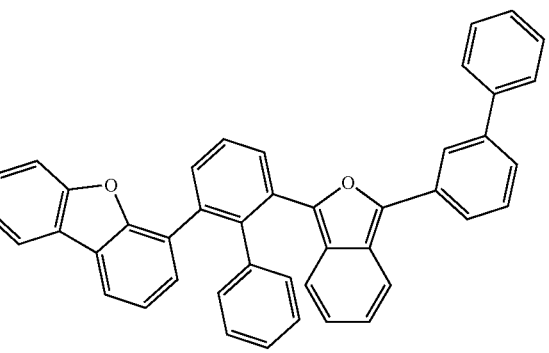
284
285
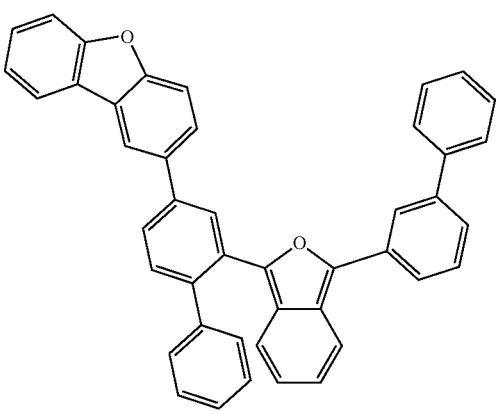

286
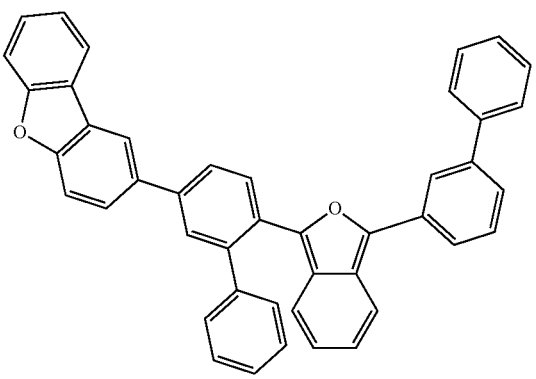
287
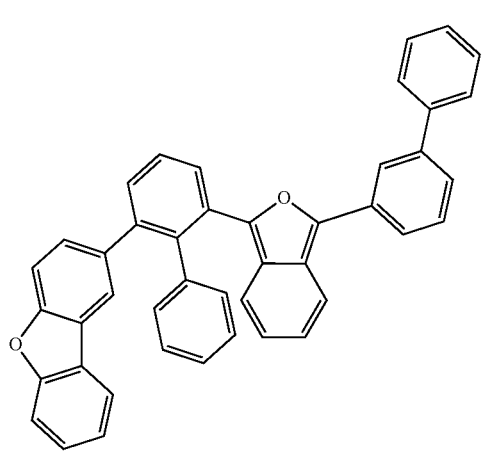
288
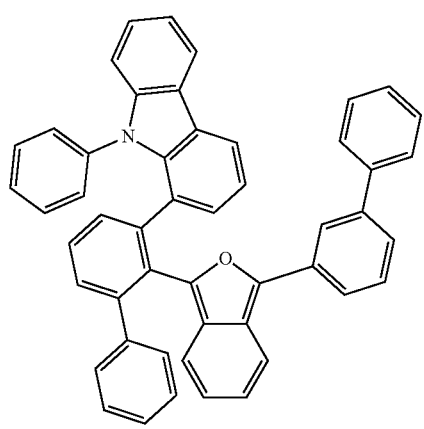
289
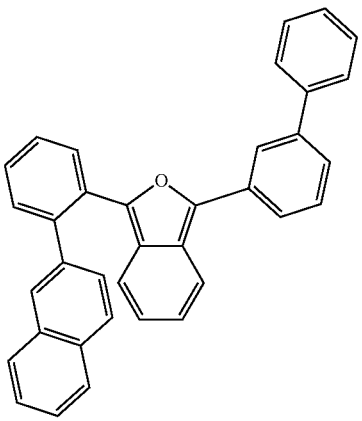
290
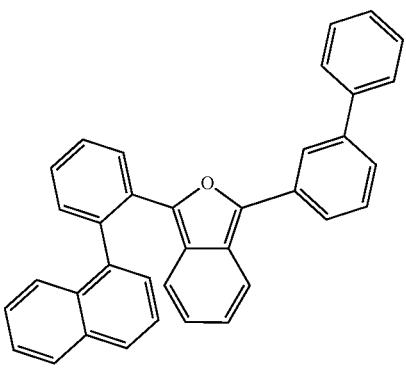
291
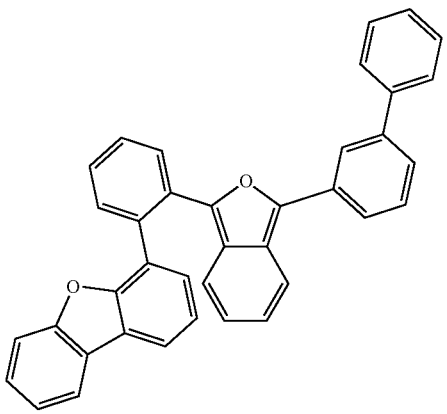
292
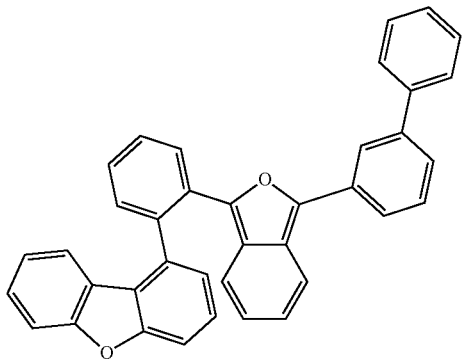

293
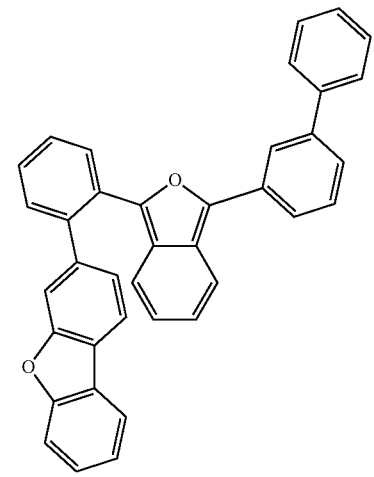
294
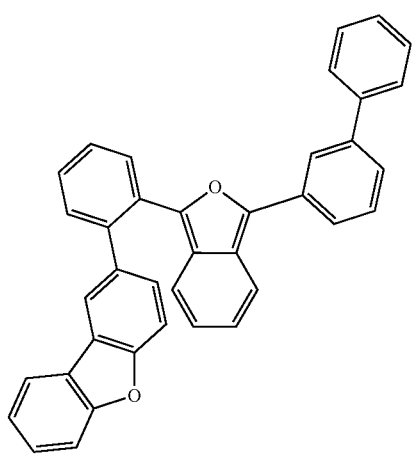
295
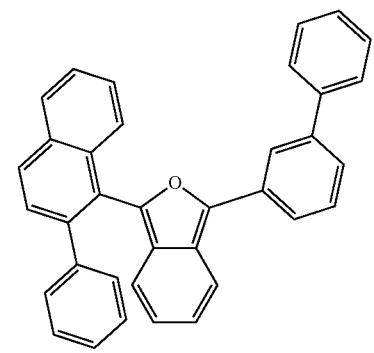
296
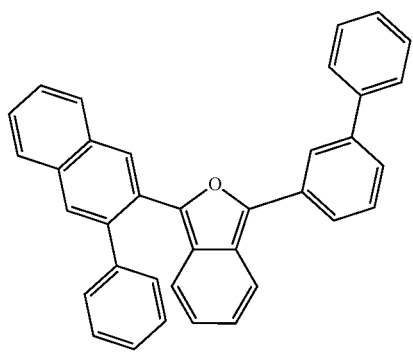
297
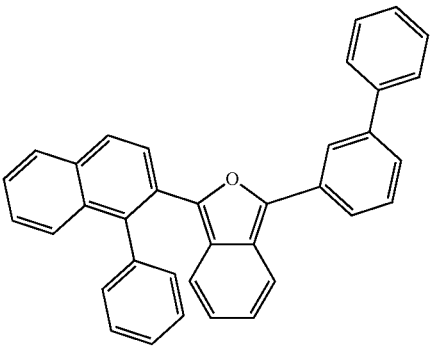
298
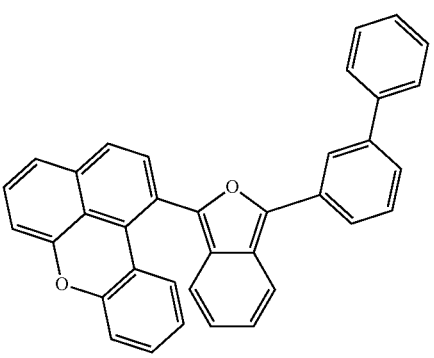
299
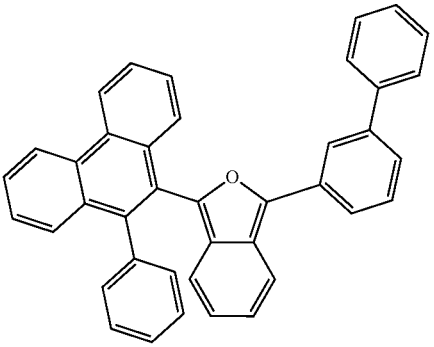
300
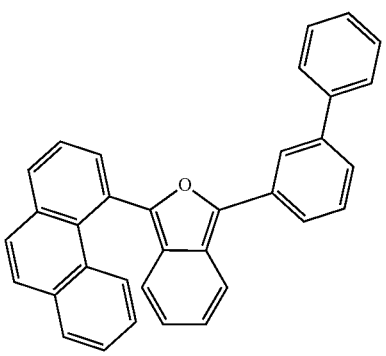

301
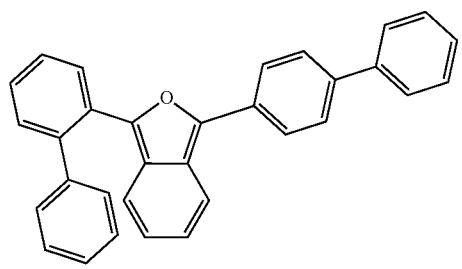
302
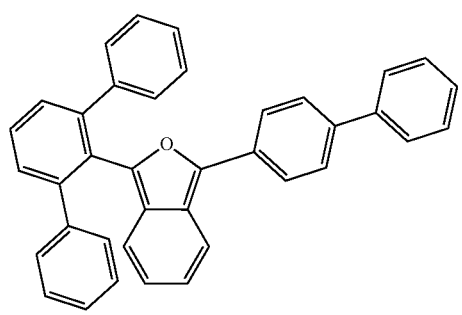
303
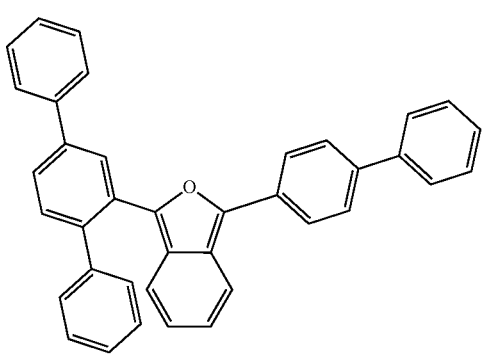
304
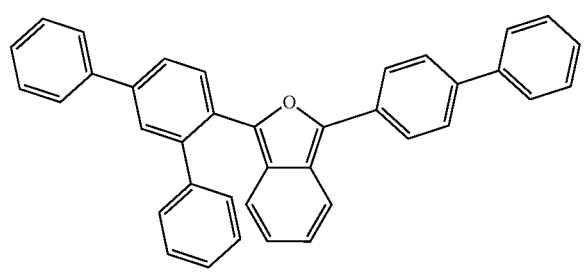
305
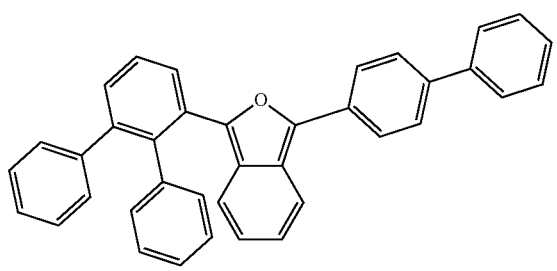
306
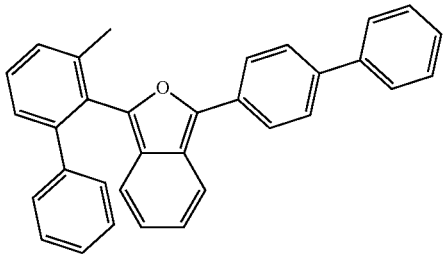
307
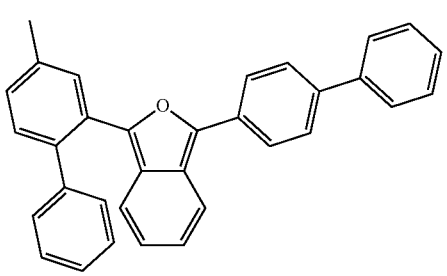
308
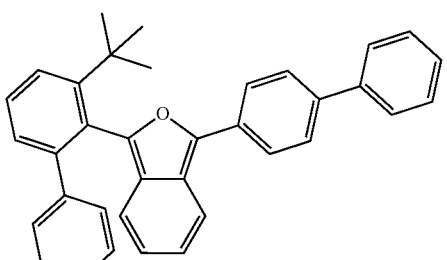
309
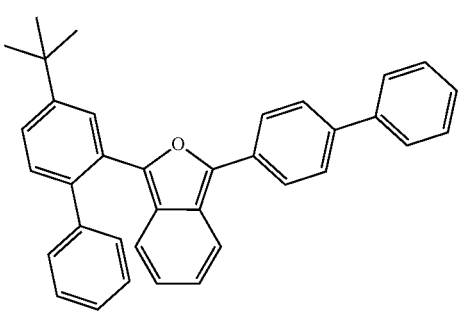
310
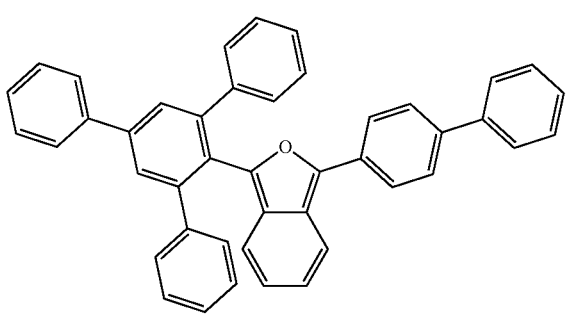

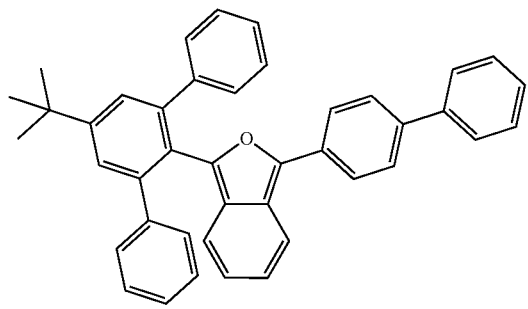
311
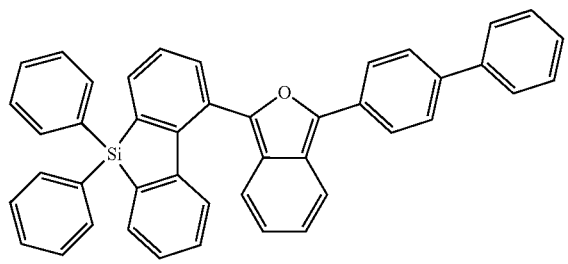
316
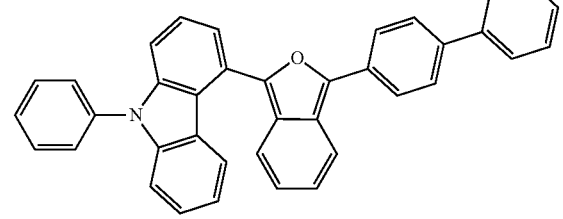
317
312
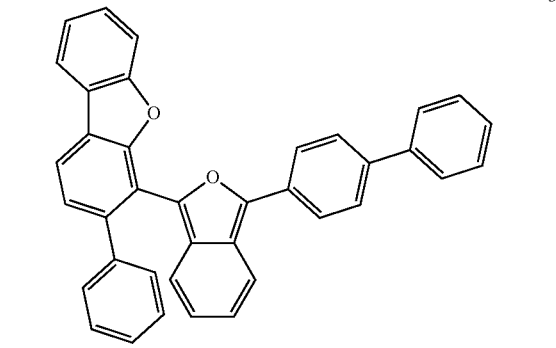
318
313
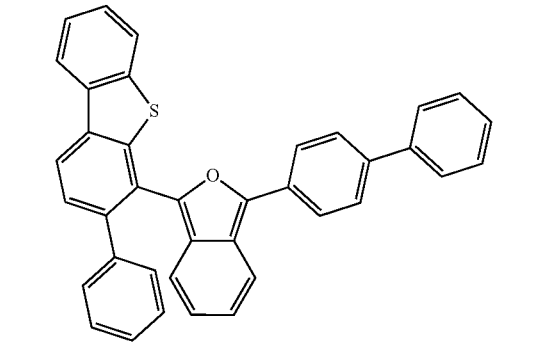
319
314
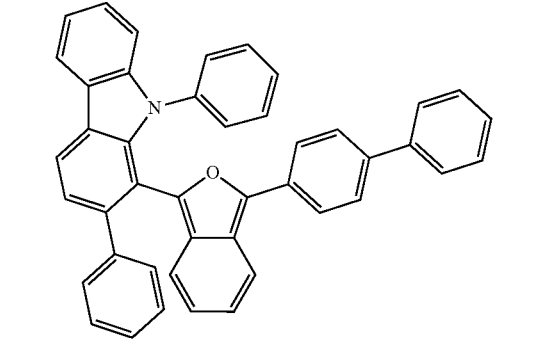
320
315

321
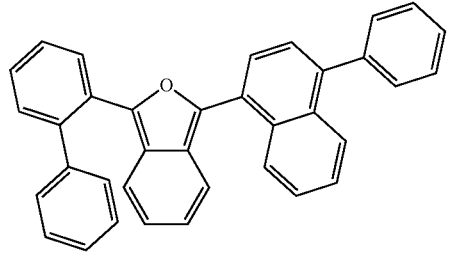
322
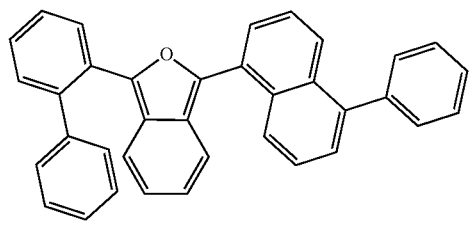
323
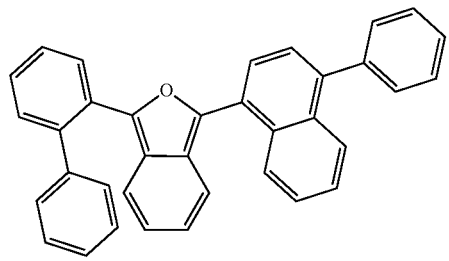
324
325
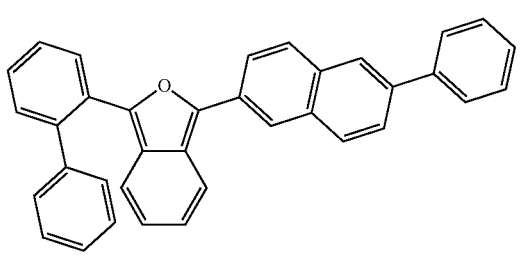
326
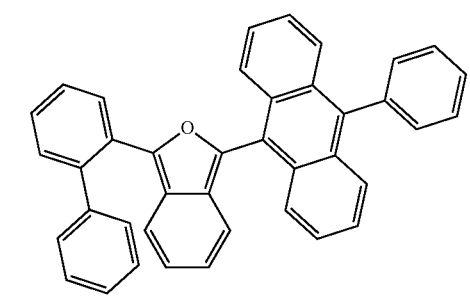
327
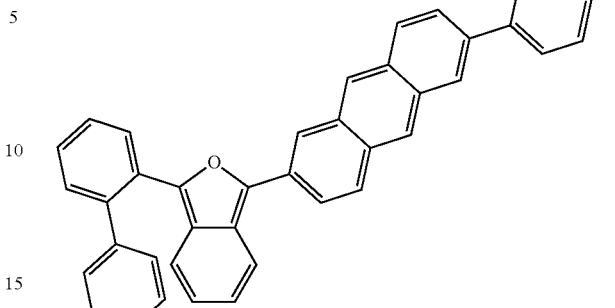
328
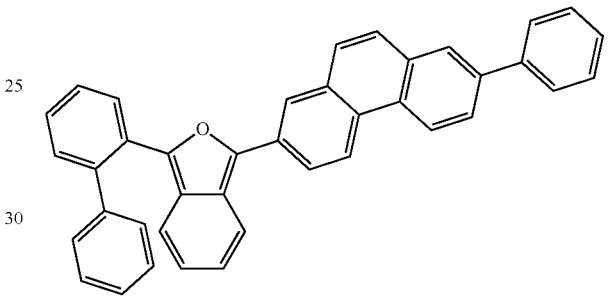
329
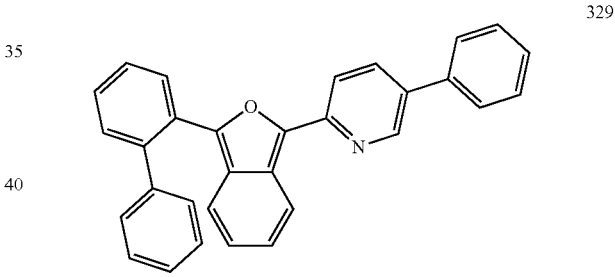
330
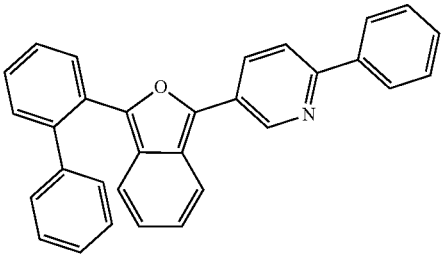
331
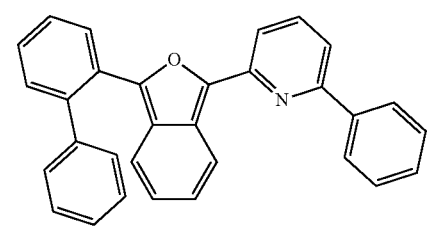

| | |
|---|---|
| 332 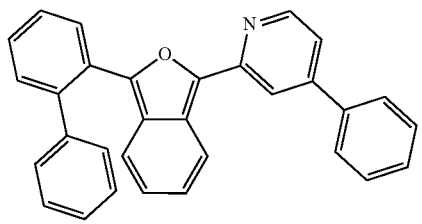 | 338 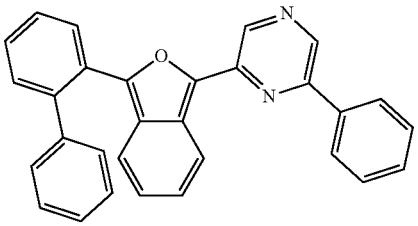 |
| 333 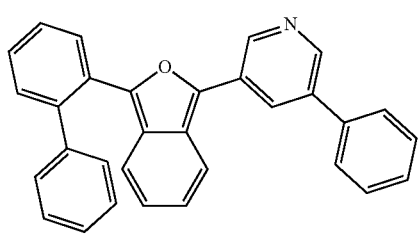 | 339 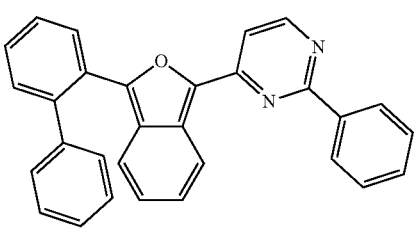 |
| 334 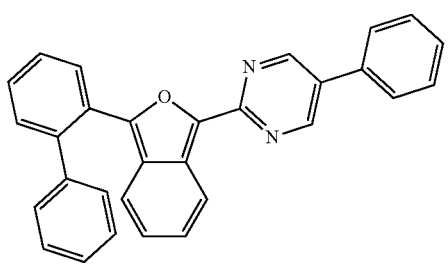 | 340 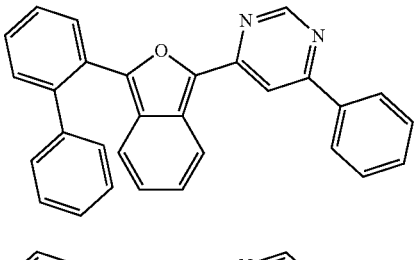 |
| 335 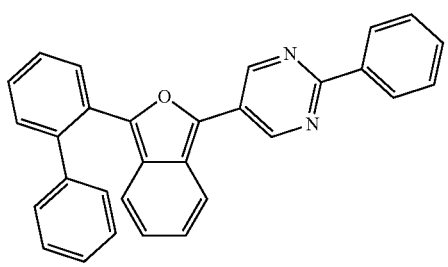 | 341 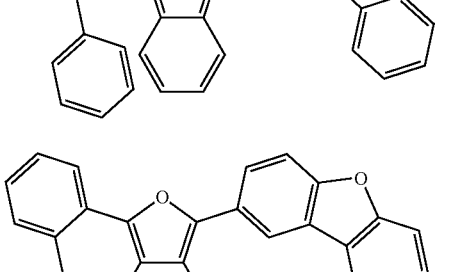 |
| 336 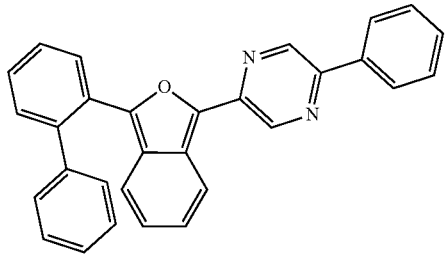 | 342 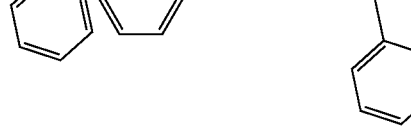 |
| 337 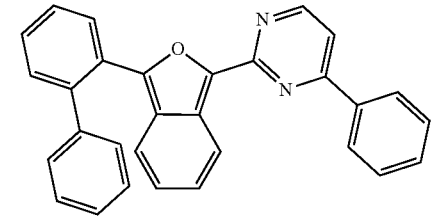 | 343 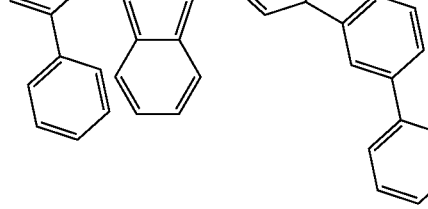 |

103
-continued
344
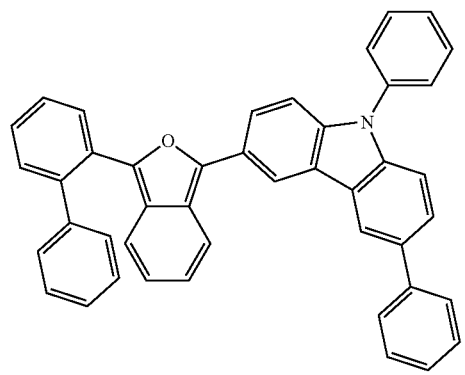
345
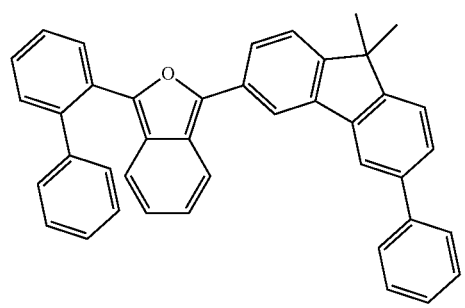
346
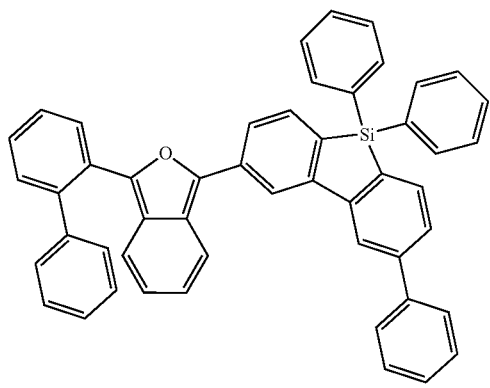
347
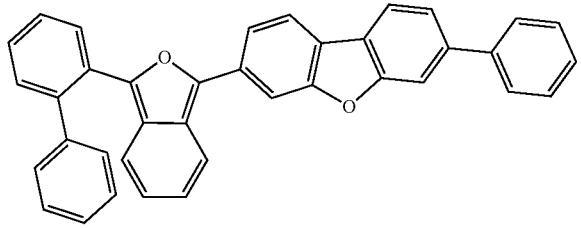
348
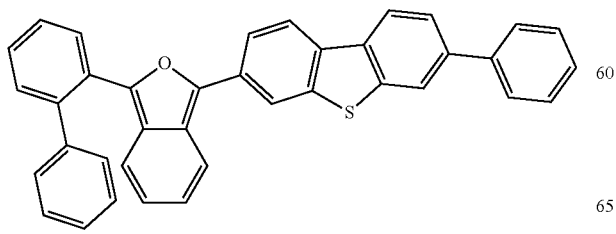
104
-continued
349
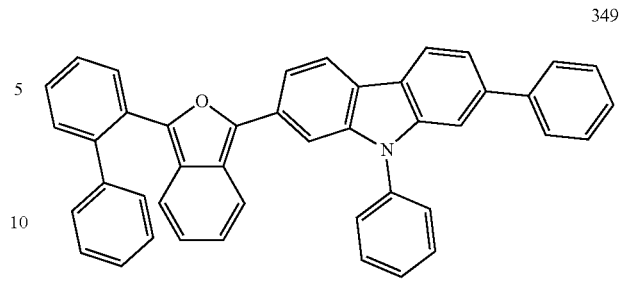
350
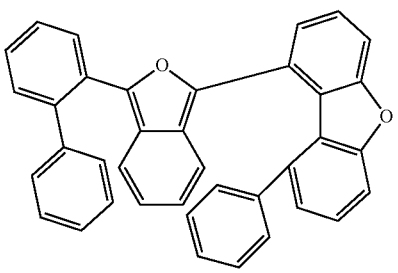
351
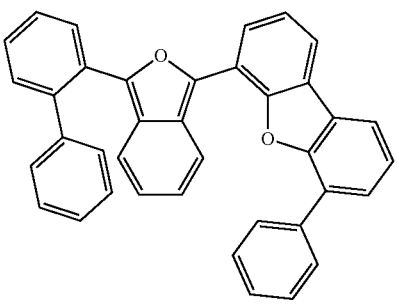
352
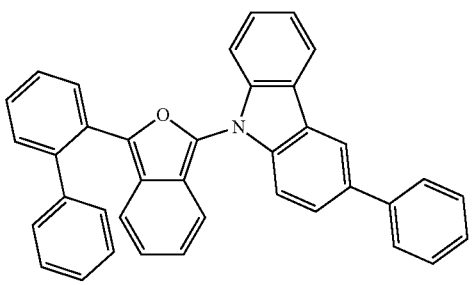
353
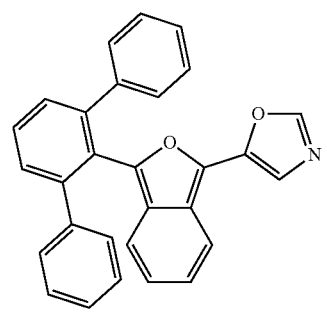

| | |
|---|---|
| 354 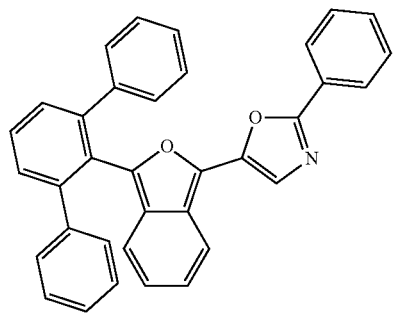 | 359 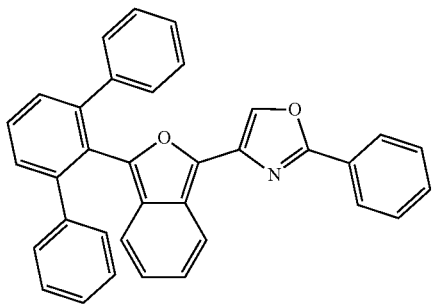 |
| 355 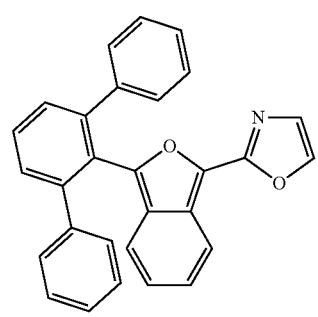 | 360 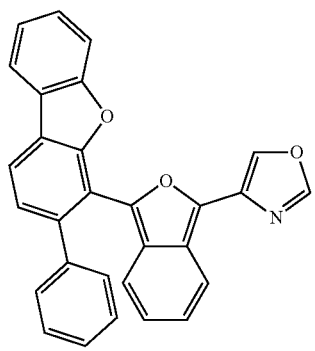 |
| 356 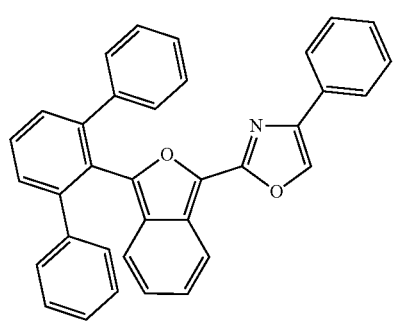 | 361 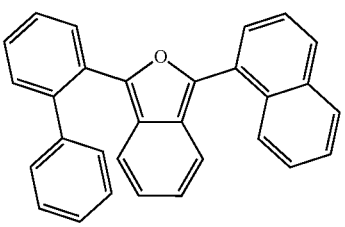 |
| 357 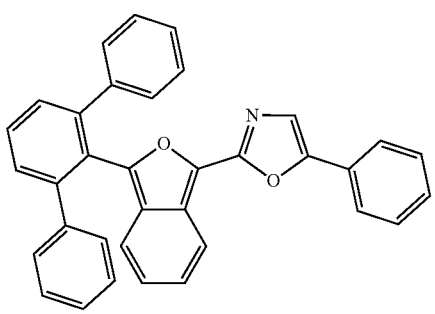 | 362 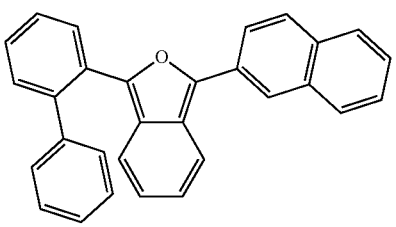 |
| 358 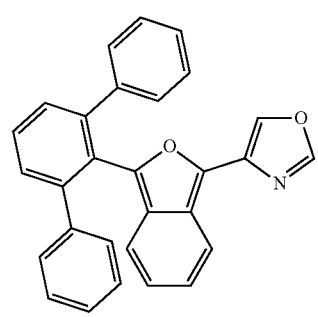 | 363 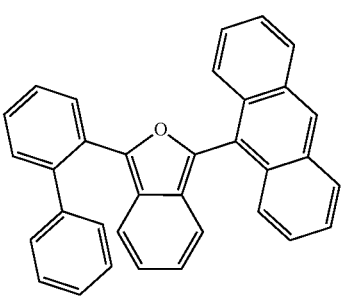 |

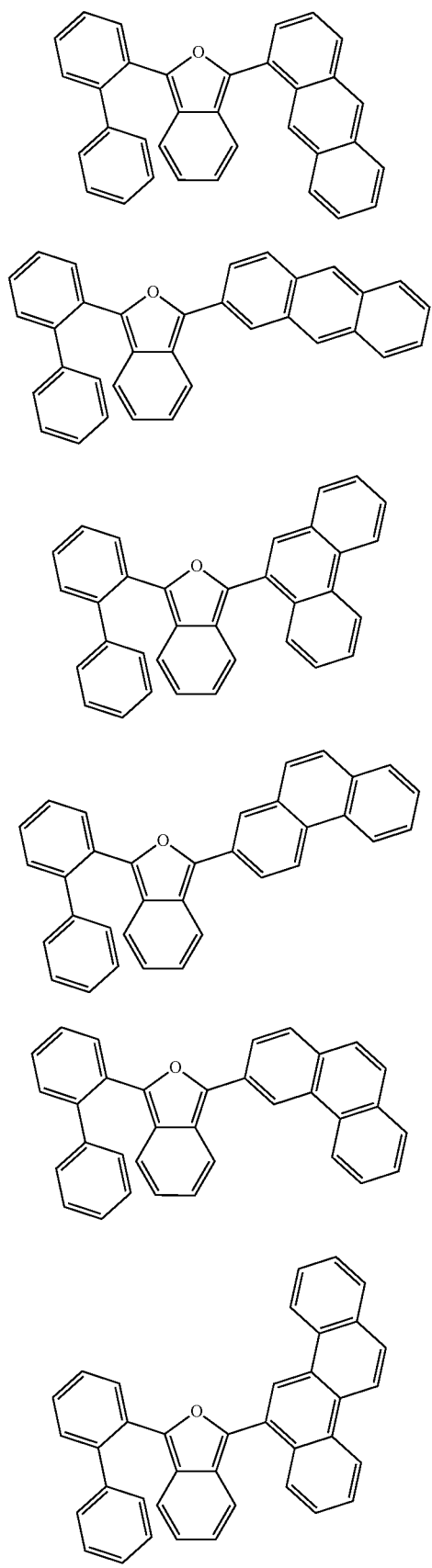
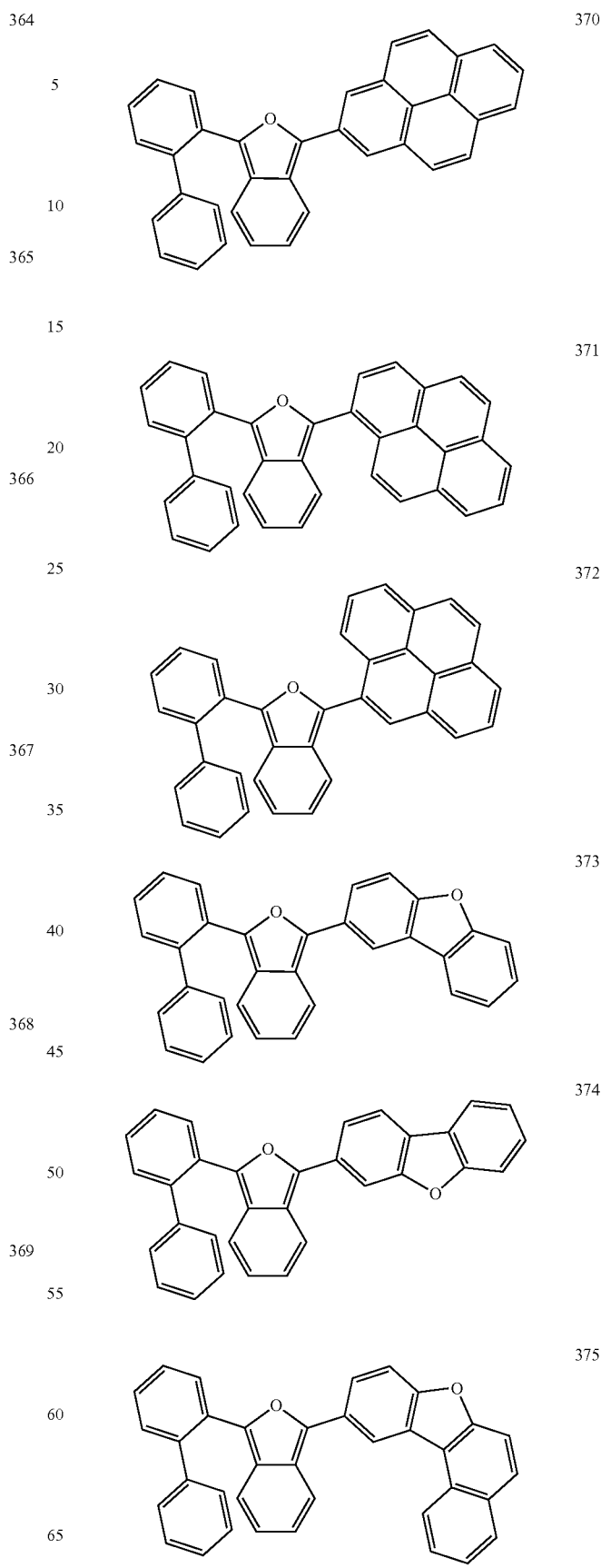

376 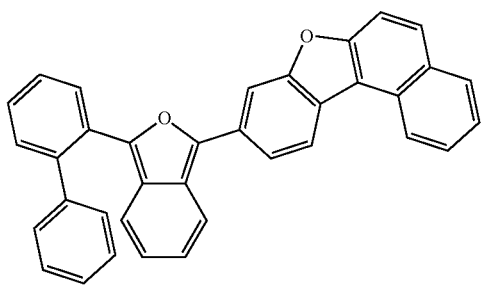
377 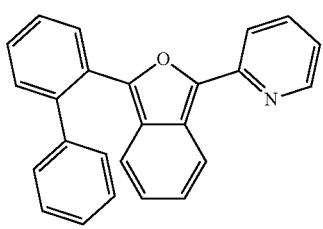
378 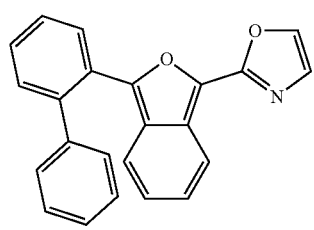
379 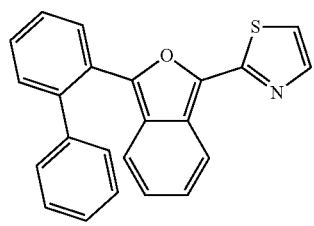
380 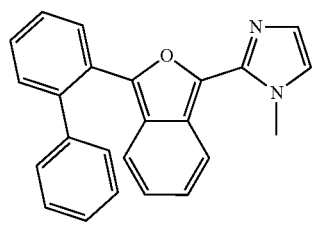
381 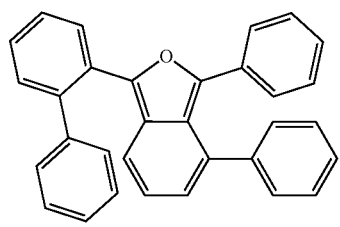
382 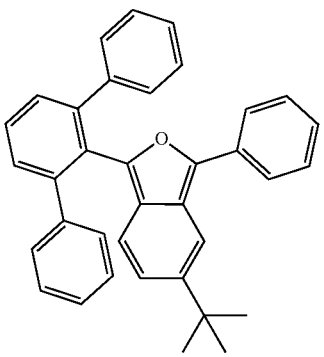
383 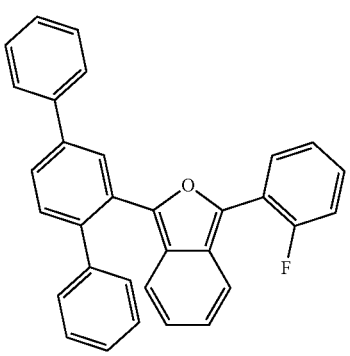
384 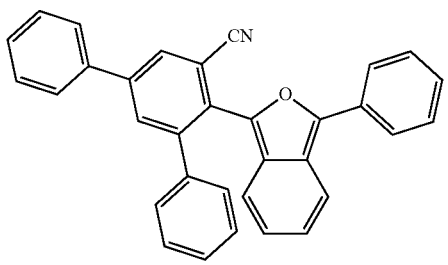
385 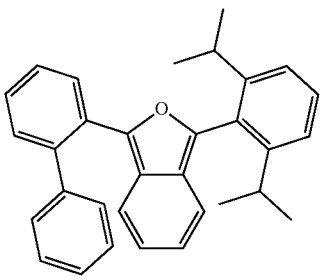
386 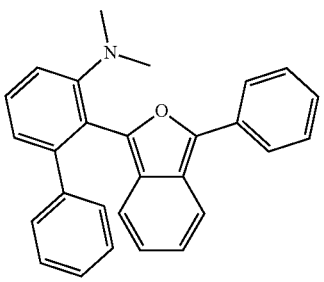

387 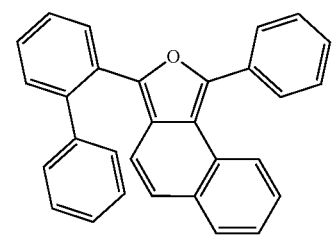
388 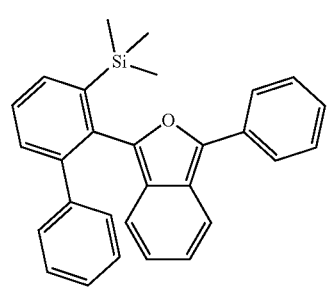
389 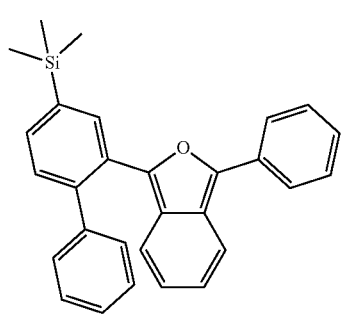
390 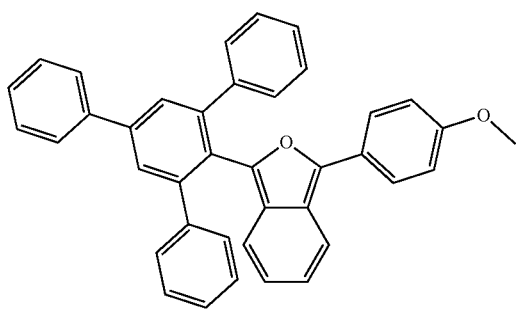
391 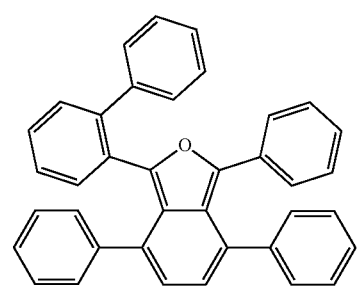
392 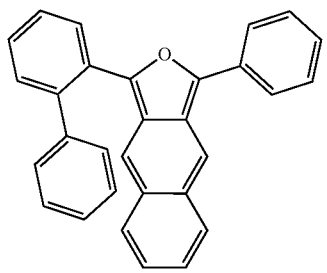
393 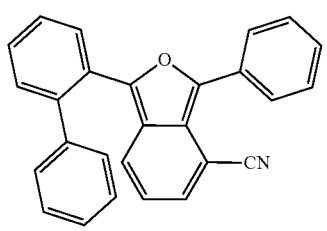
394 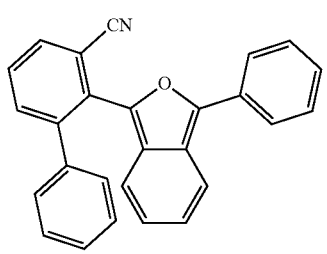
395 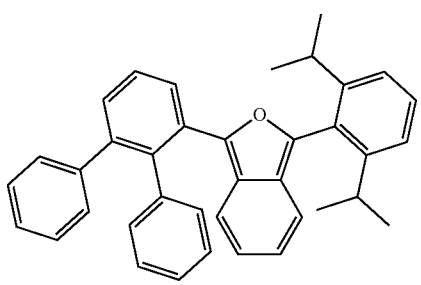
396 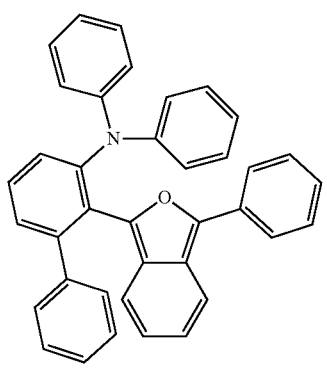

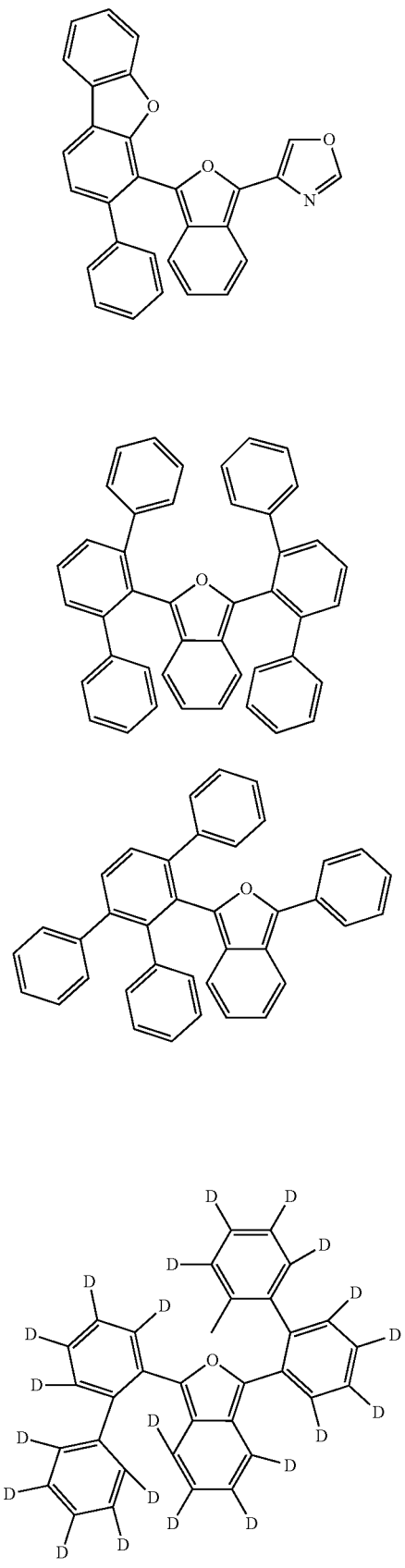
397
398
399
400
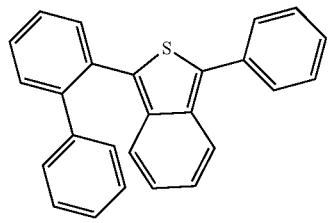
401
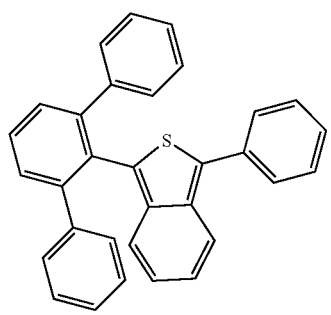
402
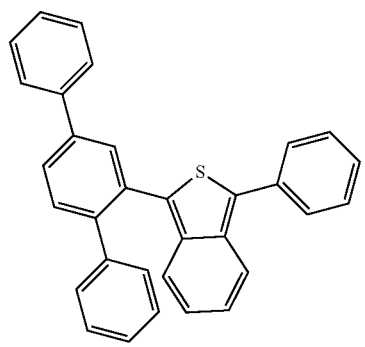
403
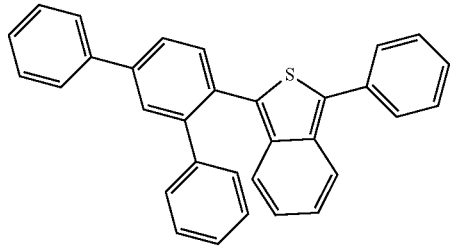
404
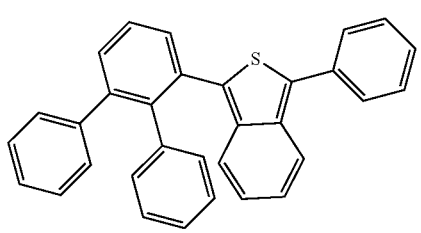
405
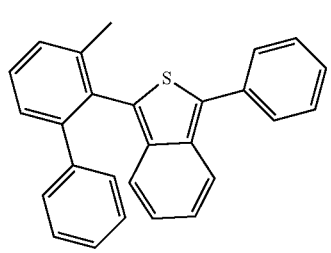
406

407
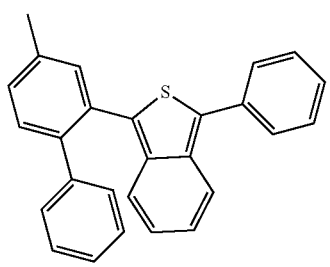
408
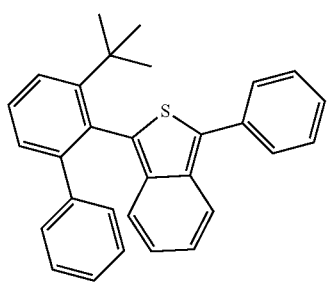
409
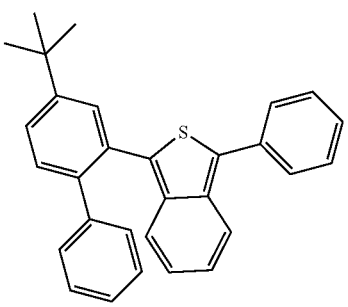
410
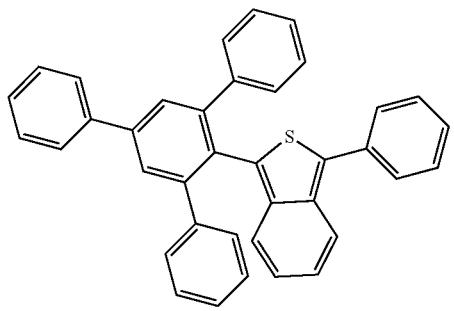
411
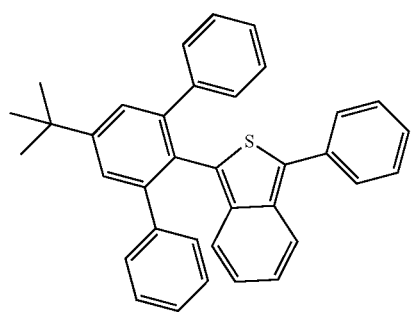
412
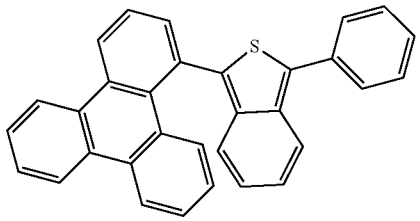
413
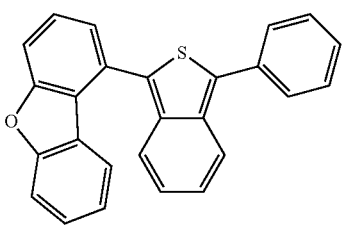
414
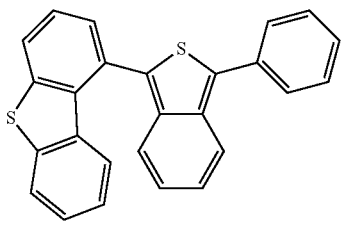
415
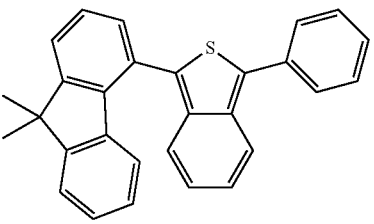
416
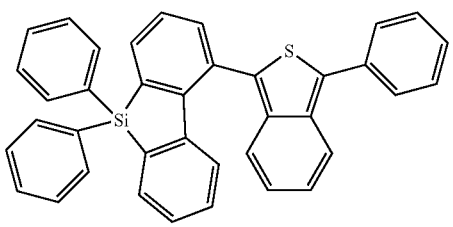
417
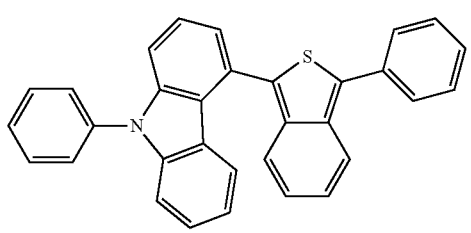

418
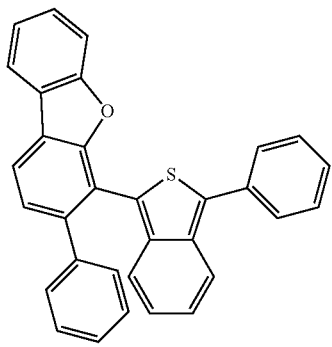
419
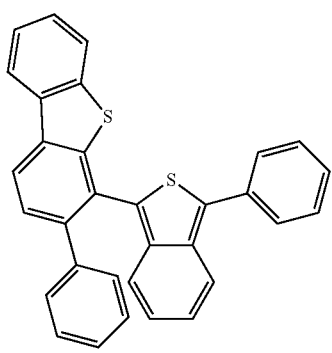
420
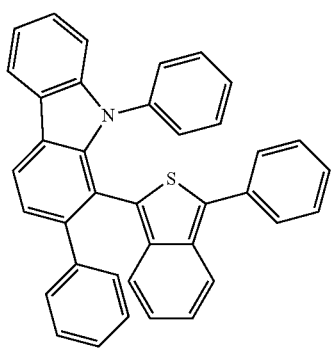
421
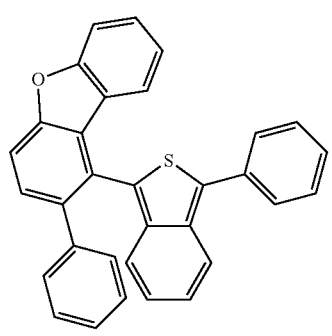
422
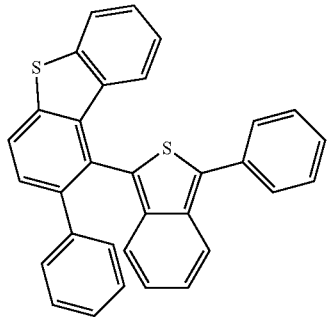
423
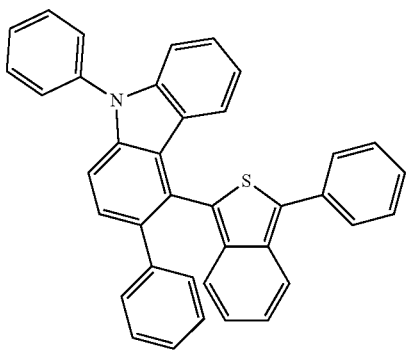
424
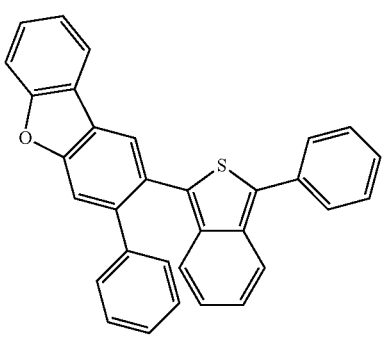
425
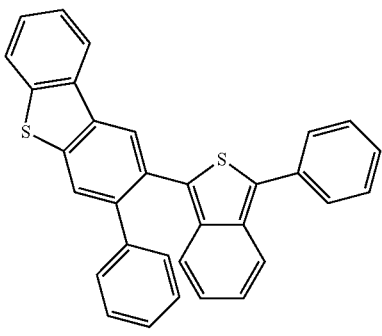

426
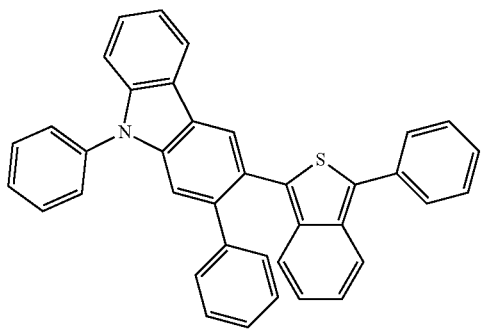
427
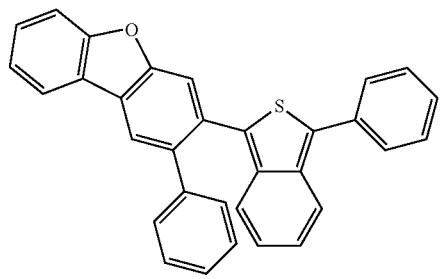
428
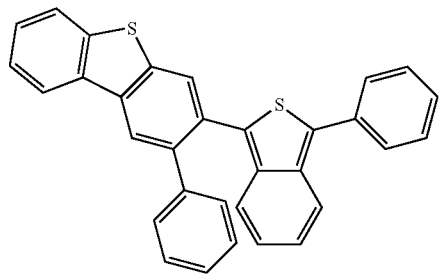
429
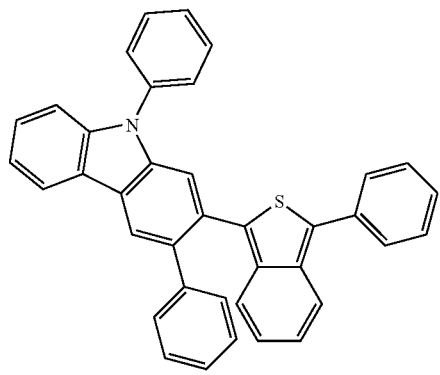
430
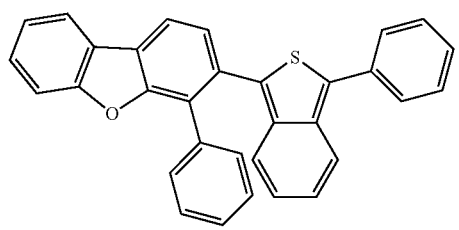
431
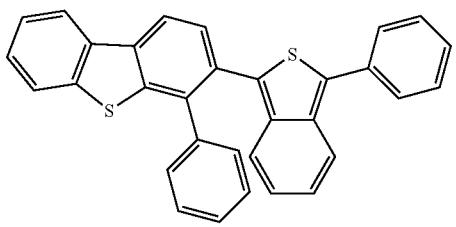
432
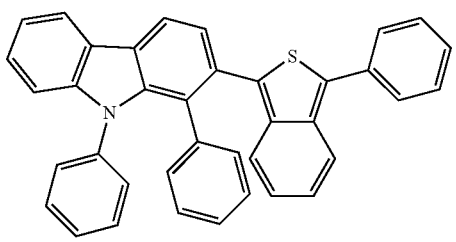
433
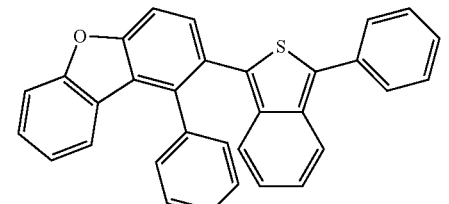
434
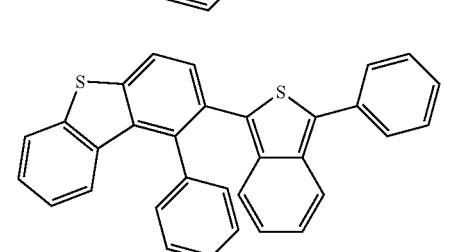
435
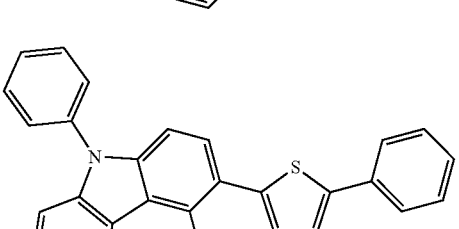
436
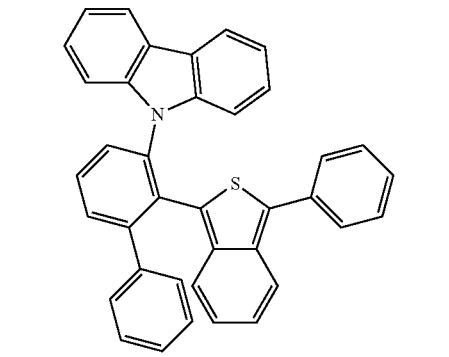

437
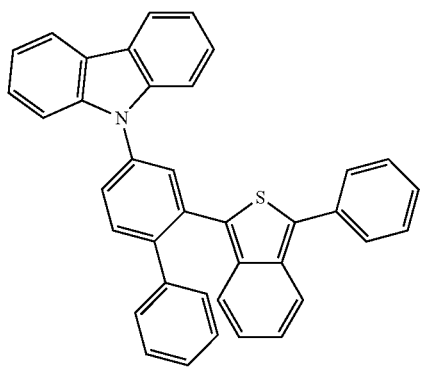
441
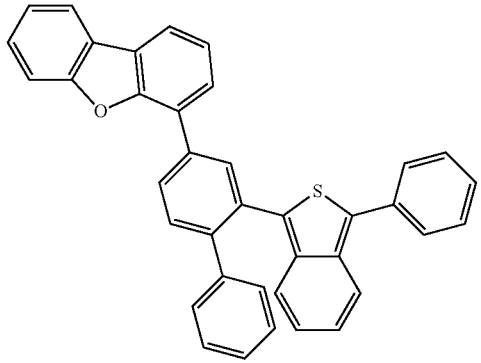
438
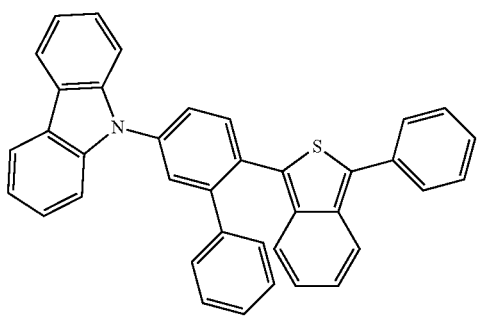
442
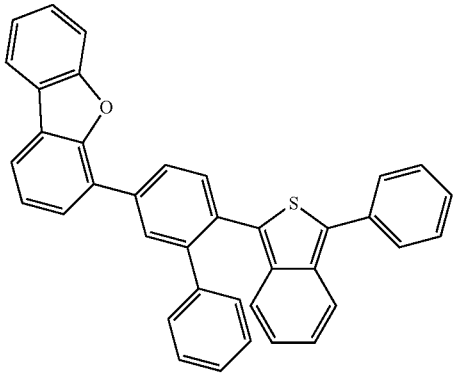
439
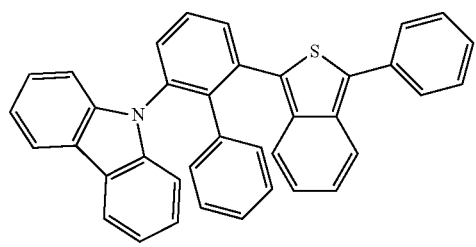
443
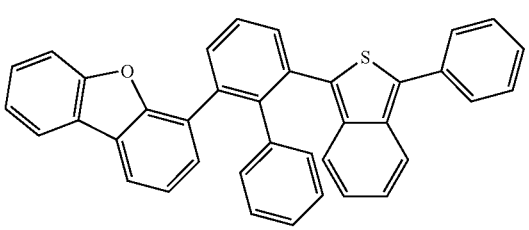
440
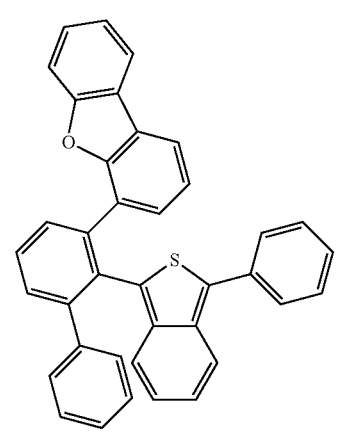
444
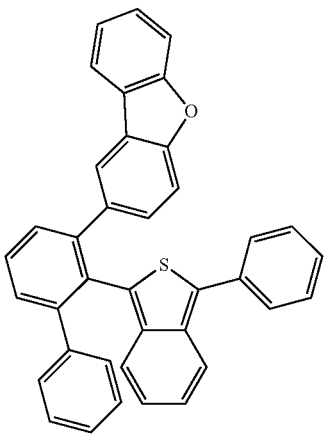

| | |
|---|---|
| 445 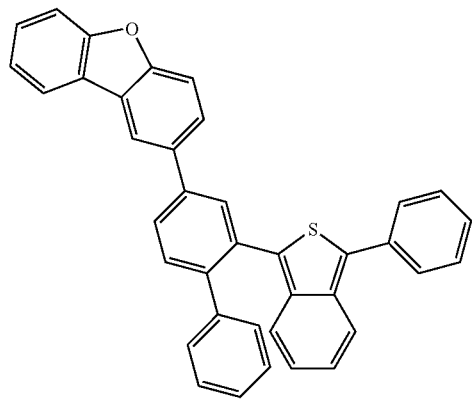 | 449 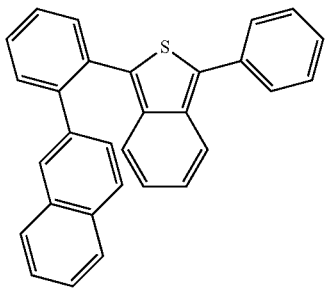 |
| 446 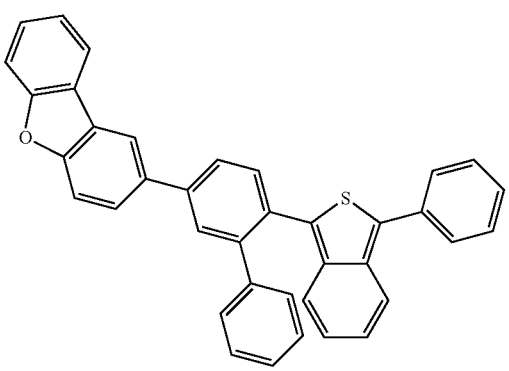 | 450 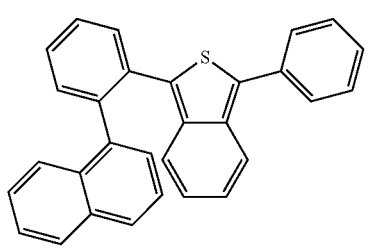 |
| | 451 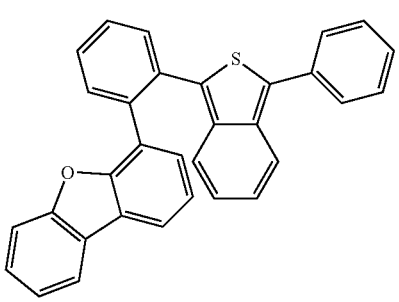 |
| 447 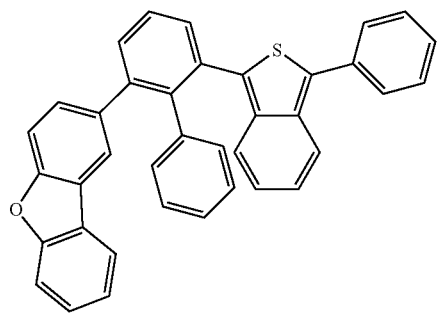 | 452 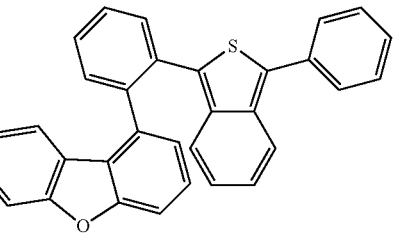 |
| 448 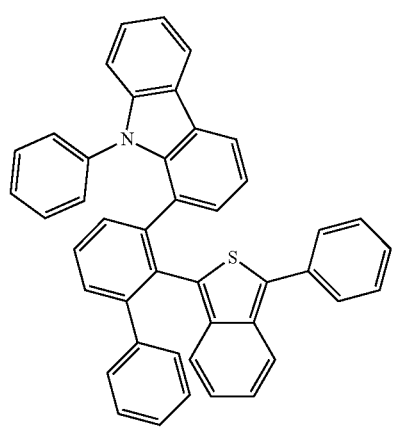 | 453 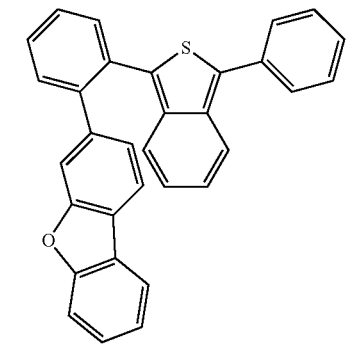 |

454 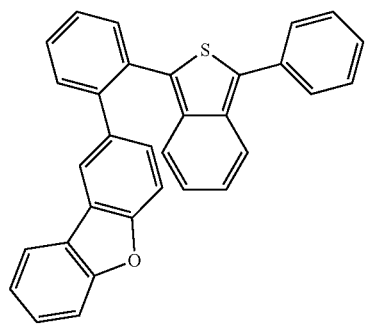
455 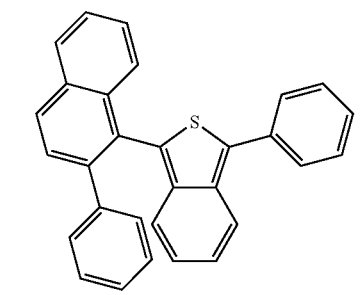
456 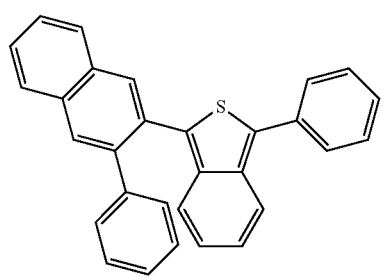
457 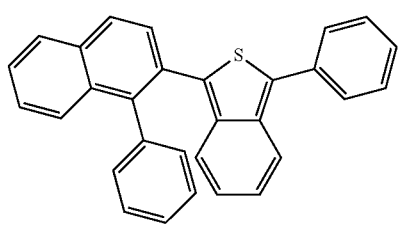
458 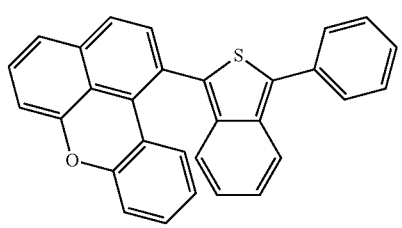
459 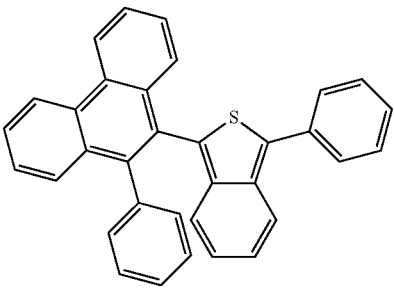
460 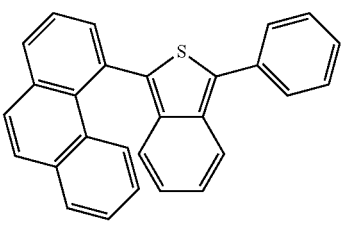
461 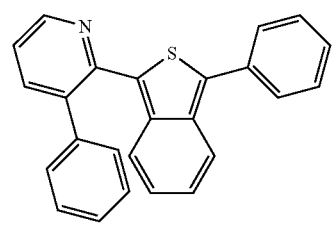
462 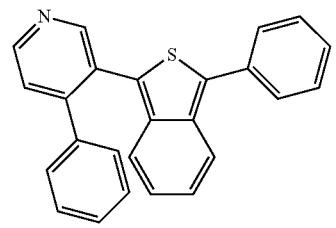
463 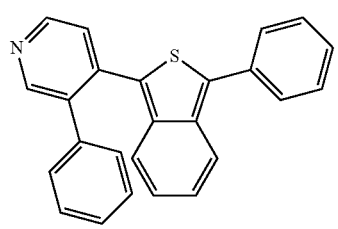
464 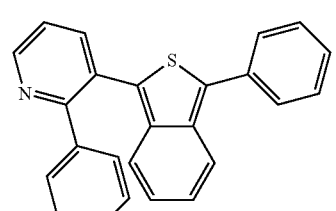

-continued
465
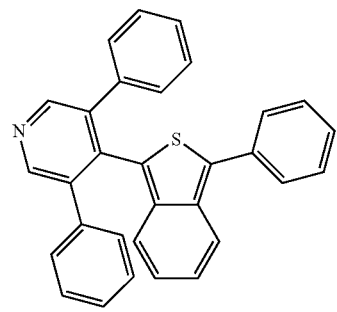
466
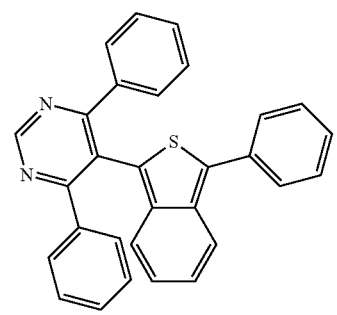
467
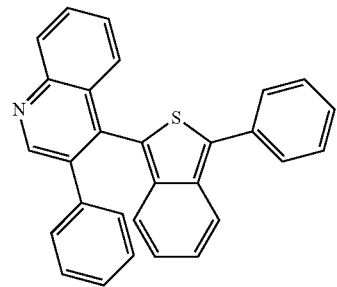
468
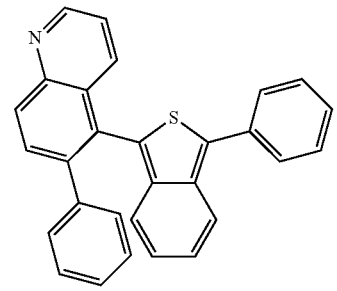
469
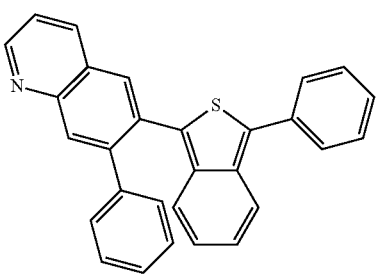
-continued
470
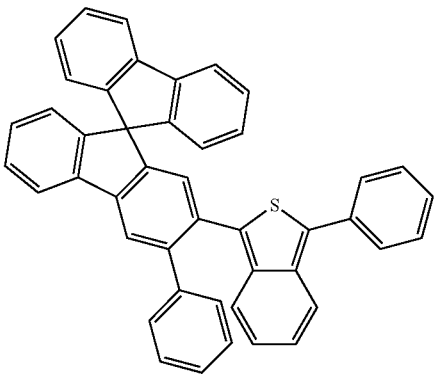
471
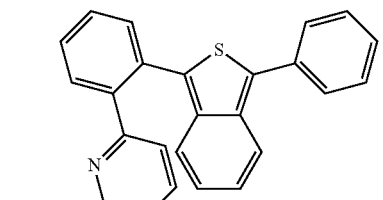
472
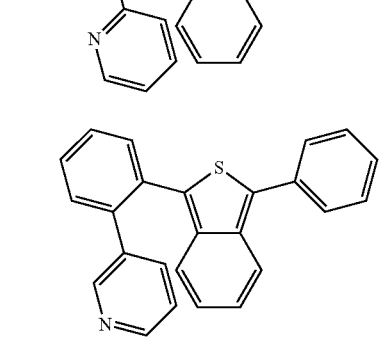
473
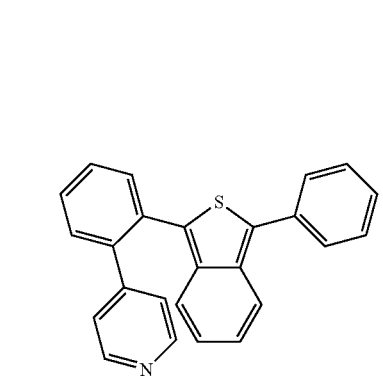
474
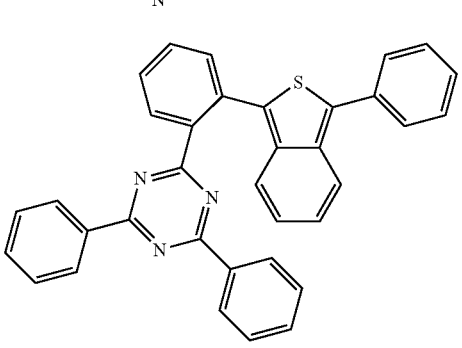

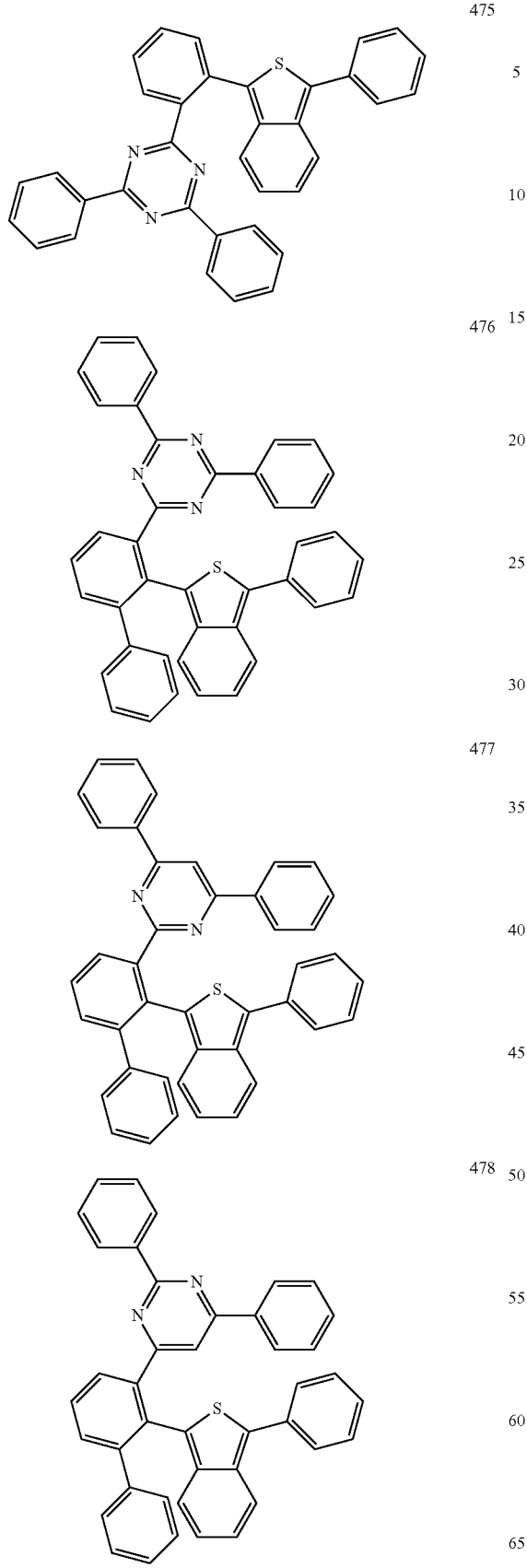
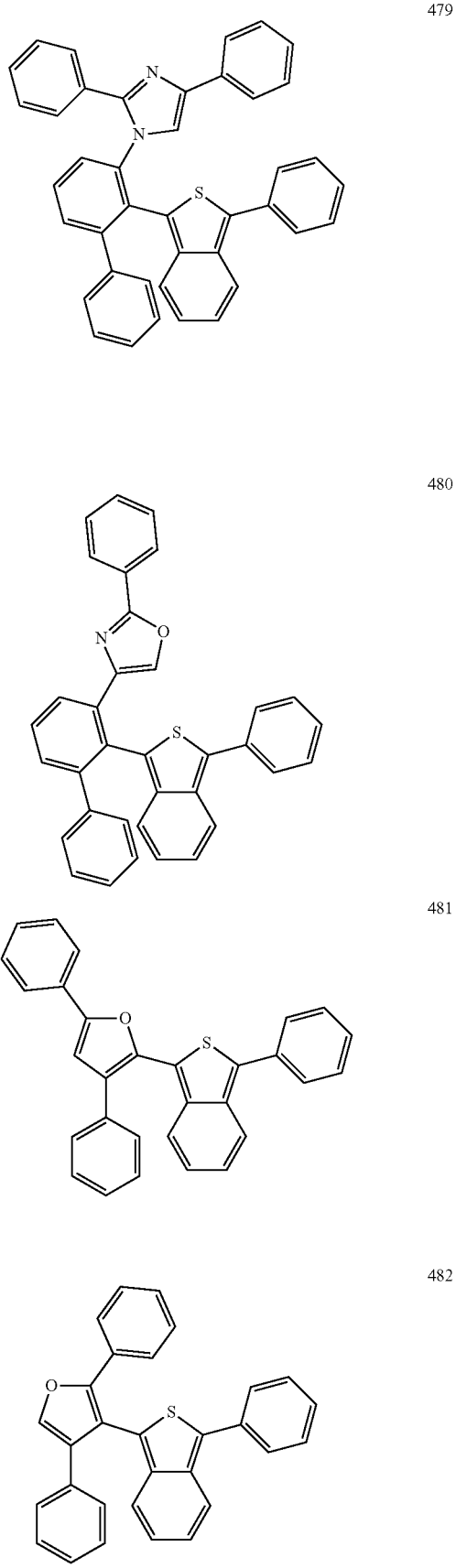

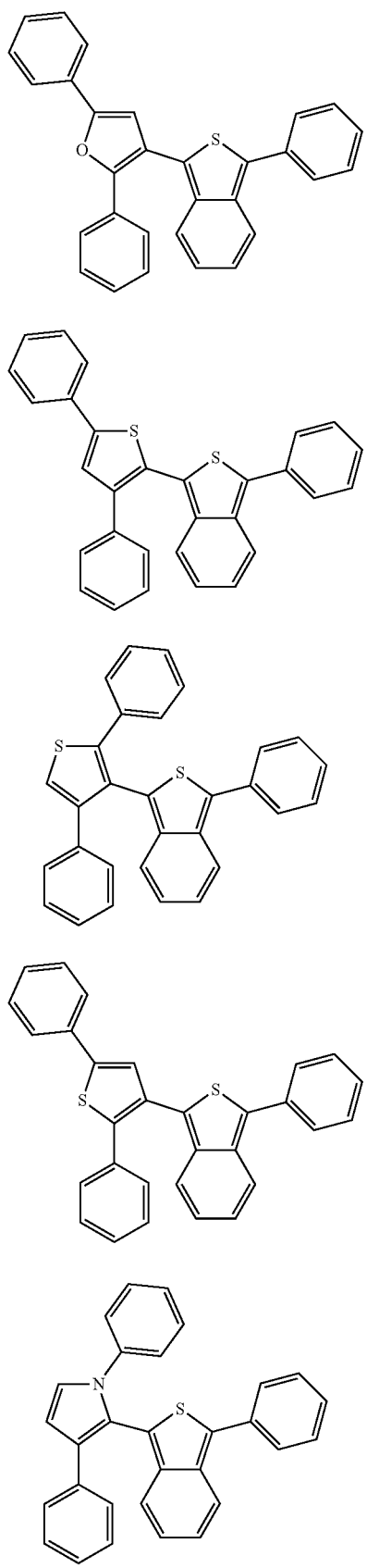
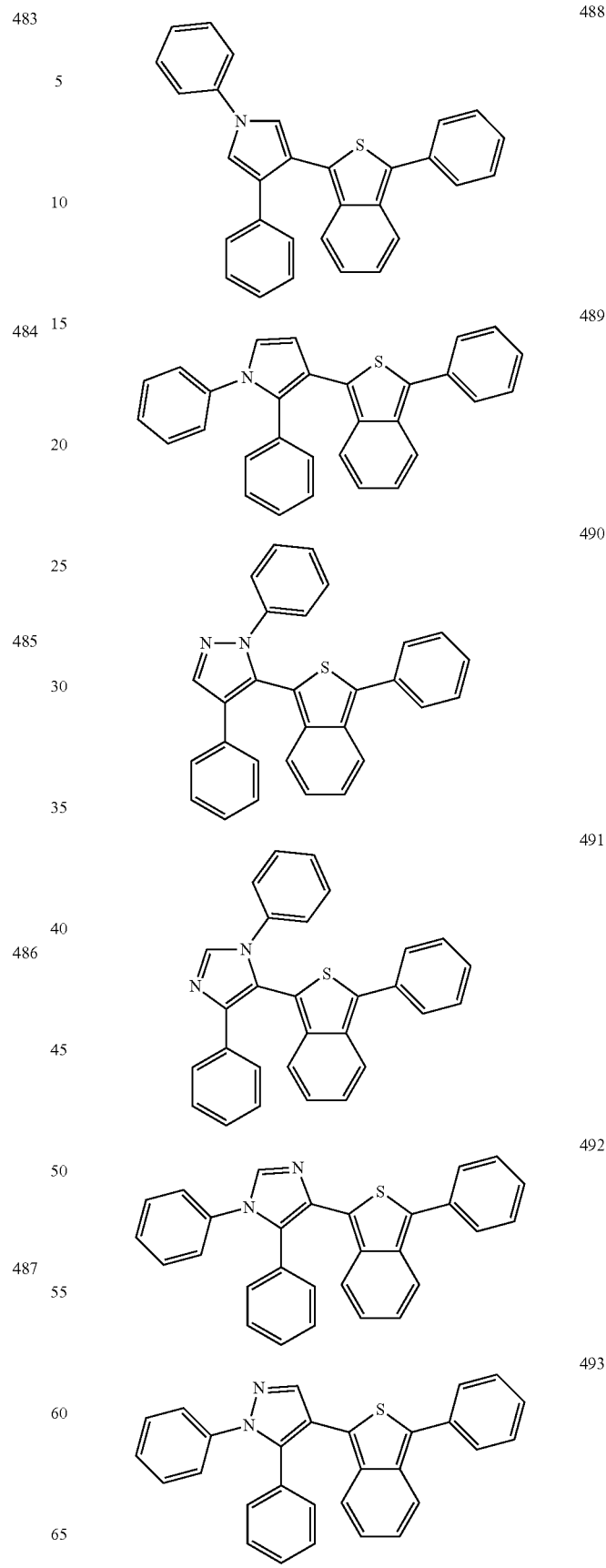

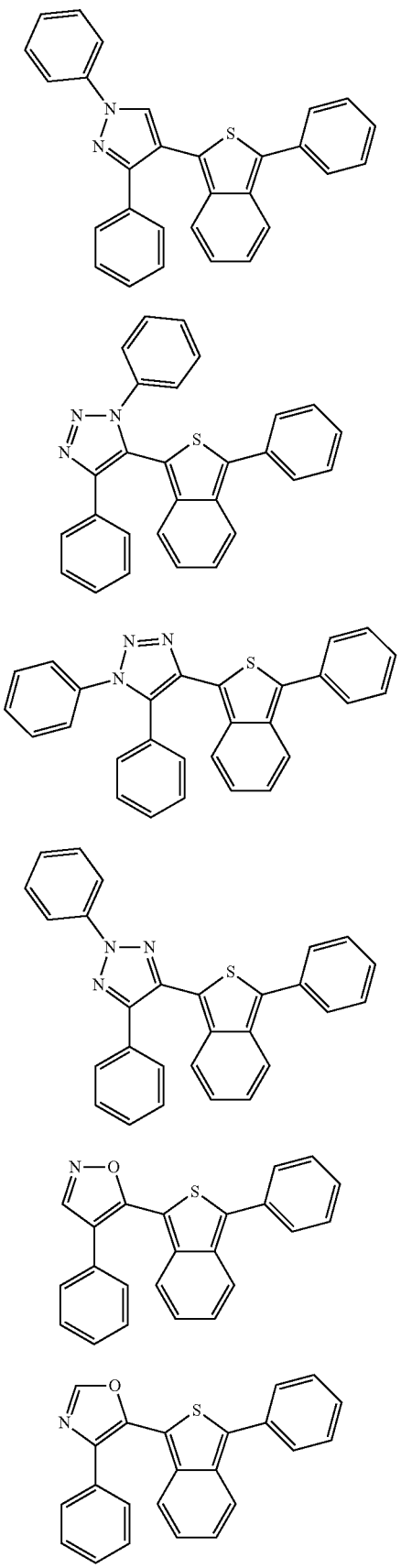
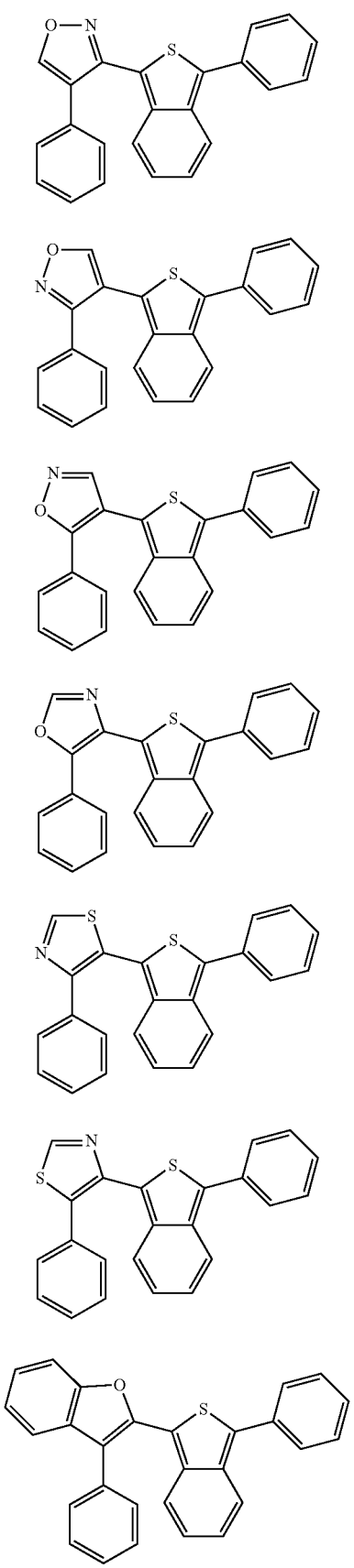

| 507 | 512 |
|---|---|
| 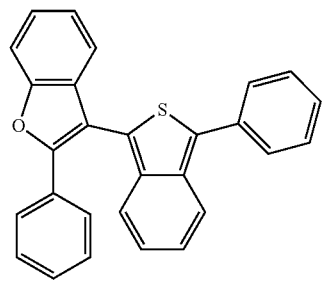 | 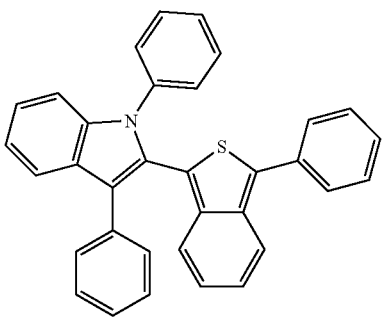 |
| 508 | 513 |
| 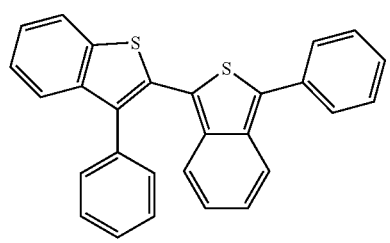 | 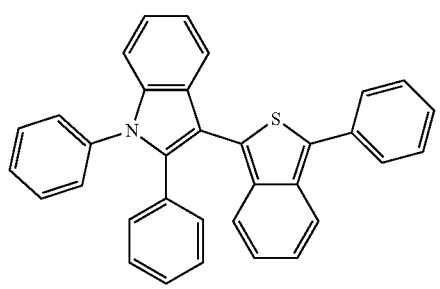 |
| 509 | 514 |
| 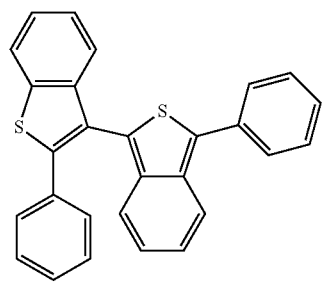 | 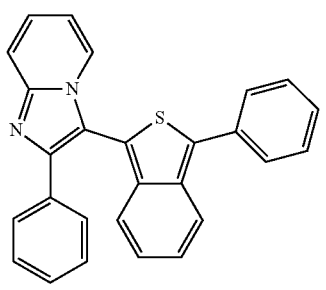 |
| 510 | 515 |
| 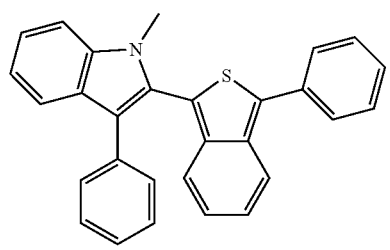 | 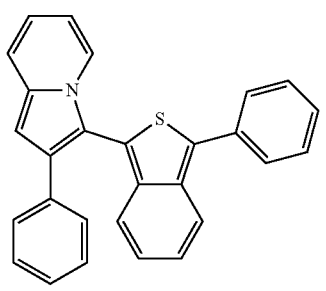 |
| 511 | 516 |
| 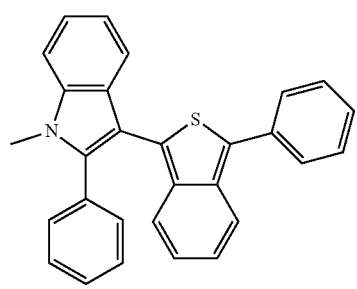 | 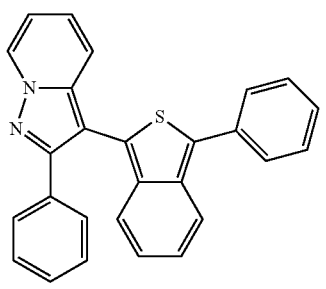 |

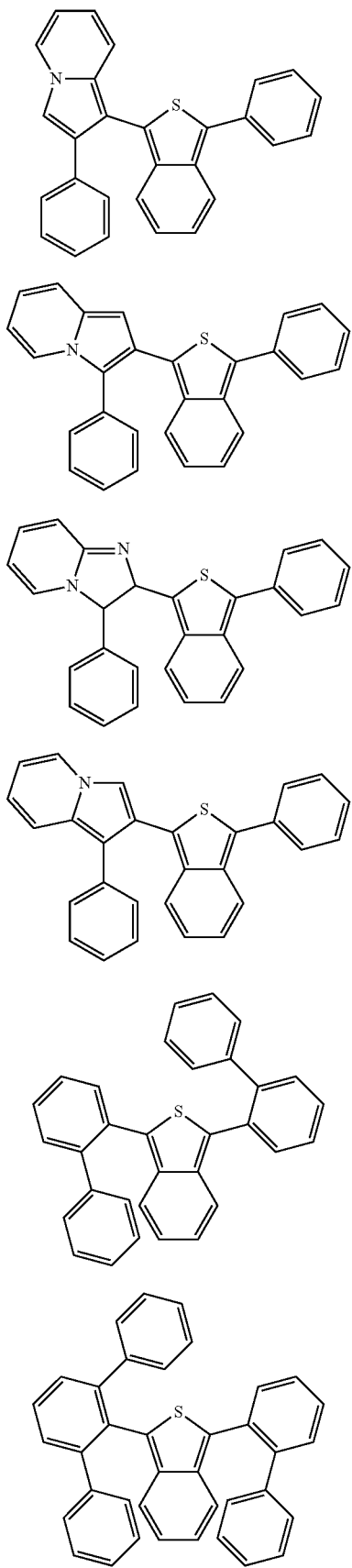
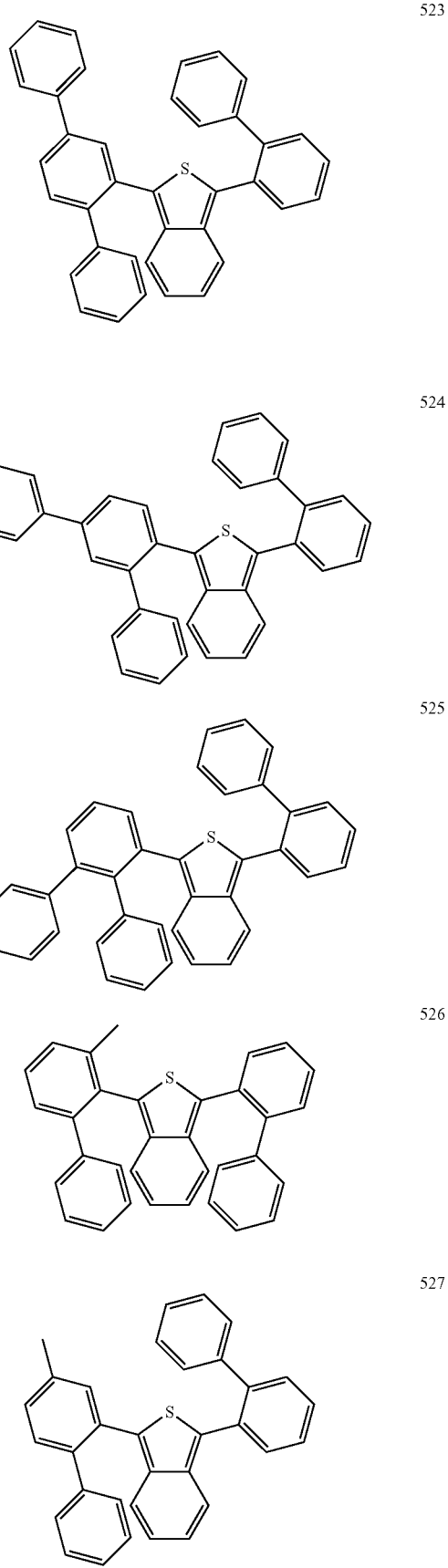

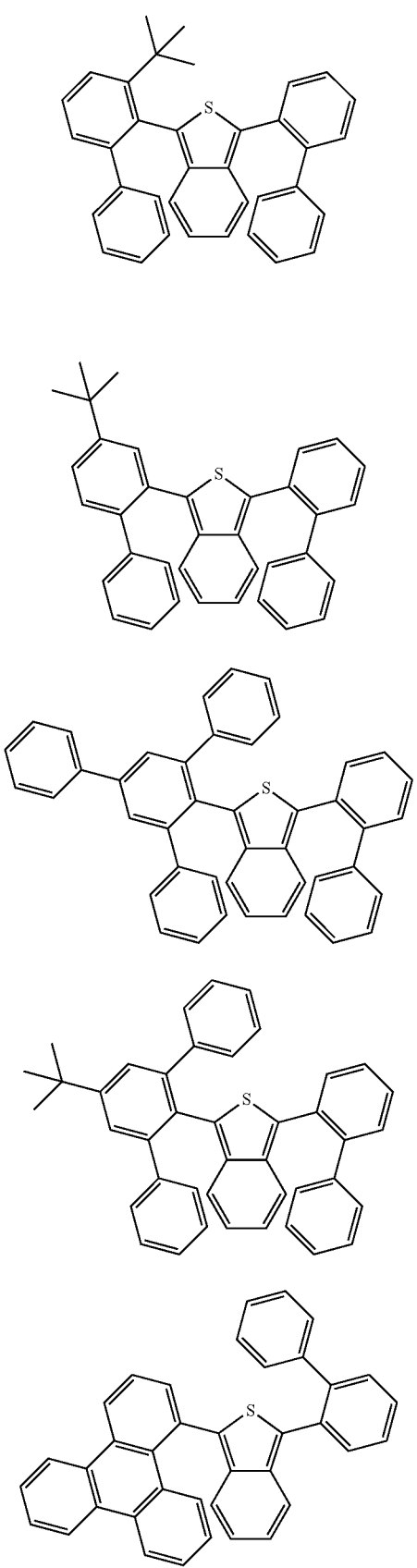
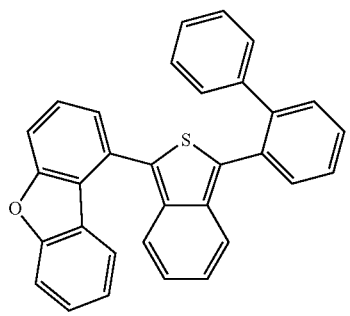
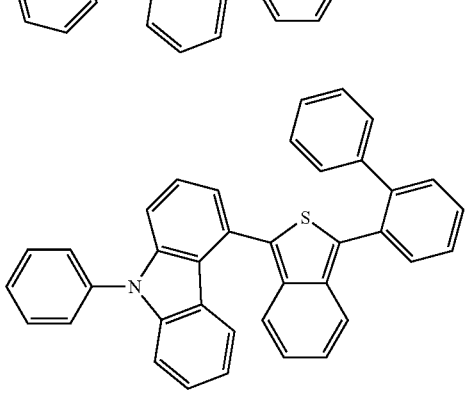

538
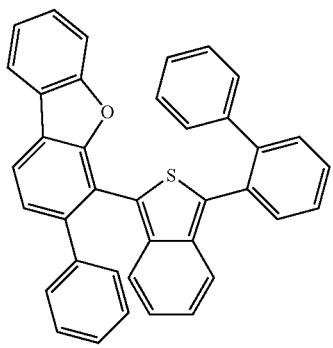
539
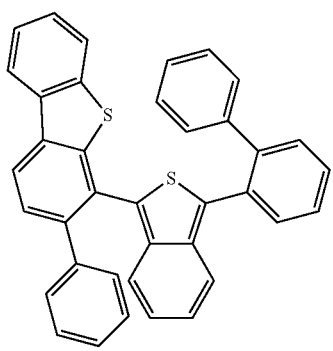
540
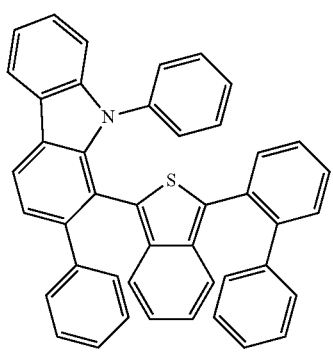
541
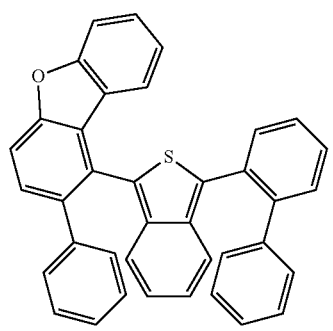
542
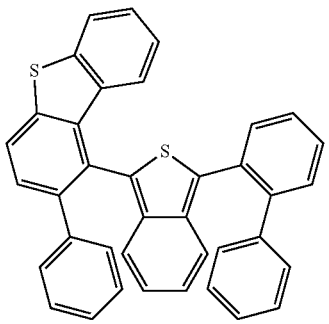
543
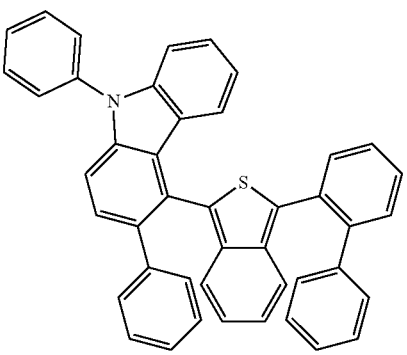
544
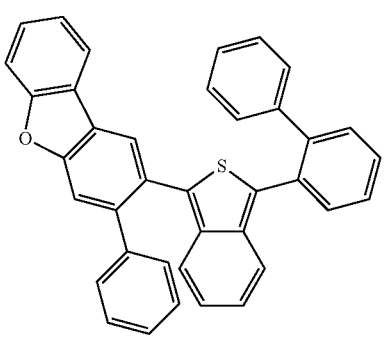
545
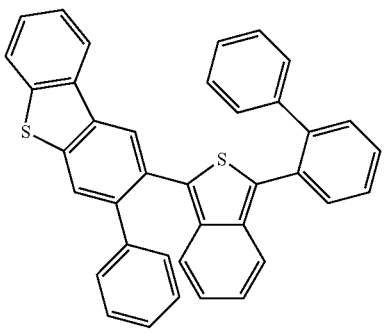

546
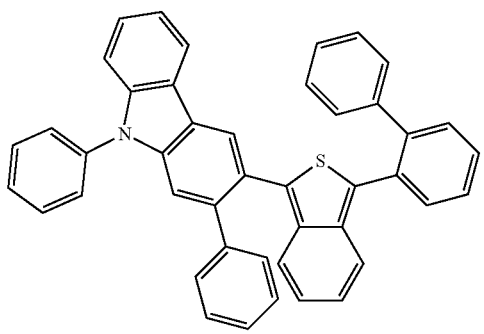
547
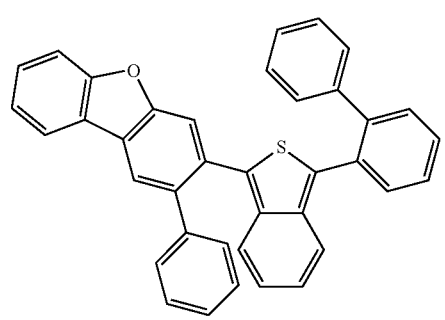
548
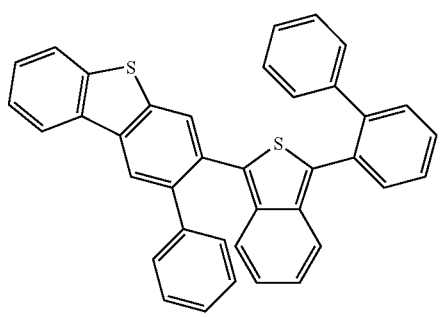
549
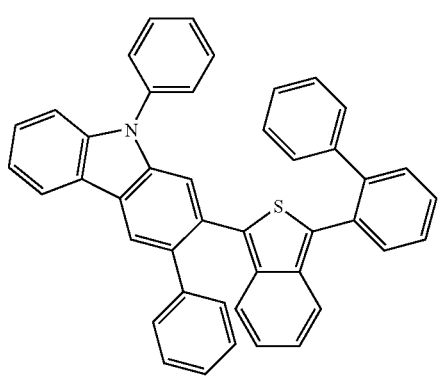
550
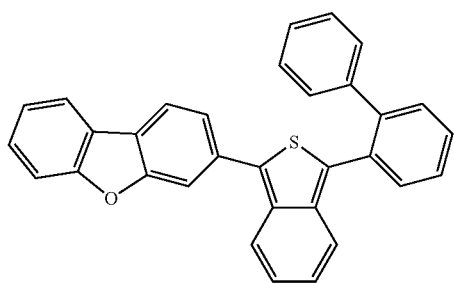
551
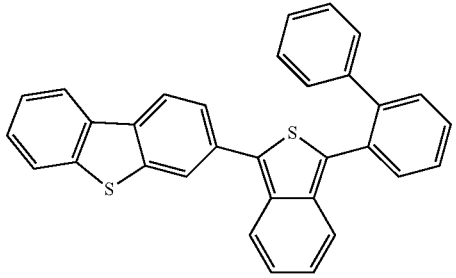
552
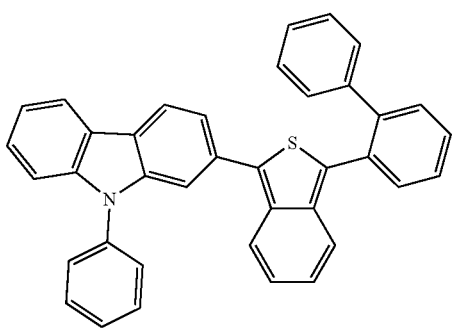
553
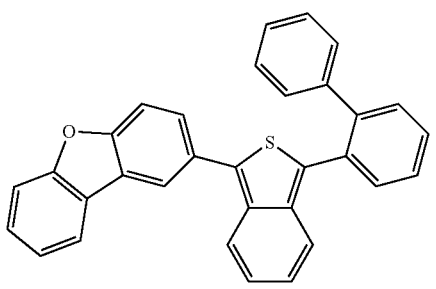
554
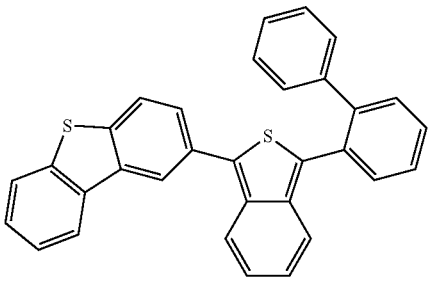
555
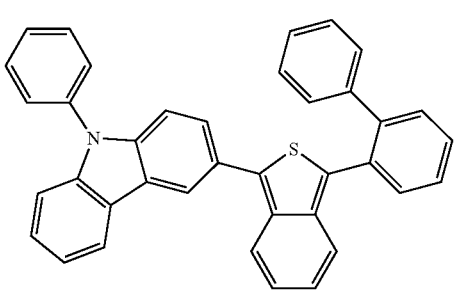

556
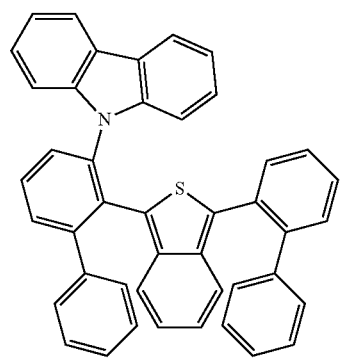
557
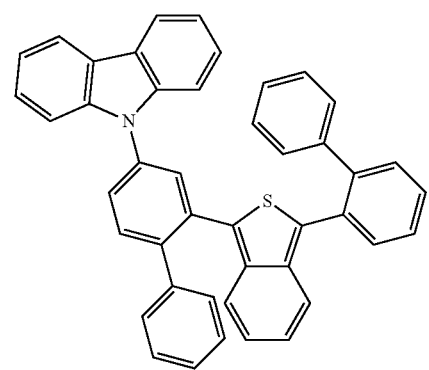
558
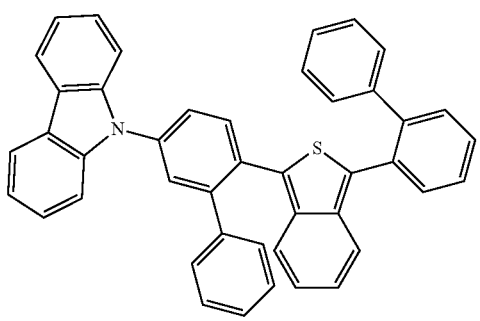
559
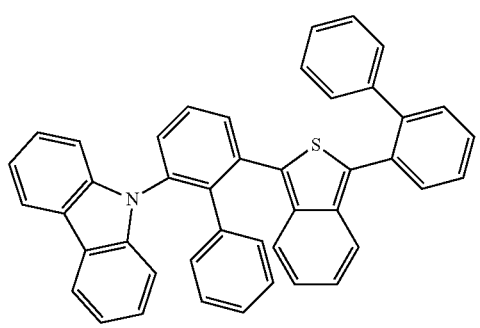
560
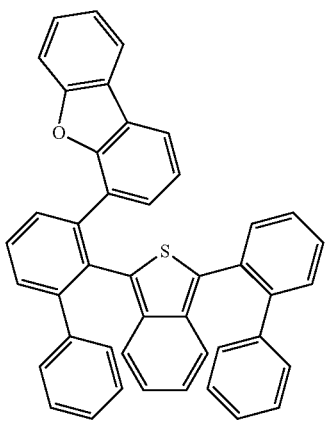
561
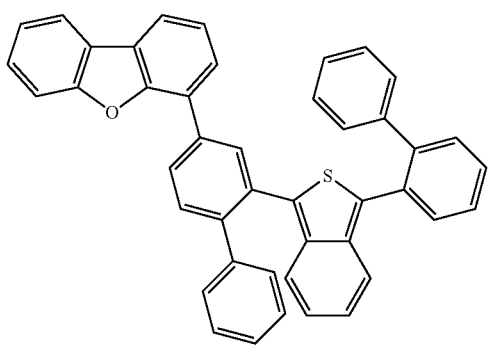
562
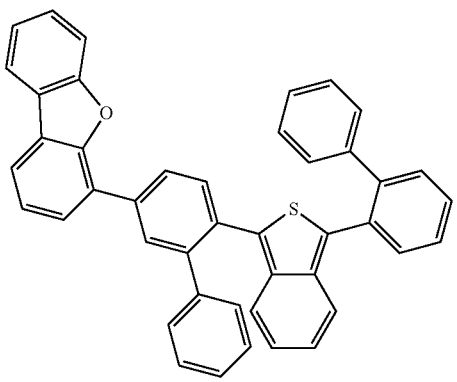
563
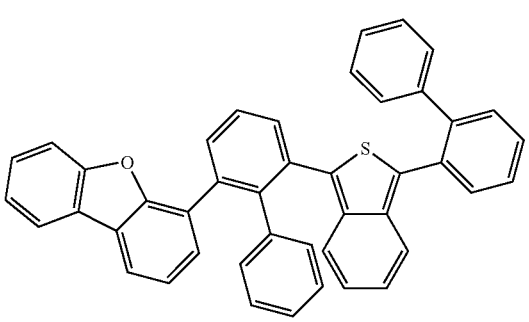

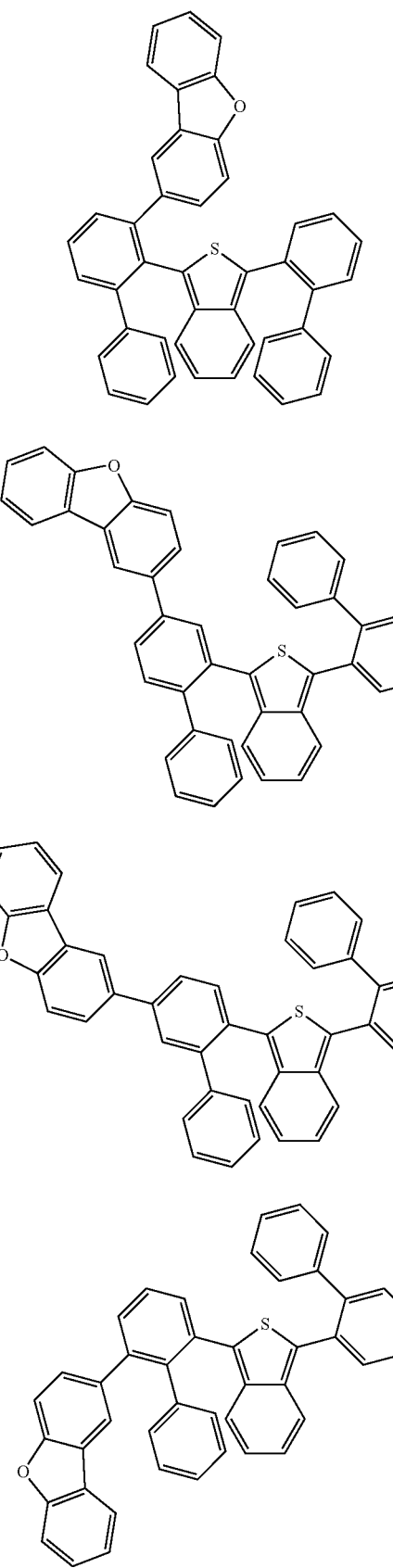
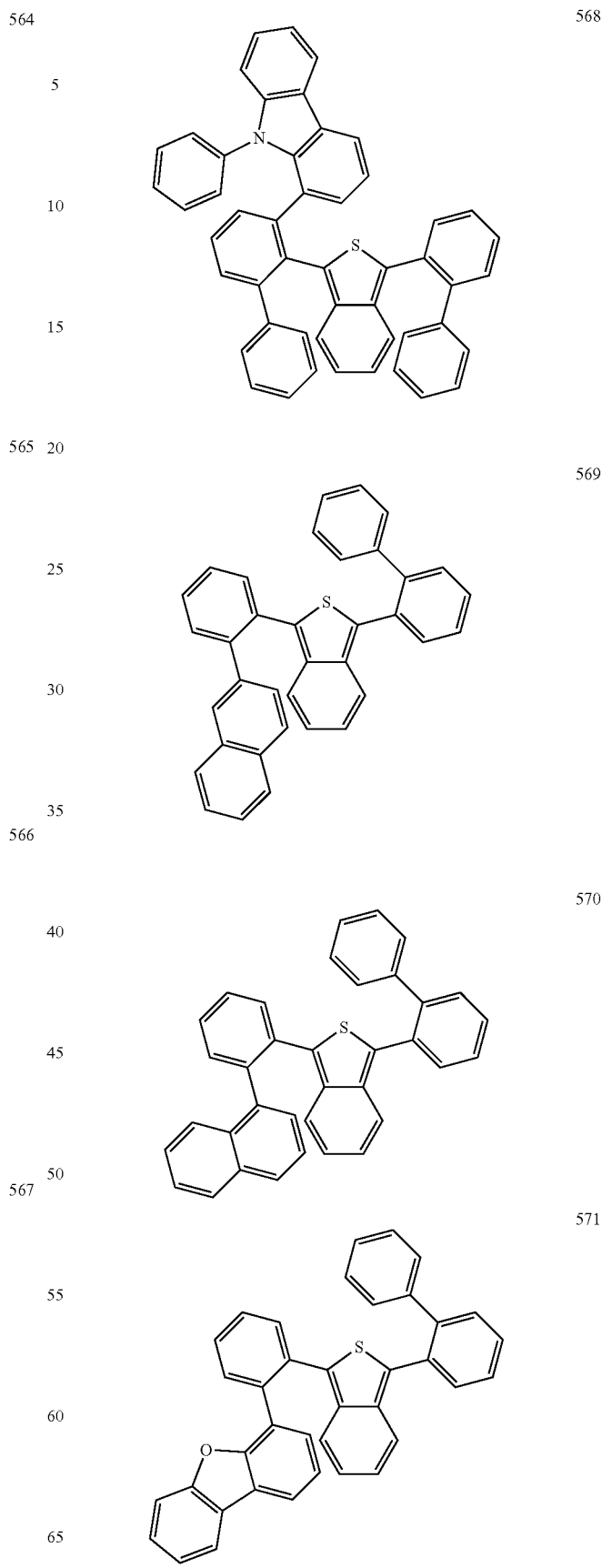

572
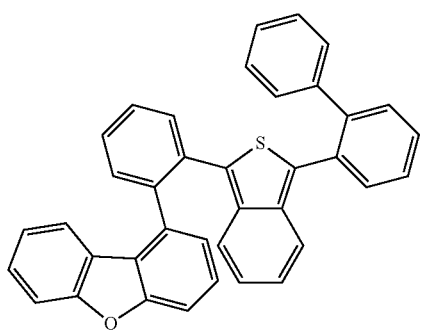
573
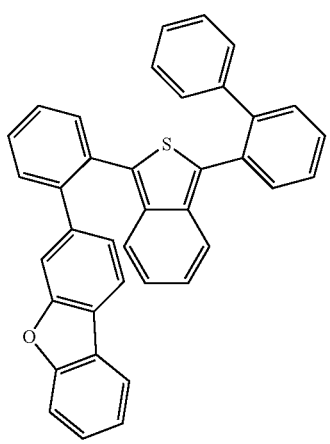
574
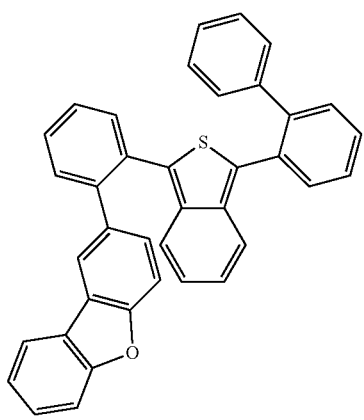
575
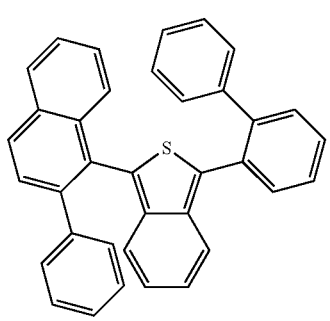
576
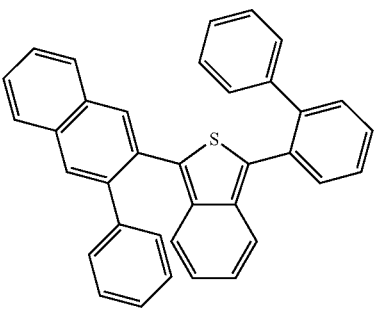
577
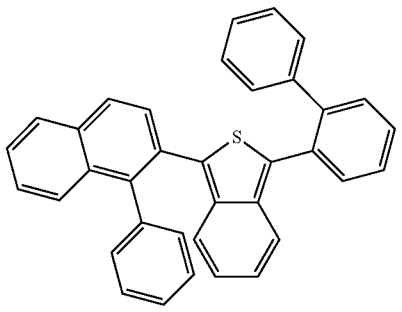
578
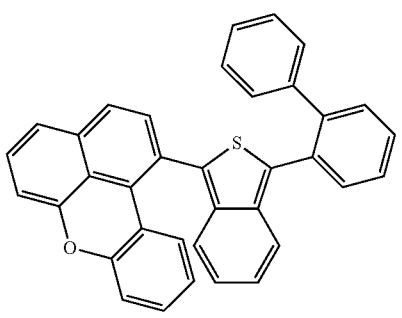
579
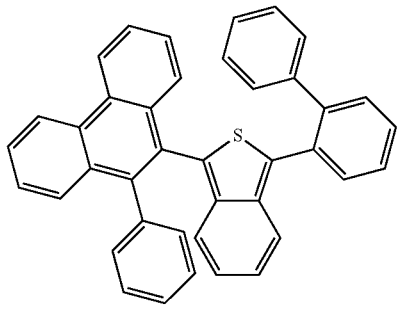
580
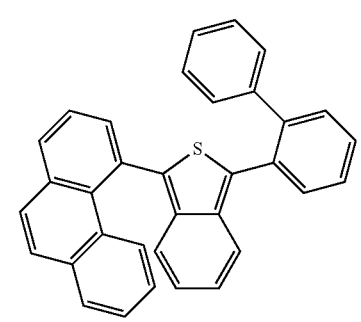

-continued
581
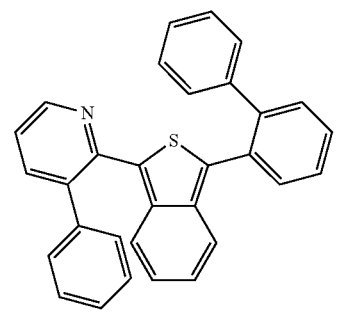
582
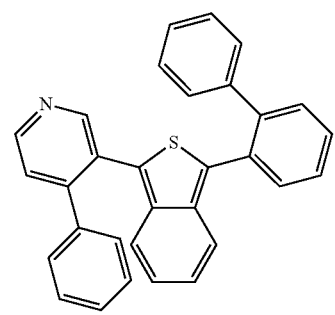
583
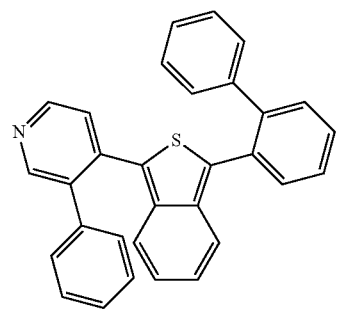
584
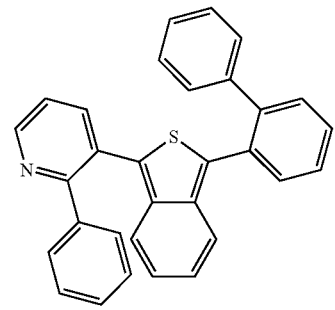
585
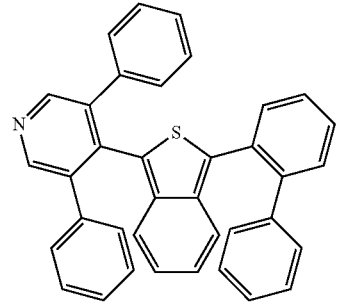
-continued
586
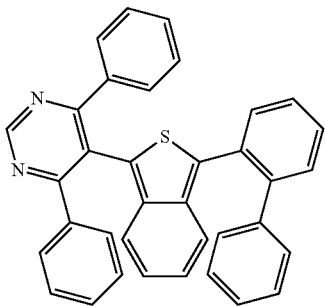
587
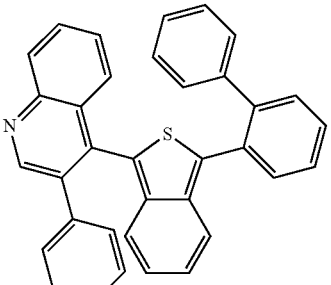
588
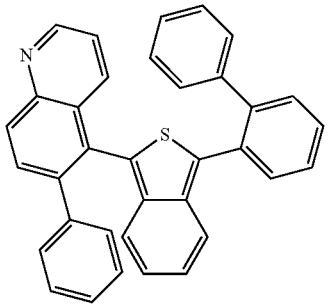
589
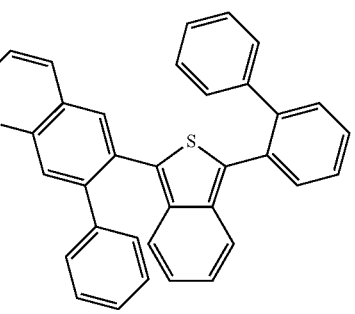
590
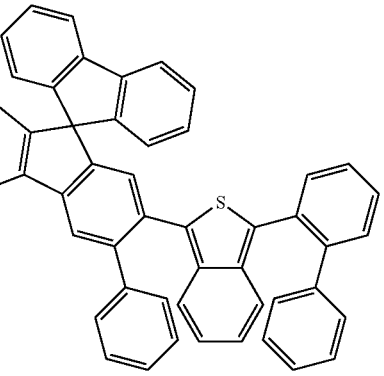

591
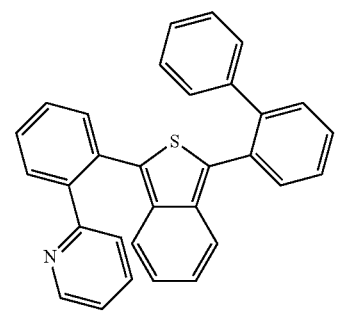
592
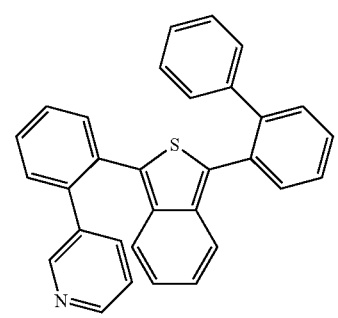
593
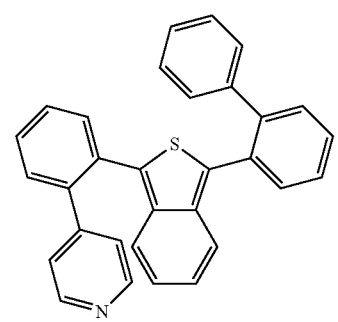
594
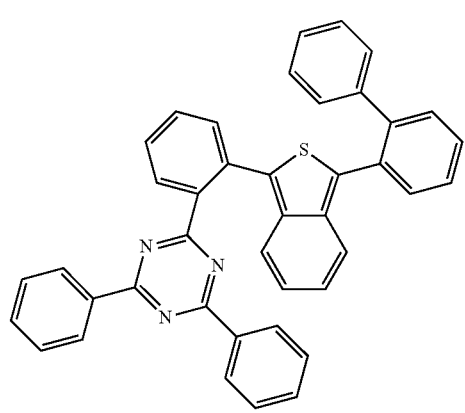
595
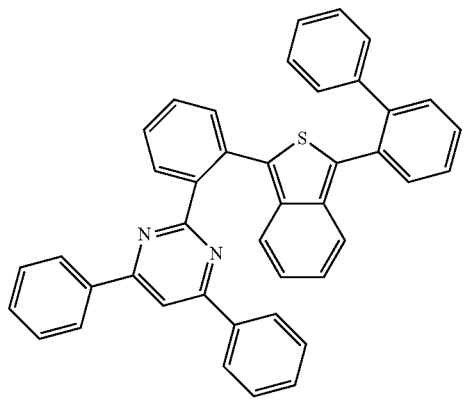
596
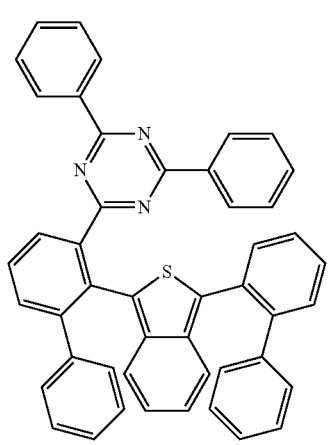
597
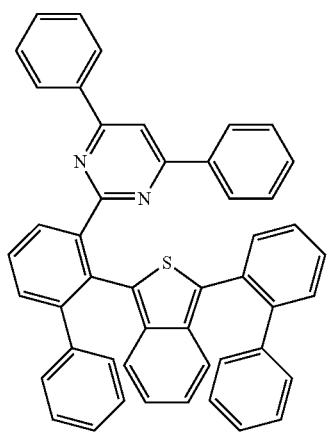

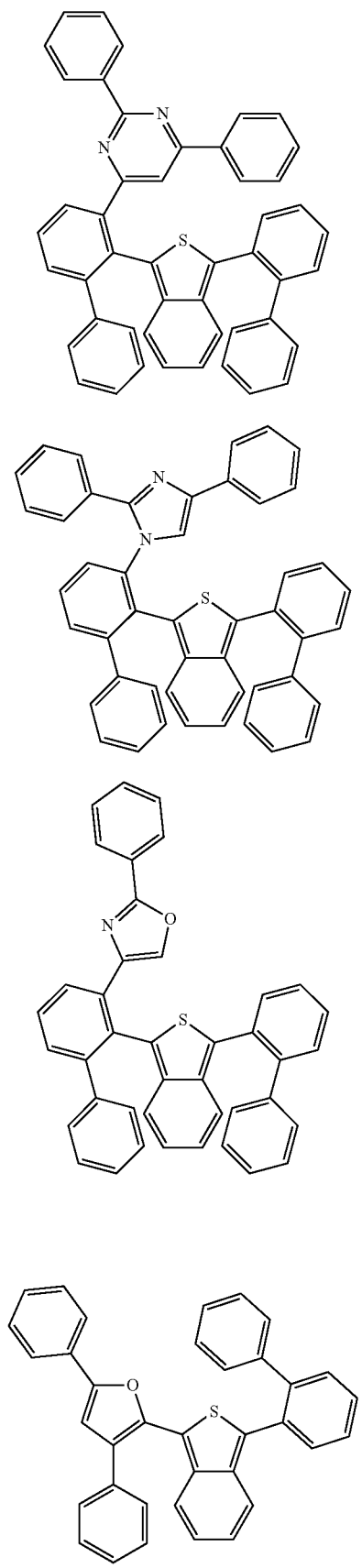
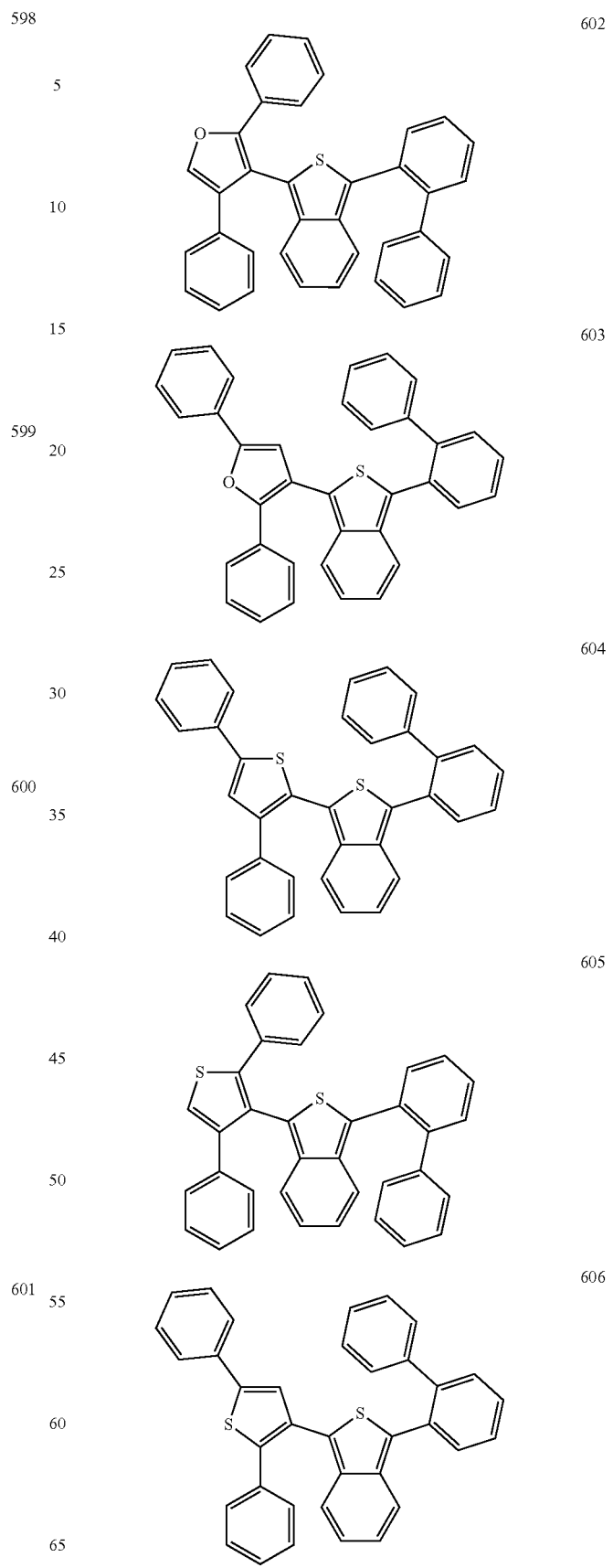

607
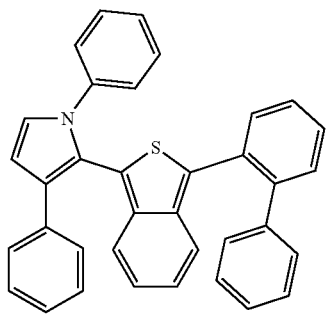
608
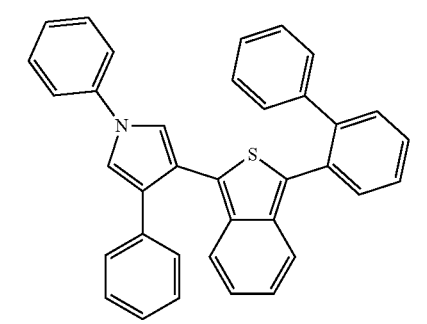
609
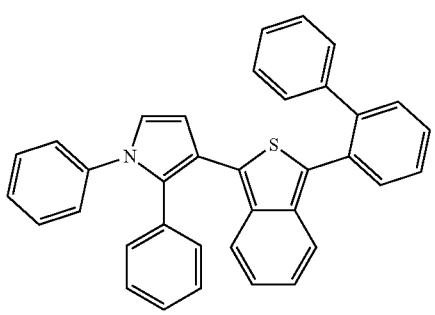
610
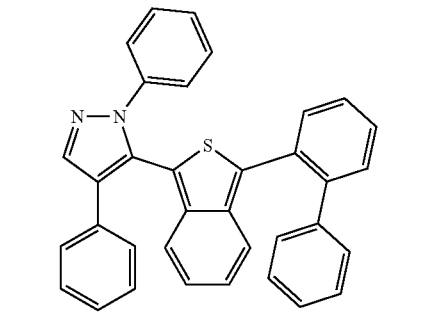
611
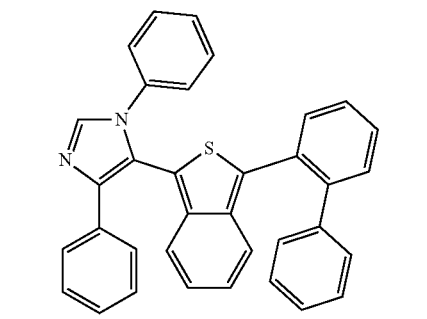
612
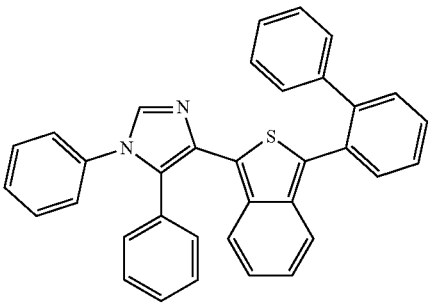
613
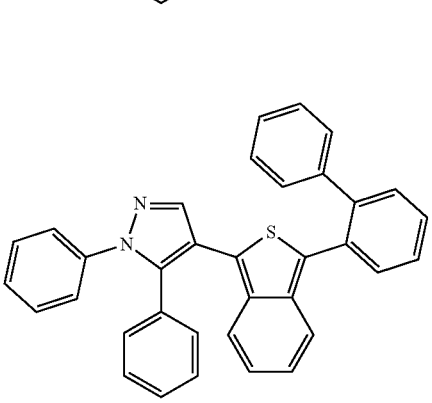
614
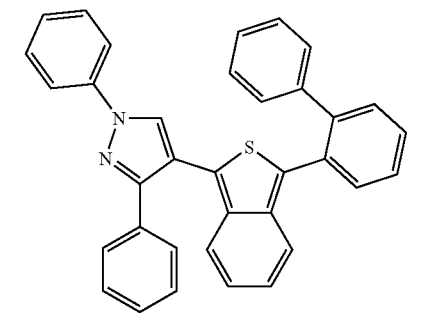
615
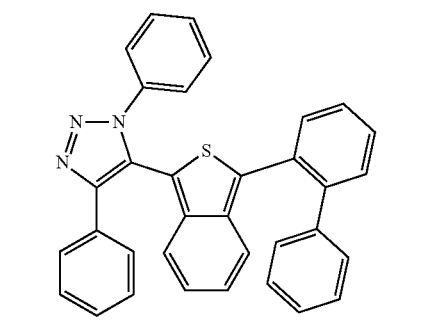
616
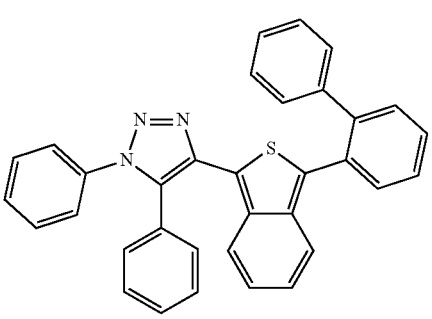

617
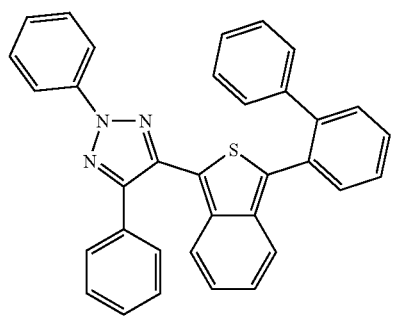
618
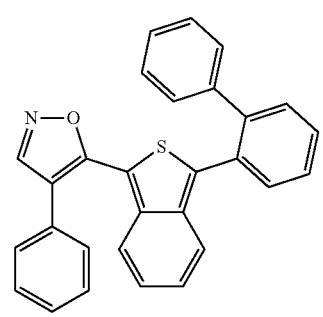
619
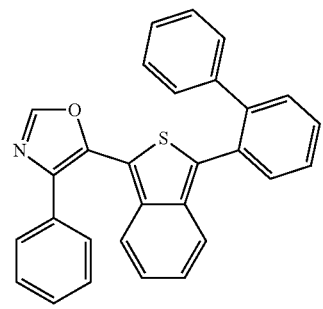
620
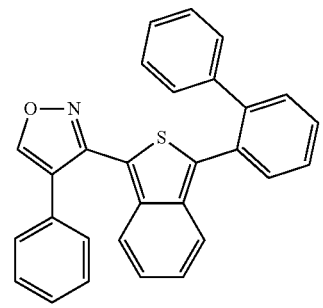
621
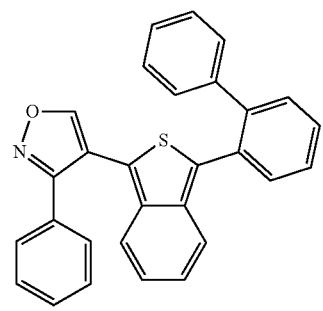
622
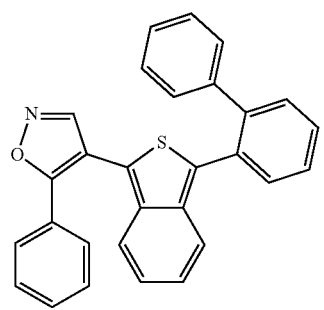
623
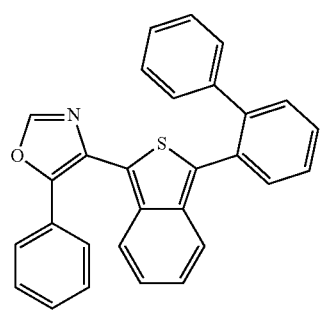
624
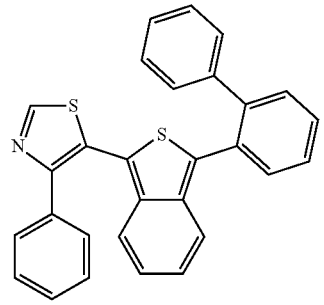
625
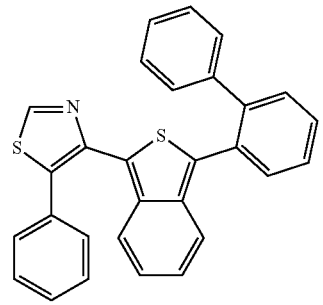
626
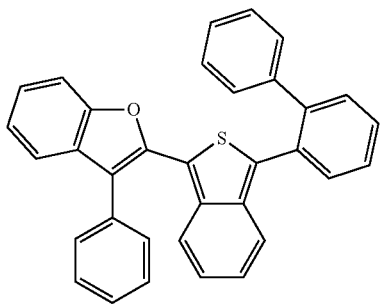

627
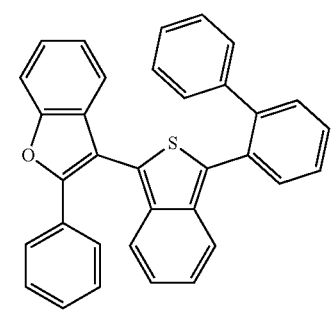
628
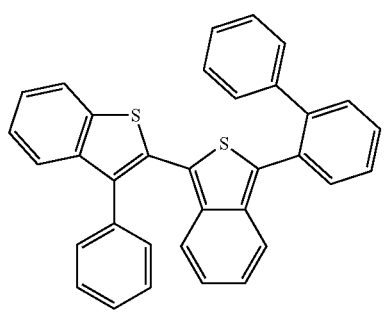
629
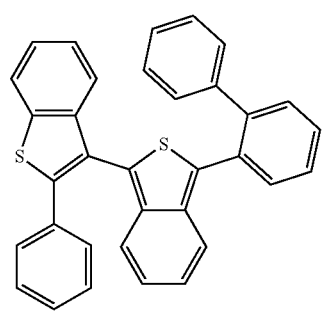
630
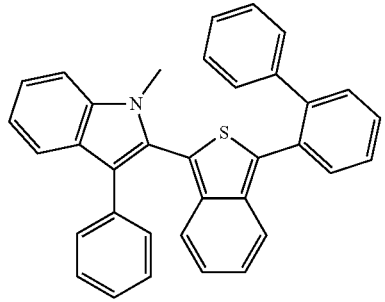
631
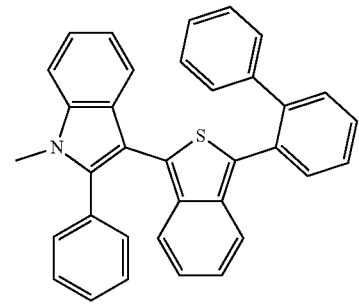
632
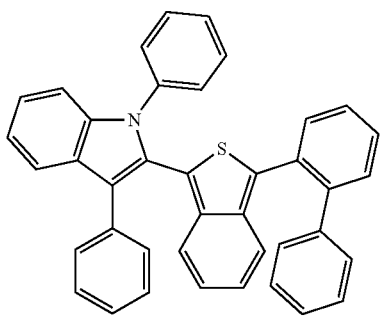
633
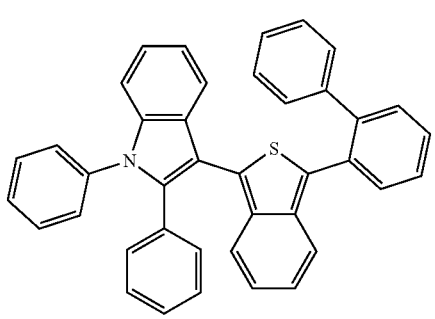
634
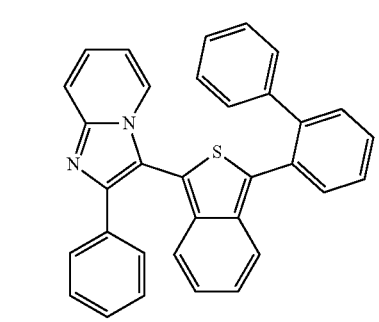
635
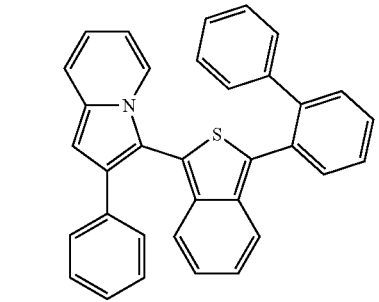
636
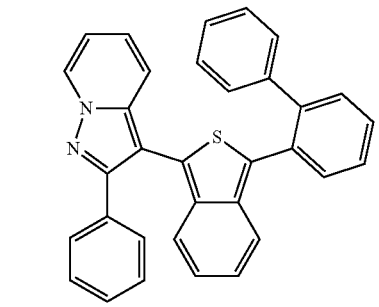

637
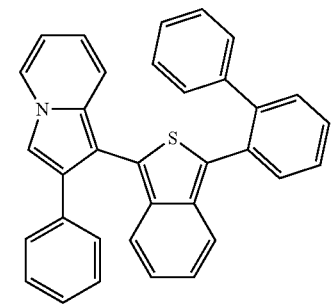
638
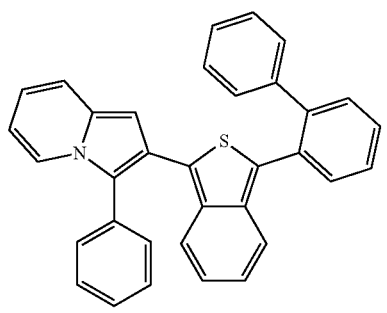
639
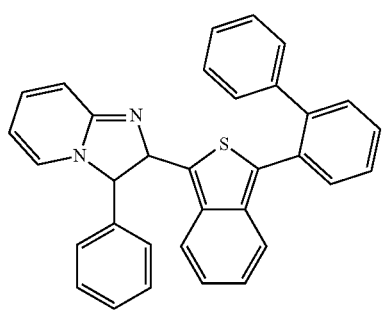
640
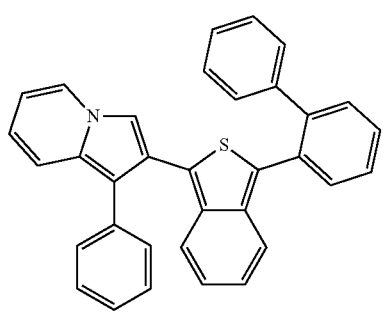
641
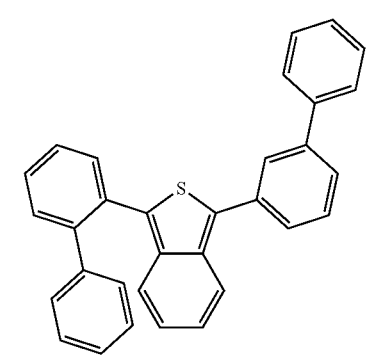
642
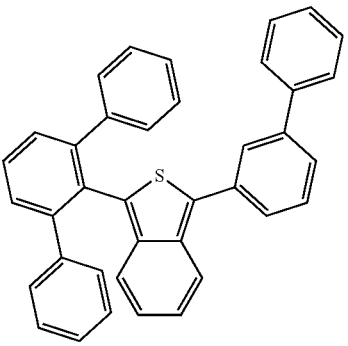
643
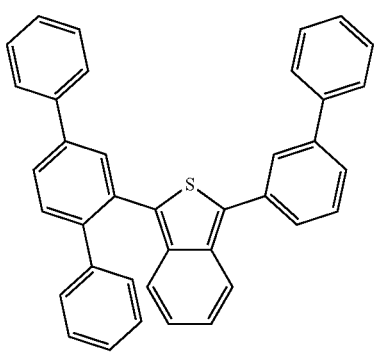
644
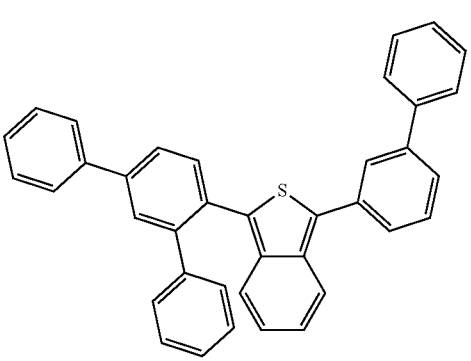
645
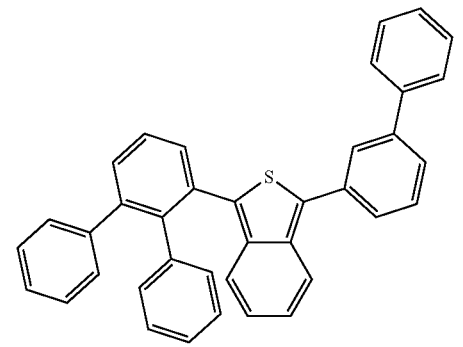

646
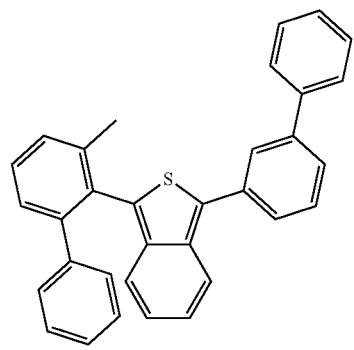
647
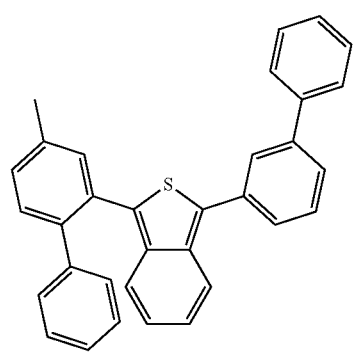
648
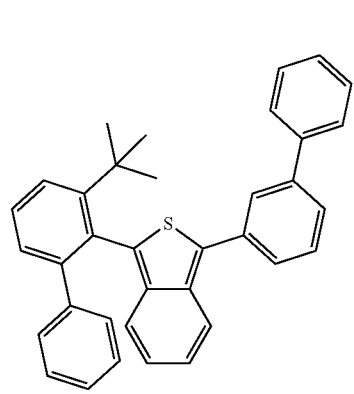
649
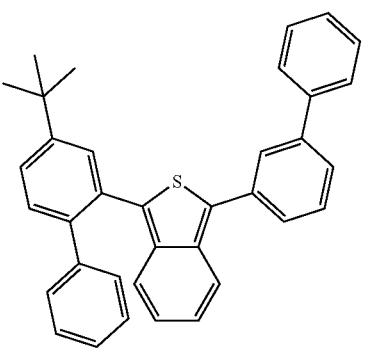
650
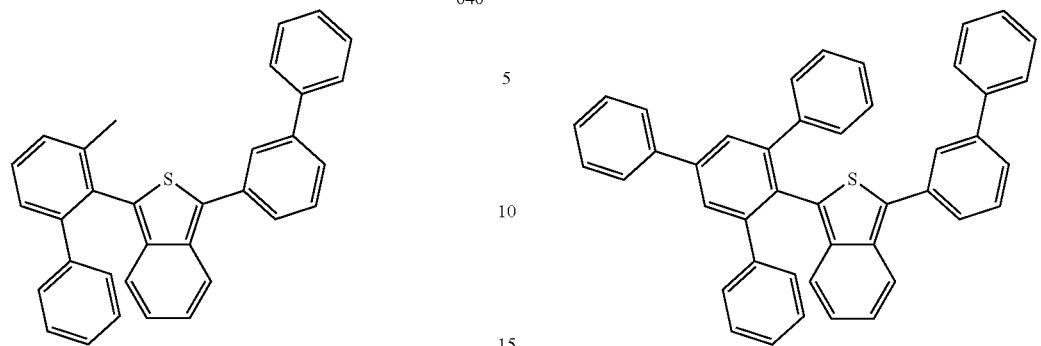
651
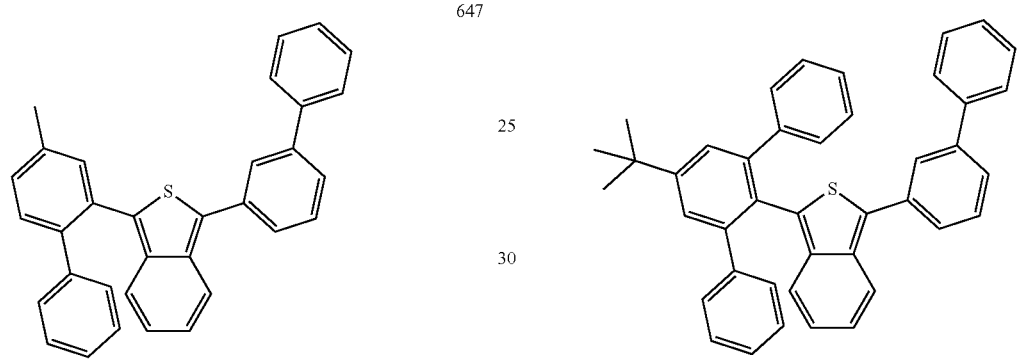
652
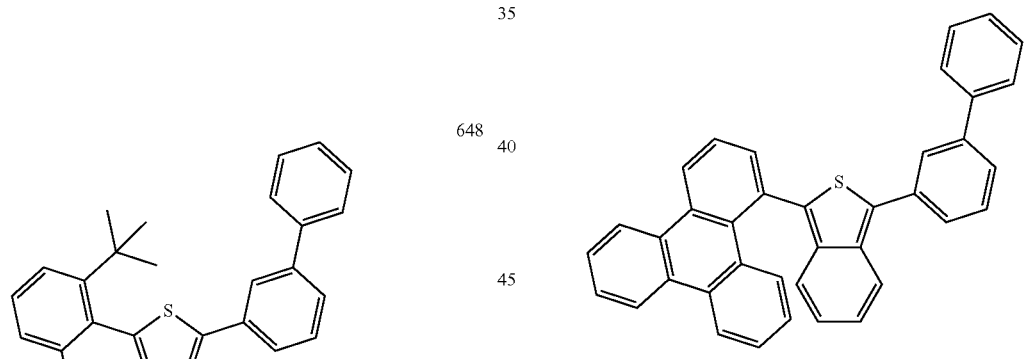
653
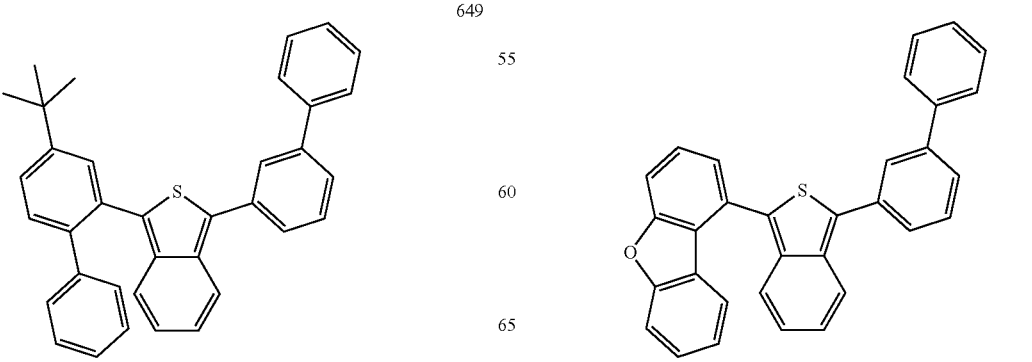

654
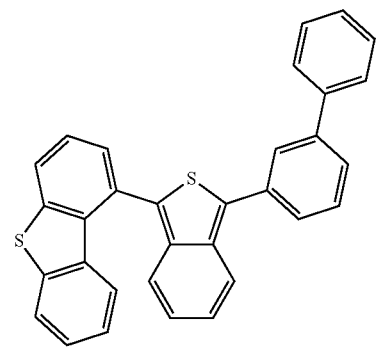
655
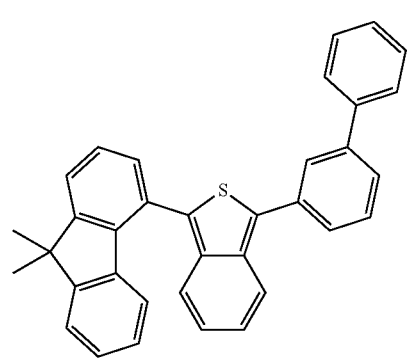
656
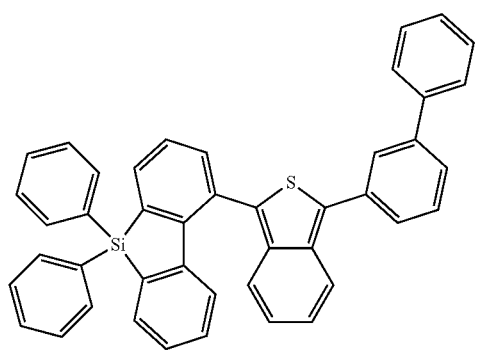
657
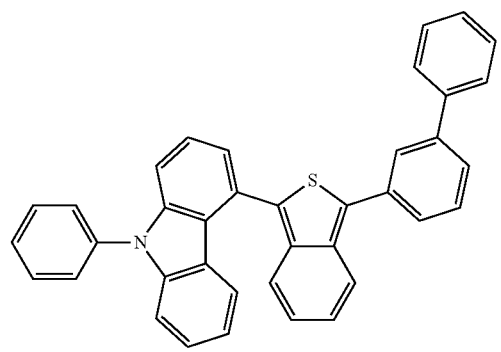
658
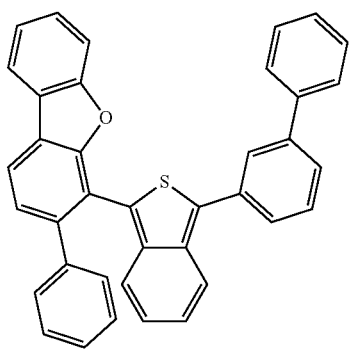
659
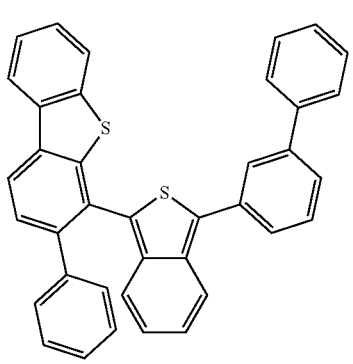
660
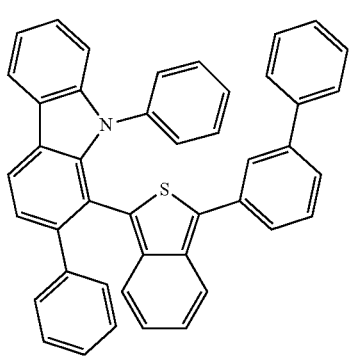
661
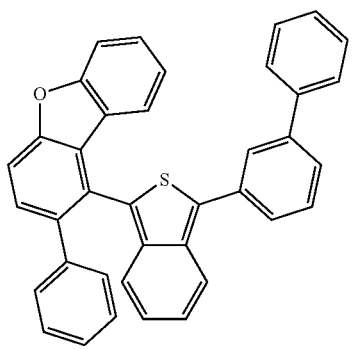

169
-continued
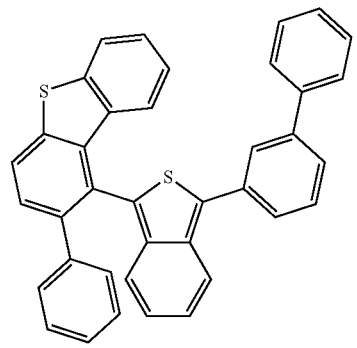
662
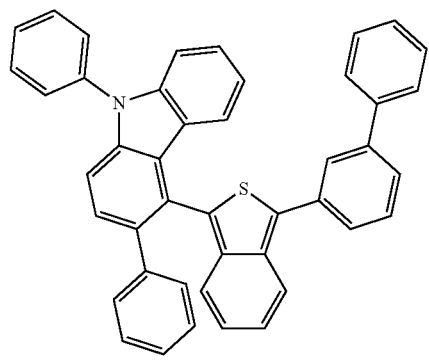
663
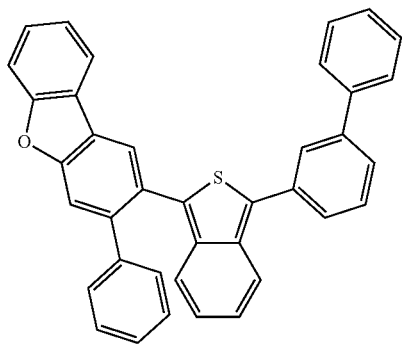
664
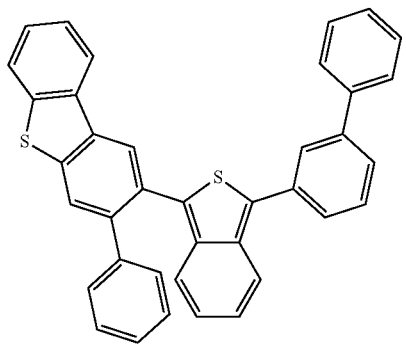
665
170
-continued
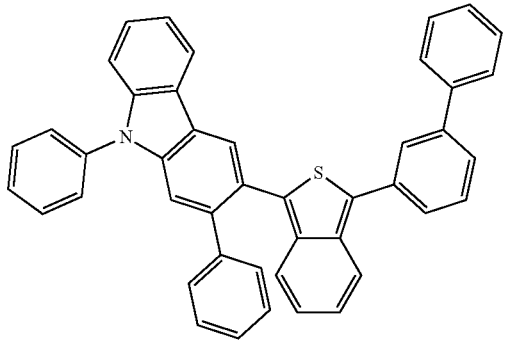
666
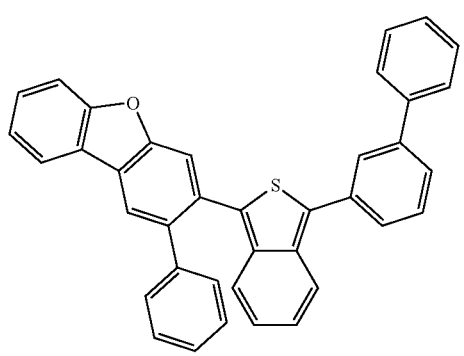
667
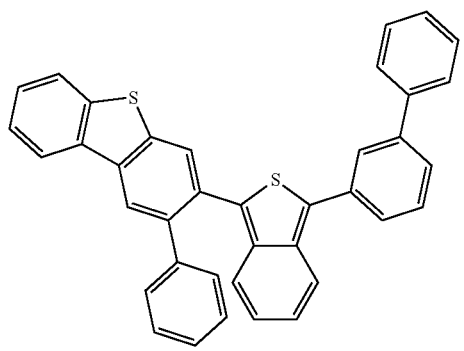
668
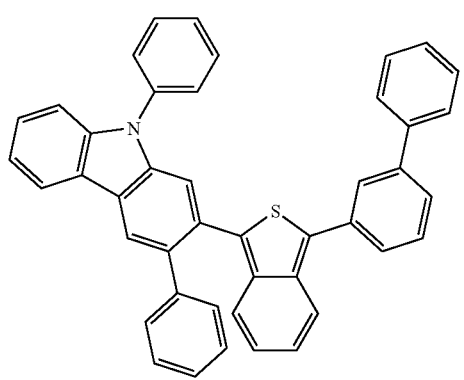
669

171
-continued
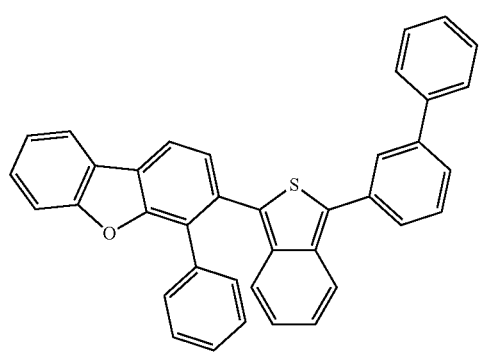
670
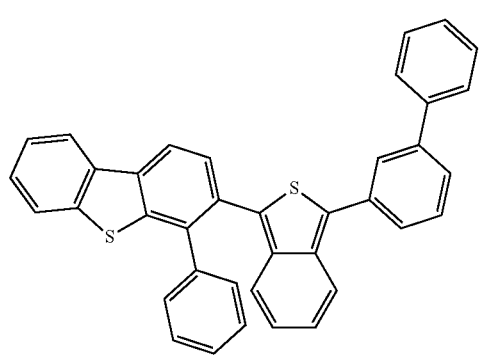
671
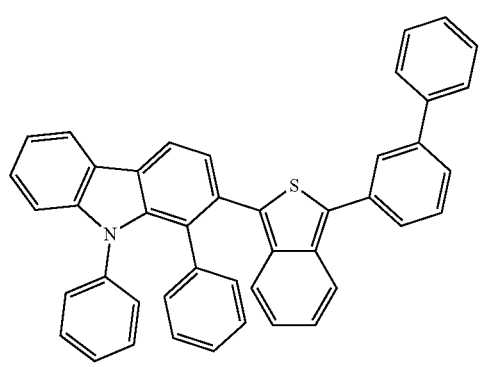
672
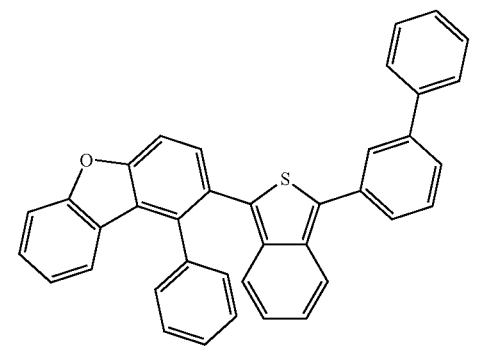
673
172
-continued
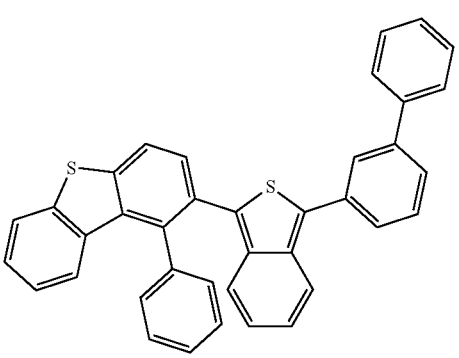
674
675
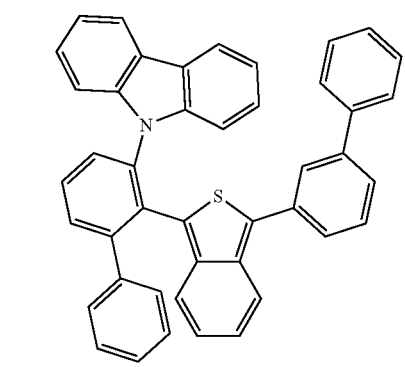
676
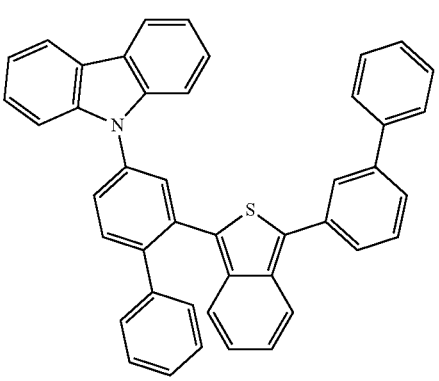
677

173
-continued
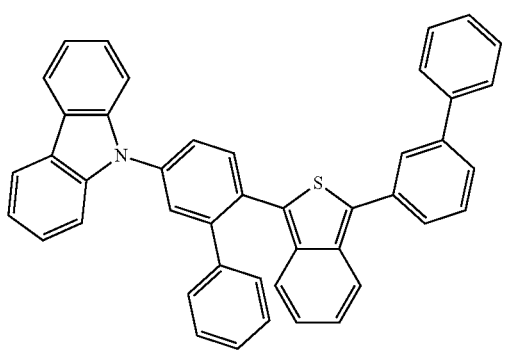
678
679
680
681
174
-continued
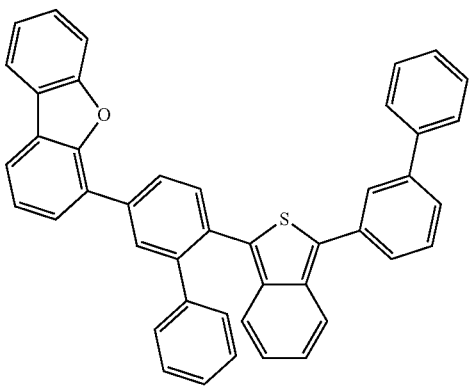
682
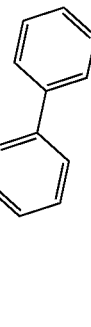
683
684
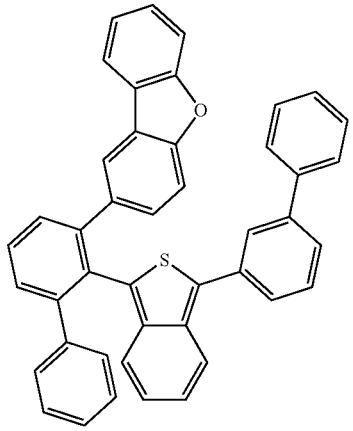
685
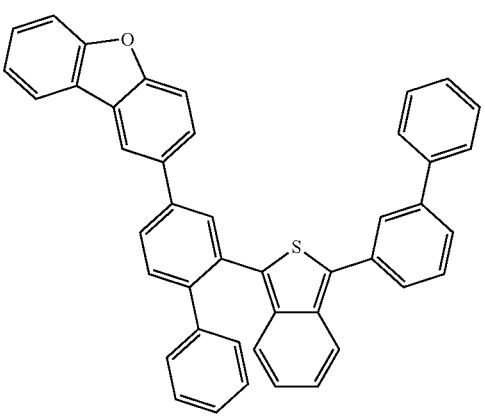

686
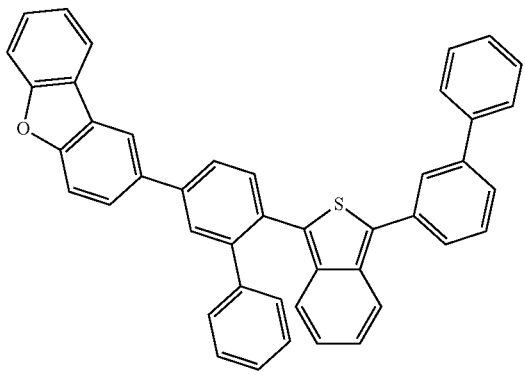
687
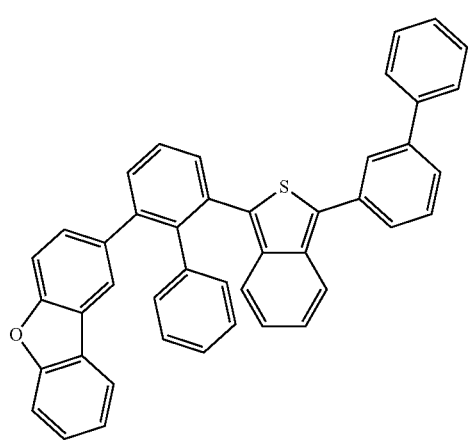
688
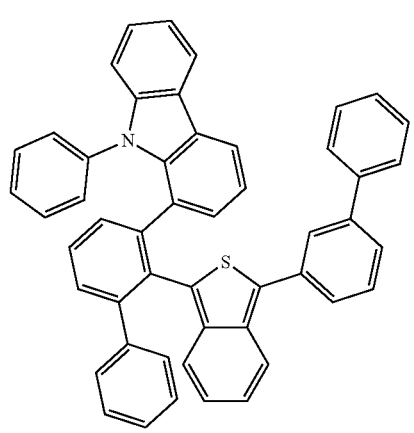
689
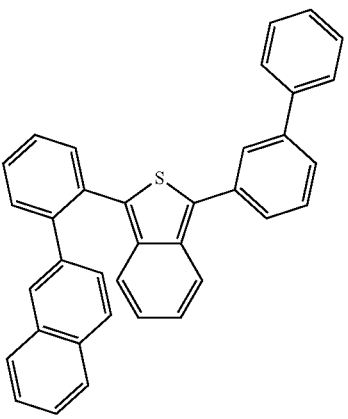
690
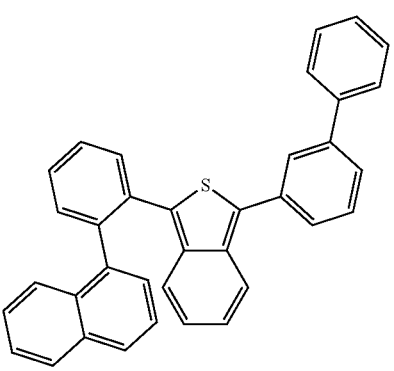
691
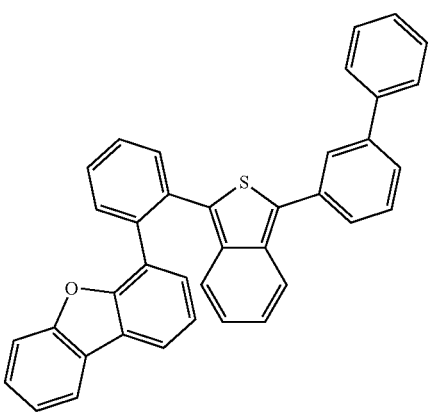
692
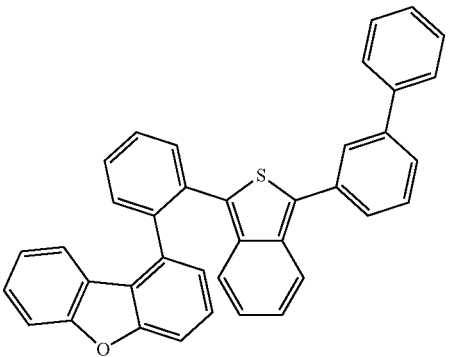

693
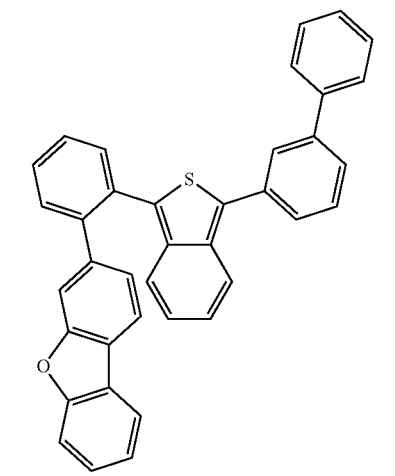
694
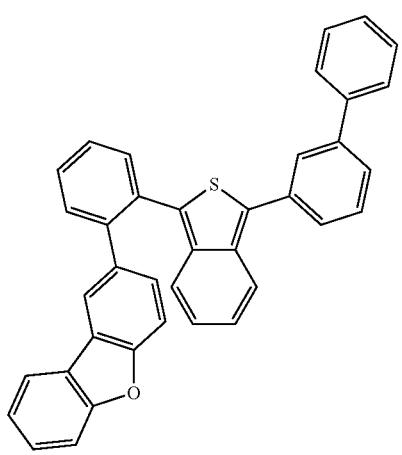
695
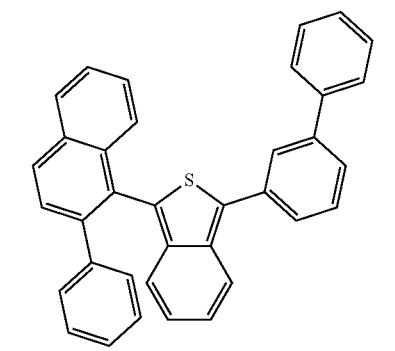
696
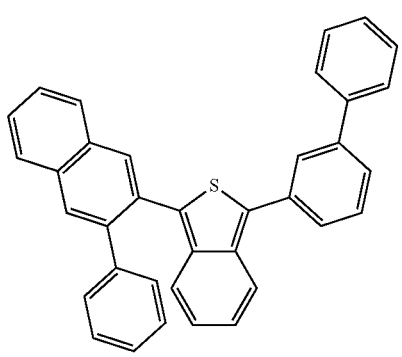
697
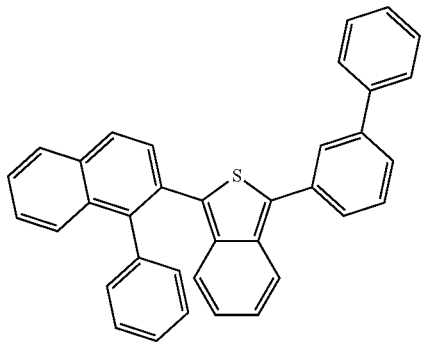
698
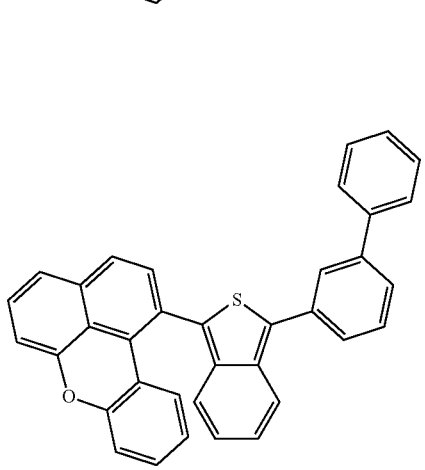
699
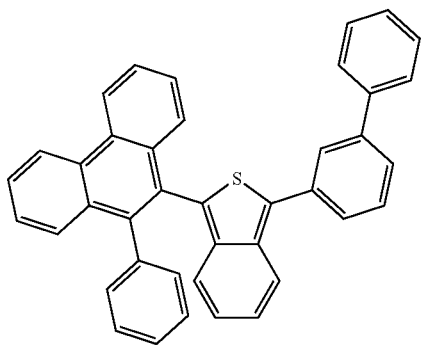
700
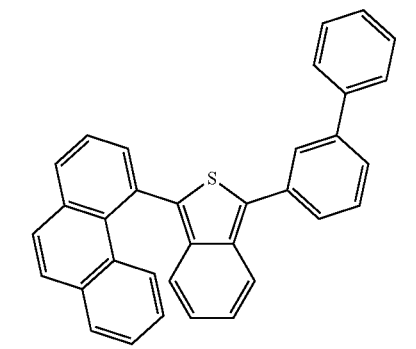

-continued
701
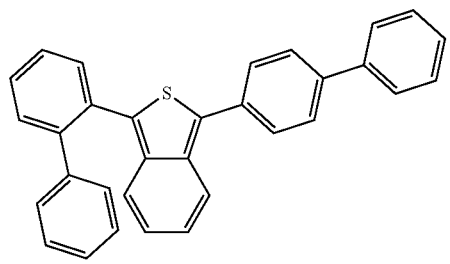
702
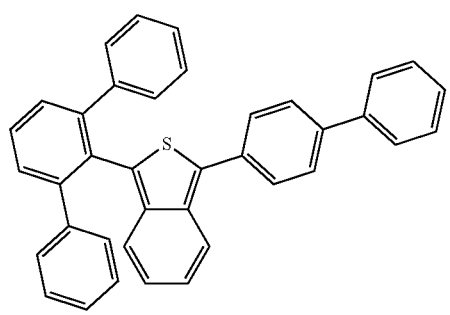
703
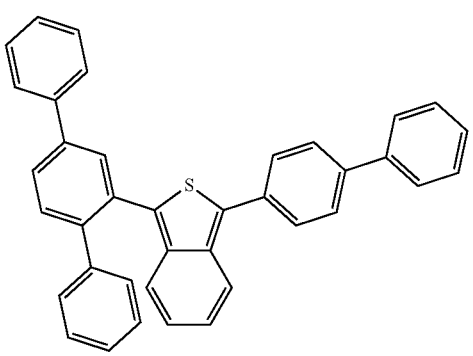
704
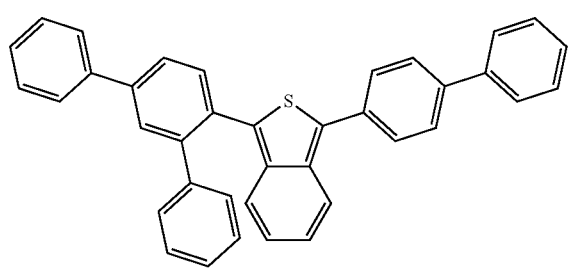
705
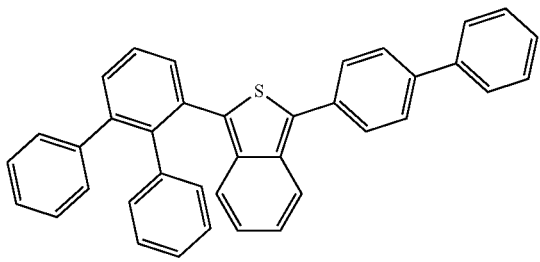
-continued
706
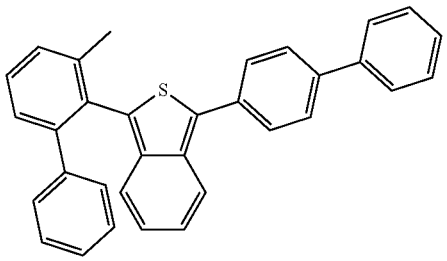
707
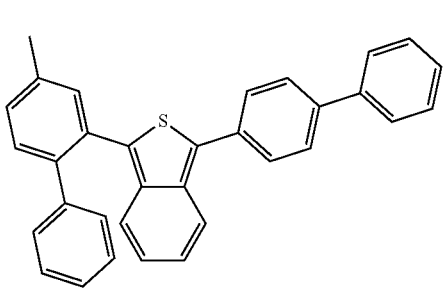
708
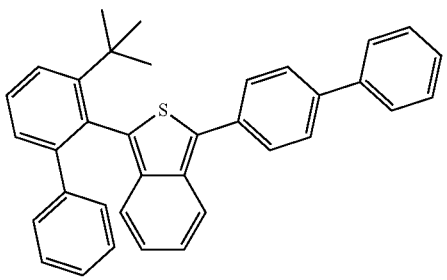
709
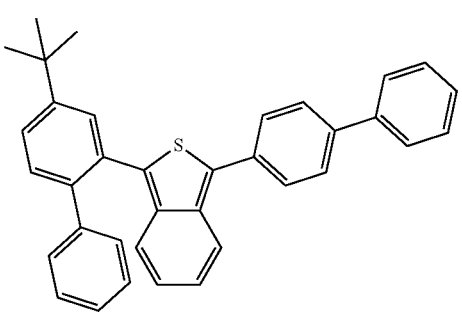
710
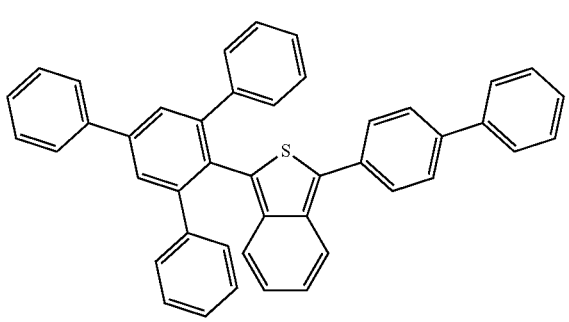

711
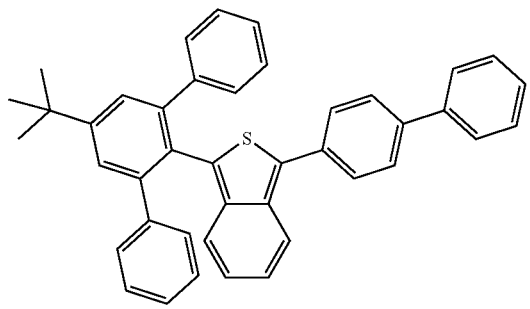
712
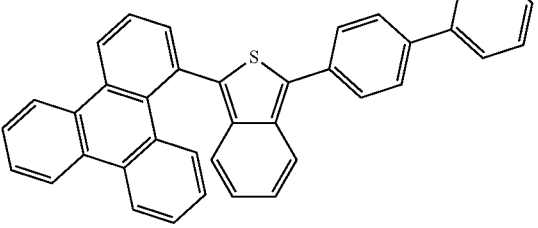
713
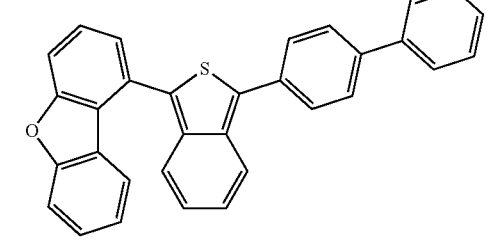
714
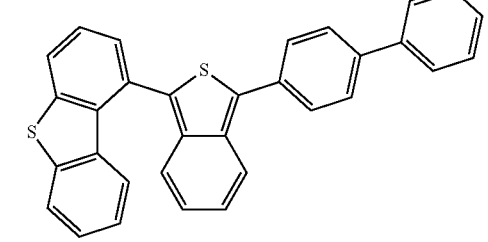
715
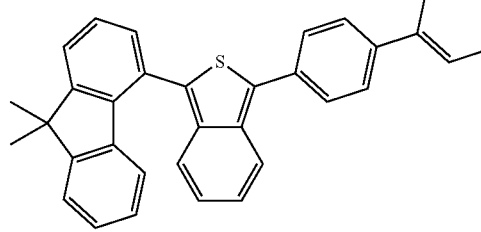
716
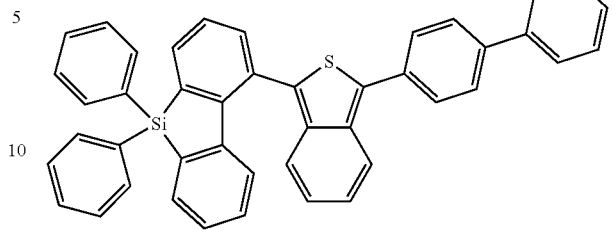
717
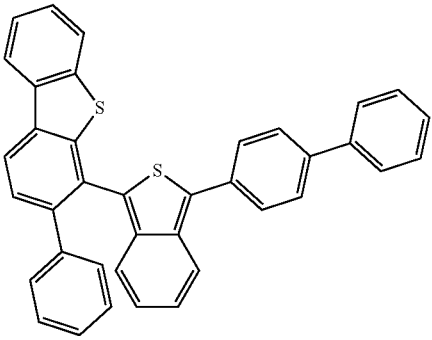
718
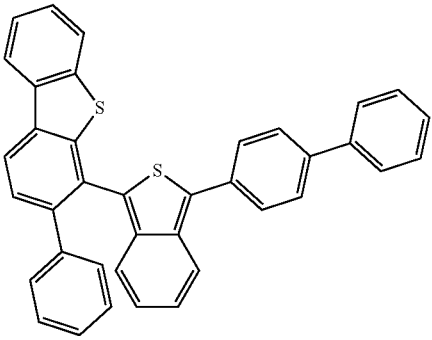
719
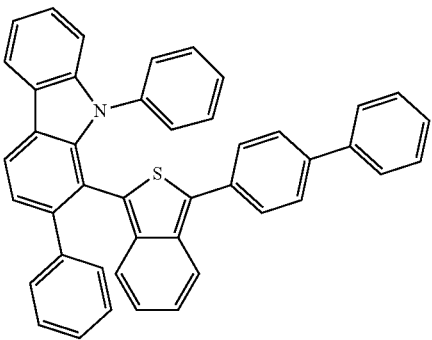
720
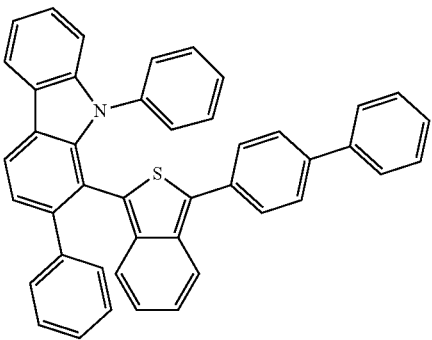

721
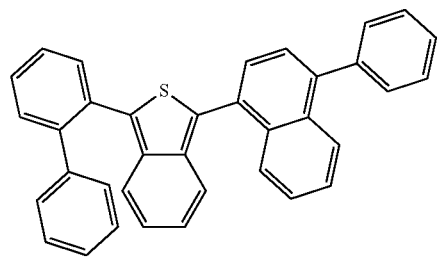
722
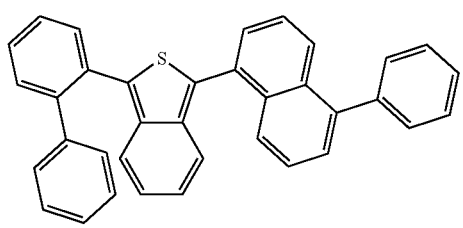
723
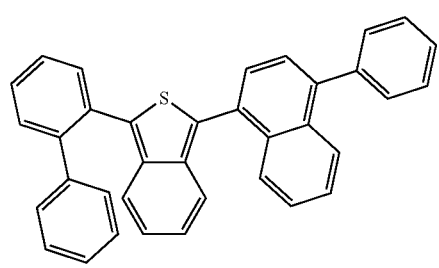
724
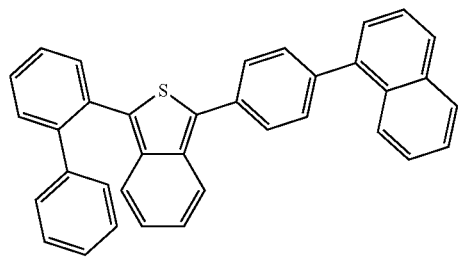
725
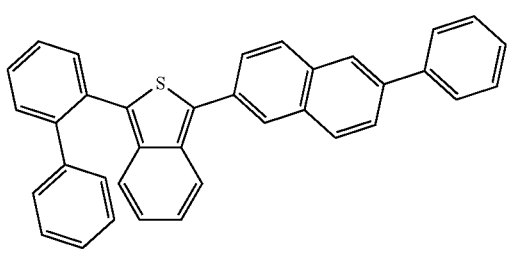
726
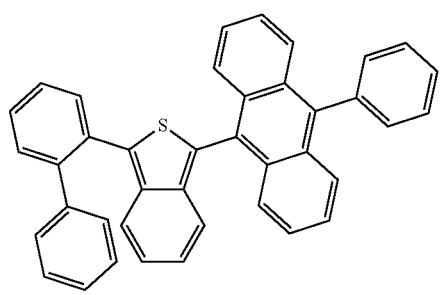
727
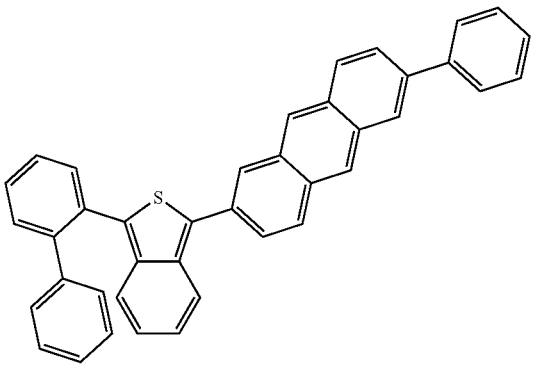
728
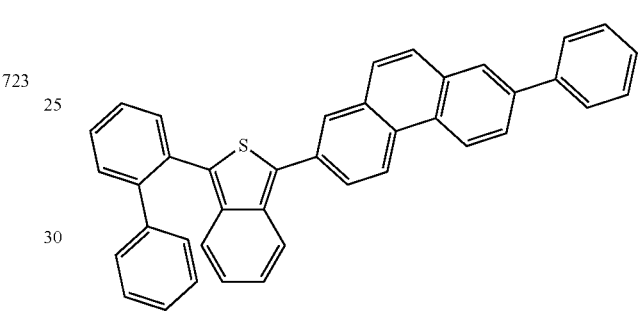
729
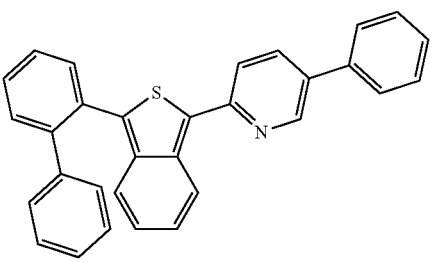
730
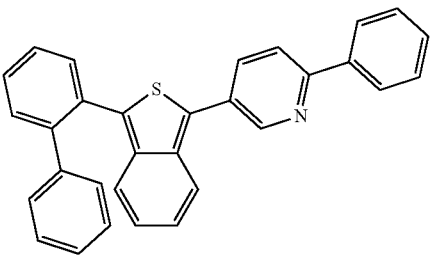
731
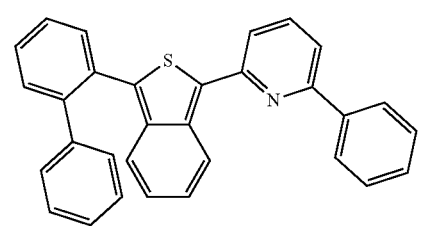

732
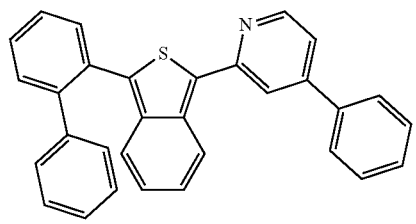
733
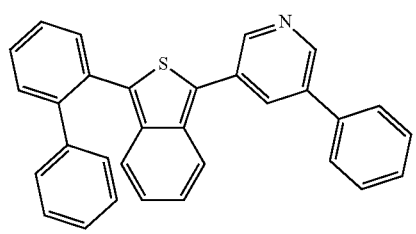
734
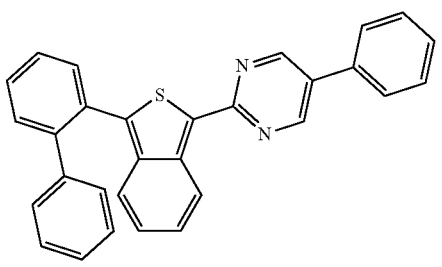
735
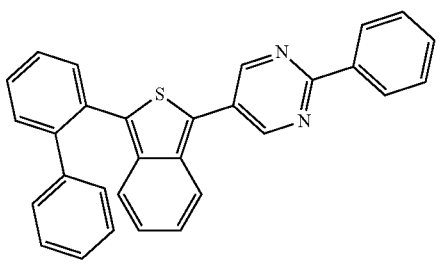
736
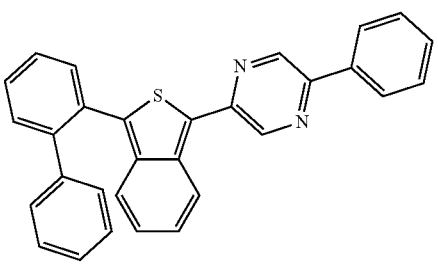
737
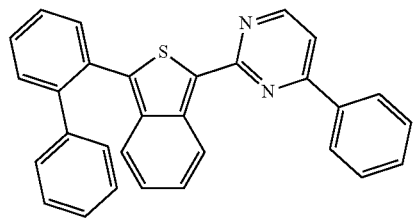
738
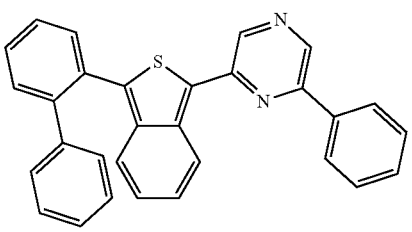
739
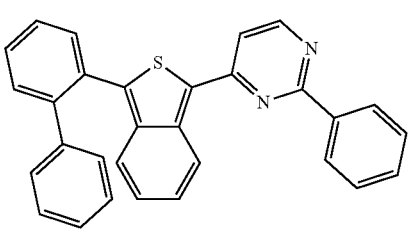
740
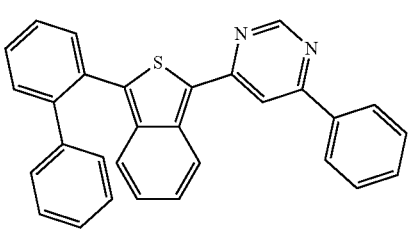
741
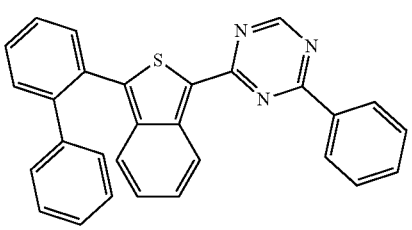
742
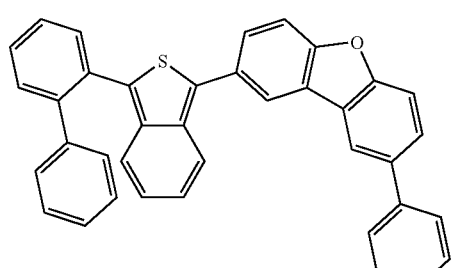
743
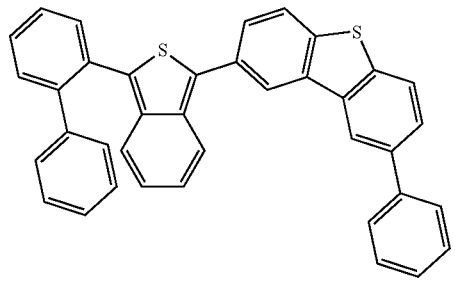

744
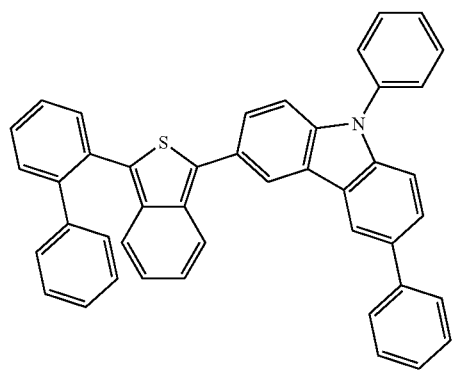
745
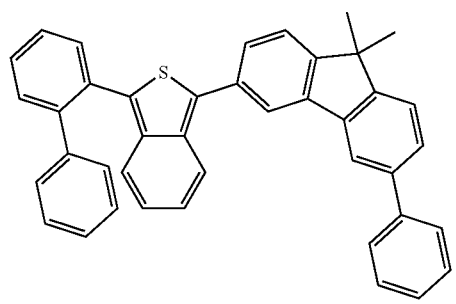
746
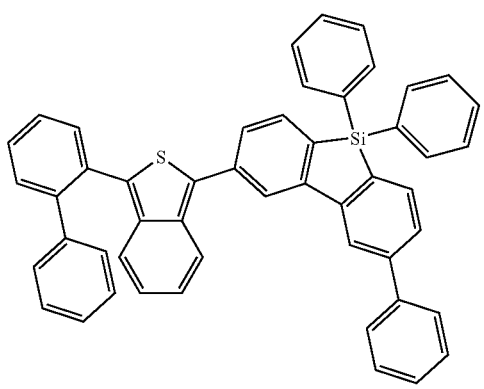
747
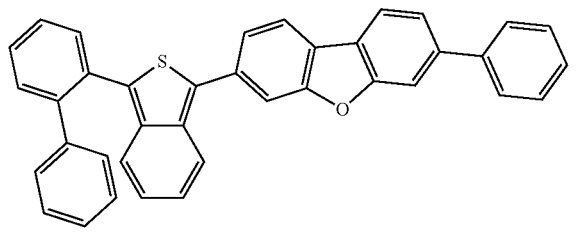
748
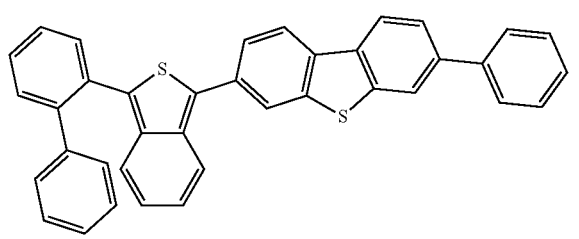
749
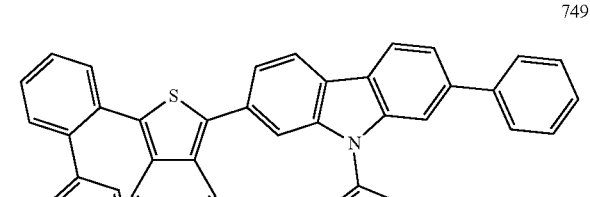
750
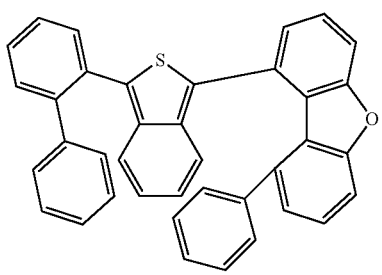
751
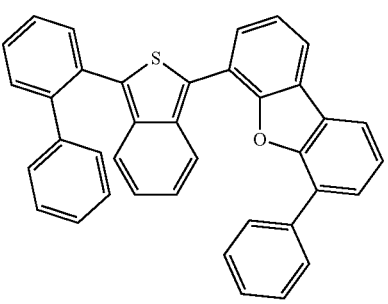
752
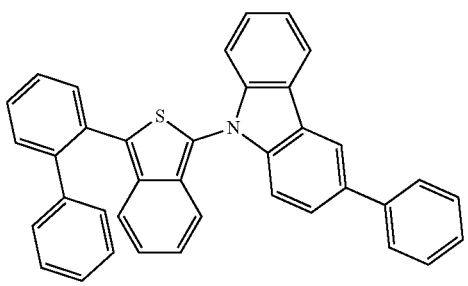
753
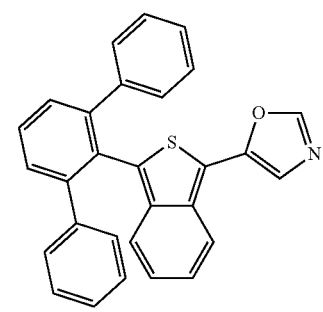

754 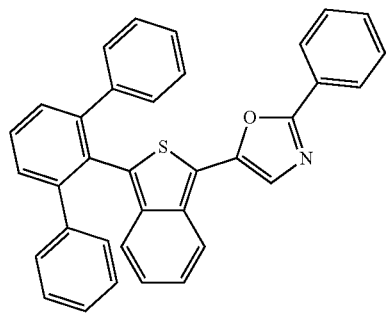
755 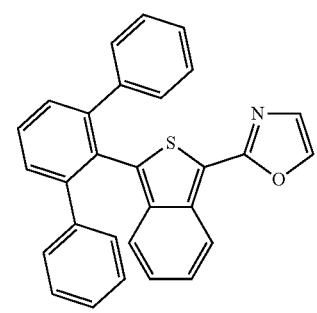
756 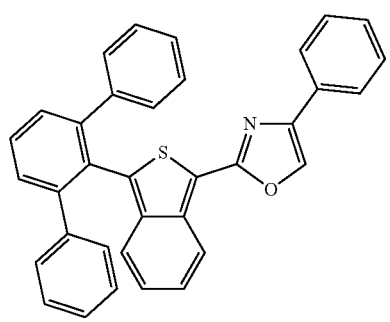
757 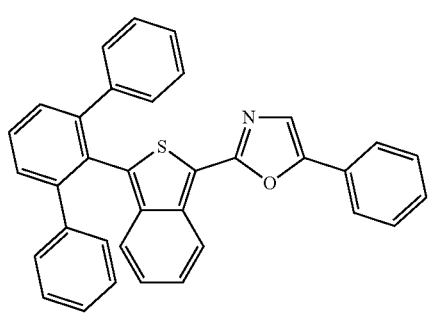
758 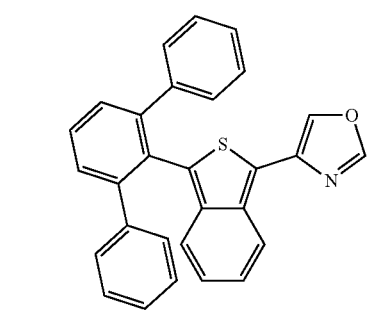
759 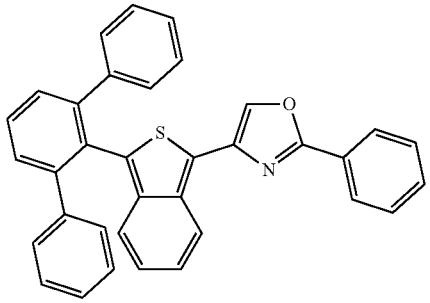
760 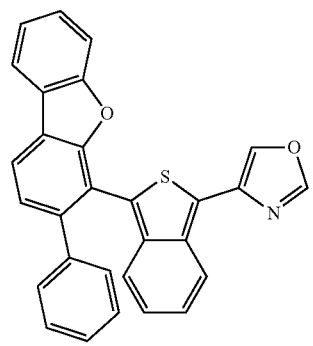
761 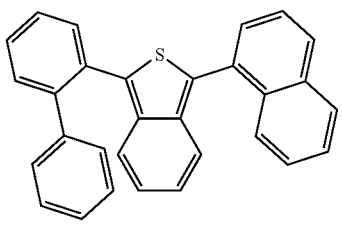
762 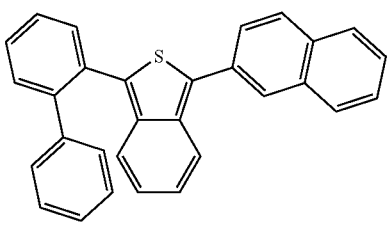
763 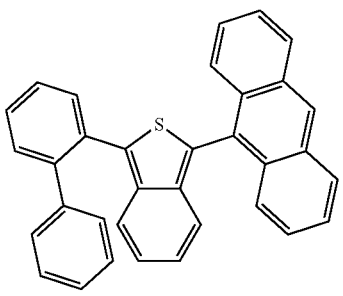

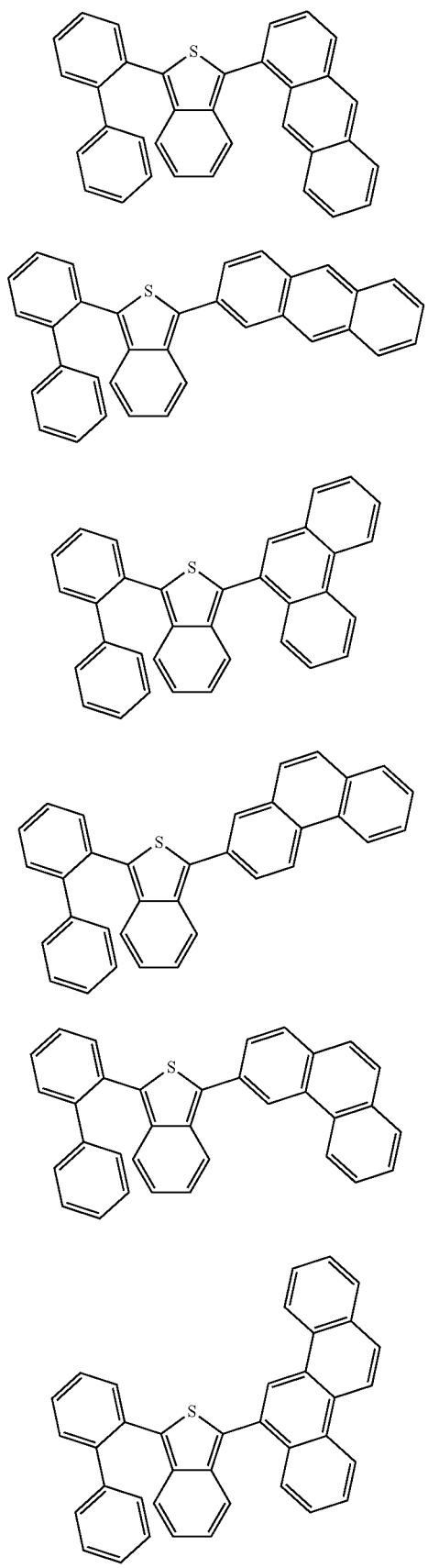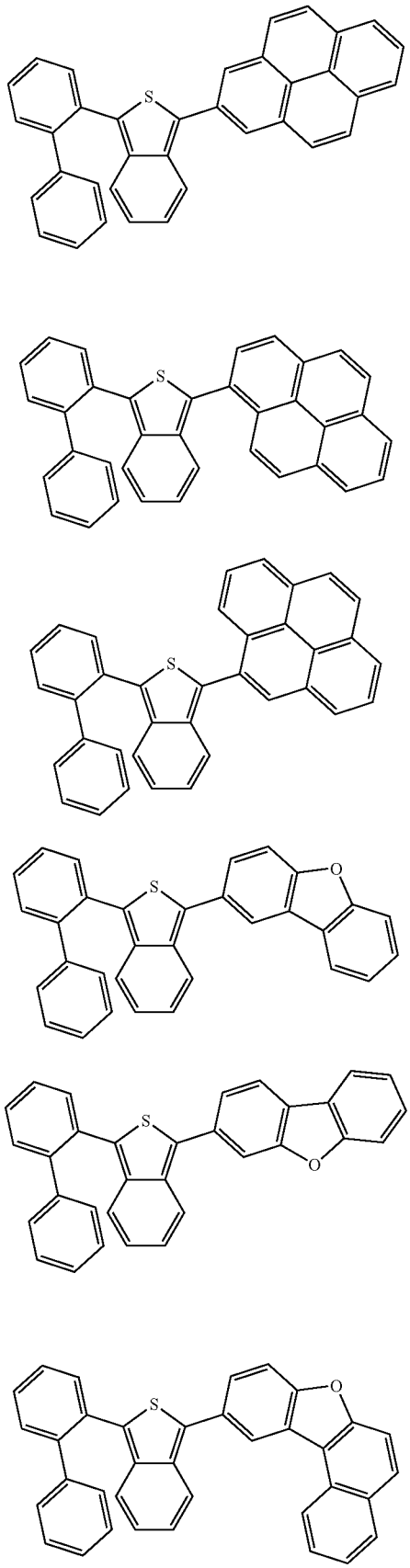

776 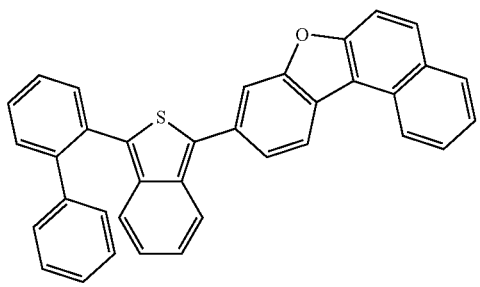
777 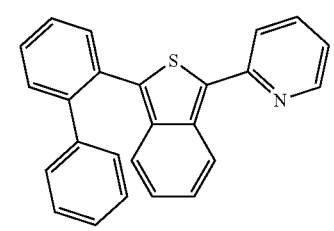
778 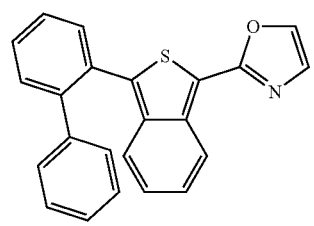
779 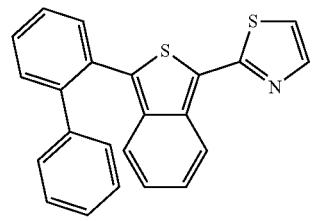
780 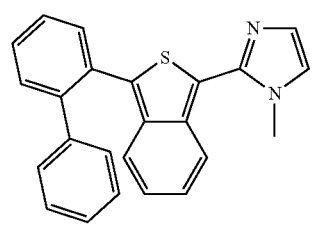
781 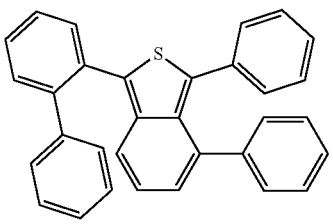
782 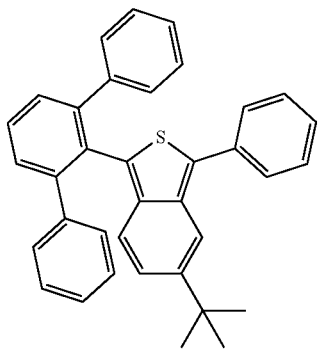
783 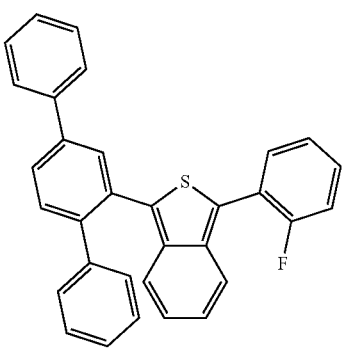
784 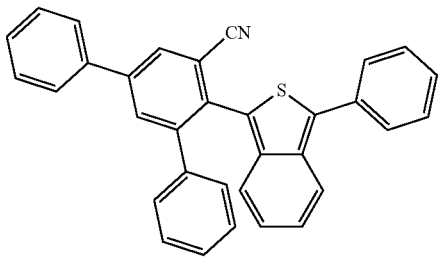
785 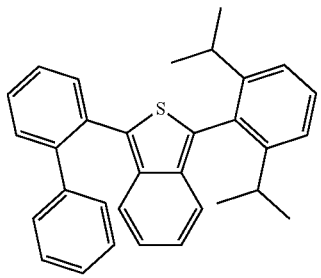
786 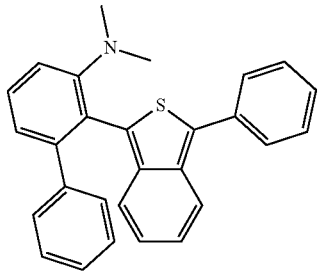

| | |
|---|---|
| 787 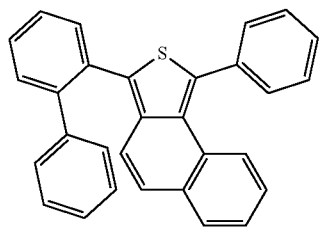 | 792 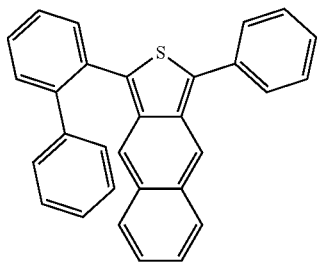 |
| 788 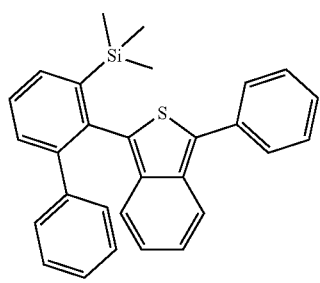 | 793 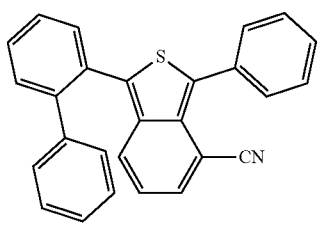 |
| 789 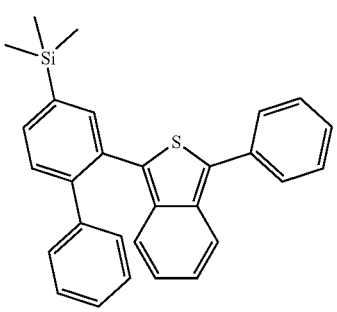 | 794 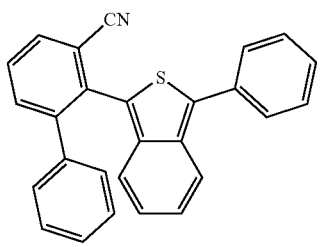 |
| 790 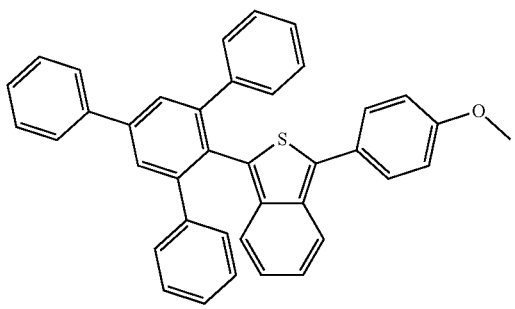 | 795 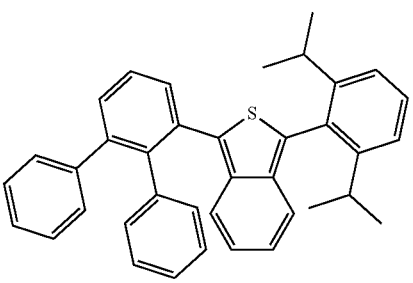 |
| 791 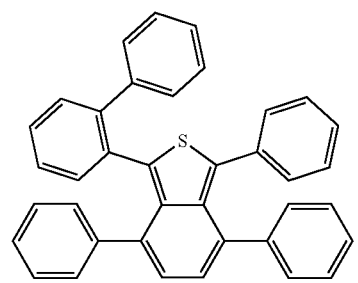 | 796 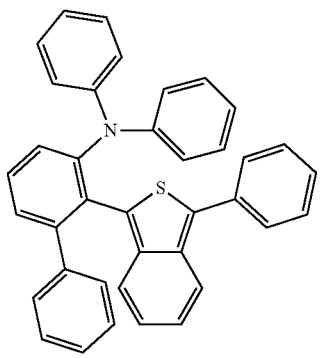 |

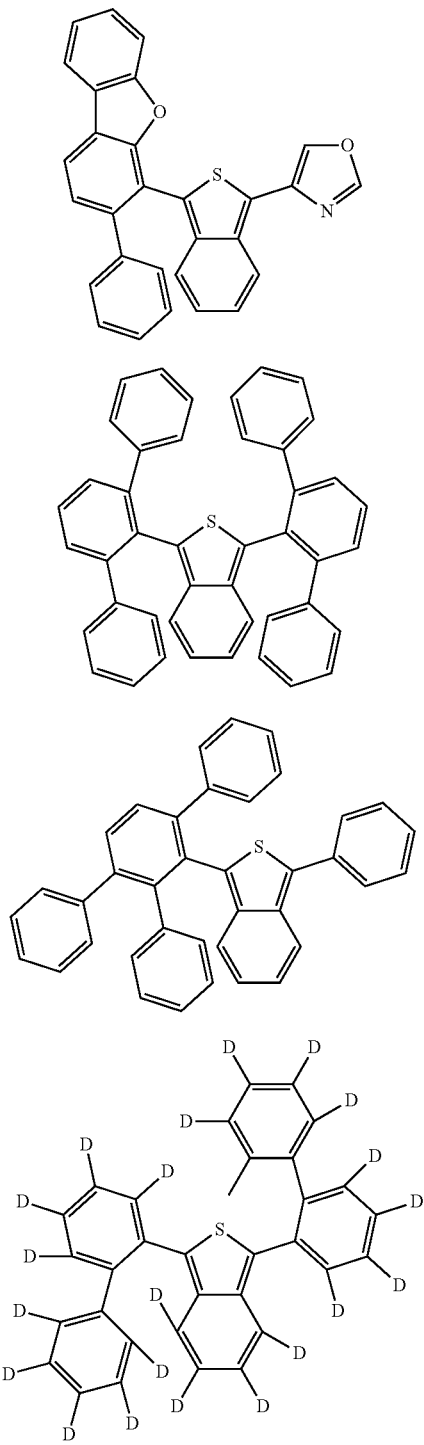

Since, in Formula 1, $Ar_{12}$ is linked to the $A_1$ ring at an ortho position with respect to the isobenzofuran or isobenzothiophene, the effect of elongation of π-conjugation length may be reduced as compared to when linked at a para or meta position, the condensed cyclic compound represented by Formula 1 may have a relative high lowest excitation singlet ($S_1$) energy level as compared to compounds in which $Ar_{12}$ and the isobenzofuran or isobenzothiophene core are linked in a para or meta position.

In one or more embodiments, the condensed cyclic compound may satisfy Inequality 1 and Inequality 2, so that two triplet excitons may collide by the mechanism of triplet-triplet fusion (TTF) to generate singlet excitons. For example, when the condensed cyclic compound is used as a host material of an emission layer, singlet excitons may be effectively generated by the mechanism of TTF and transferred to a dopant material of the emission layer, thus improving fluorescence emission efficiency.

Since, in general, the exciton generation of electrons and holes follows the mechanism in which excitons are generated in a host and transferred to a dopant, most triplet excitons are generated in a host, and due to a higher concentration of hosts in the emission layer than that of dopants, the probability of collision of the triplet excitons also increases. Accordingly, when the condensed cyclic compound according to one or more embodiments is used as a host material of the emission layer, TTF phenomenon may occur more effectively as compared to when used as dopants, leading to further improved emission efficiency.

Furthermore, since the condensed cyclic compound according to one or more embodiments has a difference smaller than 0.5 eV between twice of the lowest excitation triplet energy level E(T1) and the lowest excitation singlet energy level E(S1), singlet conversion by the TTF mechanism may occur more efficiently. Moreover, since the condensed cyclic compound according to one or more embodiments has a high delayed fluorescence ratio (TTF ratio), an electronic device, for example, an organic light-emitting device, including the condensed cyclic compound, may have high internal quantum efficiency.

As described above, the condensed cyclic compound represented by Formula 1 may have electric characteristics suitable for use as a material of an organic light-emitting device, for example, a host material in an emission layer, and specifically, for use in a blue light-emitting device. Thus, an organic light-emitting device including the condensed cyclic compound may have high efficiency and/or long lifespan.

For example, the results of evaluation of the HOMO, LUMO, $S_1$, $T_1$ and $T_2$ energy level of some of the above-listed compounds using a DFT method of Gaussian program structurally optimized at a level of B3LYP, 6-31G(d,p) are shown in Table 1.

TABLE 1

| Compound No. | HOMO (eV) | LUMO (eV) | $S_1$ energy level (eV) | $T_1$ energy level (eV) | $T_2$ energy level (eV) |
|---|---|---|---|---|---|
| 1 | −4.78 | −1.58 | 2.95 | 1.59 | 3.05 |
| 2 | −4.77 | −1.46 | 3.00 | 1.64 | 3.07 |
| 5 | −4.77 | −1.53 | 2.96 | 1.62 | 3.06 |
| 6 | −4.82 | −1.48 | 3.05 | 1.65 | 3.15 |
| 8 | −4.83 | −1.44 | 3.10 | 1.66 | 3.16 |
| 36 | −4.82 | −1.55 | 2.95 | 1.64 | 2.98 |
| 48 | −4.74 | −1.47 | 2.96 | 1.63 | 3.04 |
| 122 | −4.78 | −1.24 | 3.18 | 1.76 | 3.07 |
| 355 | −4.93 | −1.63 | 3.05 | 1.62 | 3.13 |
| 358 | −4.78 | −1.43 | 3.06 | 1.62 | 3.05 |
| 382 | −4.71 | −1.38 | 3.01 | 1.69 | 3.06 |
| 385 | −4.88 | −1.35 | 3.17 | 1.77 | 3.10 |
| 387 | −4.95 | −1.36 | 3.22 | 2.05 | 2.94 |
| 398 | −4.74 | −1.27 | 3.07 | 1.77 | 3.08 |
| 401 | −4.98 | −1.58 | 3.10 | 1.66 | 3.20 |
| 521 | −4.97 | −1.47 | 3.15 | 1.71 | 3.20 |
| 522 | −4.95 | −1.44 | 3.14 | 1.71 | 3.19 |
| A | −4.75 | −1.47 | 2.97 | 1.66 | 3.05 |
| X1 | −4.82 | −1.69 | 2.93 | 1.52 | 3.12 |
| X2 | −4.78 | −1.77 | 2.81 | 1.48 | 2.89 |
| X3 | −4.83 | −1.70 | 2.91 | 1.53 | 3.04 |

TABLE 1-continued

| Compound No. | HOMO (eV) | LUMO (eV) | S₁ energy level (eV) | T₁ energy level (eV) | T₂ energy level (eV) |
|---|---|---|---|---|---|

<Compound A>

X1

X2

X3

Referring to Table 1, it is confirmed that the condensed cyclic compounds represented by Formula 1 have a relatively high singlet ($S_1$) energy level as compared to Comparative Compounds X1 to X3, and the HOMO, LUMO, $S_1$, $T_1$ and $T_2$ energy level thereof can be freely adjusted by control of the substituent thereof.

From Table 1, it is also confirmed that the condensed cyclic compounds represented by Formula 1 satisfy Inequalities 1 and 2. Accordingly, when the condensed cyclic compound represented by Formula 1 is used as a host material of an emission layer, singlet excitons generated according to the TTF mechanism may be effectively transferred to a dopant material.

Methods of synthesizing the condensed cyclic compound represented by Formula 1 will be understood by a person of ordinary skill in the art with reference to the synthesis examples described below.

The condensed cyclic compound represented by Formula 1 may be used as a material of an electronic device, for example, an organic light-emitting device. therefore, another aspect of the present disclosure provides an organic light-emitting device including: a first electrode; a second electrode; and an organic layer disposed between the first electrode and the second electrode and including an emission layer, wherein the organic layer include at least one of the condensed cyclic compounds represented by Formula 1.

The organic light-emitting device may include an organic layer including at least one of the condensed cyclic compounds represented by Formula 1 as described above, thereby having low driving voltage, high efficiency, high luminance, high-quantum emission efficiency, and/or long lifespan.

The condensed cyclic compound represented by Formula 1 may be used between a pair of electrodes of an organic light-emitting device. For example, the condensed cyclic compound may be included in at least one of the emission layer, a hole transport region between the first electrode and the emission layer (for example, including at least one of a hole injection layer, a hole transport layer and an electron blocking layer), and an electron transport region between the emission layer and the second electrode (for example, including at least one of a hole blocking layer, an electron transport layer, and an electron injection layer).

In one or more embodiments, the first electrode may be an anode, the second electrode may be a cathode, the organic layer may include a hole transport region disposed between the first electrode and the emission layer, and an electron transport region between the emission layer and the second electrode, the hole transport region may include a hole injection layer, a hole transport layer, an electron blocking layer, a buffer layer, or any combination thereof, and the electron transport region may include a hole blocking layer, an electron transport layer, an electron injection layer, or any combination thereof. However, embodiments are not limited thereto.

In one or more embodiments, the emission layer of the organic light-emitting device may include the condensed cyclic compound represented by Formula 1.

In one or more embodiments, the emission layer of the organic light-emitting device may include a host and a dopant, and the host may include the condensed cyclic compound represented by Formula 1. The dopant may include a fluorescent dopant. The amount of the host in the emission layer may be larger than the amount of the dopant in the emission layer. The host may further include, in addition to the condensed cyclic compound represented by Formula 1, any host.

The emission layer of the organic light-emitting device may emit red, green, or blue light. For example, the emission layer may emit blue light.

In one or more embodiments, the emission layer may be a blue emission layer including a fluorescent dopant. However, embodiments are not limited thereto.

Another aspect of the present disclosure provides an organic light-emitting device including: a first electrode; a second electrode; and an organic layer disposed between the first electrode and the second electrode and including an emission layer, wherein the emission layer includes a host and a dopant, the host includes a condensed cyclic compound represented by Formula 1 below, and the amount of the host in the emission layer is higher than that of the dopant in the emission layer.

<Formula 1>

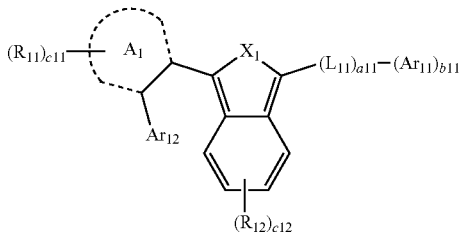

In Formula 1, $X_1$, $A_1$, $L_{11}$, a11, $Ar_{11}$, $Ar_{12}$, b11, $R_{11}$, $R_{12}$, c11, and c12 will be understood with reference to those described above.

For example, the condensed cyclic compound may serve as a host of the emission layer.

As described in the above embodiments, the condensed cyclic compound may be one of Compounds 1 to 120, 122 to 800, and Compound A. However, embodiments are not limited thereto.

As used herein, the expression "(an organic layer) includes at least one of the condensed cyclic compounds" as used herein may be construed as that the organic layer includes one condensed cyclic compound belonging to the category of Formula 1, or that the organic layer includes two or more different condensed cyclic compounds belonging to the category of Formula 1.

For example, the organic layer may include, as the condensed cyclic compound, only Compound 1. In this regard, Compound 1 may be only in the emission layer of the organic light-emitting device. In one or more embodiments, the organic layer may include, as the condensed cyclic compound, Compound 1 and Compound 2. In this regard, Compound 1 and Compound 2 may be in the same layer (for example, both Compound 1 and Compound 2 may be in the emission layer), or in different layers (for example, Compound 1 may be in the emission layer, and Compound 2 may be in a hole blocking layer).

The first electrode may be an anode, which is a hole injection electrode, and the second electrode may be a cathode, which is an electron injection electrode. In other embodiments, the first electrode may be a cathode, which is an electron injection electrode, and the second electrode may be an anode, which is a hole injection electrode.

The term "organic layer" as used herein refers to a single layer and/or a plurality of layers disposed between the first electrode and the second electrode of an organic light-emitting device. The "organic layer" may include, in addition to an organic compound, an organometallic complex including metal.

FIGURE is a schematic cross-sectional view of an organic light-emitting device 10 according to an embodiment. Hereinafter, the structure of an organic light-emitting device according to an embodiment and a method of manufacturing an organic light-emitting device according to an embodiment will be described with reference to FIGURE. The organic light-emitting device 10 may have a structure in which a first electrode 11, an organic layer 15, and a second electrode 19 which are sequentially stacked.

A substrate may be additionally disposed under the first electrode 11 or above the second electrode 19. For use as the substrate, any substrate that is used in general organic light-emitting devices may be used. The substrate may be a glass substrate or a transparent plastic substrate, each having excellent mechanical strength, thermal stability, transparency, surface smoothness, ease of handling, and water resistance.

The first electrode 11 may be formed by depositing or sputtering a material for forming the first electrode 11 on the substrate. The first electrode 11 may be an anode. The material for forming the first electrode 11 may be materials having a high work function to facilitate hole injection. The first electrode 11 may be a reflective electrode, a semi-reflective electrode, or a transmissive electrode. The material for forming the first electrode may be, for example, indium tin oxide (ITO), indium zinc oxide (IZO), tin oxide ($SnO_2$), and zinc oxide (ZnO). In one or more embodiments, the material for forming the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers. For example, the first electrode 11 may have a three-layered structure of ITO/Ag/ITO. However, embodiments are not limited thereto.

The organic layer 15 may be disposed on the first electrode 11.

The organic layer 15 may include a hole transport region, an emission layer, and an electron transport region.

The hole transport region may be disposed between the first electrode 11 and the emission layer.

The hole transport region may include at least one of a hole injection layer, a hole transport layer, an electron blocking layer, and a buffer layer.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

When the hole transport region includes a hole injection layer, the hole injection layer may be formed on the first electrode 11 by using one or more suitable methods, for example, vacuum deposition, spin coating, casting, and/or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100° C. to about 500° C., a vacuum pressure of about $10^{-8}$ to about $10^{-3}$ torr, and a deposition rate of about 0.01 Å/sec to about 100 Å/sec. However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 rpm to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to the conditions for forming the hole injection layer.

The hole transport region may include at least one of m-MTDATA, TDATA, 2-TNATA, NPB, β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonicacid (PANI/CSA), polyaniline/poly(4-styrenesulfonate) (PANI/PSS), a compound represented by Formula 201 below, a compound represented by Formula 202 below, or any combination thereof.

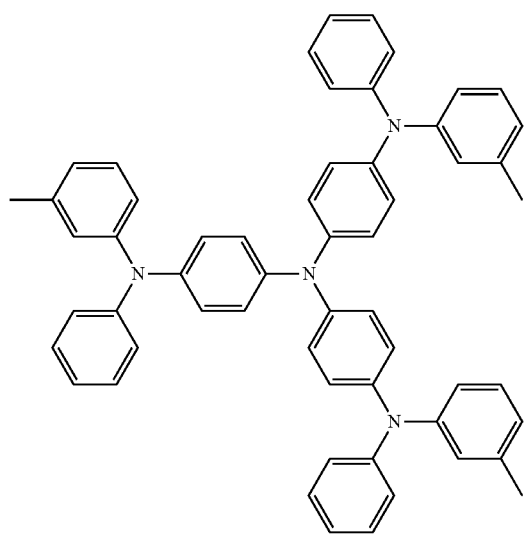

m-MTDATA

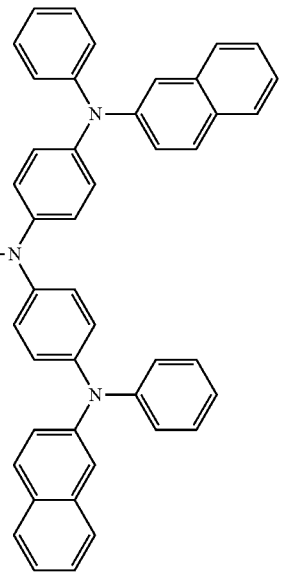

2-TNATA

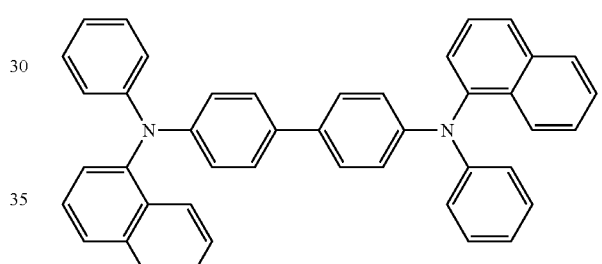

NPB

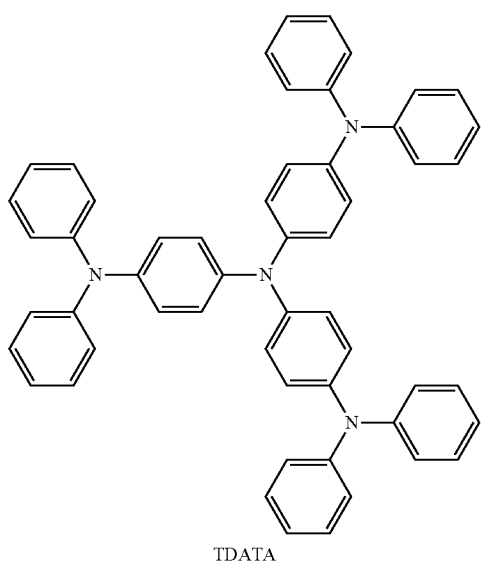

TDATA

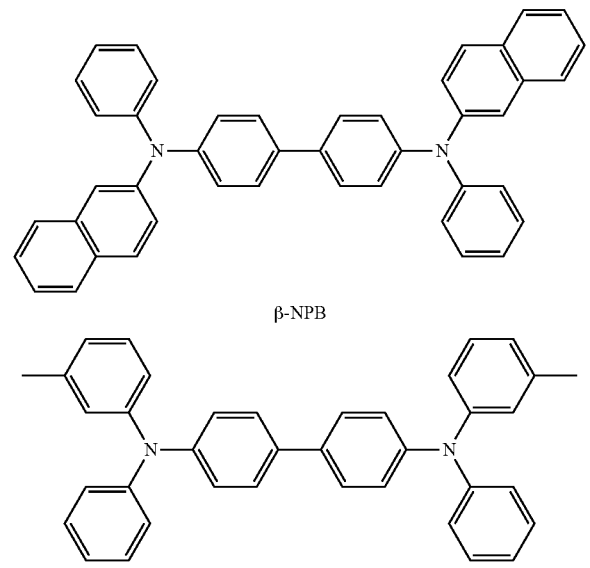

β-NPB

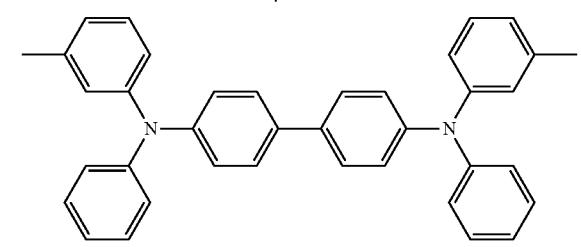

TPD

-continued

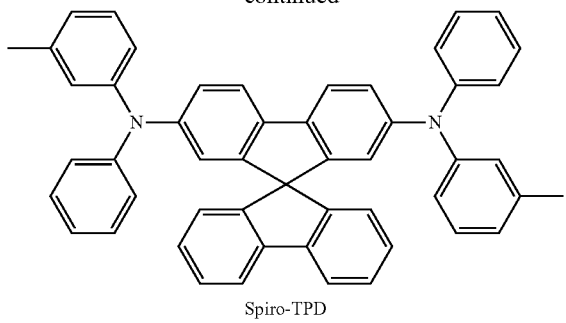
Spiro-TPD

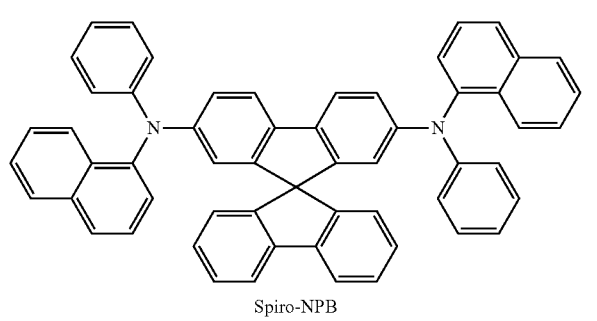
Spiro-NPB

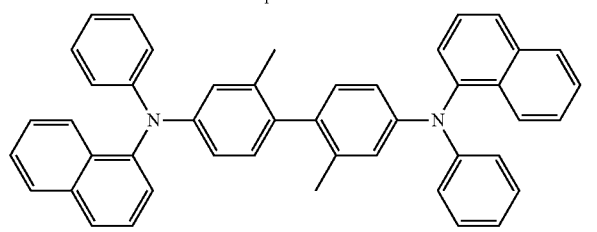
methylated NPB

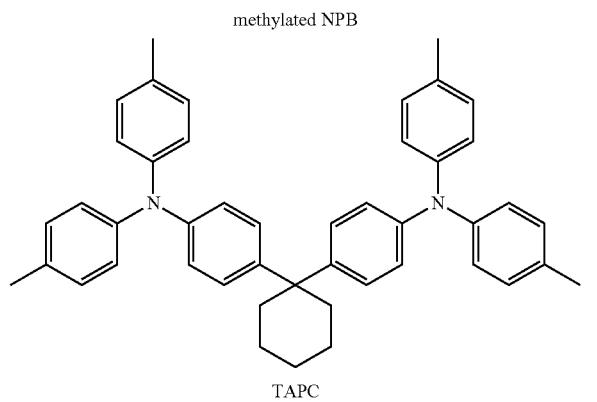
TAPC

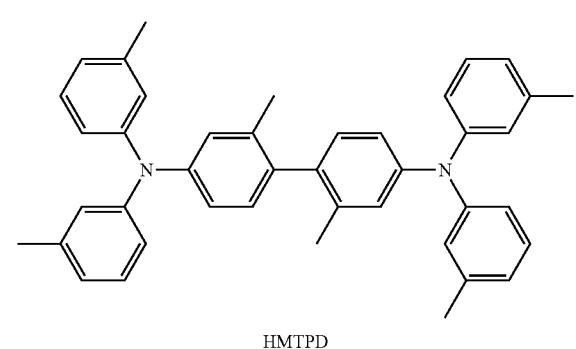
HMTPD

-continued

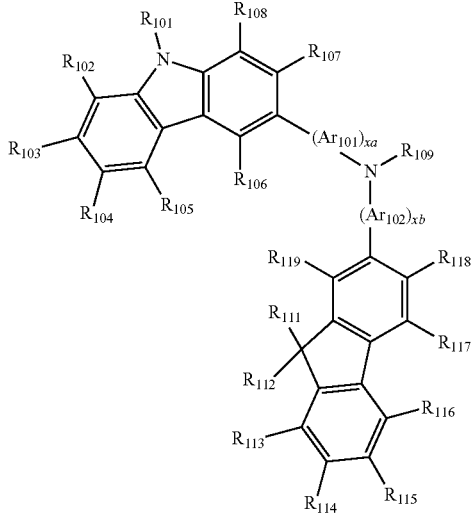

<Formula 201>

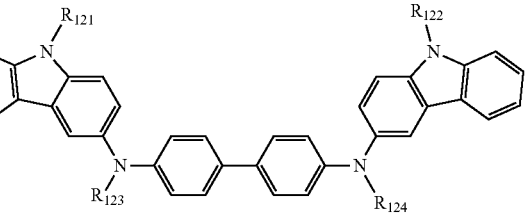

<Formula 202>

In Formula 201, $Ar_{101}$ and $Ar_{102}$ may each independently be:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group; or a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group, each substituted with at least one deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or any combination thereof.

The designations xa and xb in Formula 201 may each independently be an integer from 0 to 5, or may be 0, 1 or 2. For example, xa may be 1 and xb may be 0. However, embodiments are not limited thereto.

In Formulae 201 and 202, $R_{101}$ to $R_{108}$, $R_{111}$ to $R_{119}$, and $R_{121}$ to $R_{124}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, or the like), or a $C_1$-$C_{10}$ alkoxy group (for example, a methoxy group, an ethoxy group, a propoxy group, a butoxy group, a pentoxy group, or the like);

a $C_1$-$C_{10}$ alkyl group or a $C_1$-$C_{10}$ alkoxy group, each substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, or any combination thereof;

a phenyl group, a naphthyl group, an anthracenyl group, a fluorenyl group, or a pyrenyl group; and a phenyl group, a naphthyl group, an anthracenyl group, a fluorenyl group, or a pyrenyl group, each substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, or any combination thereof. However, embodiments are not limited thereto.

In Formula 201, $R_{109}$ may be:

a phenyl group, a naphthyl group, an anthracenyl group, or a pyridinyl group; or a phenyl group, a naphthyl group, an anthracenyl group, or a pyridinyl group, each substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyridinyl group, or any combination thereof.

In one or more embodiments, the compound represented by Formula 201 may be represented by Formula 201A. However, embodiments are not limited thereto:

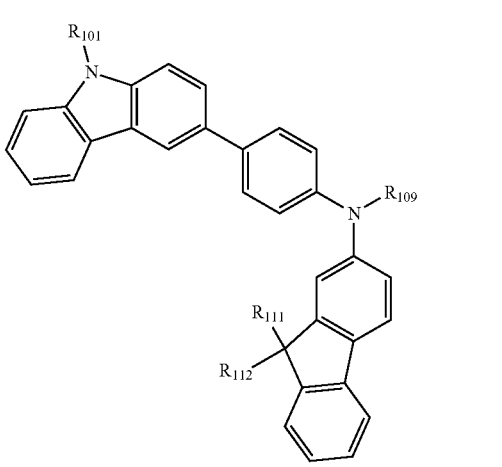

<Formula 201A>

In Formula 201A, $R_{101}$, $R_{111}$, $R_{112}$, and $R_{109}$ will be understood with reference to the above descriptions thereof.

For example, the compound represented by Formula 201 and the compound represented by Formula 202 may include Compounds HT1 to HT20 below. However, embodiments are not limited thereto:

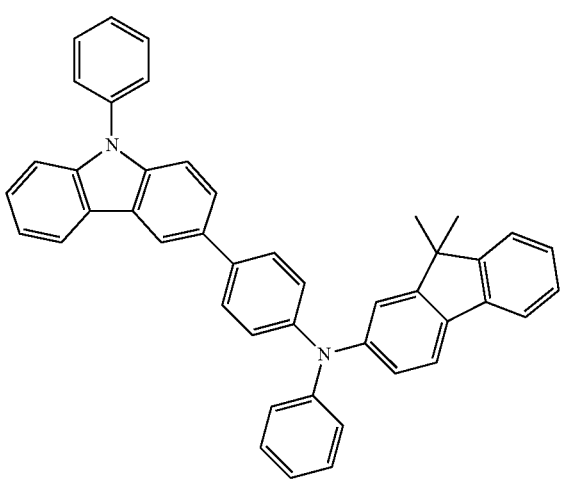

HT1

HT2
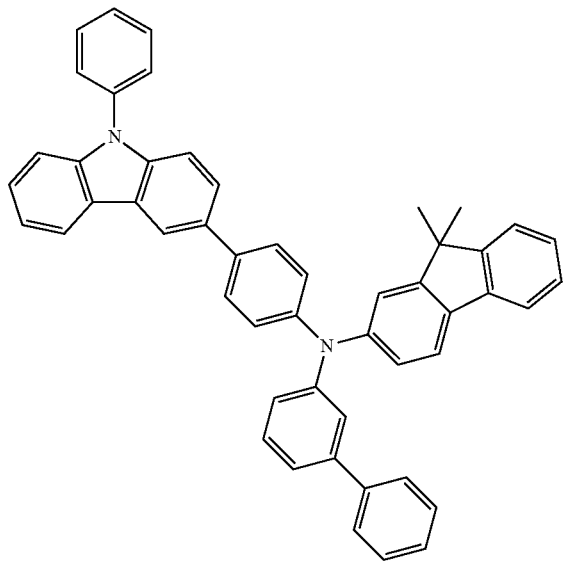
HT3
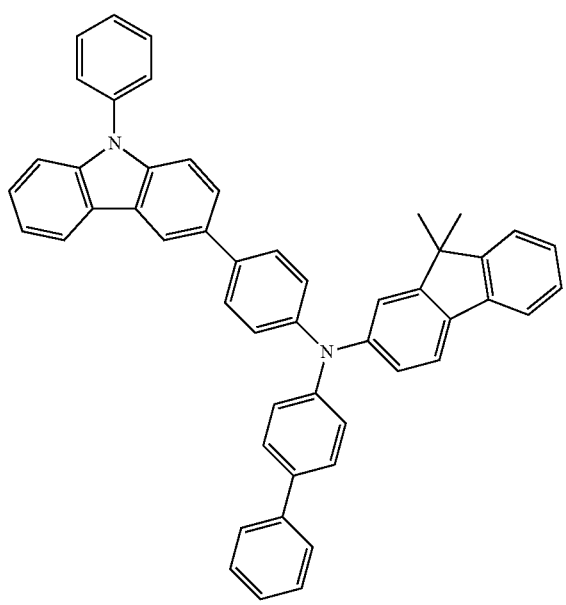
HT4
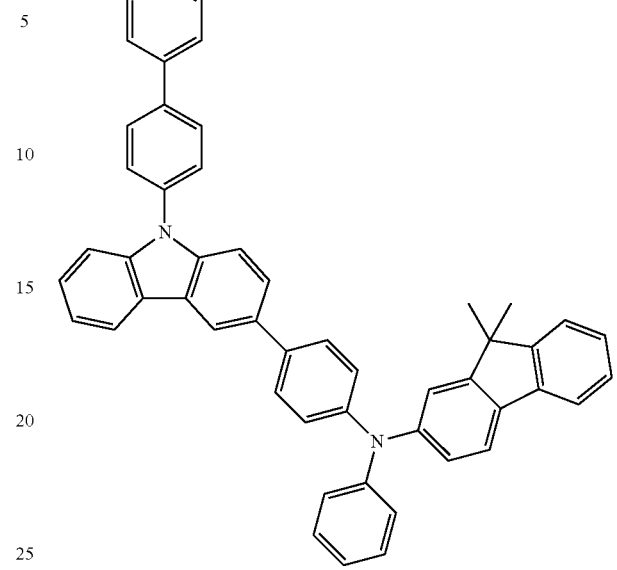
HT5
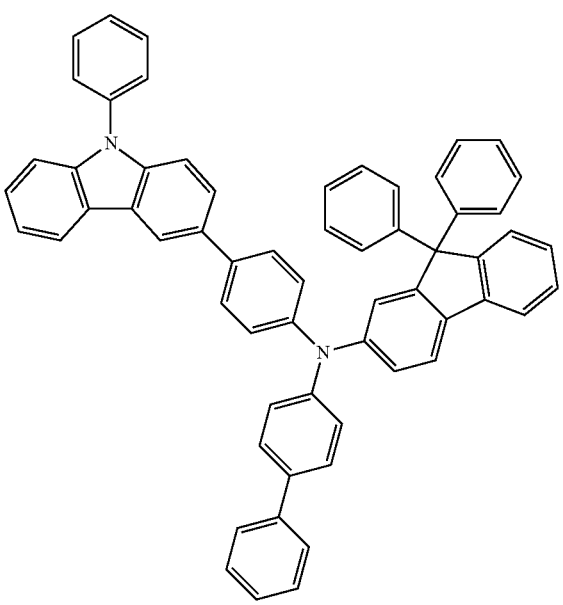

-continued
HT6
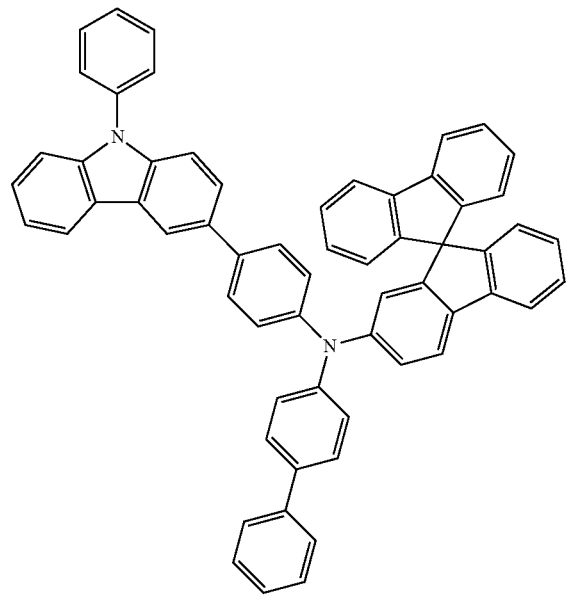
HT8
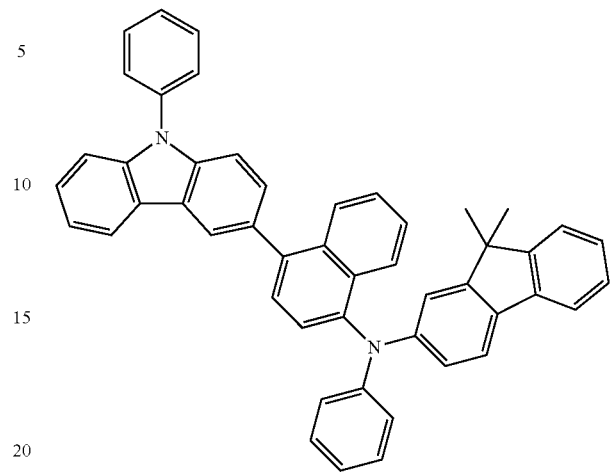
HT9
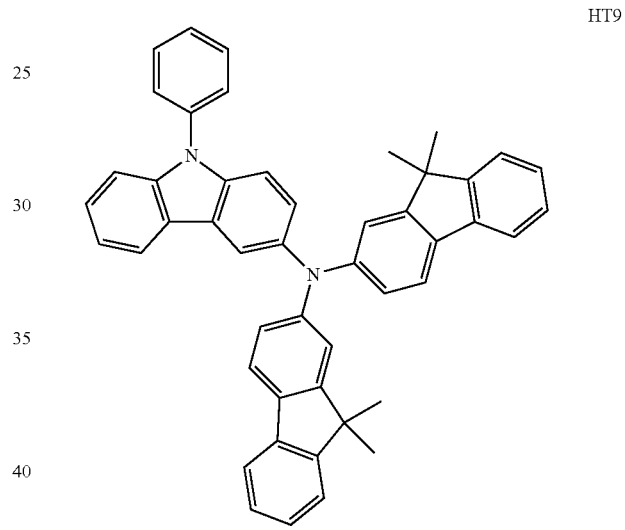
HT7
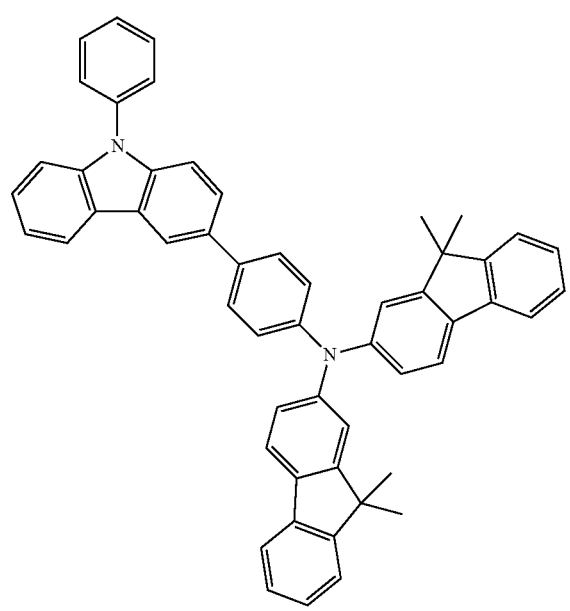
HT10
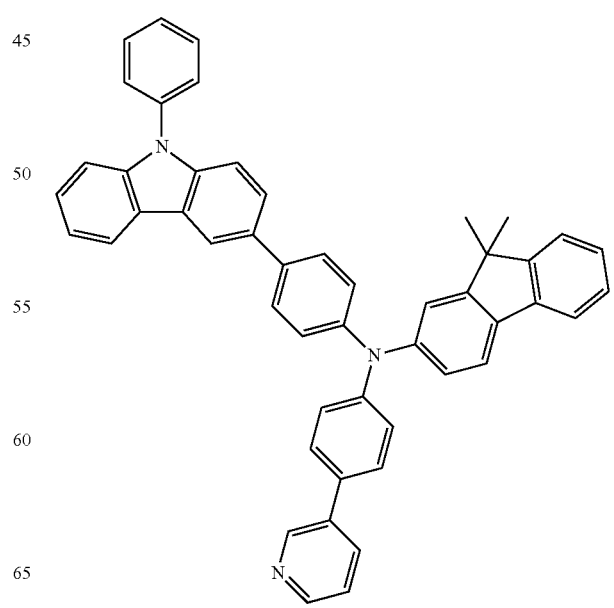

HT11
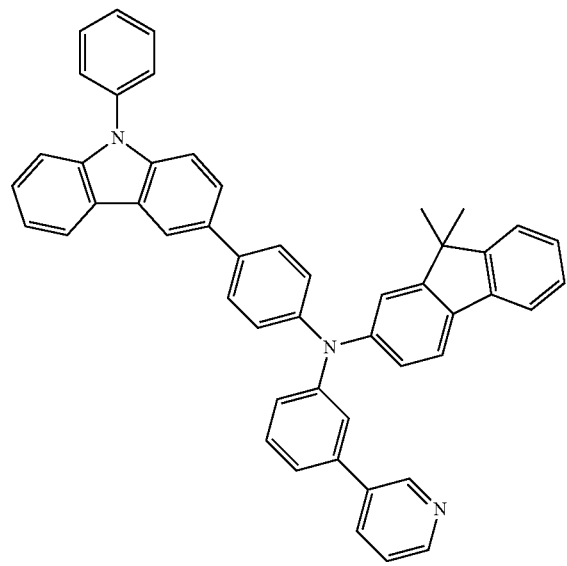
HT12
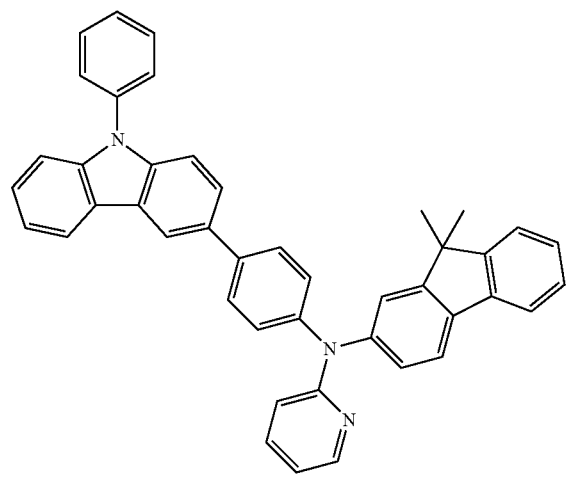
HT13
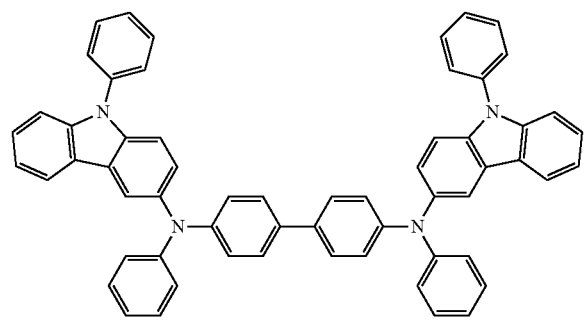
HT14
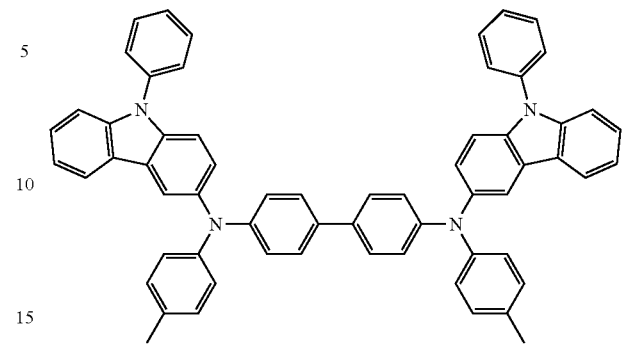
HT15
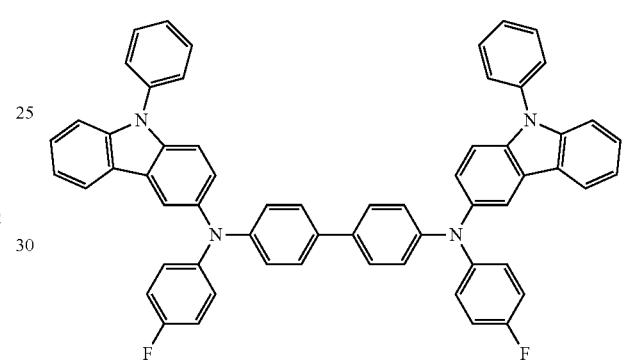
HT16
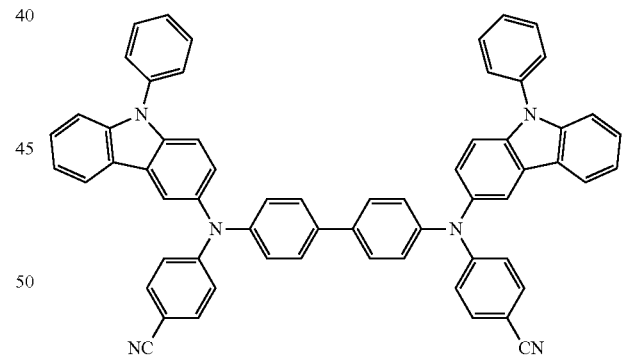
HT17
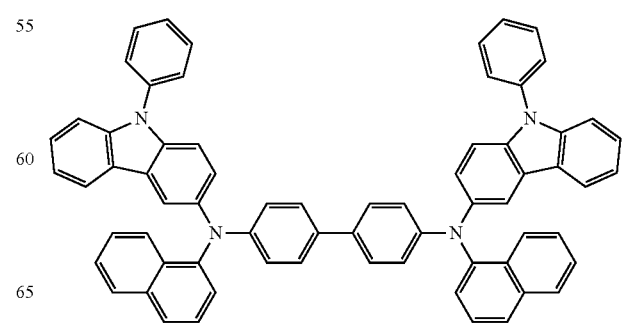

-continued

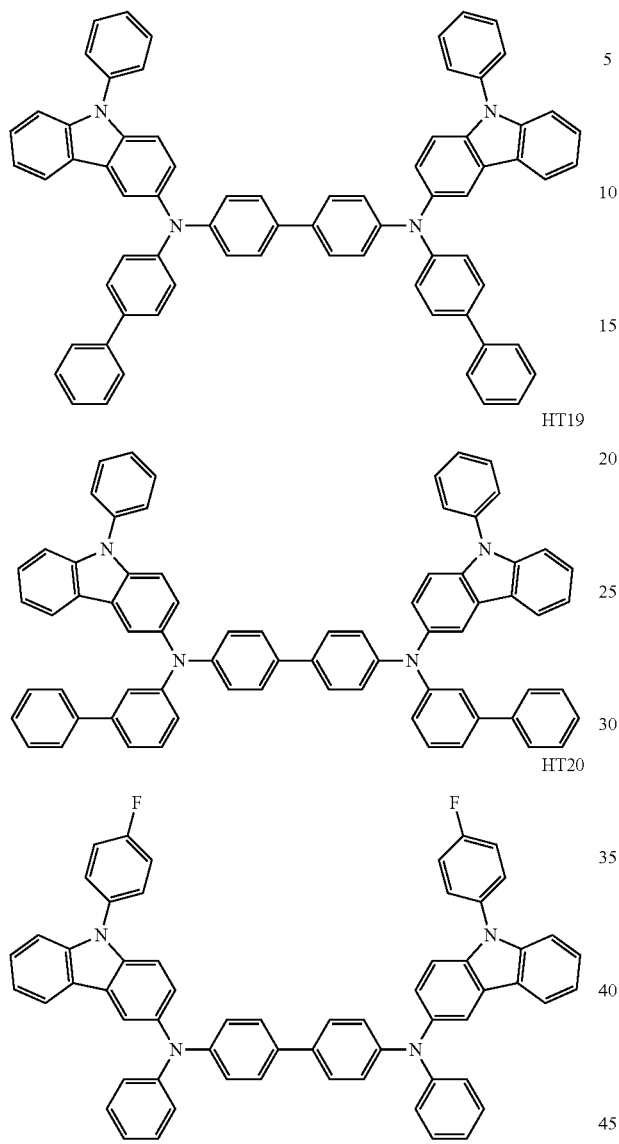

HT18

HT19

HT20

A thickness of the hole transport region may be from about 100 Å to about 10,000 Å, for example, about 100 Å to about 1,000 Å. When the hole transport region includes at least one of a hole injection layer, a hole transport layer, and an electron blocking layer, a thickness of the hole injection layer may be in a range of about 100 Å to about 10000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to the above-described materials, a charge-generation material for the improvement of conductive properties. The charge-generation material may be homogeneously or non-homogeneously dispersed in the hole transport region.

The charge-generation material may be, for example, a p-dopant. The p-dopant may be one of a quinone derivative, a metal oxide, and a cyano group-containing compound. Non-limiting examples of the p-dopant may be a quinone derivative, such as tetracyanoquinonedimethane (TCNQ), 2,3,5,6-tetrafluoro-tetracyano-1,4-benzoquinonedimethane (F4-TCNQ), and F6-TCNNQ; a metal oxide, such as a tungsten oxide or a molybdenum oxide; and a cyano group-containing compound, such as Compound HT-D1. However, embodiments are not limited thereto.

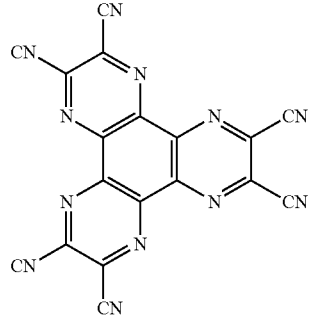

HT-D1

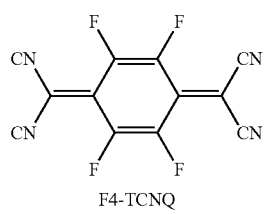

F4-TCNQ

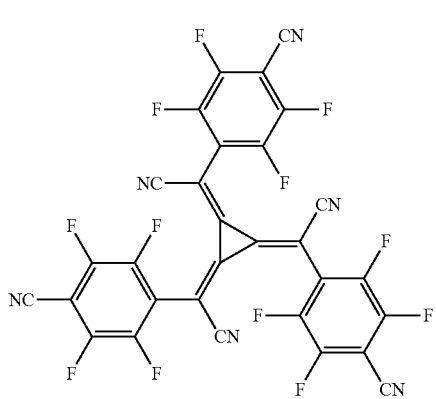

HT-D2

The hole transport region may further include a buffer layer.

The buffer layer may compensate for an optical resonance distance according to a wavelength of light emitted from the emission layer, and thus increase efficiency.

The hole transport region may further include an electron blocking layer. The electron blocking layer may include a known material, for example, mCP. However, embodiments are not limited thereto.

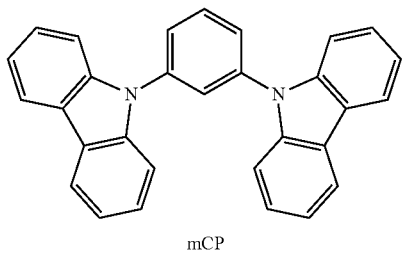 [SMILES: c1cc(-n2c3ccccc3c3ccccc32)cc(-n2c3ccccc3c3ccccc32)c1]

mCP

A thickness of the electron blocking layer may be from about 50 Å to about 1000 Å, for example, from about 70 Å to about 500 Å. When the thickness of the electron blocking layer is within these ranges, satisfactory electron blocking characteristics may be obtained without a substantial increase in driving voltage.

An emission layer may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a compound that is used to form the emission layer.

When the organic light-emitting device is a full-color organic light-emitting device, the emission layer may be patterned into a red emission layer, a green emission layer, and/or a blue emission layer. In one or more embodiments, due to having a stacked structure including a red emission layer, a green emission layer, and/or a blue emission layer, the emission layer may emit white light.

The emission layer may include the condensed cyclic compound represented by Formula 1.

For example, the emission layer may include only the condensed cyclic compound represented by Formula 1.

When the emission layer includes a host and a dopant, the amount of the dopant may be in a range of about 0.01 parts by weight to about 20 parts by weight with respect to 100 parts by weight of the emission layer. When the amount of the dopant with this range, emission can be implemented without extinction of light.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one of a hole blocking layer, an electron transport layer, and an electron injection layer.

For example, the electron transport region may have a hole blocking layer/electron transport layer/electron injection layer structure or an electron transport layer/electron injection layer structure. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP, Bphen, or any combination thereof. However, embodiments are not limited thereto.

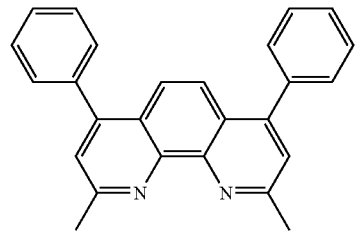

BCP

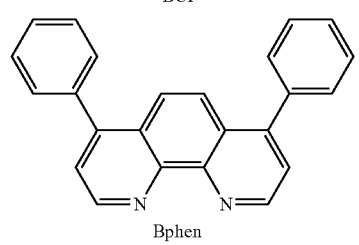

Bphen

A thickness of the hole blocking layer may be from about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may include at least one of BCP, Bphen, TPBi, $Alq_3$, BAlq, TAZ, NTAZ, or any combination thereof.

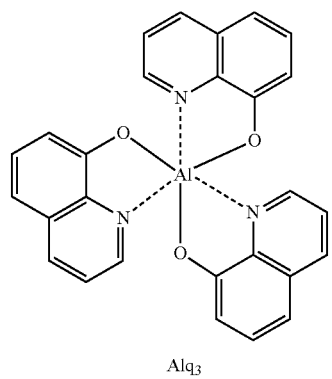

$Alq_3$

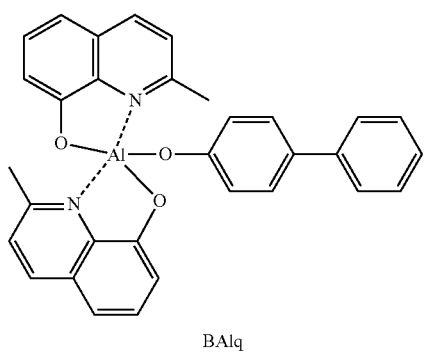

BAlq

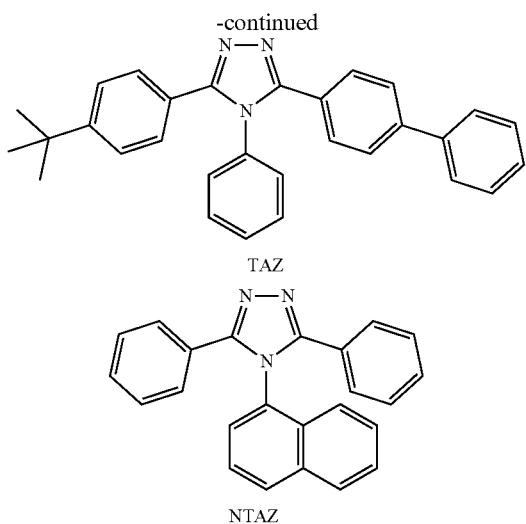

TAZ

NTAZ

In one or more embodiments, the electron transport layer may include at least one of Compounds ET1, ET2, ET3, or any combination thereof. However, embodiments are not limited thereto.

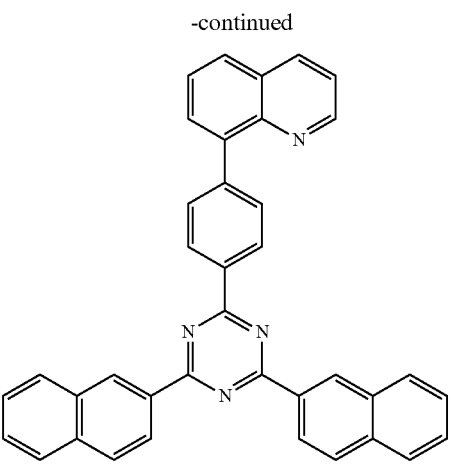

ET3

A thickness of the electron transport layer may be from about 100 Å to about 1,000 Å, for example, about 150 Å to about 500 Å. When the thickness of the electron transport layer is within the above-described ranges, the electron transport layer may have satisfactory electron transport characteristics without a substantial increase in driving voltage.

The electron transport layer may further include, in addition to the materials described above, a metal-containing material.

The metal-containing material may include a Li complex. The Li complex may include, for example, Compound ET-D1 (8-quinolinolato lithium, LiQ), Compound ET-D2, or any combination thereof

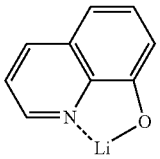

ET-D1

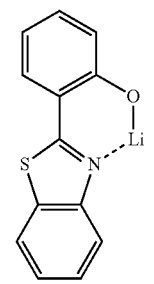

ET-D2

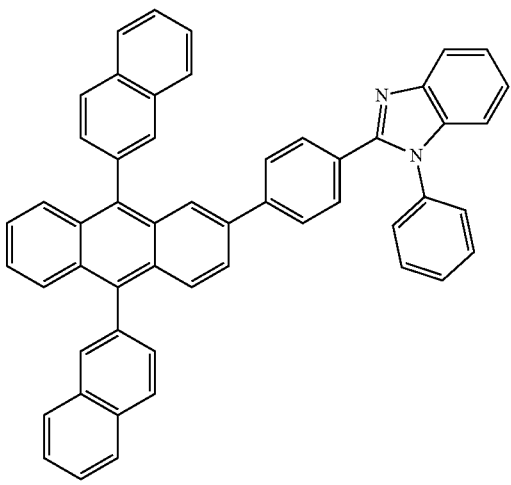

ET1

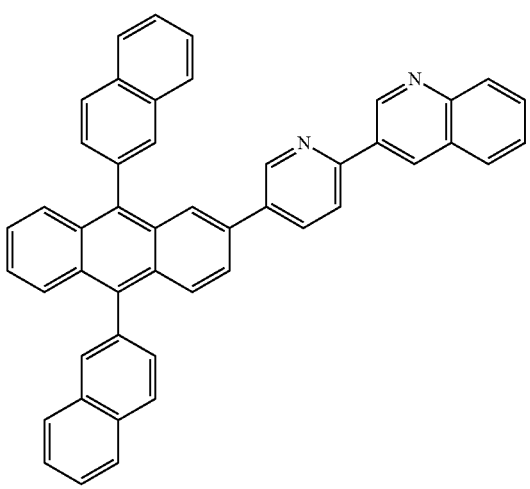

ET2

The electron transport region may include an electron injection layer that facilitates flow of electrons from the second electrode 19.

The electron injection layer may include at least one of LiQ, LiF, NaCl, CsF, Li$_2$O, BaO, or any combination thereof.

A thickness of the electron injection layer may be from about 1 Å to about 100 Å, for example, about 3 Å to about 90 Å. When a thickness of the electron injection layer is within these ranges, satisfactory electron injection characteristics may be obtained without substantial increase in driving voltage.

The second electrode 19 is disposed on the organic layer 15. The second electrode 19 may be a cathode. Examples of a material for forming the second electrode 19 may be a metal, an alloy, an electrically conductive compound, and any combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as the material for forming the second electrode 19. To manufacture a top-emission type light-emitting device, a transmissive electrode formed using ITO or IZO may be used as the second electrode 19.

Hereinbefore, the organic light-emitting device according to an embodiment has been described with reference to FIG. 1. However, embodiments are not limited thereto.

The term "$C_1$-$C_{60}$ alkyl group" as used herein refers to a linear or branched saturated aliphatic hydrocarbon monovalent group having 1 to 60 carbon atoms. Non-limiting examples of the $C_1$-$C_{60}$ alkyl group include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" used herein refers to a monovalent group represented by —$OA_{101}$ (wherein $A_{101}$ is a $C_1$-$C_{60}$ alkyl group). Non-limiting examples of the $C_1$-$C_{60}$ alkoxy group may include a methoxy group, an ethoxy group, and an isopropyloxy group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and non-limiting examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and non-limiting examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent monocyclic group having 1 to 10 carbon atoms and including, as a ring-forming atom, at least one N, O, P, Si, B, Se, Ge, Te, S, or any combination thereof and non-limiting examples thereof include a tetrahydrofuranyl group and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group having 3 to 10 carbon atoms and at least one carbon-carbon double bond in the ring thereof but no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_2$-$C_{10}$ heterocycloalkenyl group" as used herein refers to a monovalent monocyclic group having 2 to 10 carbon atoms and including, as a ring-forming atom, at least one N, O, P, Si, S, B, Se, Ge, Te, or any combination thereof, and at least one double bond in the ring thereof. Non-limiting examples of the $C_2$-$C_{10}$ heterocycloalkenyl group include a 2,3-dihydrofuranyl group and a 2,3-dihydrothiophenyl group. The term "$C_2$-$C_{10}$ heterocycloalkenylene group" as used herein refers to a divalent group having the same structure as the $C_2$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a heterocyclic aromatic system having 1 to 60 carbon atoms and including, as a ring-forming atom, at least one hetero atom N, O, P, Si, B, Se, Ge, Te, S, or any combination thereof. The term "$C_1$-$C_{60}$ heteroarylene group" as used herein refers to a divalent group having a heterocyclic aromatic system having 1 to 60 carbon atoms and including, as a ring-forming atom, at least one hetero atom N, O, P, Si, B, Se, Ge, Te, S, or any combination thereof. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" used herein indicates —$OA_{102}$ (wherein $A_{102}$ is a $C_6$-$C_{60}$ aryl group as described above), the term "$C_6$-$C_{60}$ arylthio group" used herein indicates —$SA_{103}$ (wherein $A_{103}$ is a $C_6$-$C_{60}$ aryl group as described above).

The term "monovalent non-aromatic condensed polycyclic group" as used herein refers to a monovalent group having two or more rings condensed to each other, and only carbon atoms (for example, 8 to 60 carbon atoms) as ring-forming atoms, and in which the whole molecular structure has no aromaticity. A non-limiting example of the monovalent non-aromatic condensed polycyclic group includes a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group having two or more rings condensed to each other, and including as ring-forming atoms, in addition to carbon atoms (for example 1 to 60 carbon atoms), a heteroatom N, O, P, Si, B, Se, Ge, Te, S, or any combination thereof, and in which the whole molecular structure has no aromaticity. A non-limiting example of the monovalent non-aromatic condensed heteropolycyclic group includes a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a saturated or unsaturated cyclic group having, as a ring-forming atom, 5 to 60 carbon atoms only. The $C_5$-$C_{60}$ carbocyclic group may be a monocyclic group or a polycyclic group, for example, may be a monovalent, divalent, tervalent, tetravalent, pentavalent, or hexavalent group according to the chemical structure.

The term "$C_1$-$C_{60}$ heterocyclic group" as used herein refers to a saturated or unsaturated cyclic group having, as ring-forming atoms, in addition to 1 to 60 carbon atoms, at least one hetero atom N, O, P, Si, B, Se, Ge, Te, S, or any combination thereof. The $C_1$-$C_{60}$ heterocyclic group may be a monocyclic group or a polycyclic group, for example, may be a monovalent, divalent, tervalent, tetravalent, pentavalent, or hexavalent group according to the chemical structure.

At least one of the substituents of the substituted $C_5$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{14})(Q_{15})$, —$B(Q_{16})(Q_{17})$, or any combination thereof;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each substituted with at least one deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{24})(Q_{25})$, —$B(Q_{26})(Q_{27})$, or any combination thereof; or —$Si(Q_{31})(Q_{32})(Q_{33})$, —$N(Q_{34})(Q_{35})$, or —$B(Q_{36})(Q_{37})$.

As used herein, $Q_1$ to $Q_7$, $Q_{11}$ to $Q_{17}$, $Q_{21}$ to $Q_{27}$, and $Q_{31}$ to $Q_{37}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

As used herein, * and *' indicate binding sites to adjacent atoms in the formula, unless stated otherwise.

Hereinafter, compounds and organic light-emitting devices according to embodiments will now be described in detail with reference to synthesis examples and examples. However, these examples are only for illustrative purposes and are not intended to limit the scope of the one or more embodiments of the present disclosure. The wording "B was used instead of A" used in describing synthesis examples means that the amount of A used was identical to the amount of B used, in terms of a molar equivalent.

EXAMPLES

Synthesis Example 1: Synthesis of Compound 1

Compound 1 was synthesized according to the following reaction scheme.

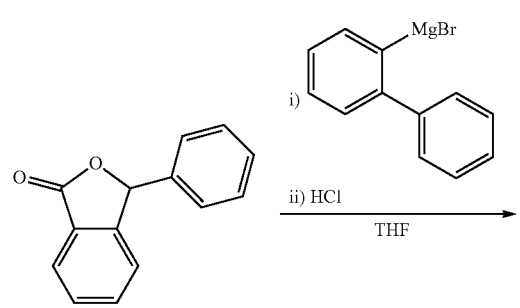

-continued

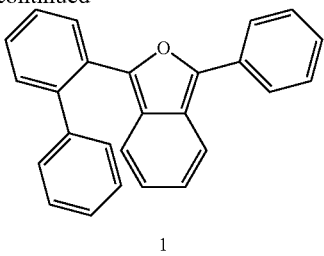

1

After 5.00 g (23.7 mmol) of 3-phenylisobenzofuran-1 (3H)-one was dissolved in 25 mL of anhydrous THF in the nitrogen atmosphere, and then cooled down to 0° C., 26.2 mL (26.2 mmol, 1.0M in THF) of a 2-biphenylmagnesium bromide solution was slowly added thereto. The temperature of the reaction mixture was slowly increased to room temperature, and then stirred for about 4 hours. After cooling again to 0° C., 10 mL of HCl and 20 mL of water were slowly added to terminate the reaction. After extraction of the reaction mixture with dichloromethane (DCM), the resulting organic layer was dried using MgSO$_4$ and then filtered to obtain a filtrate. The filtrate was concentrated under reduced pressure. The resulting product was purified by silica gel column chromatography to obtain Compound 1 (6.01 g, Yield: 73%).

LC-Mass (calcd: 346.14 g/mol, Found: M$^{+1}$=347 g/mol)

Synthesis Example 2: Synthesis of Compound A

Compound A was synthesized according to the following reaction scheme.

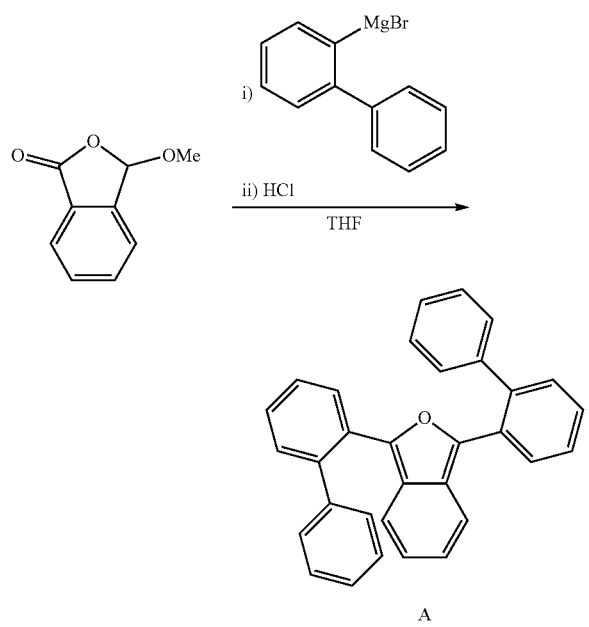

After 4.00 g (24.4 mmol) of 3-methoxyisobenzofuran-1 (3H)-one was dissolved in 25 mL of anhydrous THF under nitrogen atmosphere, and then cooled down to 0° C., 53.6 mL (53.6 mmol, 1.0M in THF) of a 2-biphenylmagnesium bromide solution was slowly added thereto. The temperature of the reaction mixture was slowly increased to room temperature, and then stirred for about 4 hours. After cooling again to 0° C., 20 mL of HCl and 40 mL of water were slowly added to terminate the reaction. After extraction of the reaction mixture with dichloromethane (DCM), the resulting organic layer was dried using MgSO$_4$ and then filtered to obtain a filtrate. The filtrate was concentrated under reduced pressure. The resulting product was purified by silica gel column chromatography to obtain Compound A (4.63 g, Yield: 45%).

LC-Mass (calcd: 422.17 g/mol, Found: M$^{+1}$=423 g/mol).

Example 1

A glass substrate (size: 50 mm×50 mm×0.5 mm) with an ITO pattern thereon was washed by ultrasonication using acetone, isopropyl alcohol and pure water for 20 minutes each, and then thermally treated at 250° C. for 10 minutes.

Subsequently, on the ITO electrode (anode) of the glass substrate, HATCN was deposited at a deposition rate of 1 Å/sec to a thickness of 100 Å to form a hole injection layer. Then, NPB was deposited on the hole injection layer at a deposition rate of 1 Å/sec to form a hole transport layer having a thickness of 800 Å.

Subsequently, mCP was deposited on the hole transport layer at a deposition rate of 1 Å/sec to form an electron blocking layer having a thickness of 50 Å.

Compound 1 (host) and Compound D1 (dopant) were co-deposited on the electron blocking rate at a deposition rate of 0.97 Å/sec and 0.3 Å/sec, respectively, to form an emission layer having a thickness of 200 Å.

After DPEPO and LiQ were co-deposited in a ratio of 1:1 on the emission layer at a rate of 0.5 Å/sec to form an electron transport layer having a thickness of 300 Å, LiQ was deposited on the electron transport layer at a rate of 0.5 Å/sec to form an electron injection layer having a thickness of 10 Å, and then Al was vacuum-deposited on the electron injection layer to form a second electrode (cathode) having a thickness of 1000 Å, thereby manufacturing an organic light-emitting device having a structure of ITO/HATCN (100 Å)/NPB (800 Å)/mCP (50 Å)/Compound 1+Compound D1 (3%) (200 Å)/DPEPO:LiQ (300 Å)/LiQ (10 Å)/Al (1000 Å).

Example 2 and Comparative Examples 1 to 3

Organic light-emitting devices were manufactured in the same manner as in Example 1, except that compounds listed in Table 2 were used, respectively, instead of Compound 1, as a host in forming the emission layer.

Evaluation Example 1: Evaluation of TTF Ratio

A TTF ratio was measured as a square of the inverse of the y-intercept value in the graph of values of 1/square root of TrEL intensities from 500 ns to 4000 ns in the decay spectrum of transient electroluminescence (TrEL) (1/sqrt (TrEL)) with respect to time.

Evaluation Example 2: Evaluation of Characteristics of Organic Light-Emitting Device The driving voltage, external quantum efficiency (EQE), and lifetime (LT$_{95}$) of each of the organic light-emitting devices manufactured in Examples 1 and 2 and Comparative Examples 1 to 3 were evaluated. The results are shown in Table 2. This evaluation was performed using a current-voltage meter (Keithley 2400) and a luminescence meter (Minolta Cs-1,000A), and the lifetime (LT$_{95}$) (at 6000 nit)

was evaluated as the time (hr) it took until the luminance was reduced to 95% with respect to 100% of the initial luminance. The external quantum efficiency (EQE) and lifetime ($LT_{95}$) were both measured under a luminance of 16000 cd/m².

In Table 2, the driving voltage, external quantum efficiency, and lifetime were represented as relative values (%) with respect to 100% of the driving voltage, external quantum efficiency, and lifetime of the organic light-emitting device of Comparative Example 1.

TABLE 2

|  | Host Compound | Driving voltage (Relative value, %) | External quantum efficiency (Relative value, %) | Lifetime (Relative value, %) | Emission color |
|---|---|---|---|---|---|
| Example 1 | Compound 1 | 85 | 121 | 147 | Sky blue |
| Example 2 | Compound A | 78 | 137 | 125 | Sky blue |
| Comparative Example 1 | X1 | 100 | 100 | 100 | Sky blue |
| Comparative Example 2 | X2 | 105 | 78 | 67 | Sky blue |
| Comparative Example 3 | X3 | 98 | 109 | 113 | Sky blue |

<Compound 1>

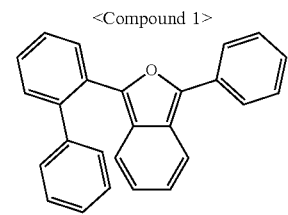

<Compound A>

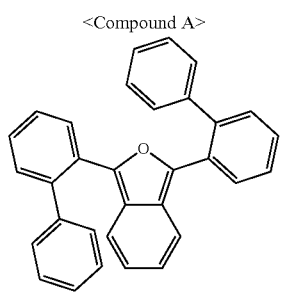

<Compound X1>

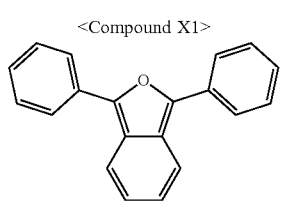

<Compound X2>

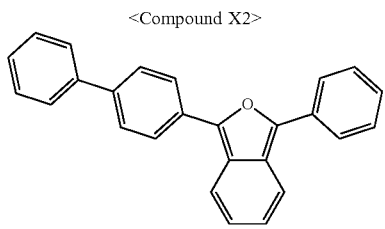

TABLE 2-continued

|  | Driving voltage (Relative value, %) | External quantum efficiency (Relative value, %) | Lifetime (Relative value, %) | Emission color |
|---|---|---|---|---|
| Host Compound |  |  |  |  |

<Compound X3>

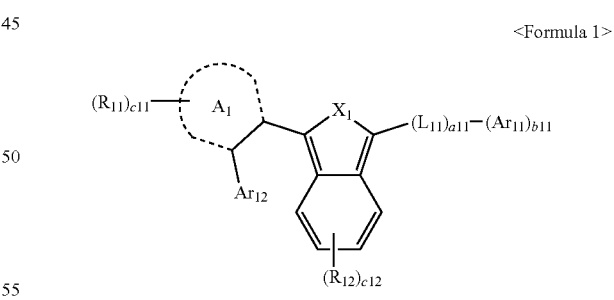

Referring to Table 2, the organic light-emitting devices of Examples 1 and 2 were found to have a low driving voltage, excellent external quantum efficiency, and long lifespan, as compared to those of the organic light-emitting devices of Comparative Examples 1 to 3.

According to the one or more embodiment, the condensed cyclic compound represented by Formula 1 has high singlet energy, excellent electric characteristics and thermal stability, and thus an organic light-emitting device using the condensed cyclic compound may have a low driving voltage, high efficiency, high power, high quantum efficiency, and long lifespan characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope as defined by the following claims.

What is claimed is:

1. A condensed cyclic compound represented by Formula 1:

<Formula 1>

$(R_{11})_{c11} \text{—} A_1 \text{—} \begin{matrix} X_1 \\ \end{matrix} \text{—} (L_{11})_{a11} \text{—} (Ar_{11})_{b11}$ $Ar_{12}$ $(R_{12})_{c12}$ wherein, in Formula 1,
$X_1$ is O or S,
$A_1$ is a $C_5$-$C_{60}$ carbocyclic group or a $C_1$-$C_{60}$ heterocyclic group,
$L_{11}$ is a substituted or unsubstituted $C_5$-$C_{60}$ carbocyclic group, or a substituted or unsubstituted $C_1$-$C_{60}$ heterocyclic group,
a11 is an integer 0 to 3,
$Ar_{11}$ and $Ar_{12}$ are each independently a $C_6$-$C_{60}$ aryl group, a $C_1$-$C_{60}$ heteroaryl group, a monovalent non-aromatic condensed polycyclic group, or a monovalent non-aromatic condensed heteropolycyclic group, each unsubstituted or substituted with at least one $R_a$, b11 is an integer 1 to 5, $R_{11}$, $R_{12}$, and $R_a$ are each independently hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), or —B($Q_6$)($Q_7$), c11 is an integer 1 to 20, c12 is an integer 1 to 4, when c11 is 2 or greater, two adjacent $R_{11}$(s) are optionally linked to each other to form a substituted or unsubstituted $C_5$-$C_{30}$ carbocyclic group or a substituted or unsubstituted $C_1$-$C_{30}$ heterocyclic group, when c12 is 2 or greater, two adjacent $R_{12}$(s) are optionally linked to each other to form a substituted or unsubstituted $C_5$-$C_{30}$ carbocyclic group or a substituted or unsubstituted $C_1$-$C_{30}$ heterocyclic group, $A_1$ and $Ar_{12}$ are optionally condensed with each other via a first linking group of a single bond, *—$Ar_{31}$—*', *—O—*', *—S—*', *—[C($R_{31}$)($R_{32}$)]$_{k11}$—*', *—C($R_{31}$)=*', *=C($R_{31}$)—*', *—C($R_{31}$)=C($R_{32}$)—', *—C(=O)—', *—C(=S)—*', *—C≡C—*', *—N($R_{31}$)—*', *—P($R_{31}$)—*', *—[Si($R_{31}$)($R_{32}$)]$_{k11}$—*', or *—P($R_{31}$)($R_{32}$)—*' to form a substituted or unsubstituted $C_5$-$C_{30}$ carbocyclic group or a substituted or unsubstituted $C_1$-$C_{30}$ heterocyclic group, a12 is an integer of 0 or 1, $Ar_{31}$ is a $C_5$-$C_{30}$ carbocyclic group, $R_{31}$ and $R_{32}$ are each independently the same as defined in connection with $R_{11}$, k11 is 1, 2, 3, or 4, at least one of substituents of the substituted $C_5$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is: deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), —B($Q_{16}$)($Q_{17}$), or any combination thereof;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each substituted with at least one deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), —B($Q_{26}$)($Q_{27}$), or any combination thereof; or —Si($Q_{31}$)($Q_{32}$)($Q_{33}$), —N($Q_{34}$)($Q_{35}$), or —B($Q_{36}$)($Q_{37}$), and $Q_1$ to $Q_7$, $Q_{11}$ to $Q_{17}$, $Q_{21}$ to $Q_{27}$, and $Q_{31}$ to $Q_{37}$ are each independently hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group, provided that the condensed cyclic compound represented by Formula 1 is not Compound A or Compound 1:

<Compound A>

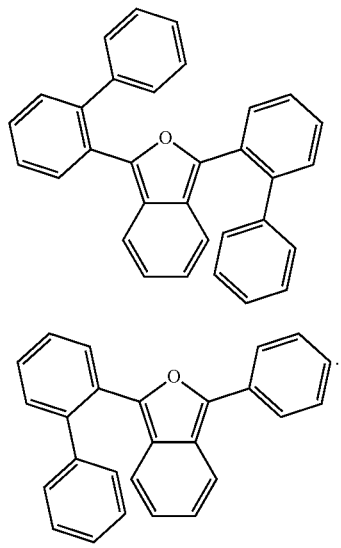

Compound 1

2. The condensed cyclic compound of claim 1, wherein $A_1$ is a benzene group, a naphthalene group, an anthracene group, a phenanthrene group, a fluorene group, a spirobifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, an imidazopyridine group, an indolizine group, a pyrazolopyridine group, an indole group, a benzofuran group, a benzothiophene group, an isobenzothiophene group, a benzoxazole group, an isobenzoxazole group, a triazole group, a tetrazole group, an oxadiazole group, a thiadiazole group, a triazine group, a dibenzofuran group, a dibenzothiophene group, or a dibenzosilole group.

3. The condensed cyclic compound of claim 1, wherein $A_1$ is a benzene group, a naphthalene group, a phenanthrene group, a fluorene group, a spiro-fluorene group, a pyrrole group, a thiophene group, a furan group, an imidazole group, a pyrazole group, a thiazole group, an isothiazole group, an oxazole group, an isoxazole group, a pyridine group, a pyrimidine group, a quinoline group, a carbazole group, an imidazopyridine group, an indolizine group, a pyrazolopyridine group, an indole group, a benzofuran group, a benzothiophene group, an indole group, a triazole group, a dibenzofuran group, or a dibenzosilole group.

4. The condensed cyclic compound of claim 1, wherein $A_1$ is a group represented by one of Formulae 2-1 to 2-52:

2-1

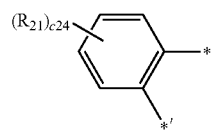

2-2

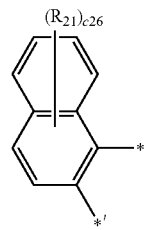

2-3

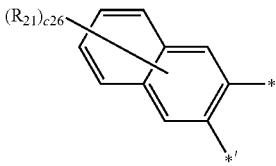

2-4

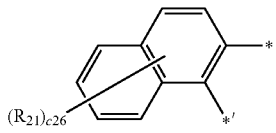

2-5

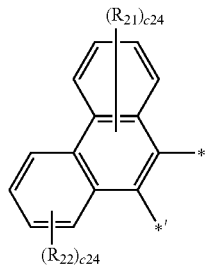

2-6

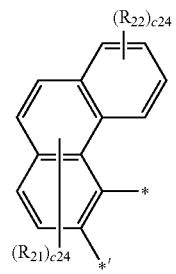

2-7

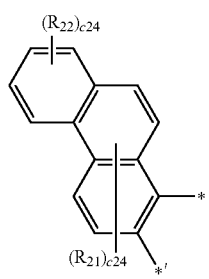

2-8

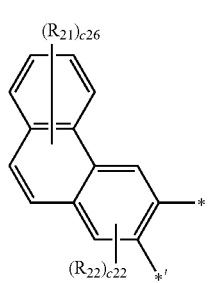

233
-continued
2-9
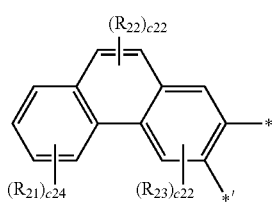
2-10
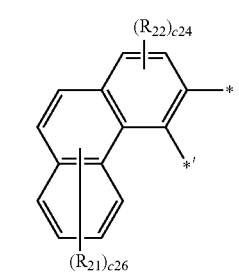
2-11
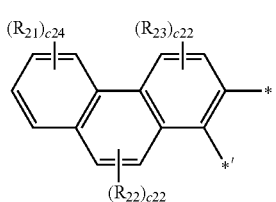
2-12
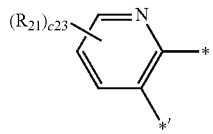
2-13
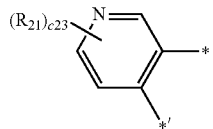
2-14
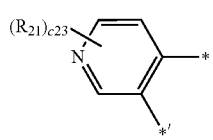
2-15
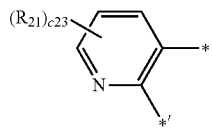
2-16
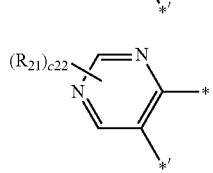
2-17
234
-continued
2-18
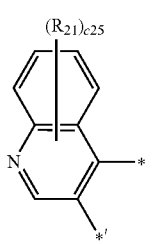
2-19
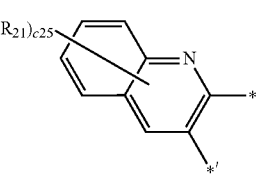
2-20
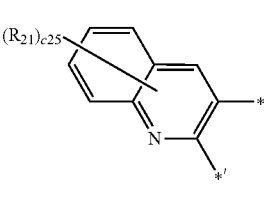
2-21
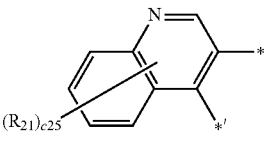
2-22
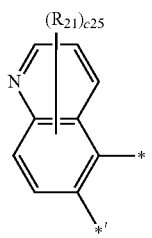
2-23
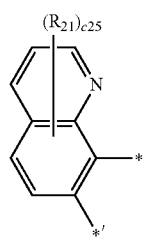
2-24
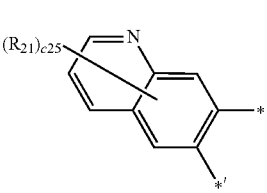
2-25
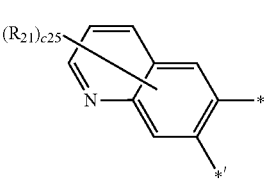

-continued 2-26
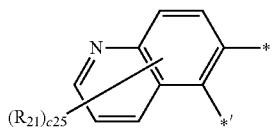

2-27
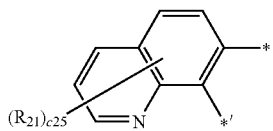

2-28
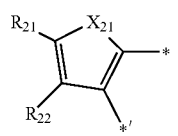

2-29
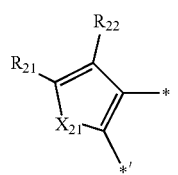

2-30
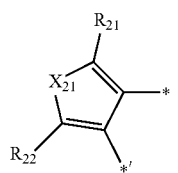

2-46
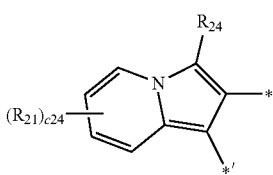

2-47
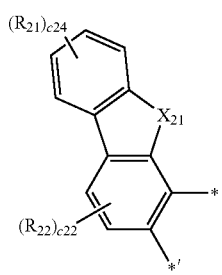

2-48
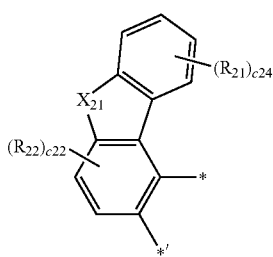

-continued 2-49
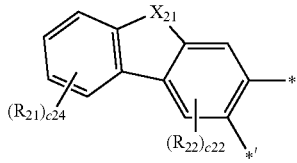

2-50
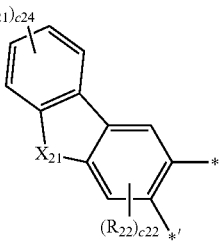

2-51
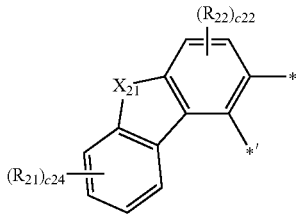

2-52
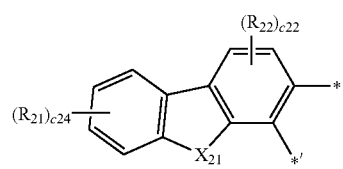

wherein, in Formulae 2-1 to 2-52,
$X_{21}$ is O, S, $N(R_{24})$, $C(R_{24})(R_{25})$, or $Si(R_{24})(R_{25})$,
$R_{21}$ to $R_{25}$ are each independently the same as defined in connection with $R_{11}$ in Formula 1,
c22 is 1 or 2,
c23 is an integer of 1 to 3,
c24 is an integer of 1 to 4,
c25 is an integer of 1 to 5,
c26 is an integer of 1 to 6, and
* and *' are binding sites to adjacent atoms.

5. The condensed cyclic compound of claim 4, wherein the group represented by Formula 2-1 is a group represented by one of Formulae 2-1(1) to 2-1(10):

2-1(1)
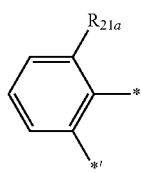

2-1(2)
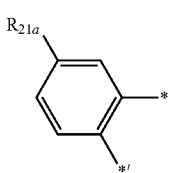

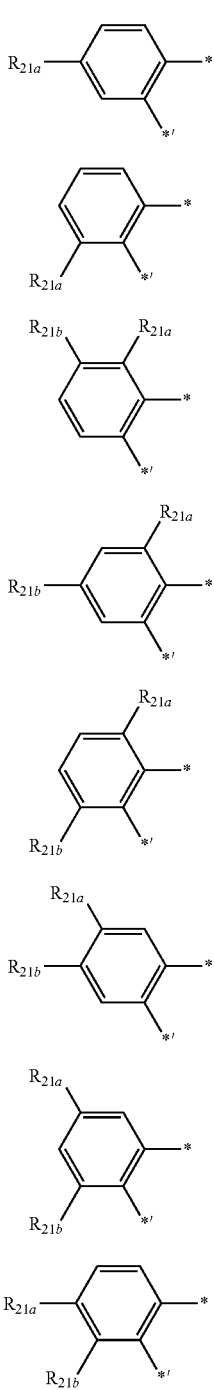

2-1(3)
2-1(4)
2-1(5)
2-1(6)
2-1(7)
2-1(8)
2-1(9)
2-1(10)

wherein, in Formulae 2-1(1) to 2-1(10),
$R_{21a}$ and $R_{21b}$ are each independently the same as defined with reference to $R_{21}$ in Formula 2-1, and
* and *' are binding sites to adjacent atoms.

6. The condensed cyclic compound of claim 1, wherein $L_{11}$ is a cyclopentylene group, a cyclohexylene group, a cyclopentenylene group, a cyclohexenylene group, a cycloheptenylene group, a phenylene group, a biphenylene group, a ter-phenylene group, a pentalenylene group, an indenylene group, a naphthylene group, an azulenylene group, a heptalenylene group, an indacenylene group, an acenaphthylene group, a fluorenylene group, a spiro-bifluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoxazolylene group, a benzimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a dibenzosilolylene group, a benzocarbazolylene group, a dibenzocarbazolylene group, an imidazopyrimidinylene group, an imidazopyridinylene group, a pyridoindolylene group, a benzofuropyridinylene group, a benzothienopyridinylene group, a pyrimidoindolylene group, a benzofuropyrimidinylene group, a benzothienopyrimidinylene group, a phenoxazinylene group, a pyridobenzoxazinylene group, or a pyridobenzothiazinylene group, each unsubstituted or substituted with at least one deuterium, —F, —Cl, —Br, —I, a hydroxyl group, a cyano group, a nitro group, an amino group, a $C_1$-$C_{60}$ alkyl group, a $C_1$-$C_{60}$ alkoxy group, a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzoxazinyl group, a pyridobenzothiazinyl group, or any combination thereof.

7. The condensed cyclic compound of claim 1, wherein $L_{11}$ is a group represented by one of Formulae 4-1 to 4-36:
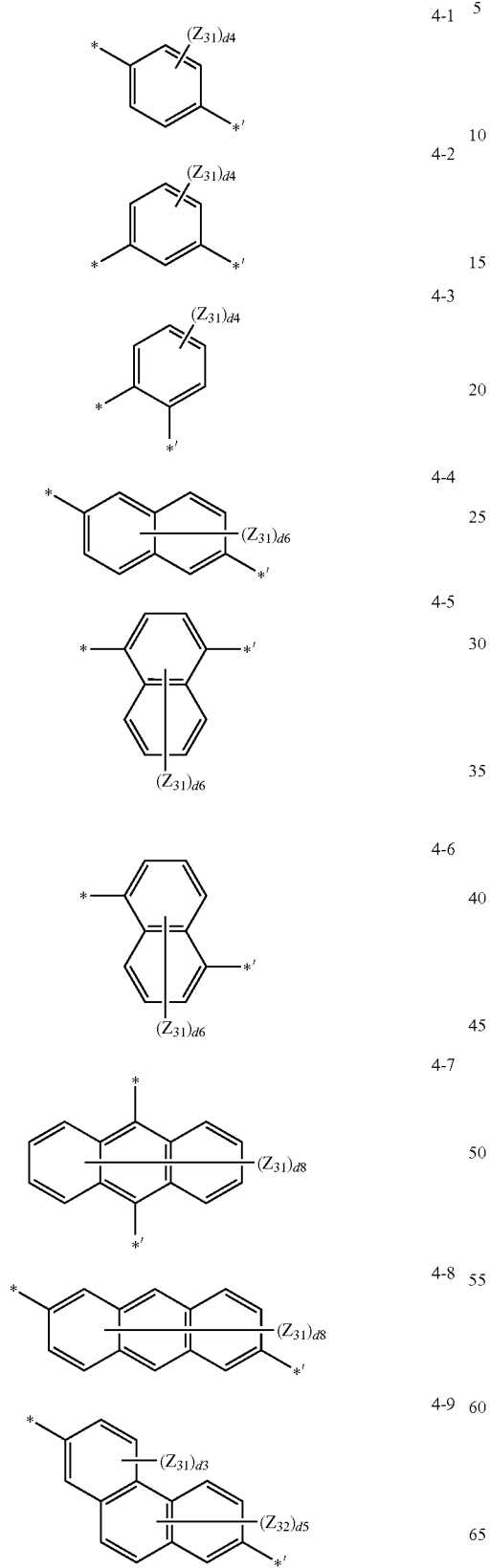
4-1
4-2
4-3
4-4
4-5
4-6
4-7
4-8
4-9
-continued
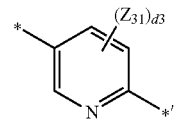
4-10
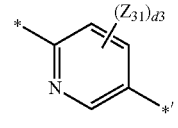
4-11
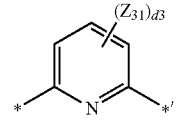
4-12
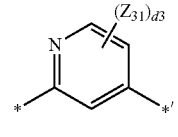
4-13
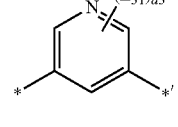
4-14
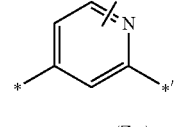
4-15
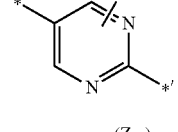
4-16
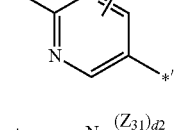
4-17
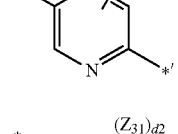
4-18
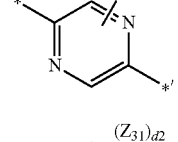
4-19
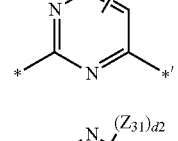
4-20
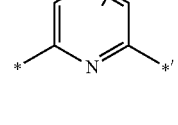
4-21

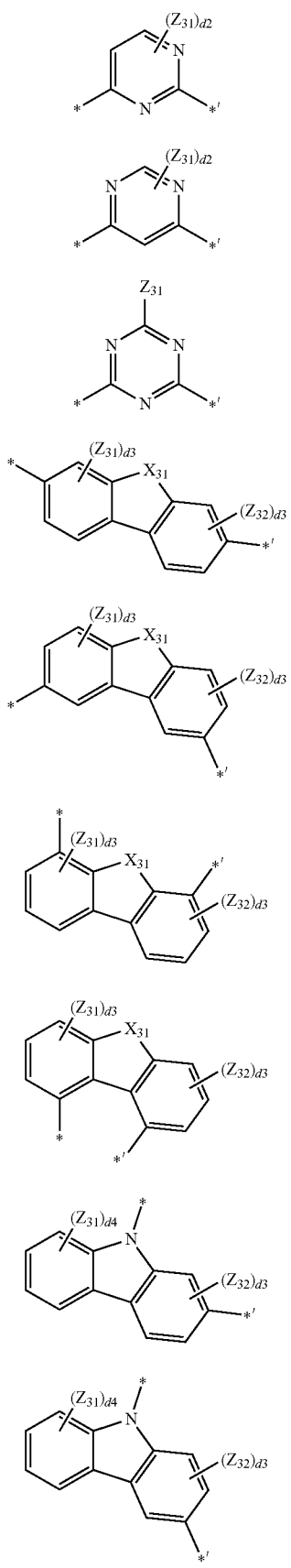

wherein, in Formulae 4-1 to 4-36, $X_{31}$ is O, S, $N(Z_{33})$, $C(Z_{33})(Z_{34})$, or $Si(Z_{33})(Z_{34})$, $Z_{31}$ to $Z_{34}$ are each independently hydrogen, deuterium, —F, —Cl, —Br, —I, a hydroxyl group, a cyano group, a nitro group, an amino group, a $C_1$-$C_{20}$ alkyl group, a $C_1$-$C_{20}$ alkoxy group, a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a spiro-bifluorenyl group, an anthracenyl group, a fluoranthenyl group, a triphenylenyl group, a pyrenyl group, a chrysenyl group, a pyrrolyl group, an imidazolyl group, a pyrazolyl group, a pyridinyl group, a pyrazinyl group, a pyrimidinyl group, a pyridazinyl group, an indolyl group, a carbazolyl group, a phenanthridinyl group, an acridinyl group, a phenanthrolinyl group, an oxazolyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, a triazinyl group, a dibenzofuranyl group, or a dibenzothiophenyl group, d2 is an integer of 1 to 2,
d3 is an integer of 1 to 3,
d4 is an integer of 1 to 4,
d5 is an integer of 1 to 5,
d6 is an integer of 1 to 6,
d8 is an integer 1 to 8, and
* and *' are binding sites to adjacent atoms.

8. The condensed cyclic compound of claim 1, wherein a11 is 0 or 1.

9. The condensed cyclic compound of claim 1, wherein $Ar_{11}$ and $Ar_{12}$ are each independently:
a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a benzofluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a naphthobenzofuranyl group, a naphthobenzothiophenyl group, a benzocarbazolyl group, a dibenzocarbazolyl group, an imidazopyridinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzoxazinyl group, or a pyridobenzothiazinyl group, each unsubstituted or substituted with at least one $R_a$.

10. The condensed cyclic compound of claim 1, wherein $Ar_{11}$ and $Ar_{12}$ are each independently a group represented by one of Formulae 5-1 to 5-48:

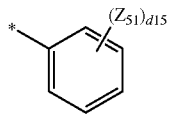

5-1

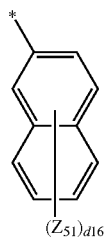

5-2

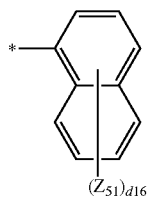

5-3

-continued

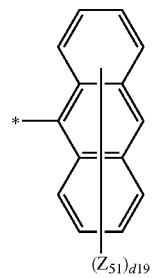

5-4

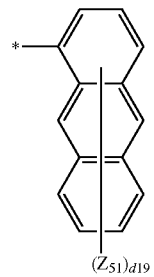

5-5

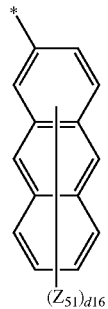

5-6

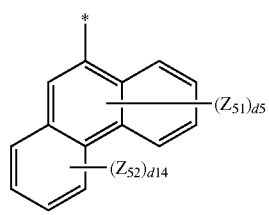

5-7

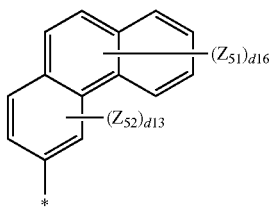

5-8

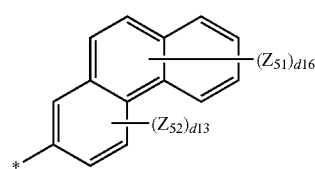

5-9

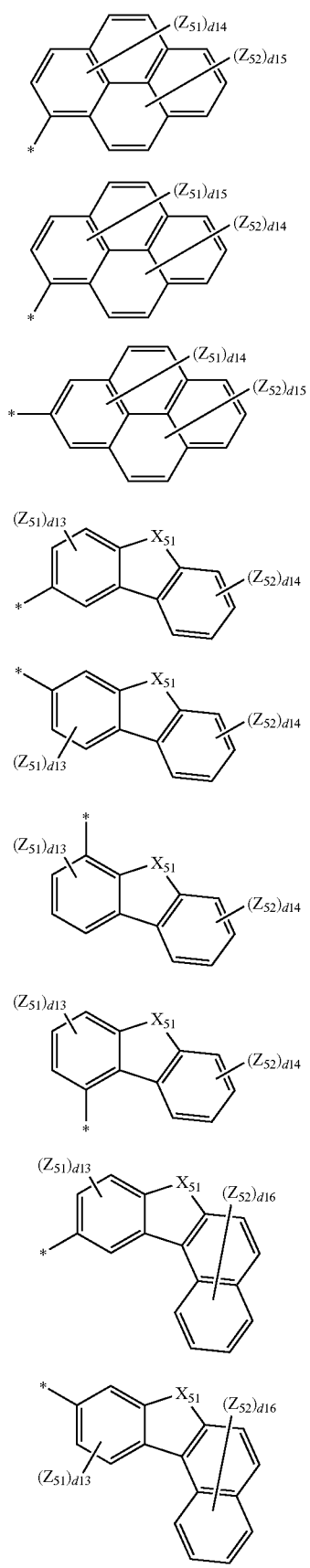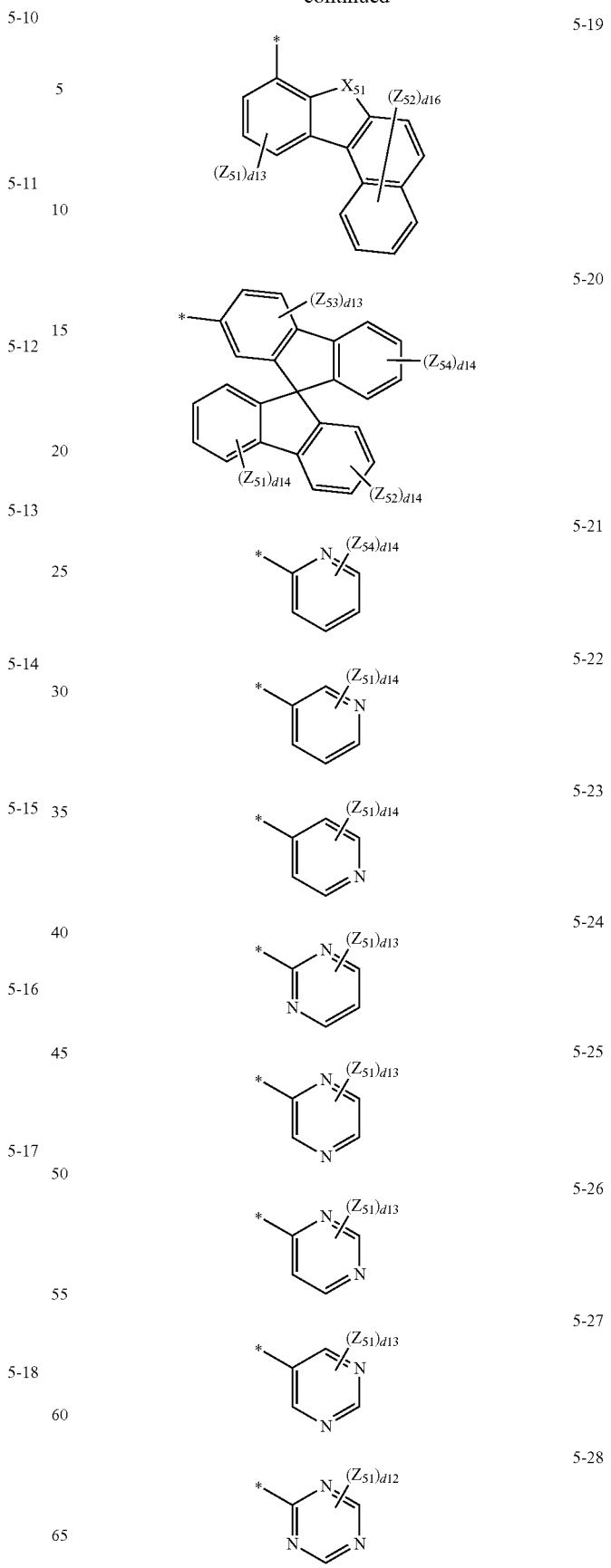

-continued
5-29 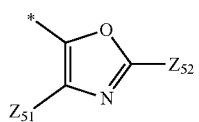
5-30 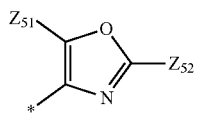
5-31 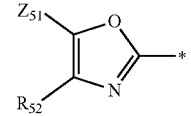
5-32 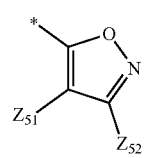
5-33 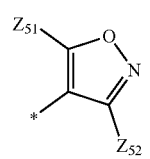
5-34 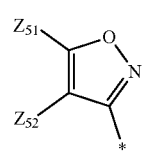
5-35 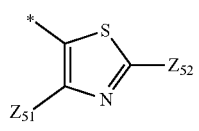
5-36 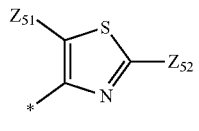
5-37 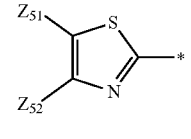
5-38 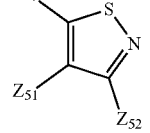
5-39 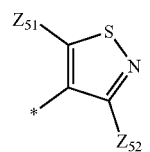
-continued
5-40 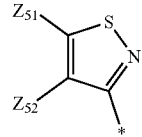
5-41 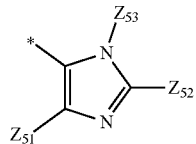
5-42 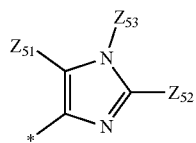
5-43 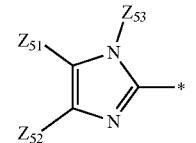
5-44 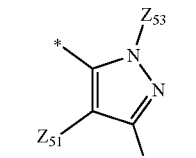
5-45 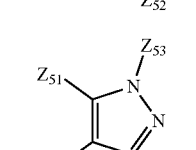
5-46 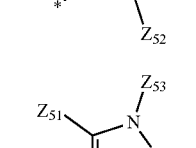
5-47 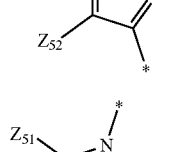
5-48 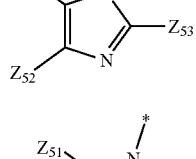
wherein, in Formulae 5-1 to 5-48,
$X_{51}$ is O, S, N($Z_{53}$), C($Z_{53}$)($Z_{54}$), or Si($Z_{53}$)($Z_{54}$),
$Z_{51}$ to $Z_{54}$ are each independently hydrogen, deuterium, —F, —Cl, —Br, —I, a hydroxyl group, a cyano group, a nitro group, an amino group, a $C_1$-$C_{20}$ alkyl group, a $C_1$-$C_{20}$ alkoxy group, a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a spiro-bifluorenyl group, an anthracenyl group, a fluoranthenyl group, a triphenylenyl group, a pyrenyl group, a chrysenyl group, a pyrrolyl group, an imidazolyl group, a pyrazolyl group, a pyridinyl group, a pyrazinyl group, a pyrimidinyl group, a pyridazinyl group, an indolyl group, a carbazolyl group, a phenanthridinyl group, an acridinyl group, a phenanthrolinyl group, an oxazolyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, a triazinyl group, a dibenzofuranyl group, or a dibenzothiophenyl group, d12 is an integer of 1 to 2,
d13 is an integer of 1 to 3,
d14 is an integer of 1 to 4,
d15 is an integer of 1 to 5,
d16 is an integer of 1 to 6,
d19 is an integer of 1 to 9, and
* is a binding site to an adjacent atom.

11. The condensed cyclic compound of claim 1, wherein $R_{11}$, $R_{12}$, and $R_a$ are each independently:

hydrogen, deuterium, —F, —Cl, —Br, —I, a hydroxyl group, a cyano group, a nitro group, an amino group, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one deuterium, —F, —Cl, —Br, —I, a hydroxyl group, a cyano group, a nitro group, an amino group, or any combination thereof;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzoxazinyl group, or a pyridobenzothiazinyl group, each unsubstituted or substituted with at least one deuterium, —F, —Cl, —Br, —I, a hydroxyl group, a cyano group, a nitro group, an amino group, a $C_1$-$C_{20}$ alkyl group, a $C_1$-$C_{20}$ alkoxy group, a phenyl group, a biphenyl group, a terphenyl group, or any combination thereof; or —Si($Q_1$)($Q_2$)($Q_3$), —N($Q_4$)($Q_5$), or —B($Q_6$)($Q_7$), and $Q_1$ to $Q_7$ are each independently hydrogen, deuterium, a $C_1$-$C_{10}$ alkyl group, a phenyl group, a naphthyl group, a fluorenyl group, a carbazolyl group, a dibenzofuranyl group, a dibenzothiophenyl group, or a biphenyl group.

12. The condensed cyclic compound of claim 1, wherein the condensed cyclic compound satisfies Inequality 1 and Inequality 2:

$$E(T1) < E(S1) < 2E(T1) \qquad \text{<Inequality 1>}$$

$$2E(T1) - E(S1) < 0.5 \text{ eV} \qquad \text{<Inequality 2>}$$

wherein, in Inequalities 1 and 2,
E(T1) is a lowest excitation triplet energy level (eV) of the condensed cyclic compound, and
E(S1) is a lowest excitation singlet energy level (eV) of the condensed cyclic compound.

13. The condensed cyclic compound of claim 1, wherein the condensed cyclic compound is one of Compounds 2 to 120 and Compounds 122 to 800:

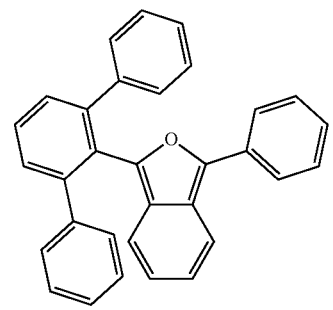

2

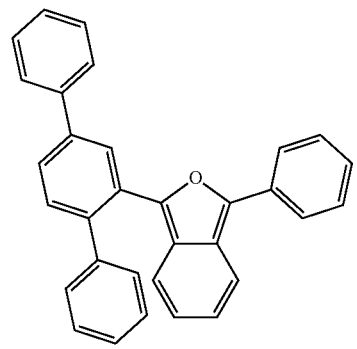

3

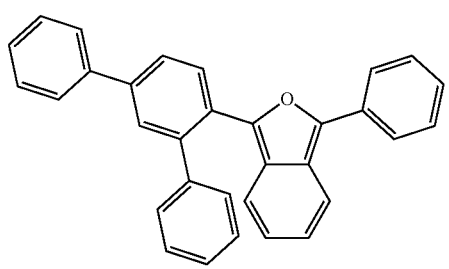

4

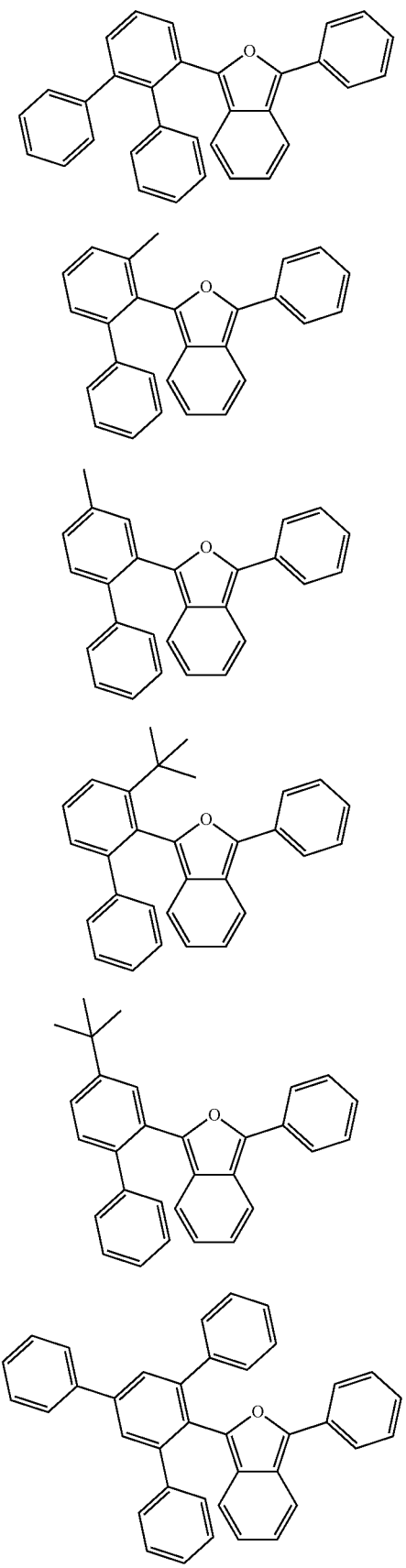
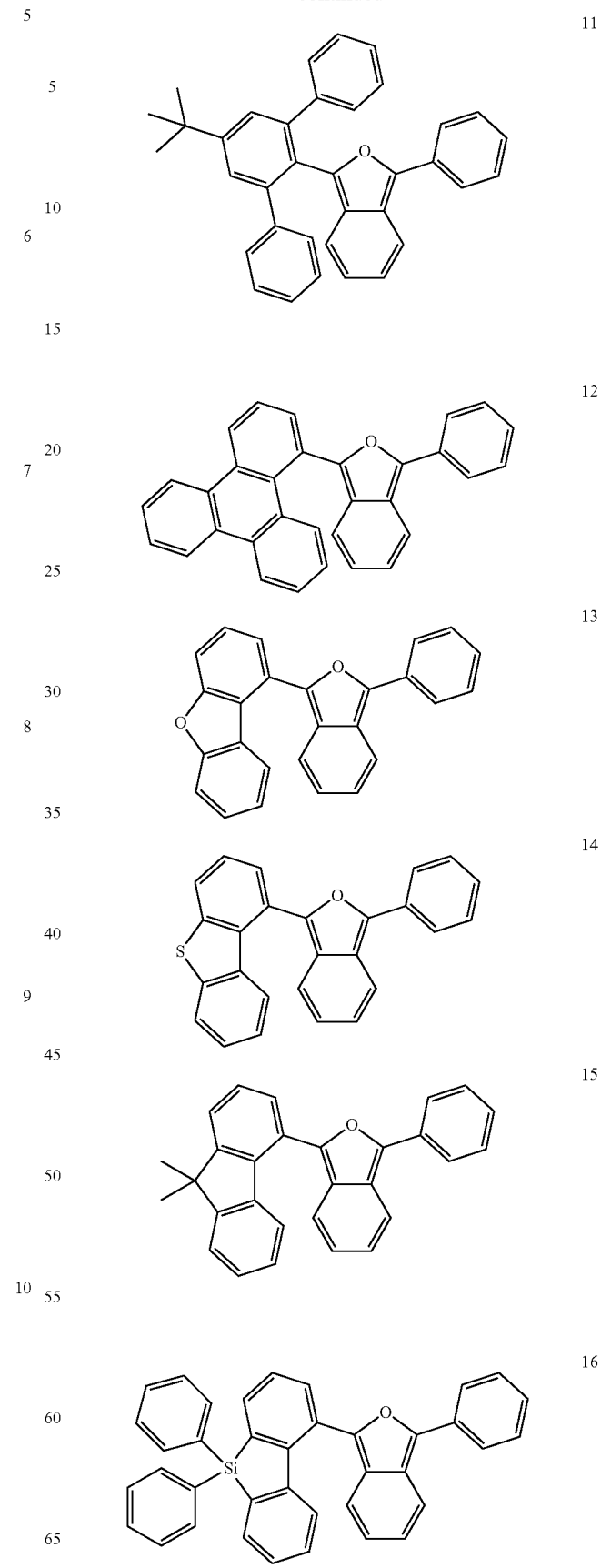

17
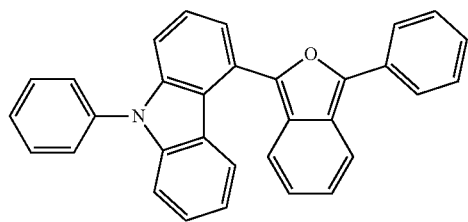
18
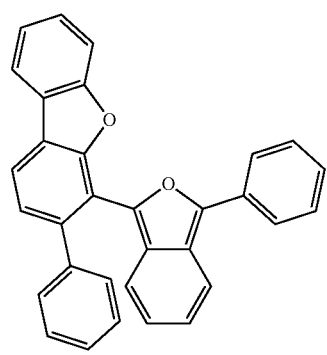
19
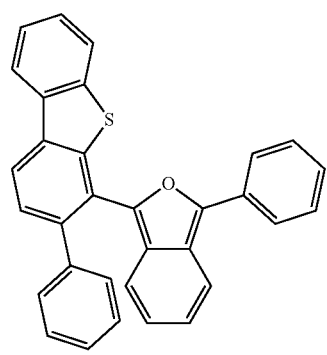
20
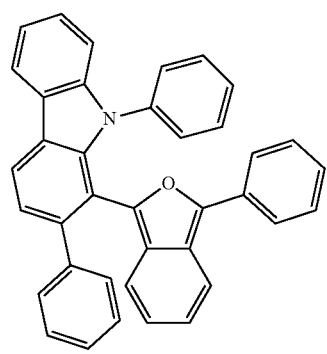
21
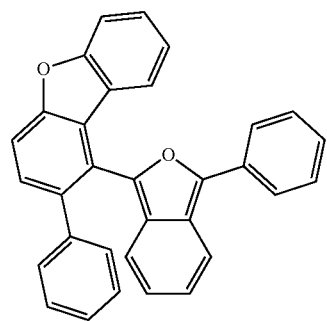
22
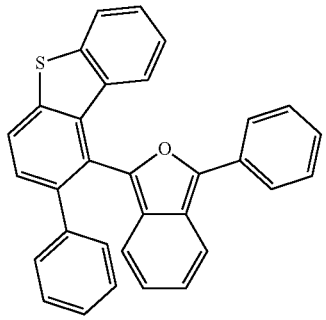
23
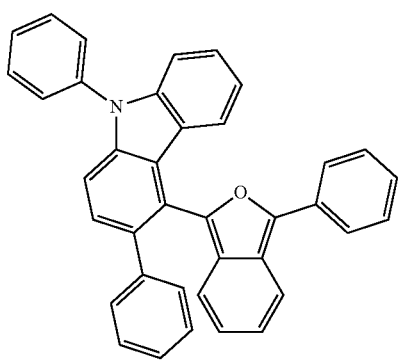
24
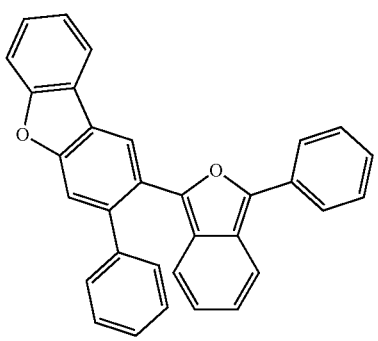
25
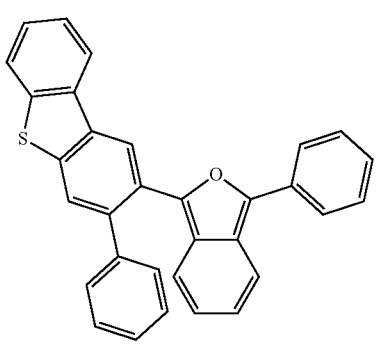

26
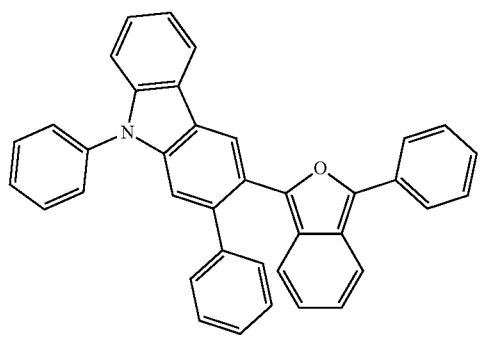
27
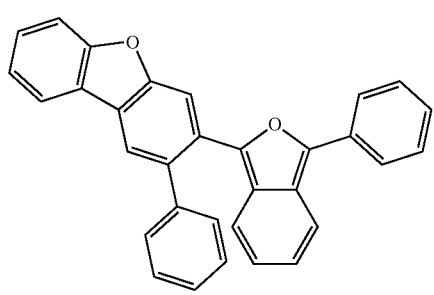
28
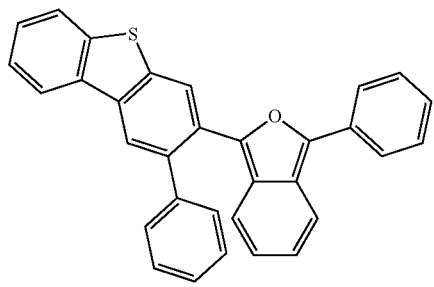
29
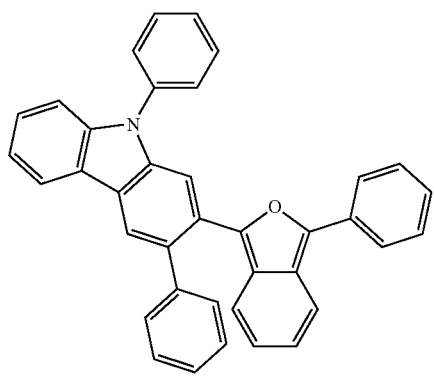
30
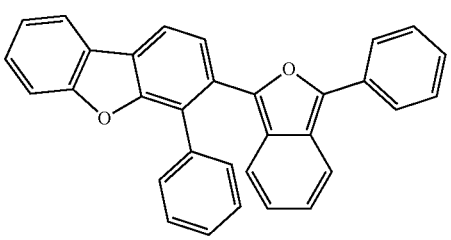
31
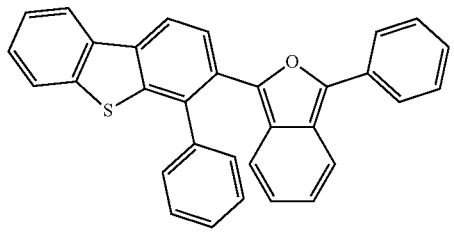
32
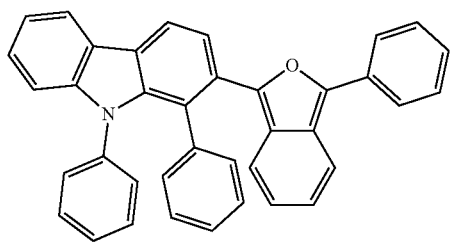
33
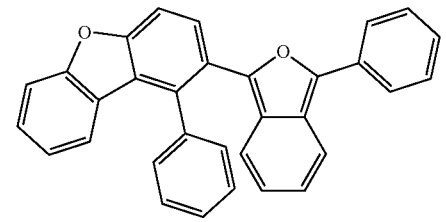
34
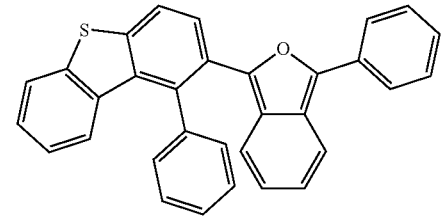
35
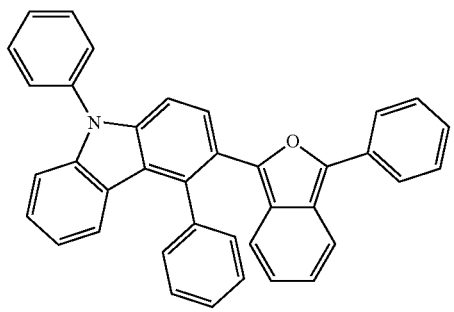
36
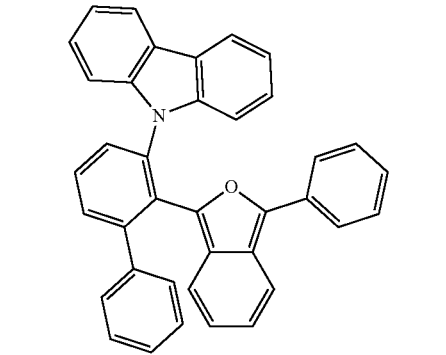

37
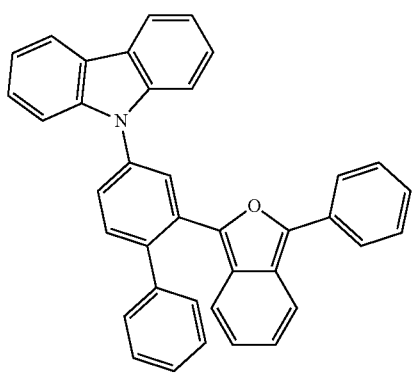
38
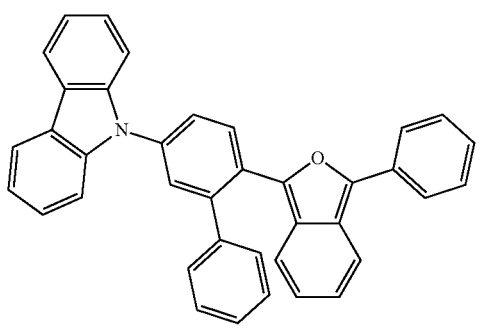
39
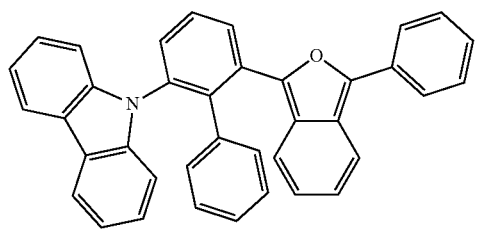
40
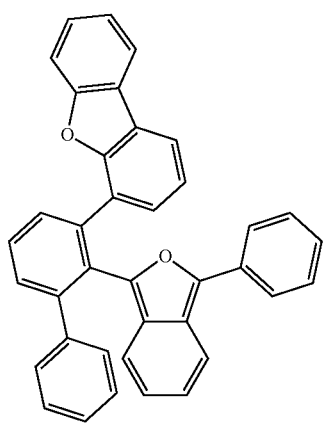
41
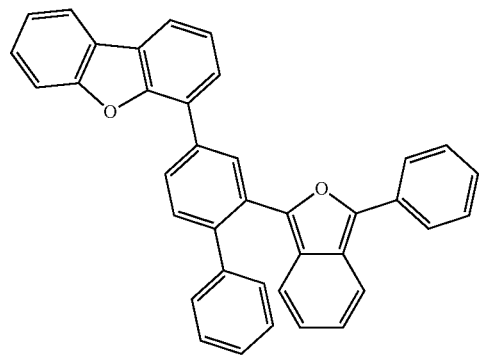
42
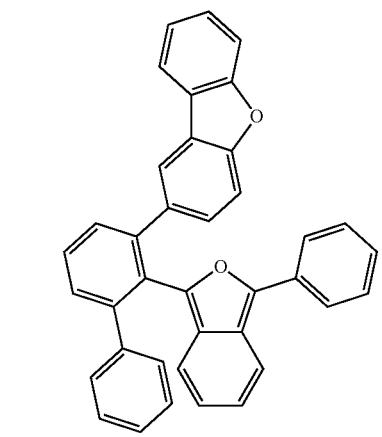
43
44

45
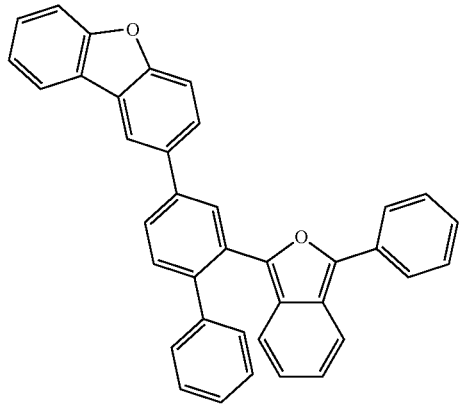
46
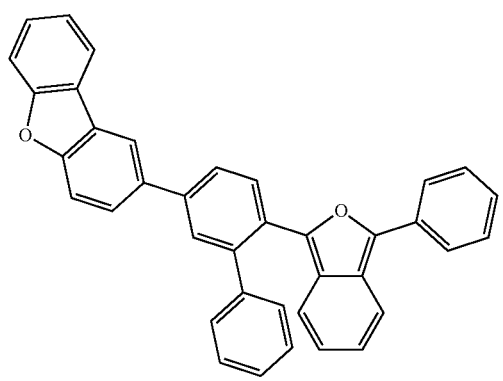
47
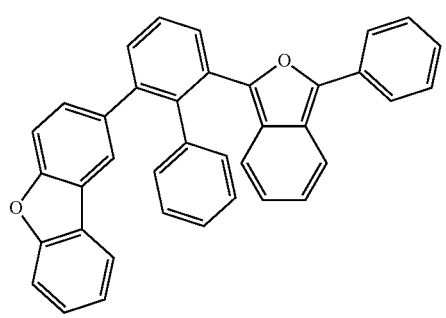
48
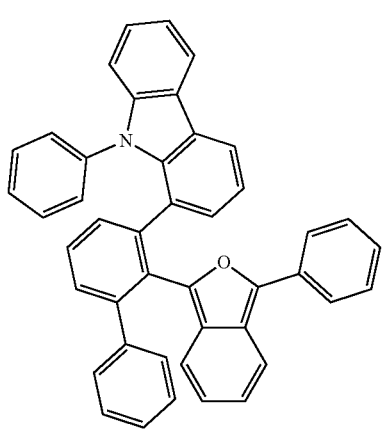
49
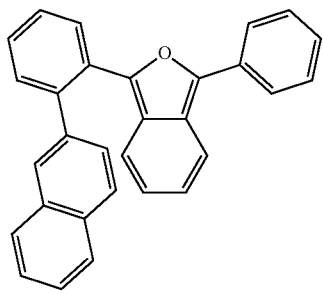
50
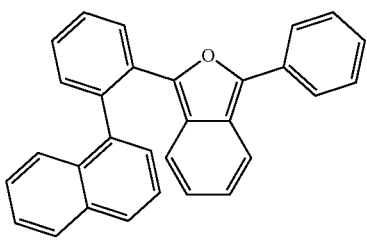
51
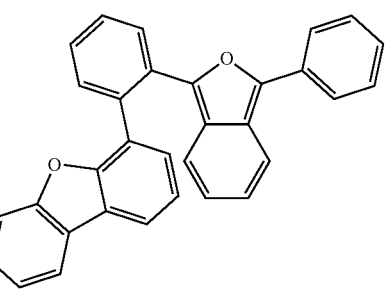
52
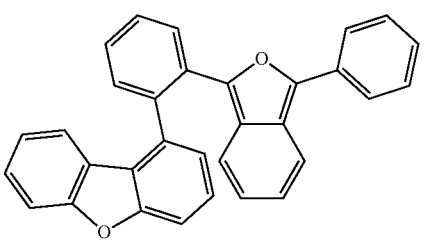
53
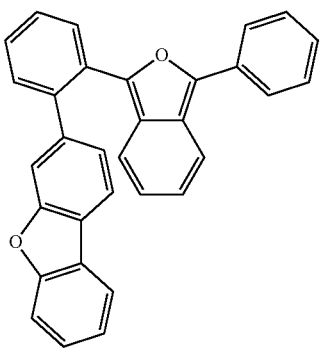

54
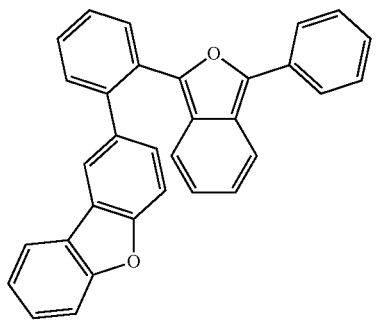
55
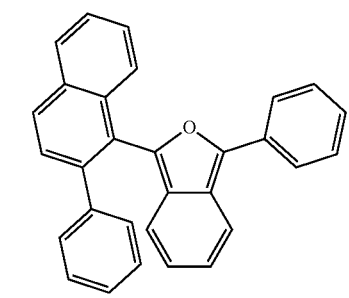
56
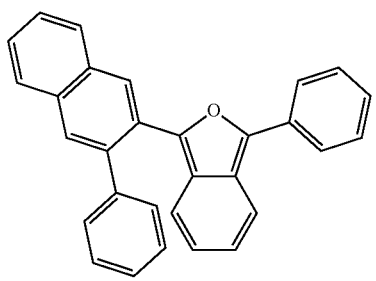
57
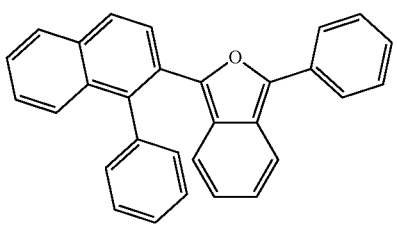
58
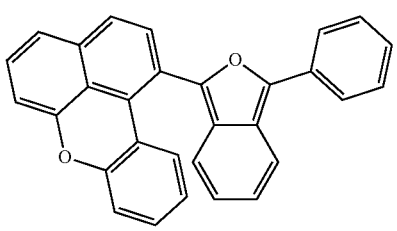
59
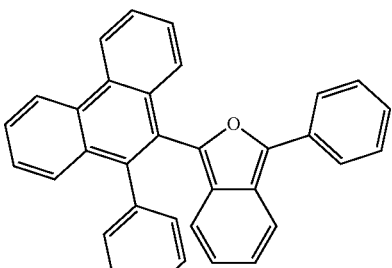
60
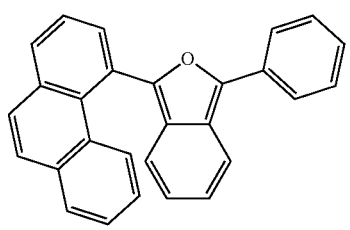
61
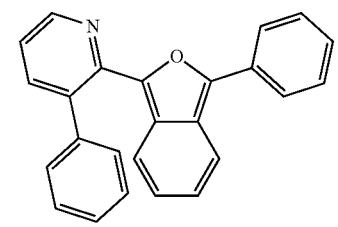
62
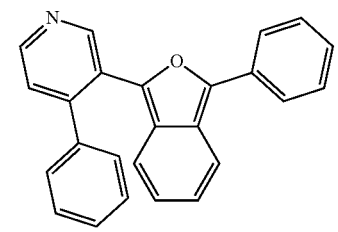
63
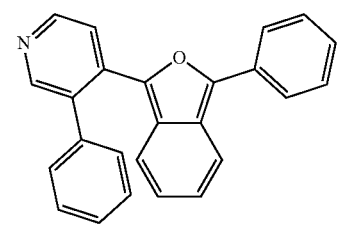
64
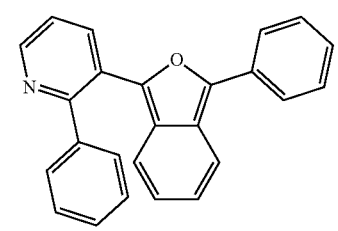

65
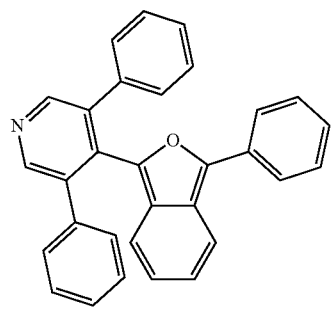
66
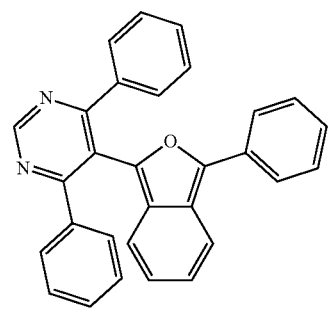
67
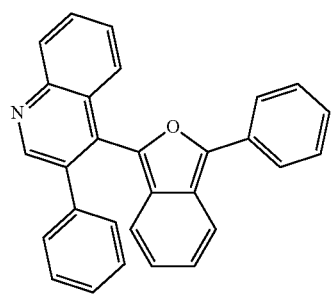
68
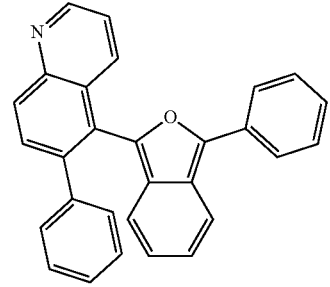
69
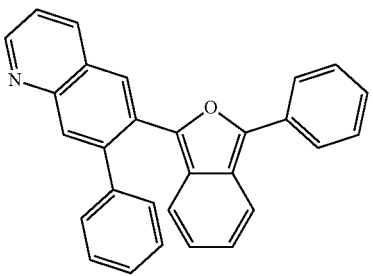
70
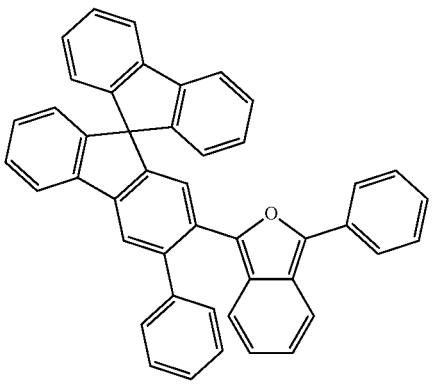
71
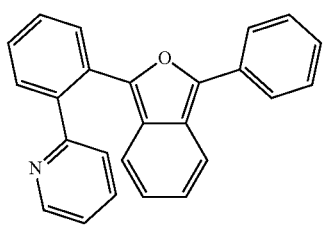
72
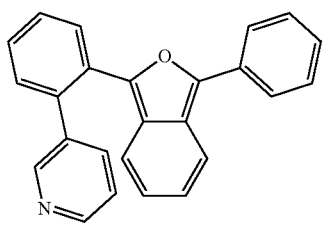 [SMILES: c1ccc(-c2ccccc2-c2oc(-c3ccccc3)c3ccccc23)cc1]
73
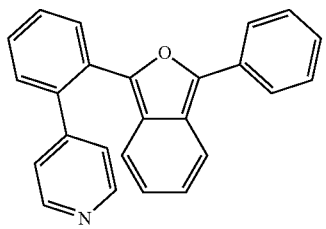
74
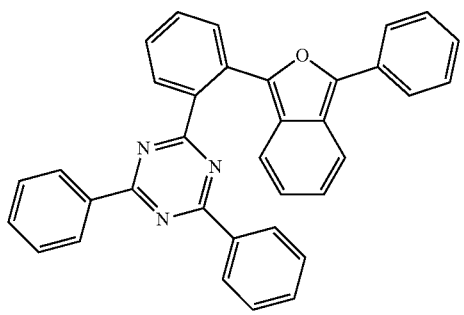

265
-continued
75
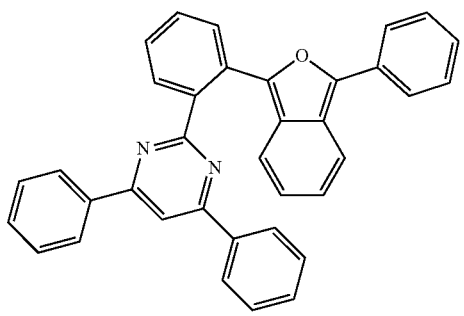
76
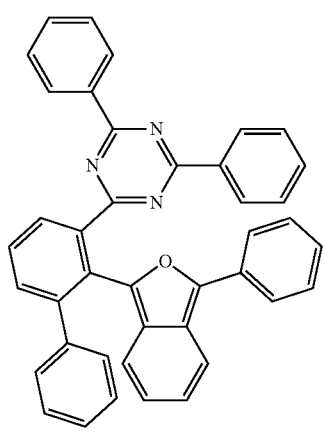
77
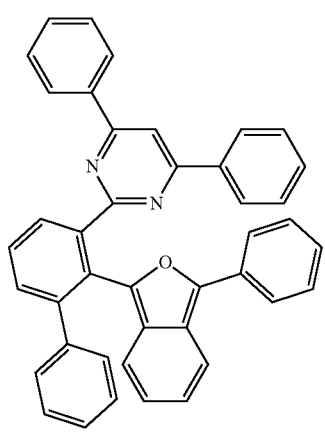
78
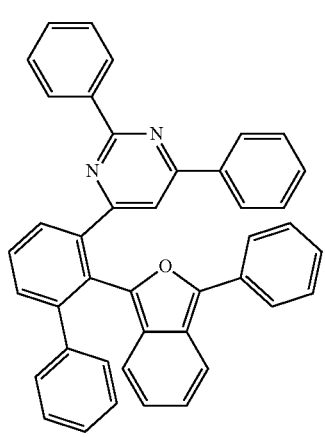
266
-continued
79
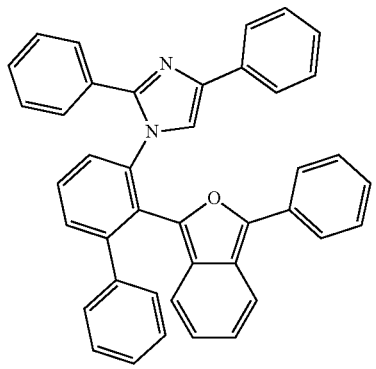
80
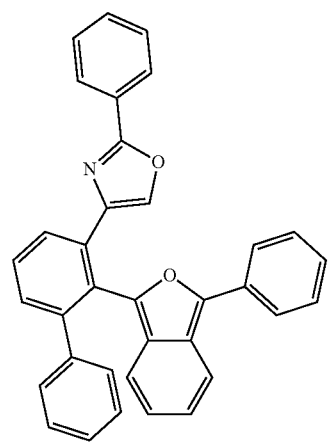
81
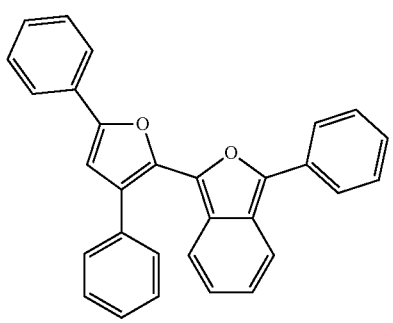
82
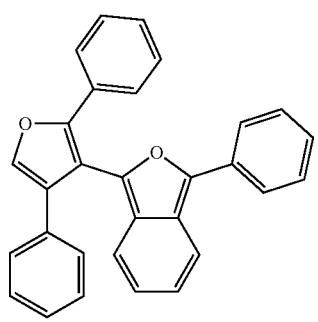

83
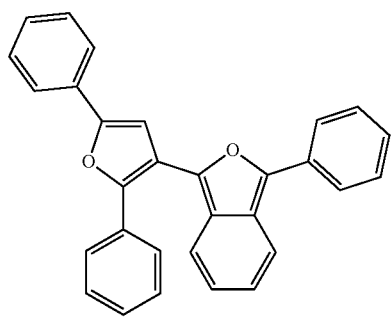
84
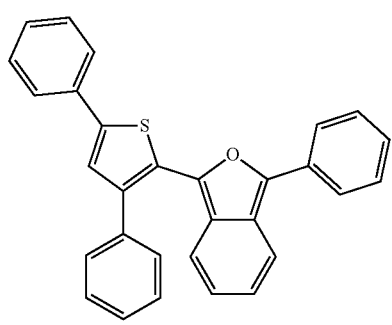
85
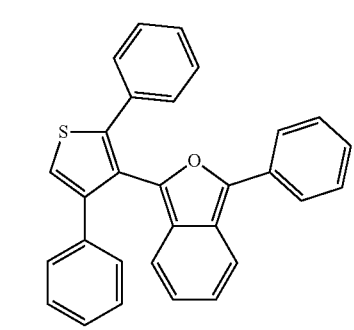
86
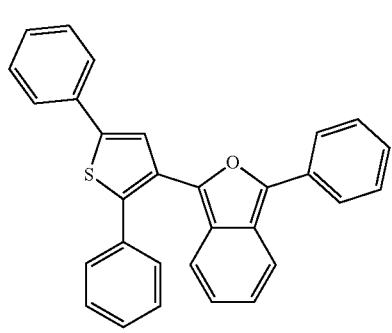
87
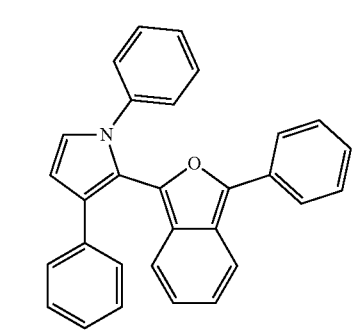
88
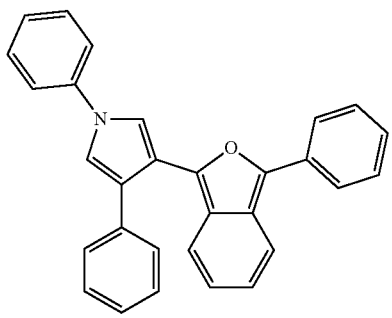
89
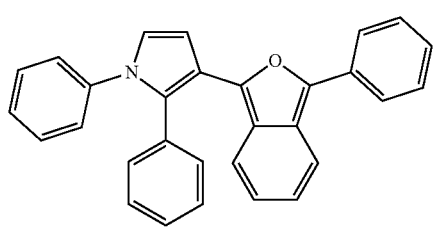
90
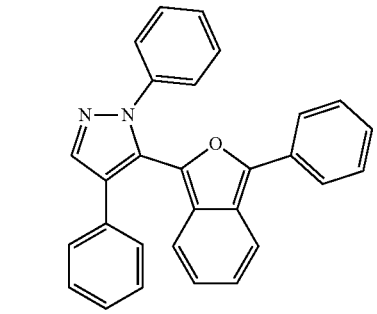
91
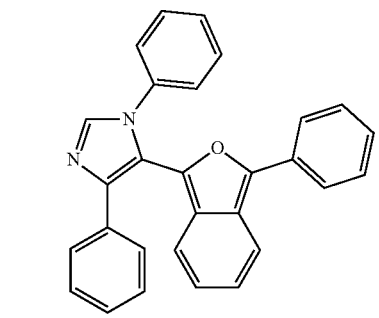
92
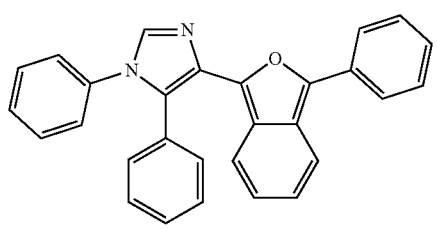
93
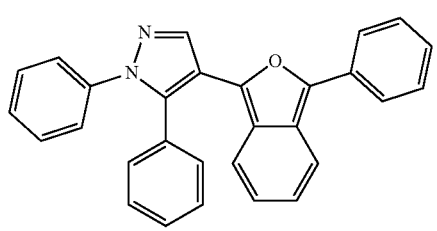

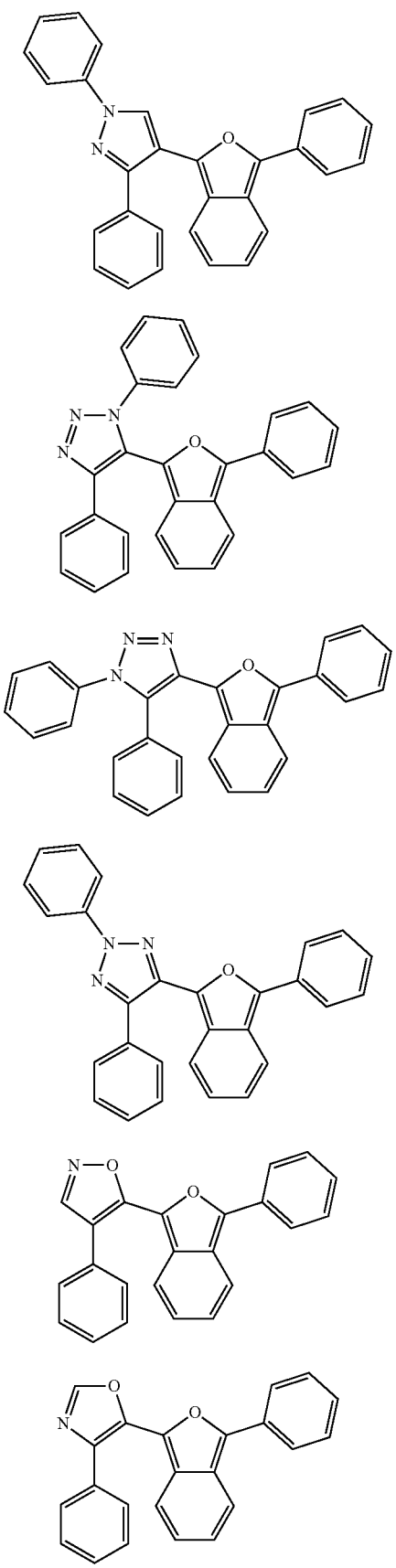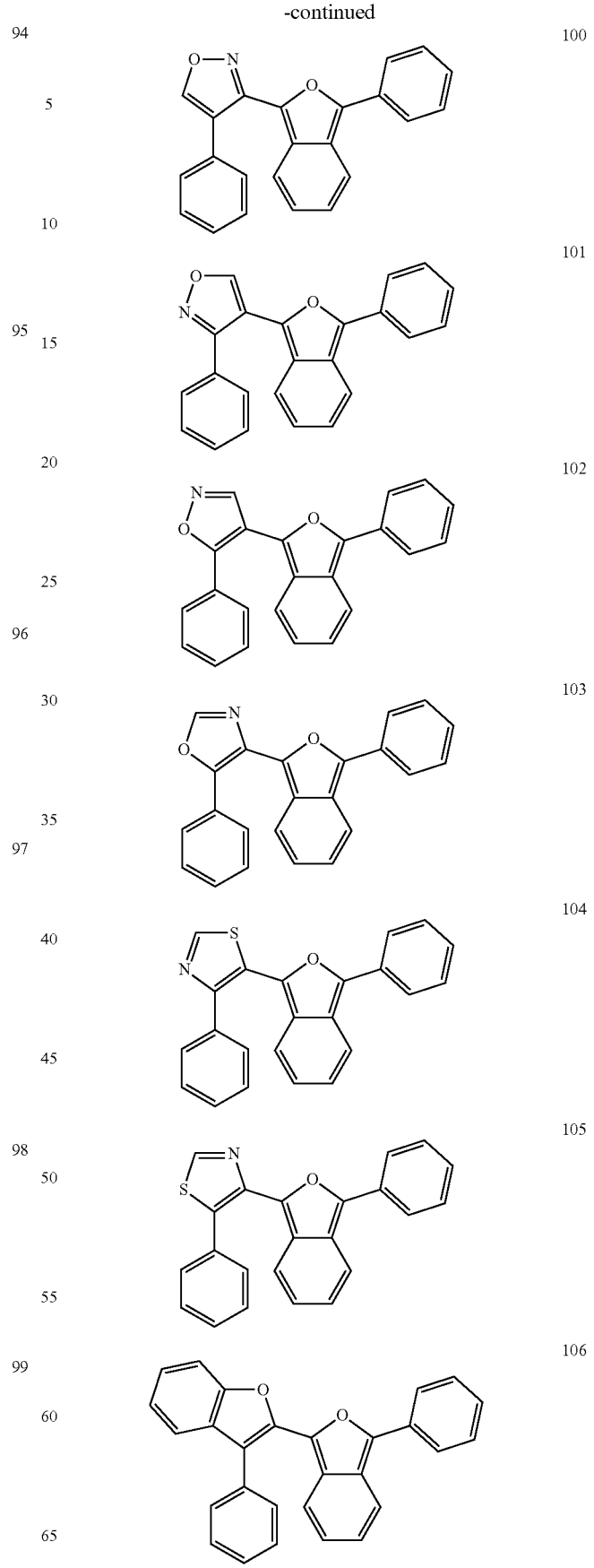

107 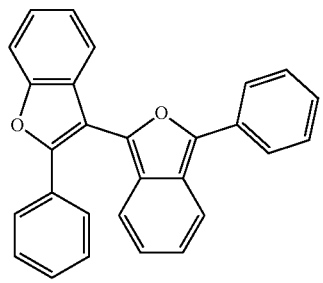
108 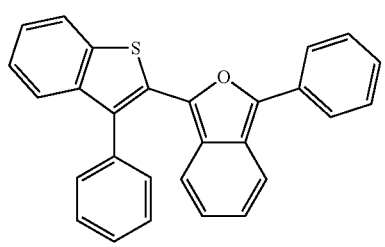
109 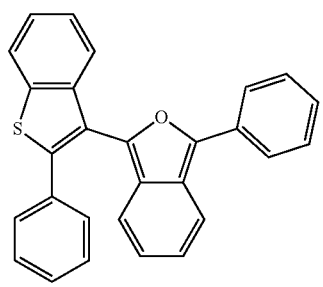
110 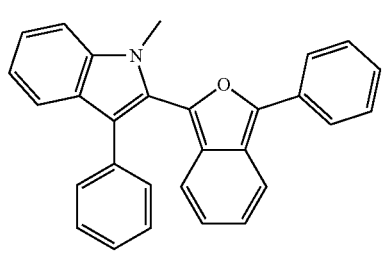
111 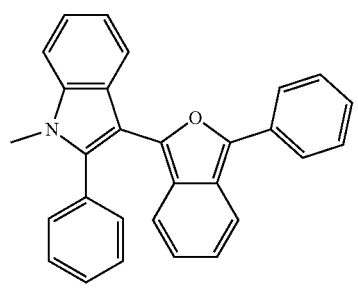
112 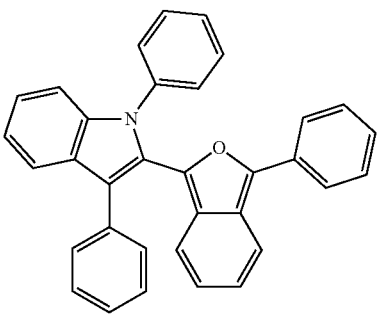
113 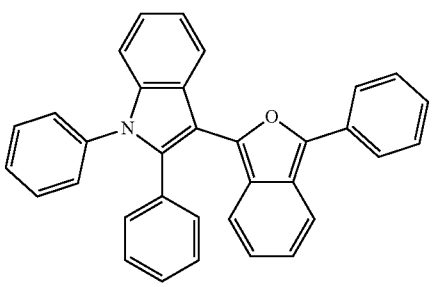
114 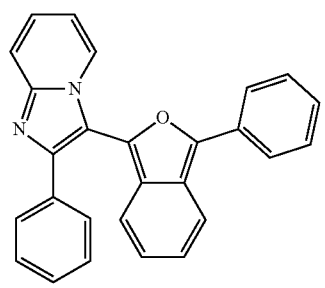
115 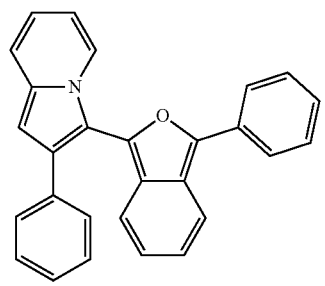
116 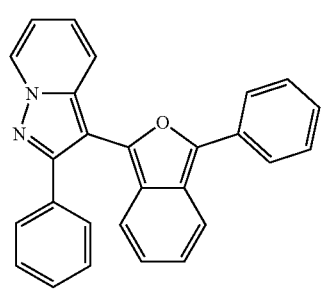

117
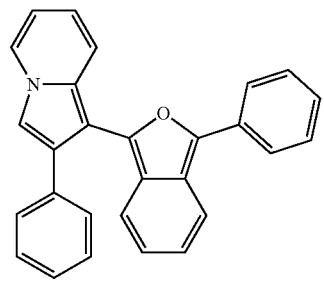
118
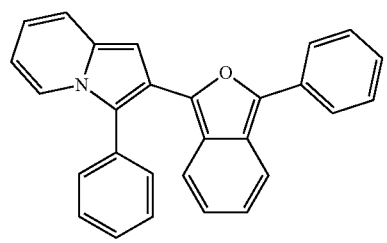
119
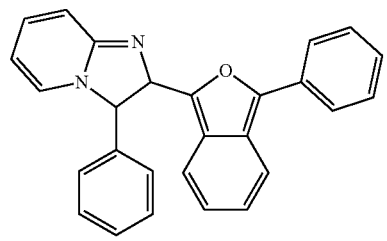
120
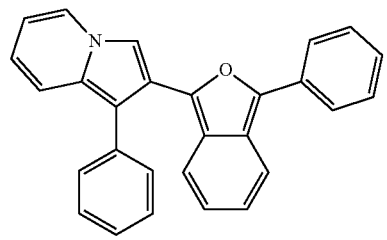
122
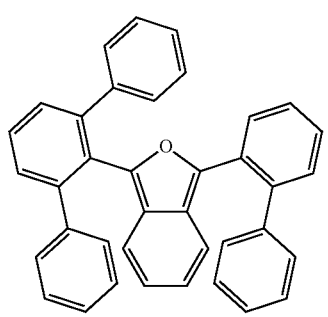
123
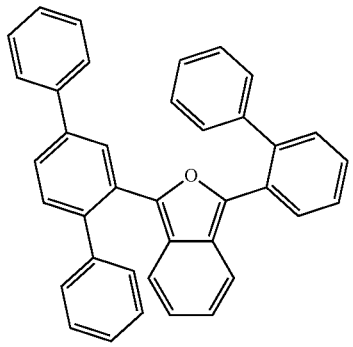
124
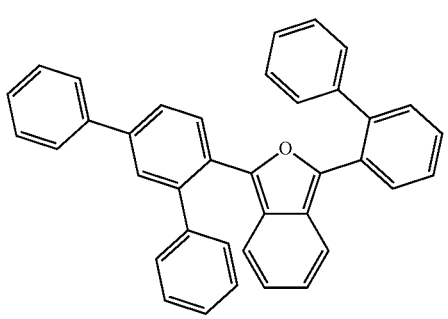
125
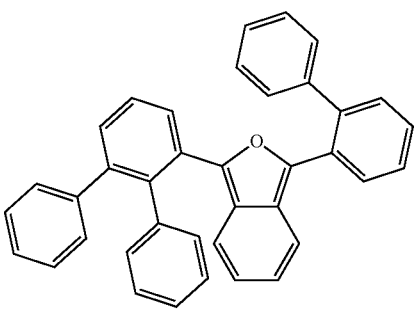
126
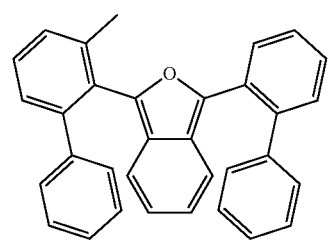
127
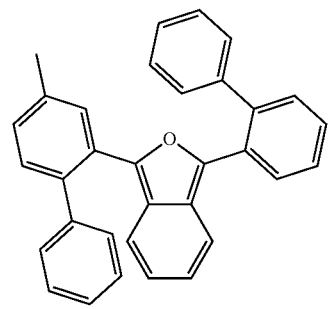

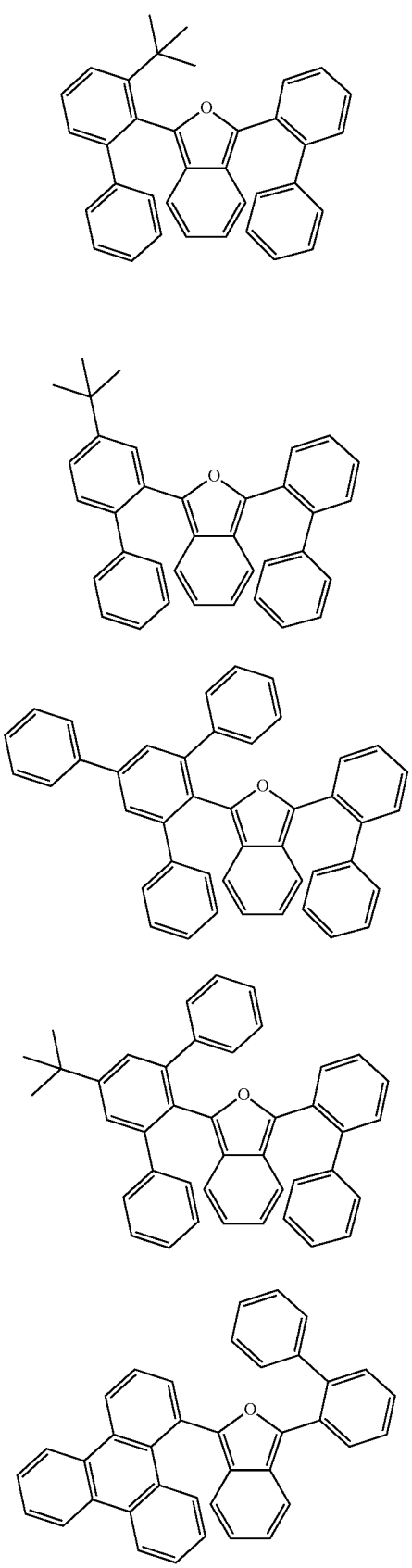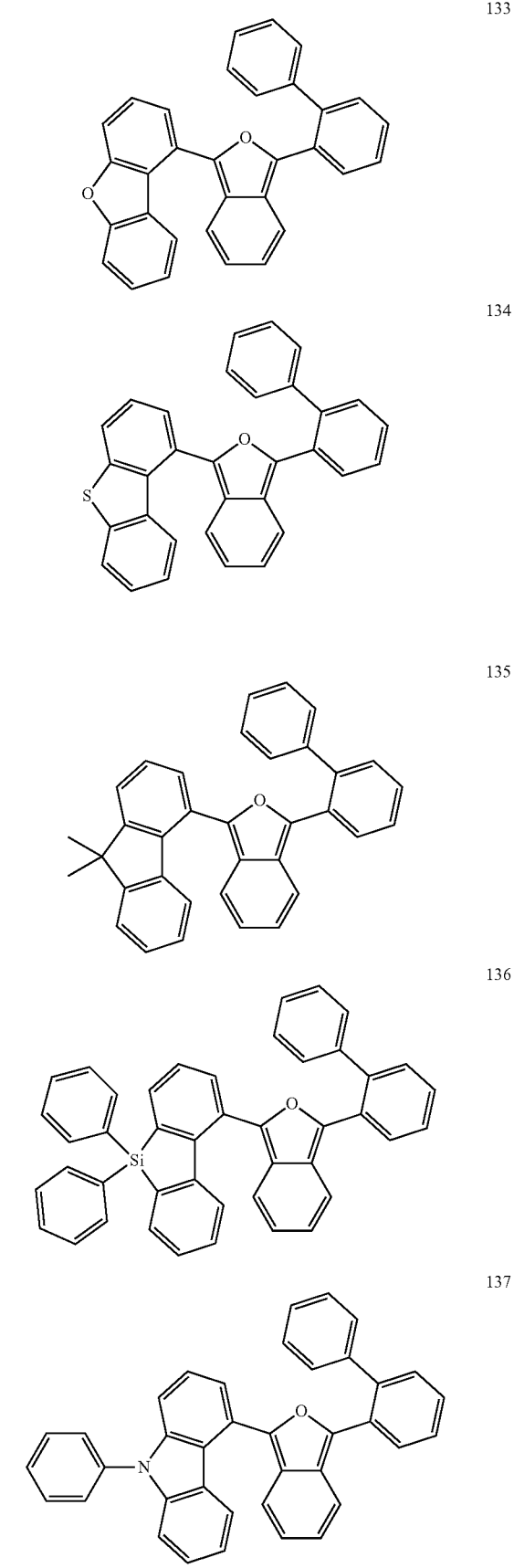

138
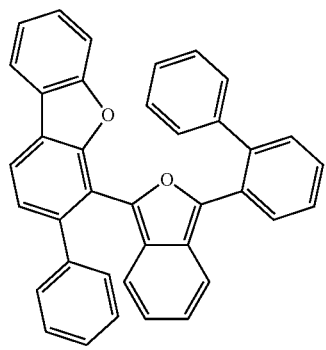
139
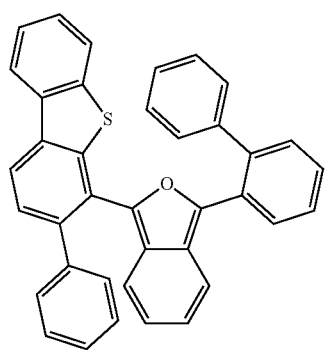
140
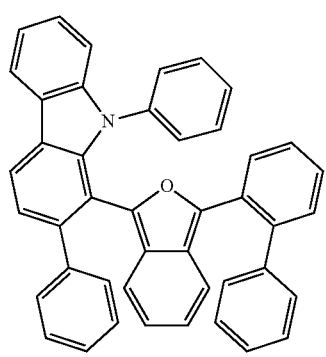
141
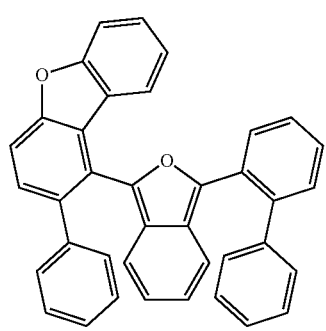
142
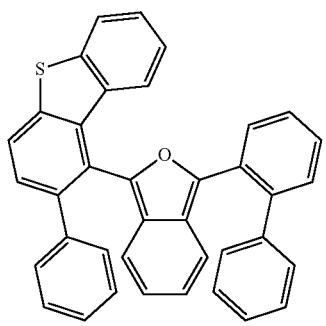
143
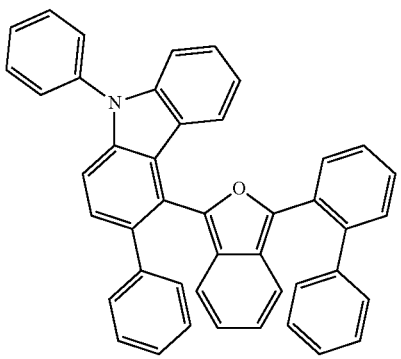
144
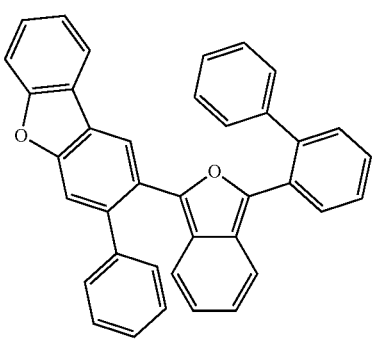
145
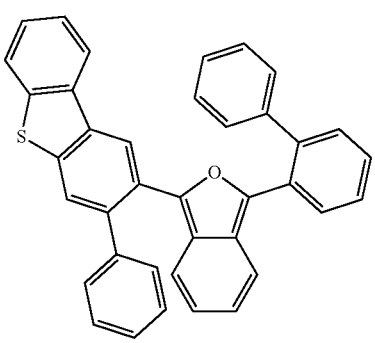

146
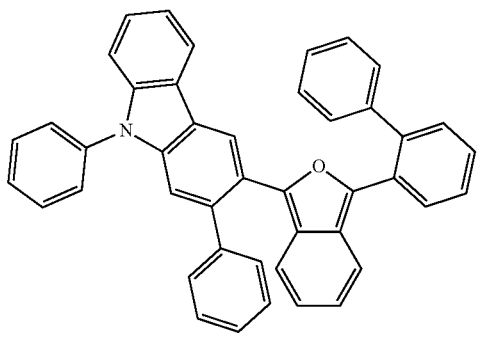
147
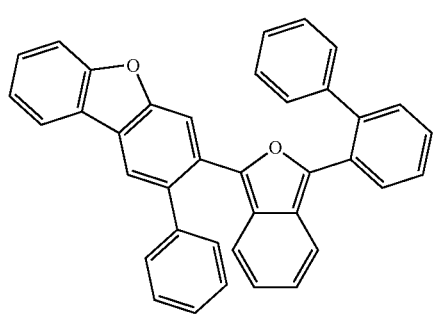
148
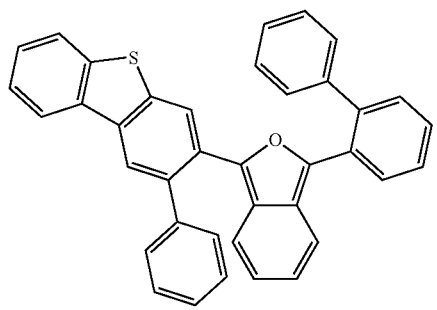
149
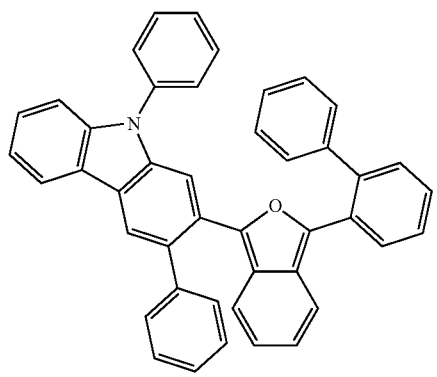
150
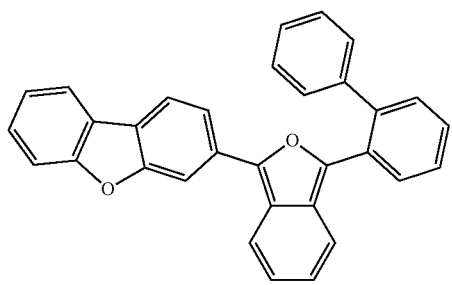
151
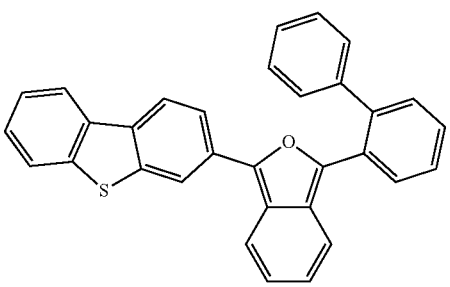
152
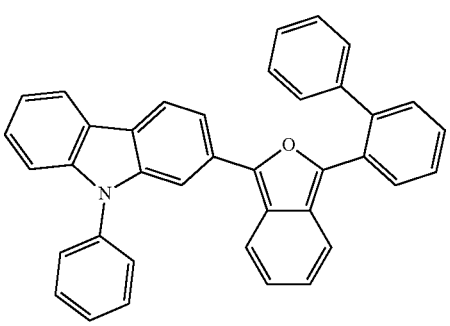
153
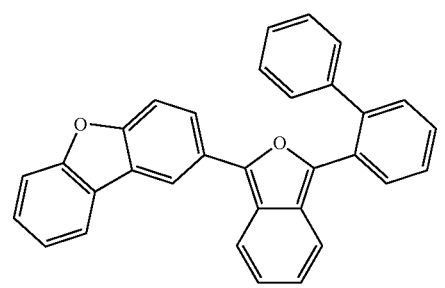
154
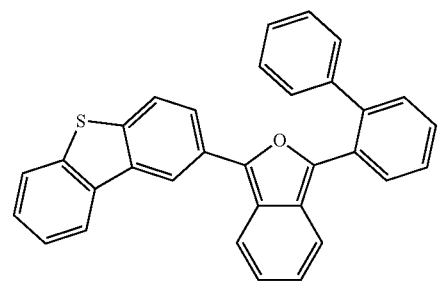
155
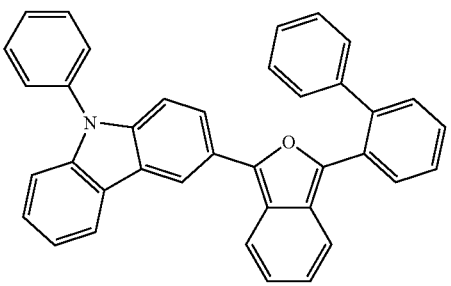

156
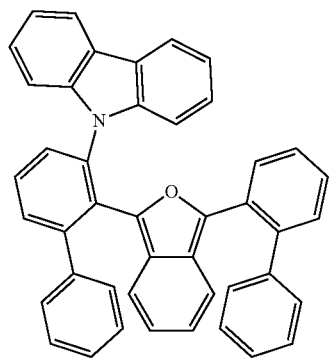
157
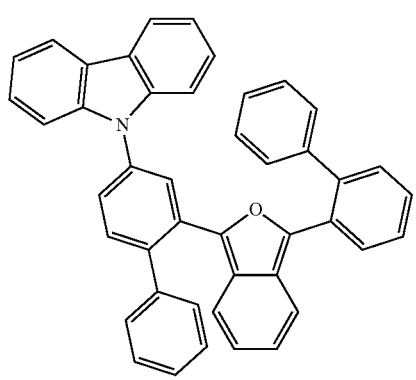
158
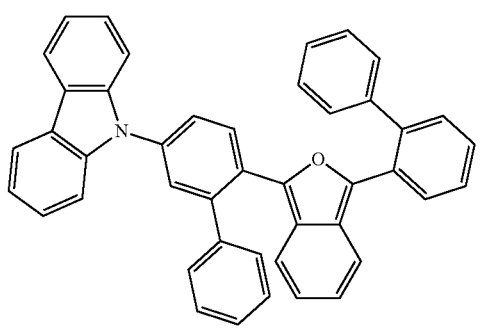
159
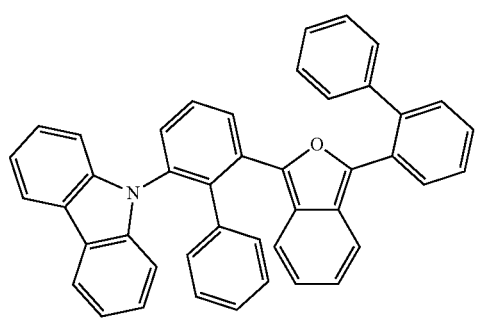
160
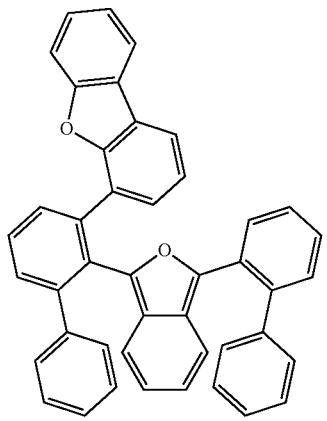
161
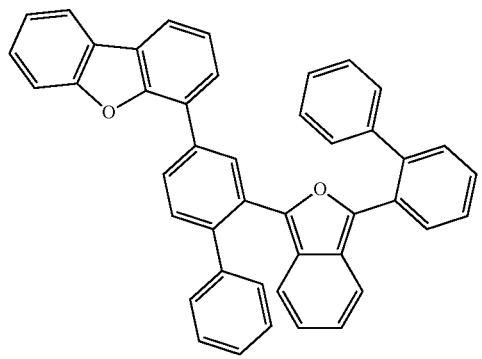
162
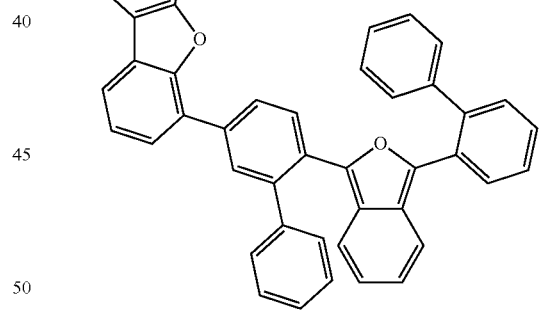
163
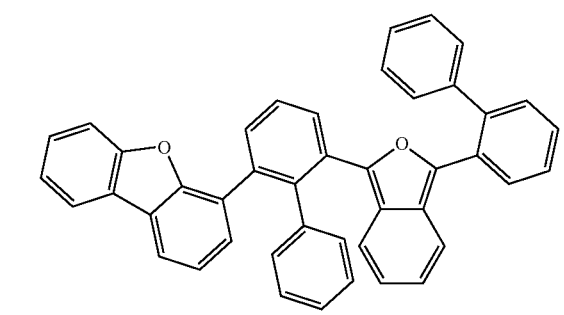

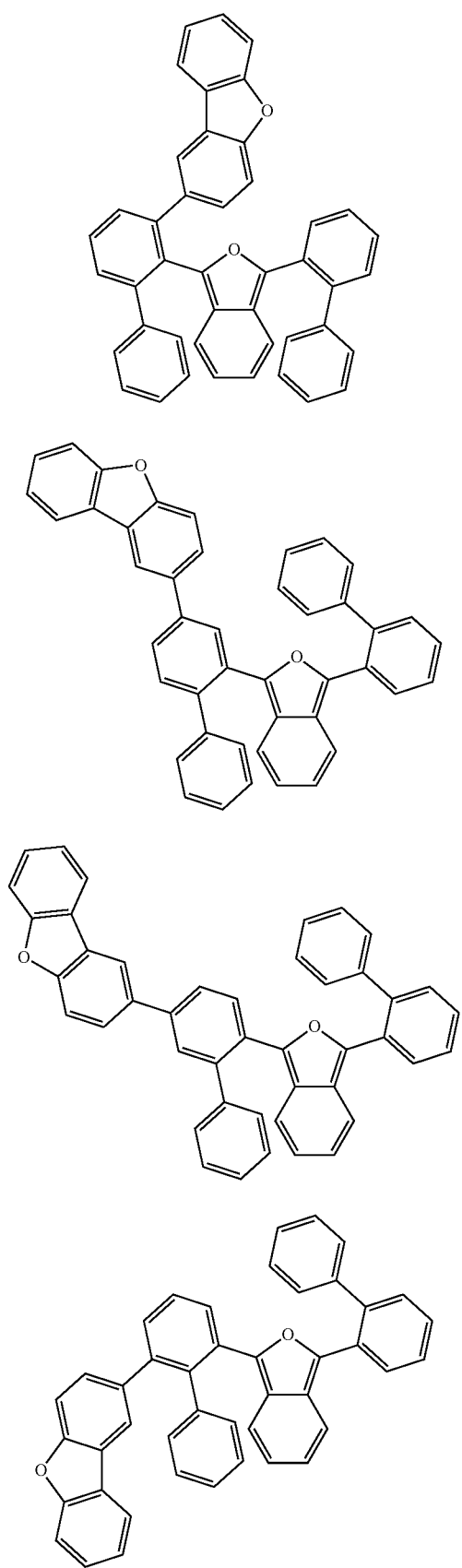
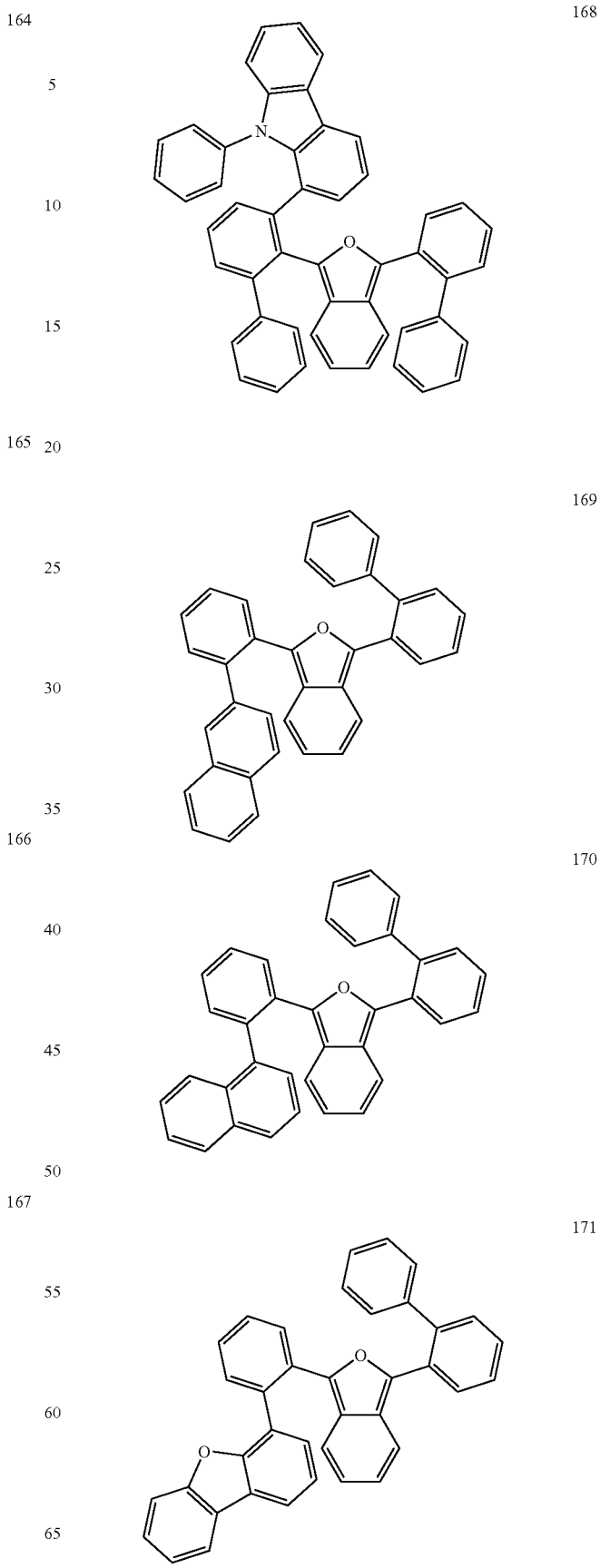

172 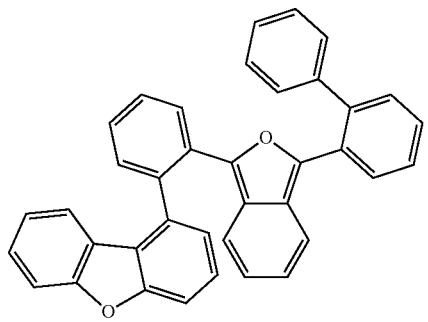
173 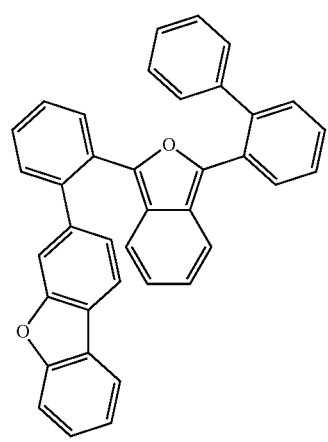
174 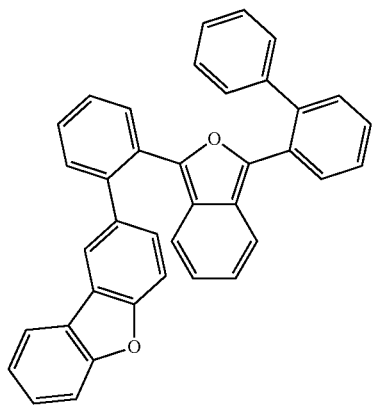
175 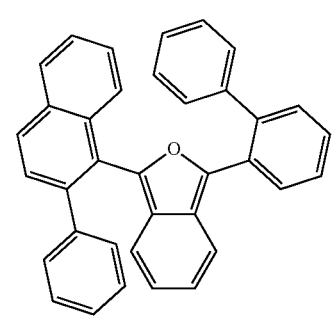
176 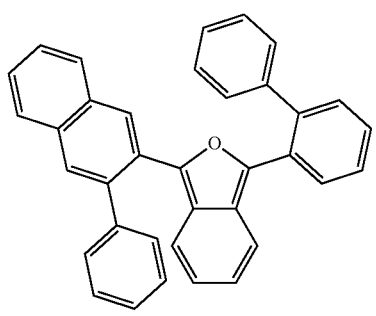
177 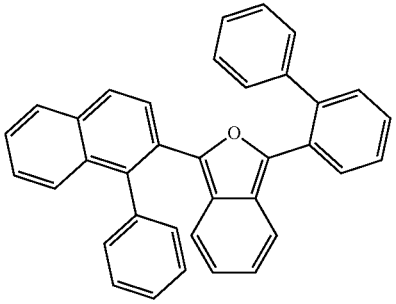
178 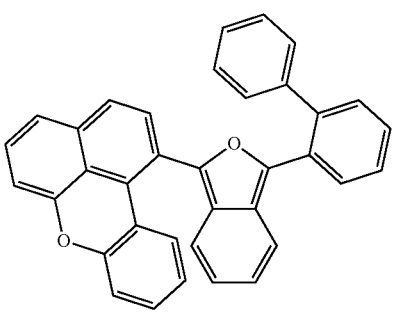
179 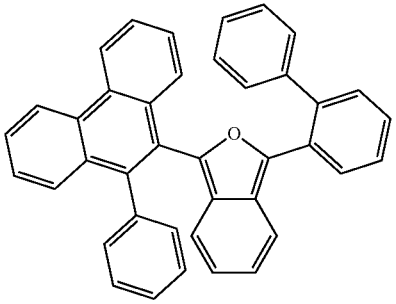
180 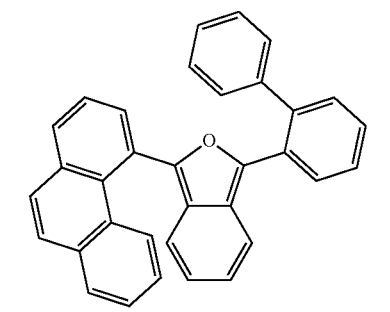

181
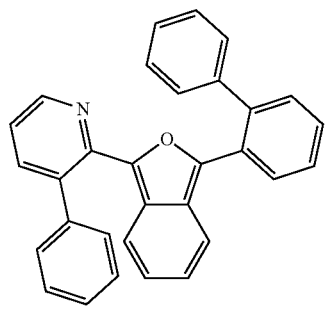
182
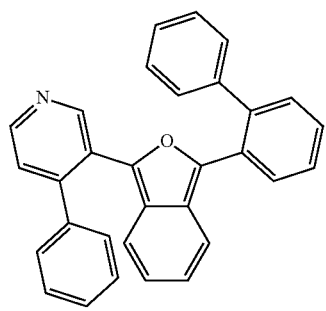
183
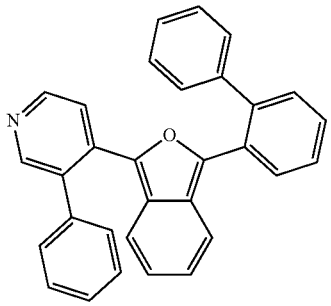
184
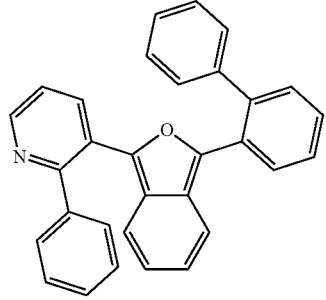 [SMILES: c1ccc(-c2ccccc2-c2oc(-c3ccccc3-c3ccccc3)c3ccccc23)cc1]
185
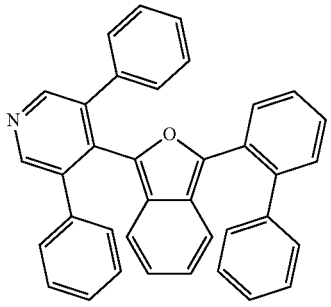
186
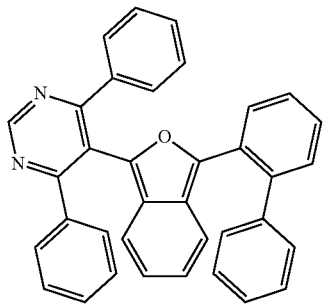
187
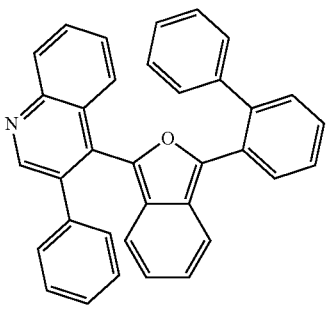
188
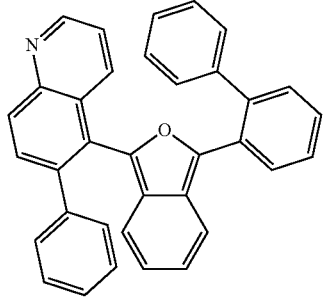
189
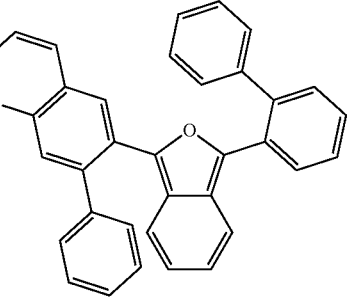
190
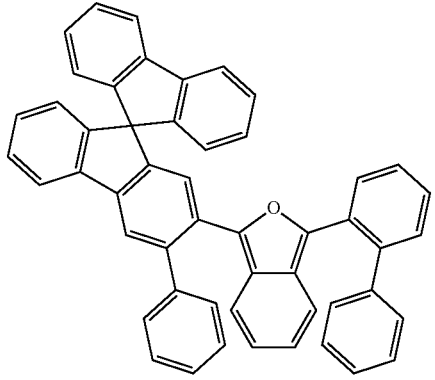

191
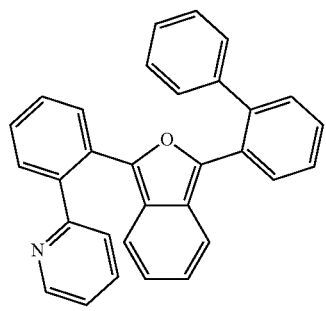
192
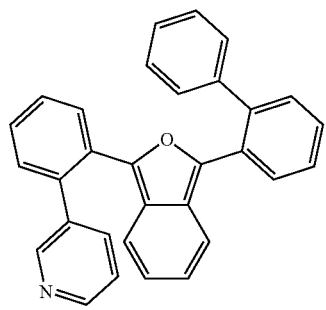
193
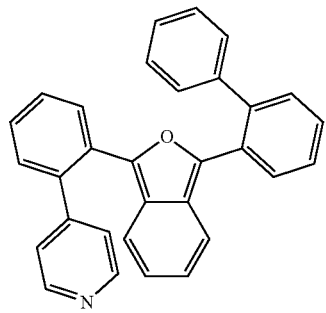
194
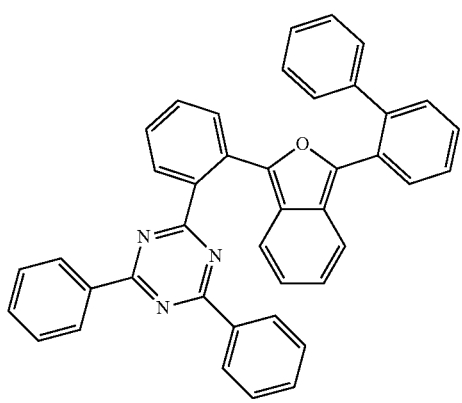
195
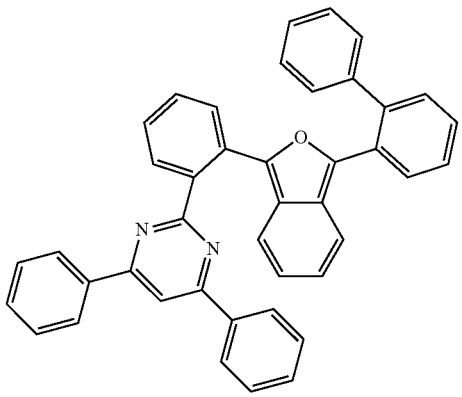
196
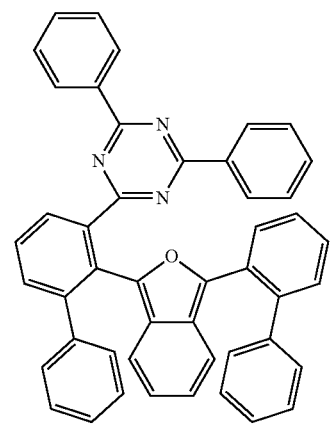
197
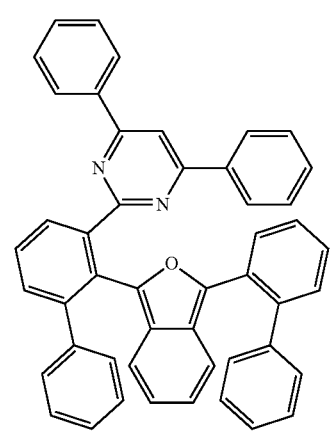

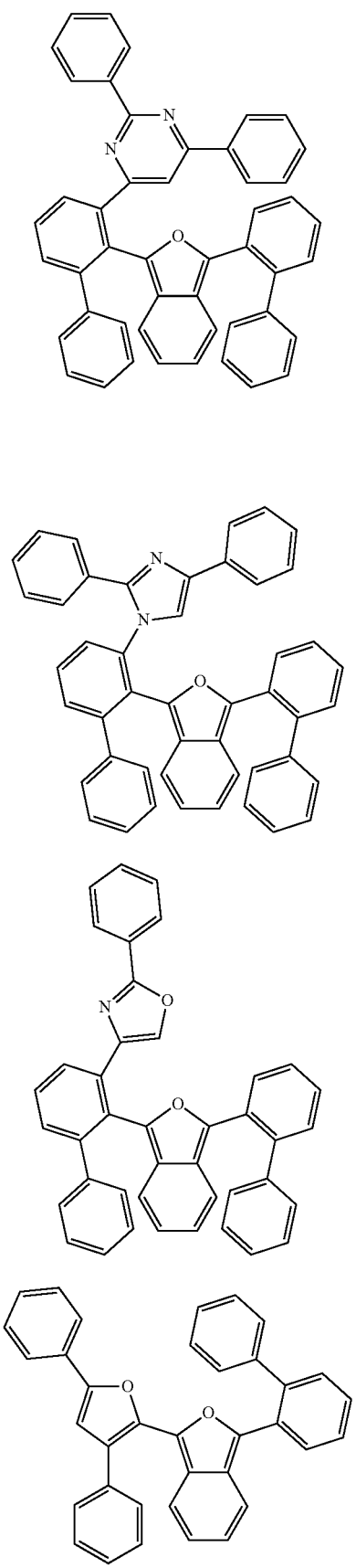
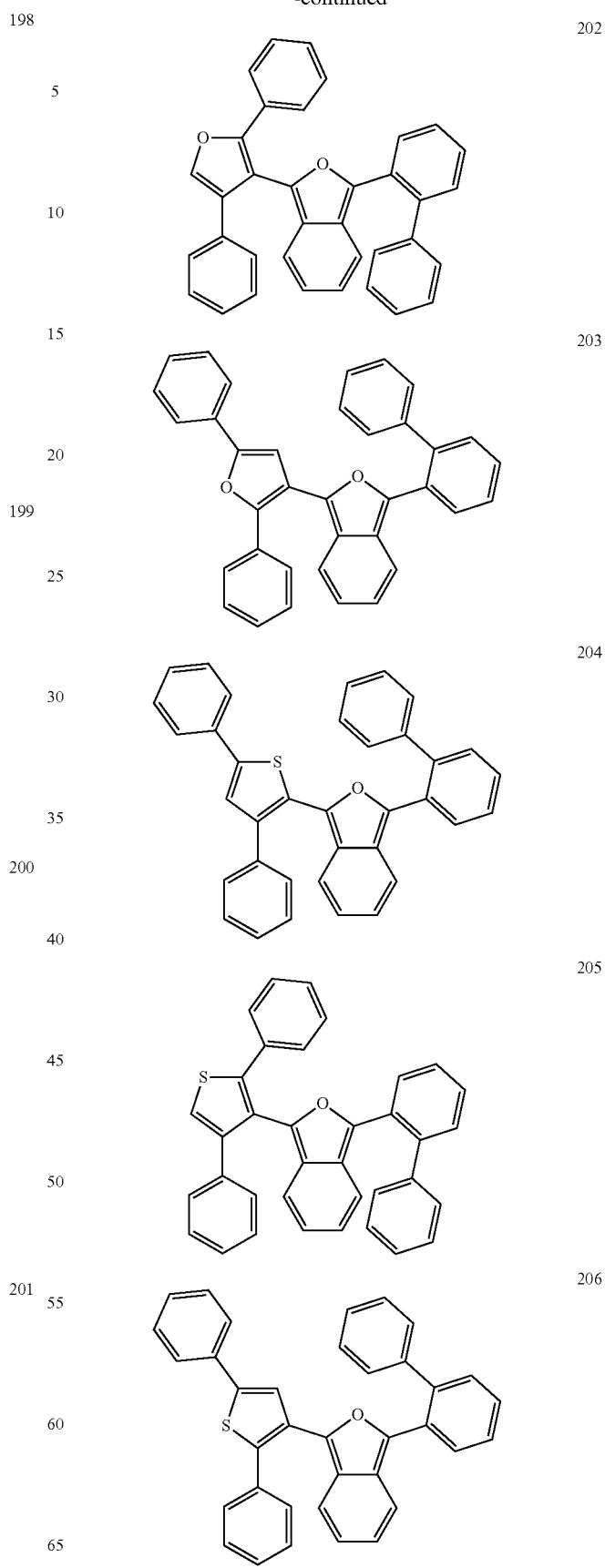

| 293 | 294 |
|---|---|
| 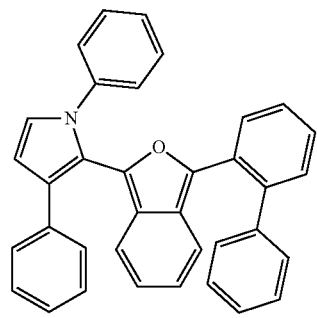 207 | 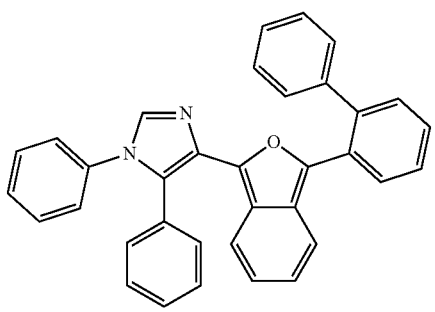 212 |
| 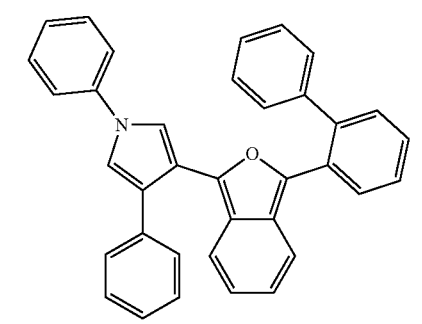 208 | 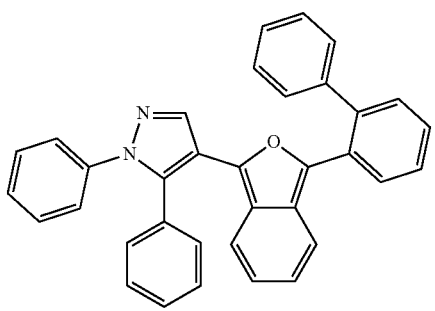 213 |
| 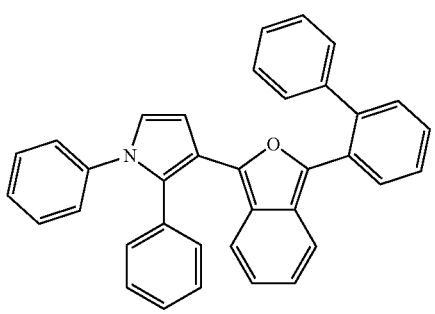 209 | 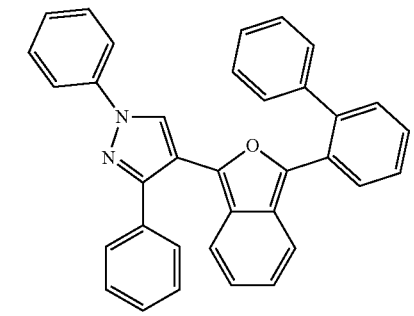 214 |
| 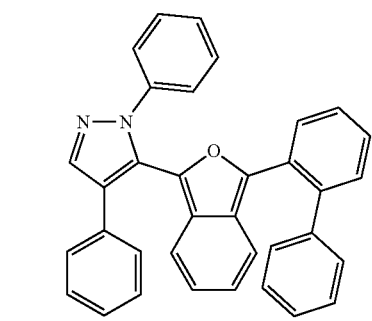 210 | 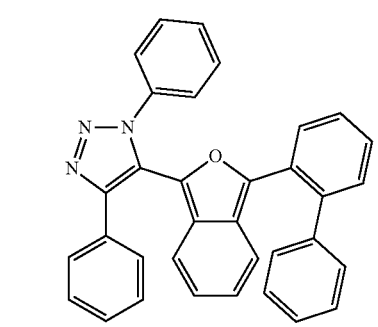 215 |
| 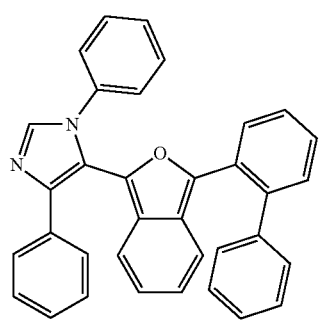 211 | 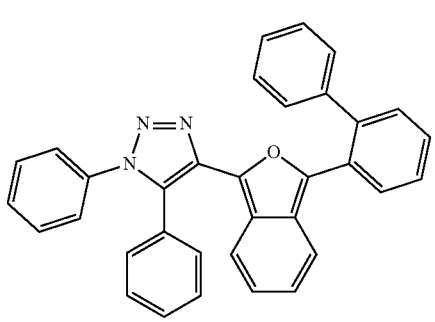 216 |

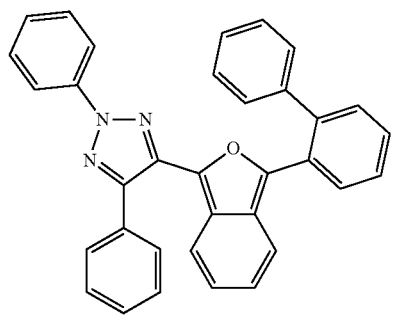
217
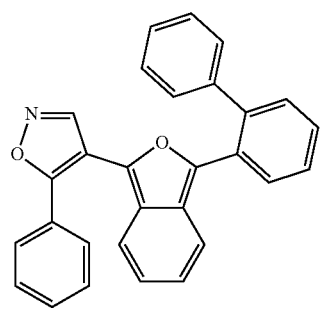
222
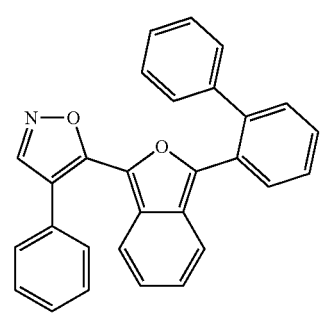
218
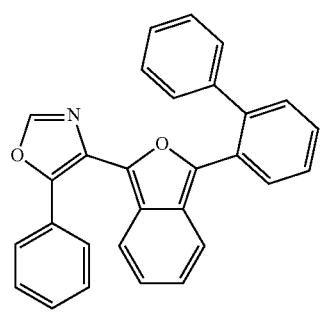
223
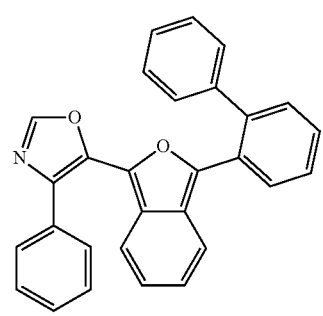
219
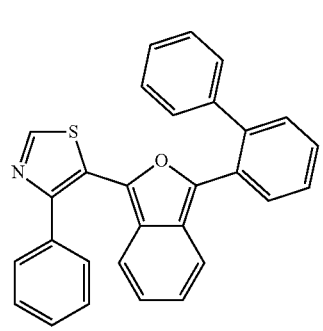
224
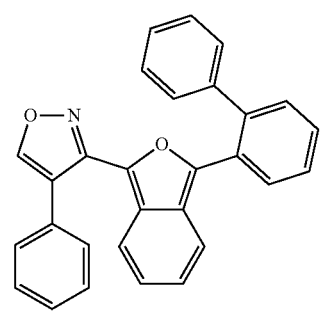
220
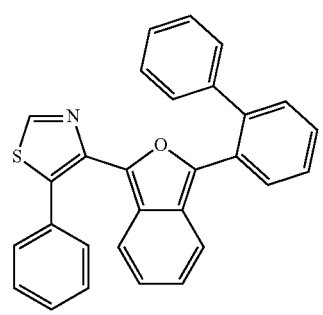
225
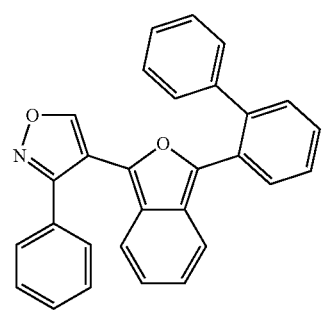
221
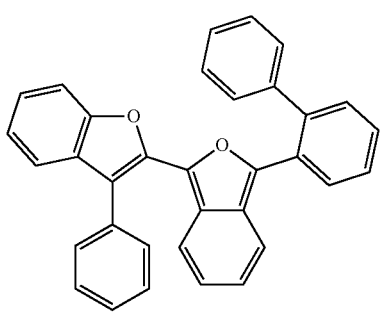
226

227
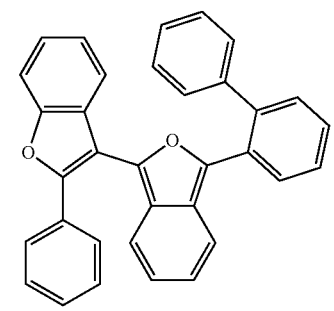
228
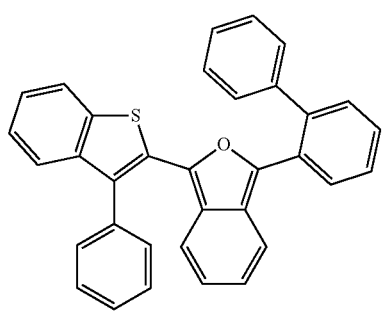
229
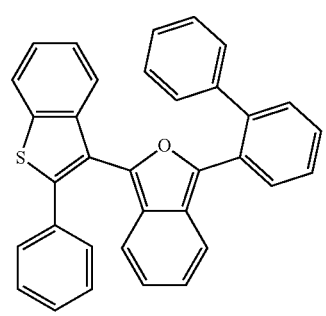
230
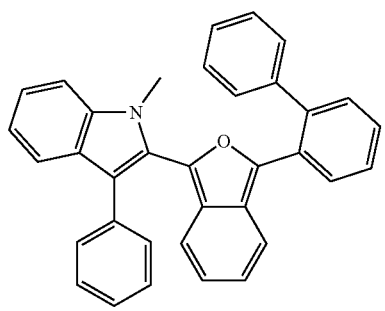
231
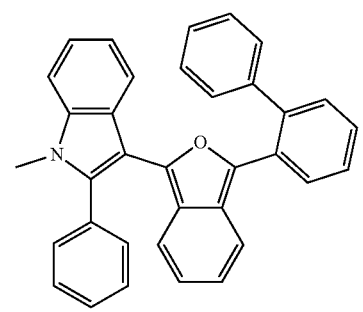
232
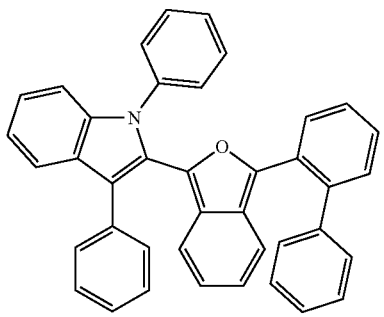
233
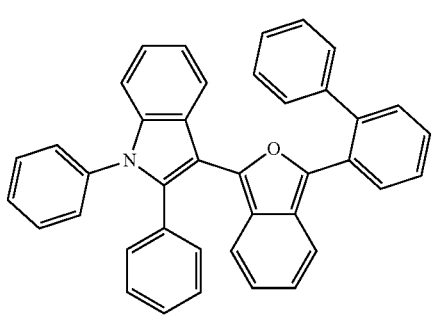
234
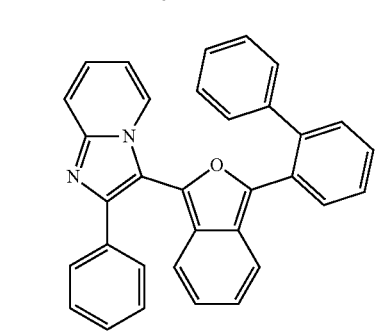
235
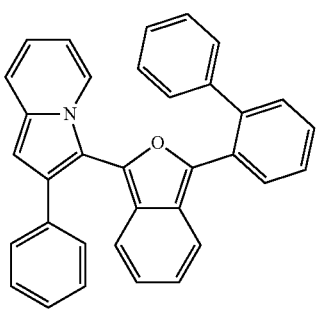
236
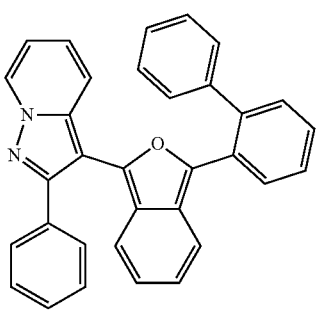

237
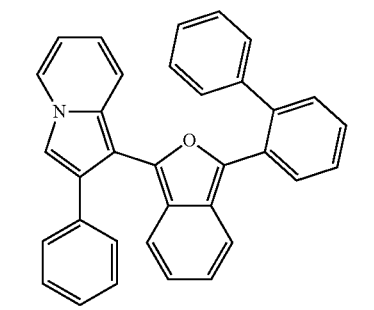
238
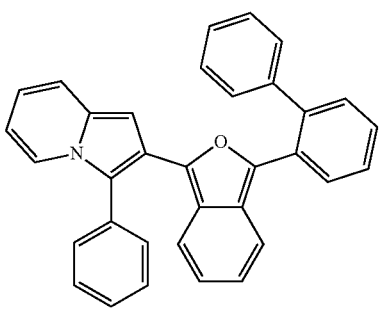
239
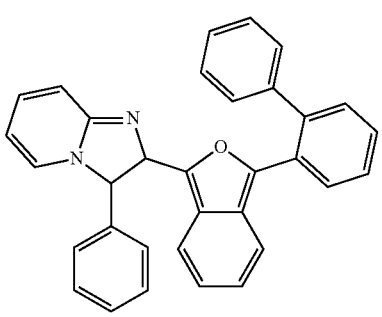
240
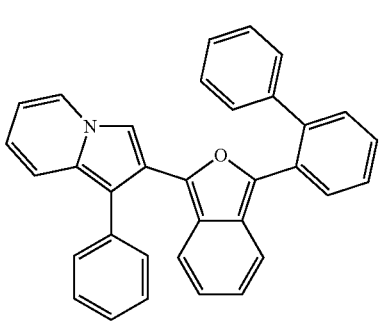
241
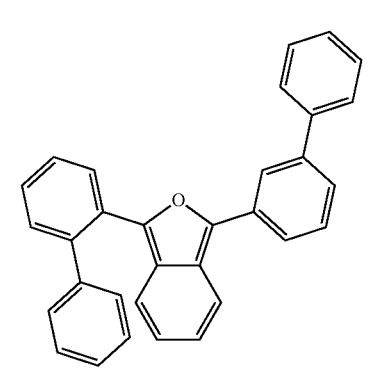
242
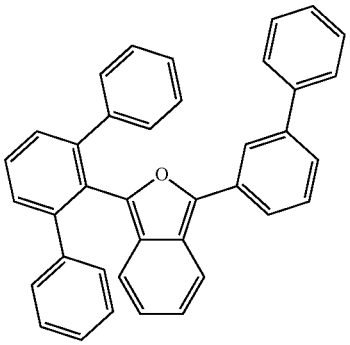
243
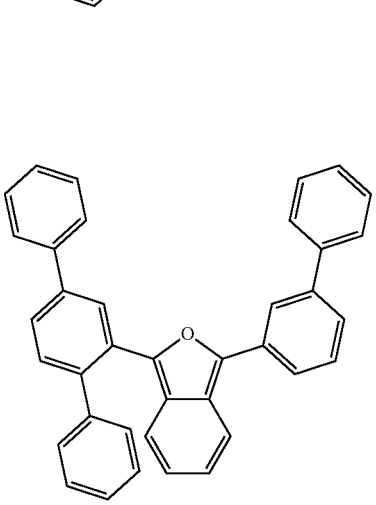
244
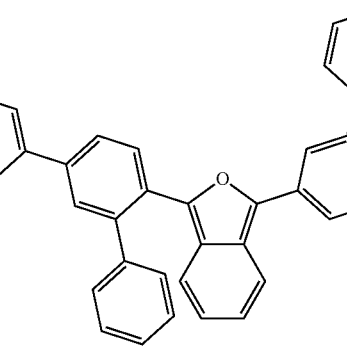
245
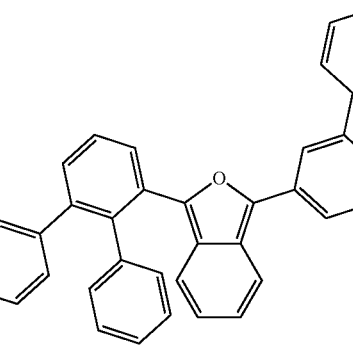

| 246 | 250 |
|---|---|
| 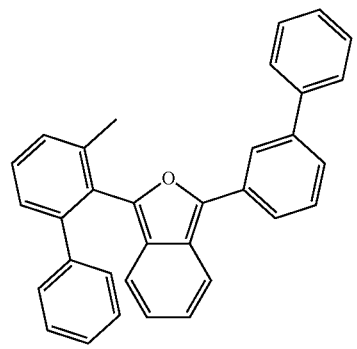 | 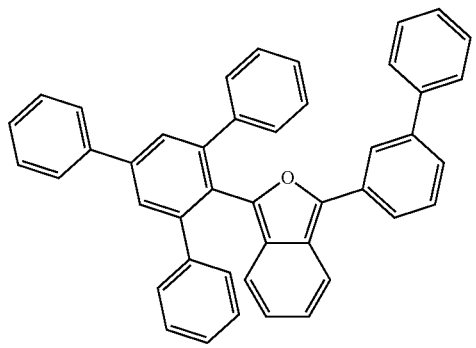 |
| 247 | 251 |
|---|---|
| 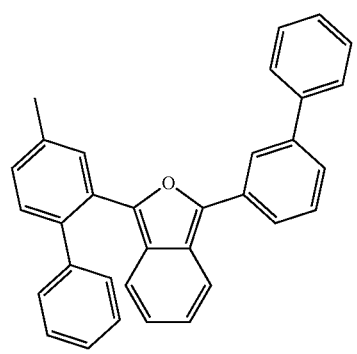 | 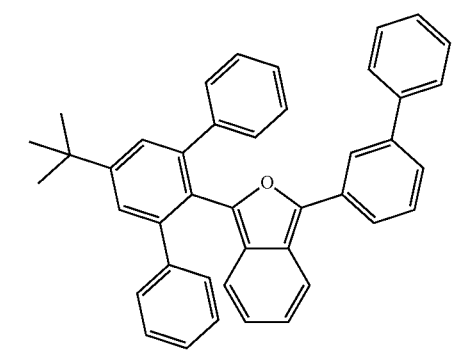 |
| 248 | 252 |
|---|---|
| 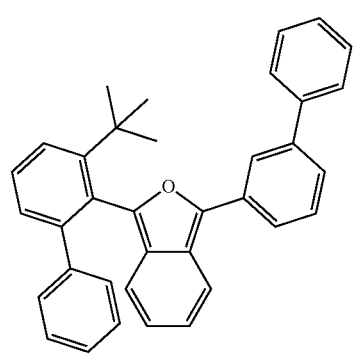 | 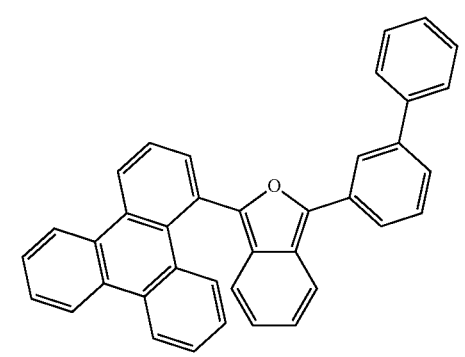 |
| 249 | 253 |
|---|---|
| 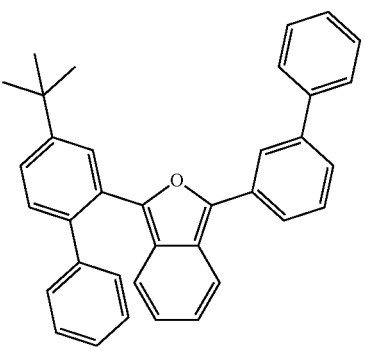 | 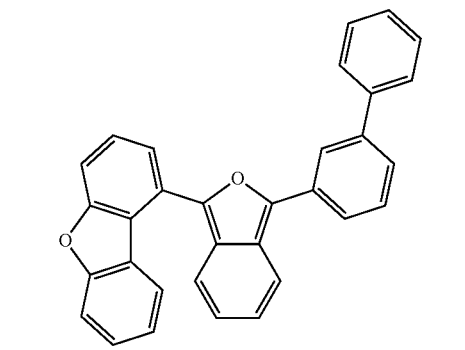 |

254
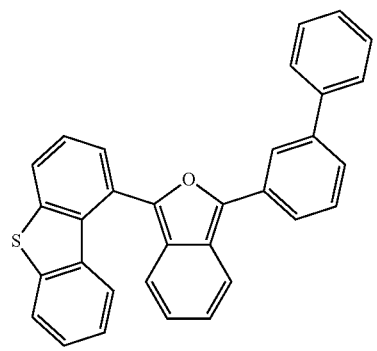
255
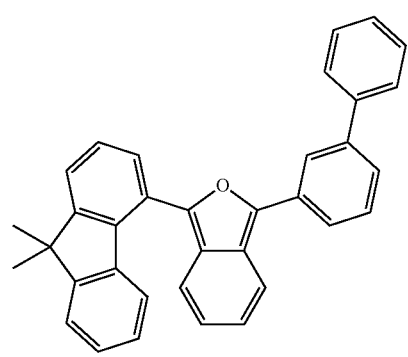
256
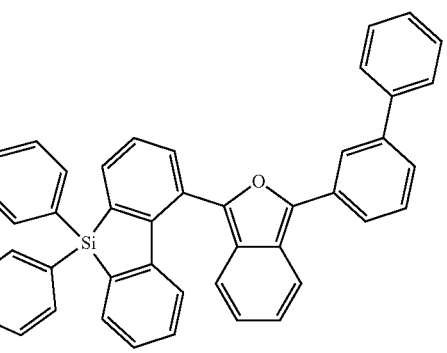
257
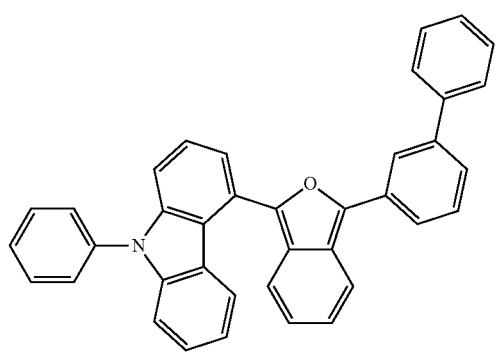
258
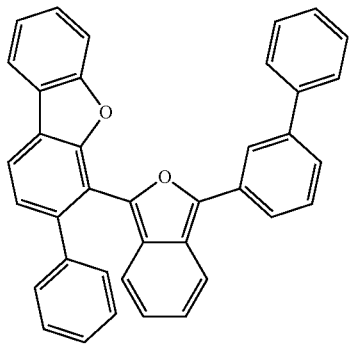
259
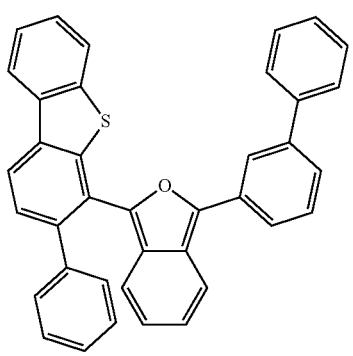
260
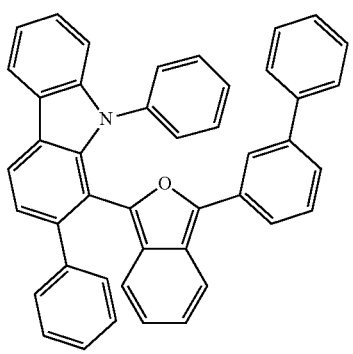
261
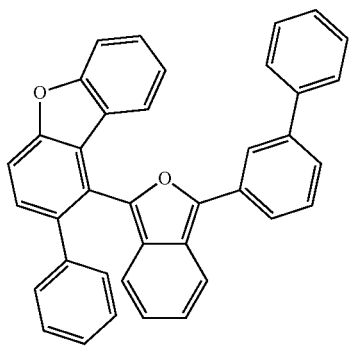

262
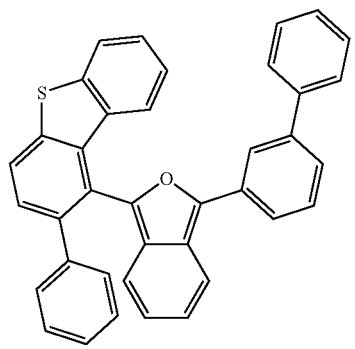
266
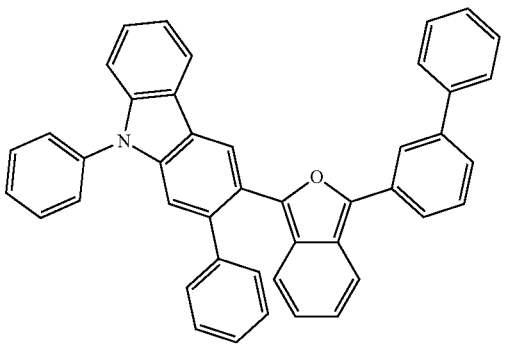
263
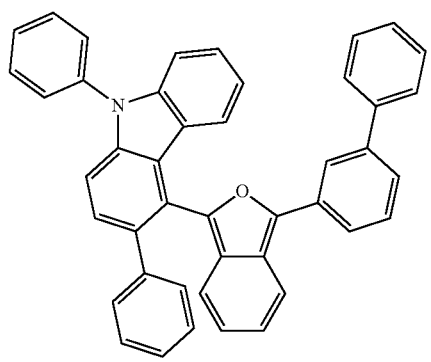
267
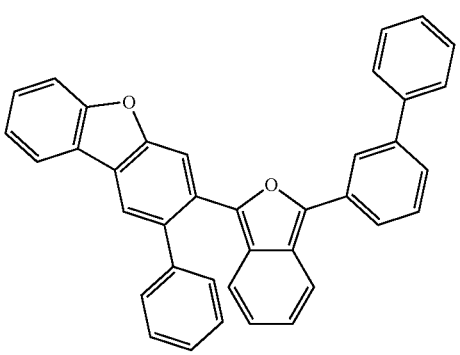
264
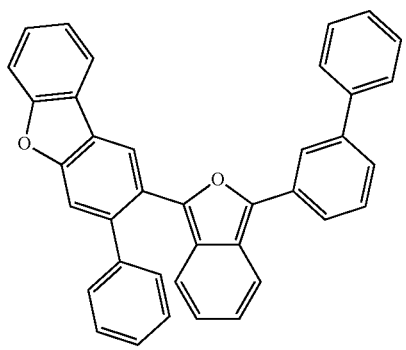
268
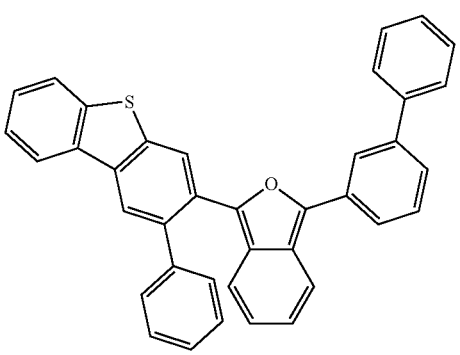
265
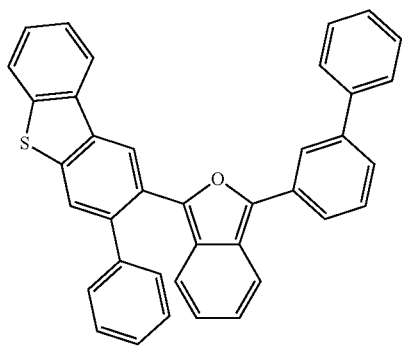
269
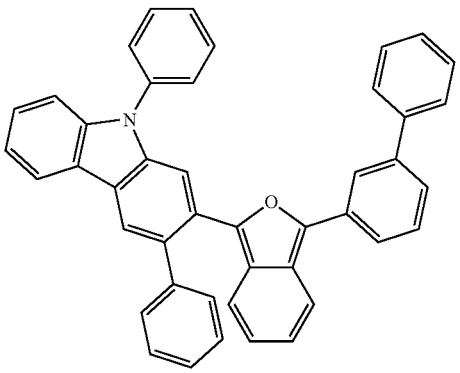

| | |
|---|---|
| 270 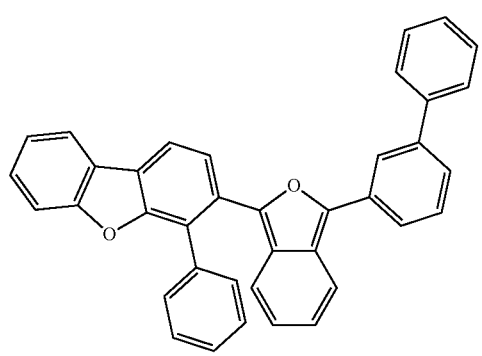 | 274 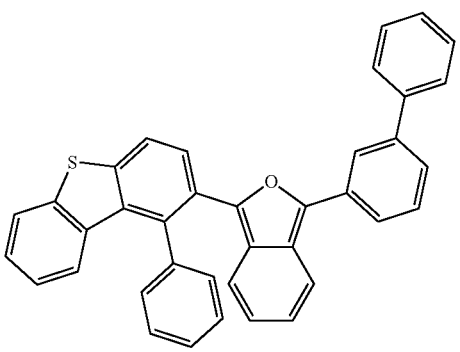 |
| 271 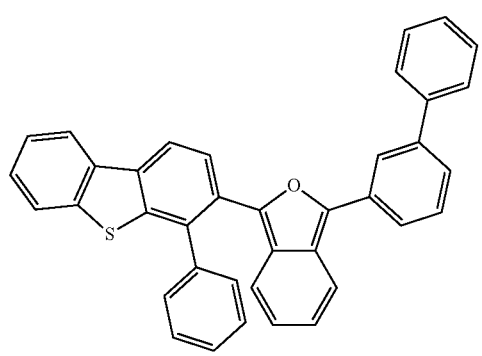 | 275 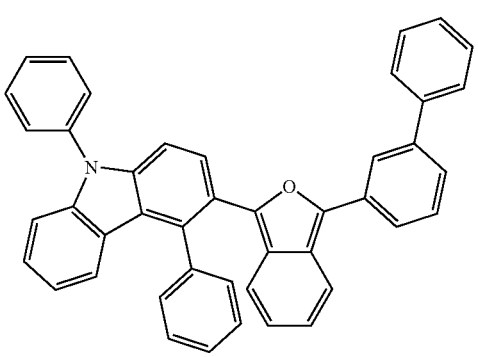 |
| 272 | 276 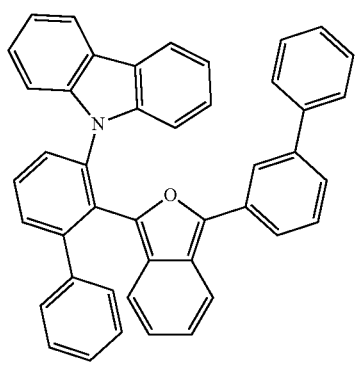 |
| 273 | 277 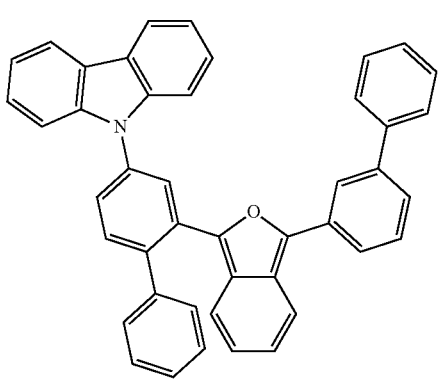 |

278
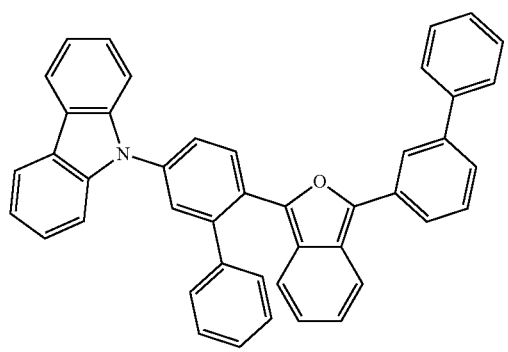
282
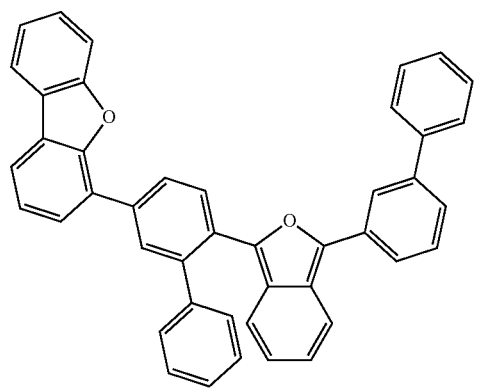
279
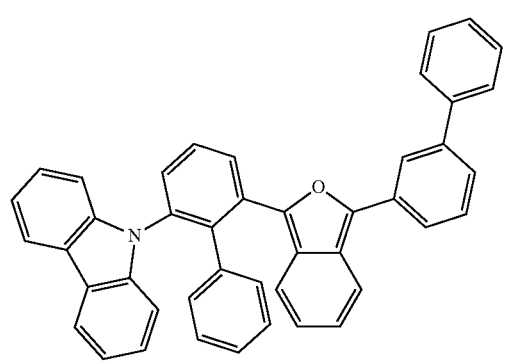
283
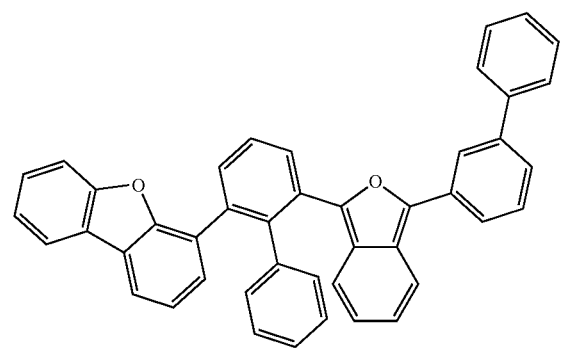
280
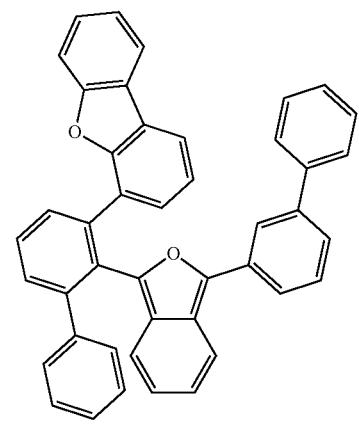
284
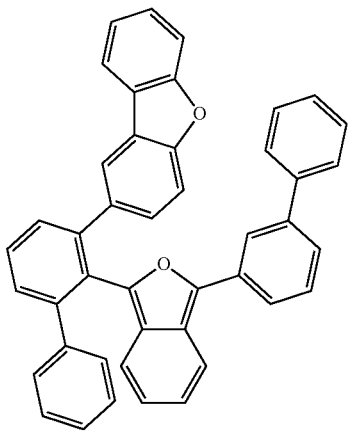
281
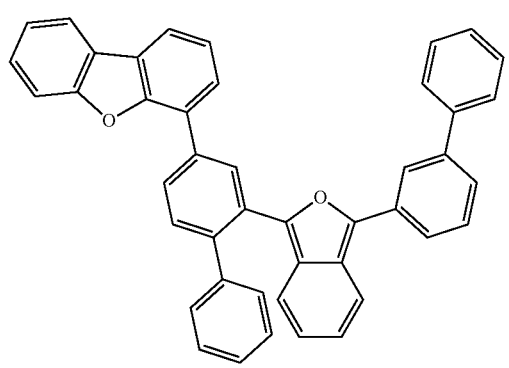
285
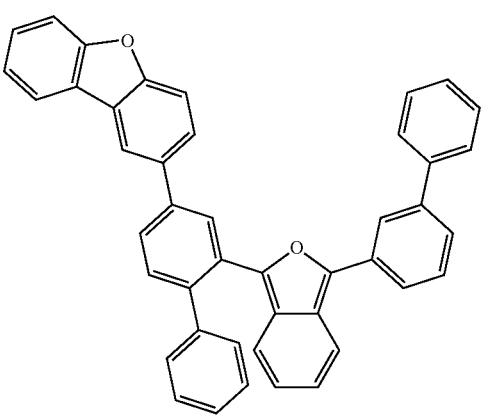

311
-continued
286
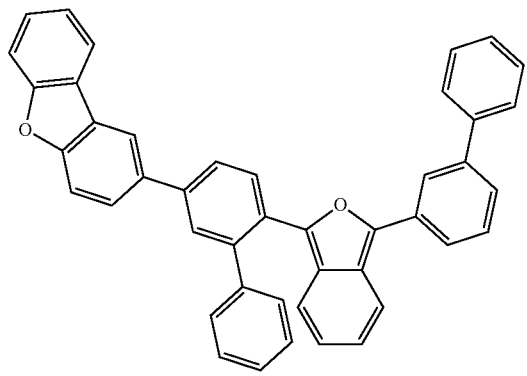
287
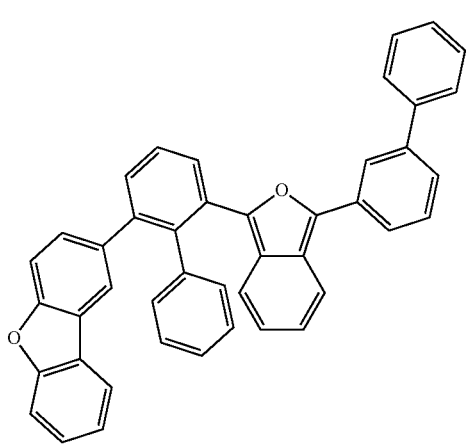
288
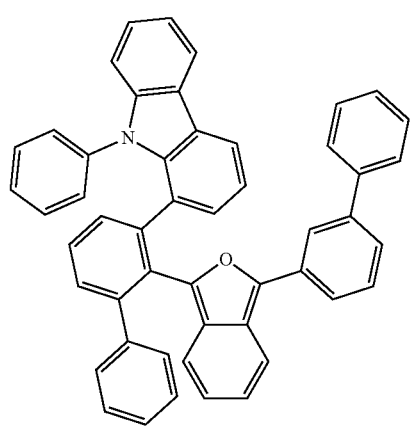
312
-continued
289
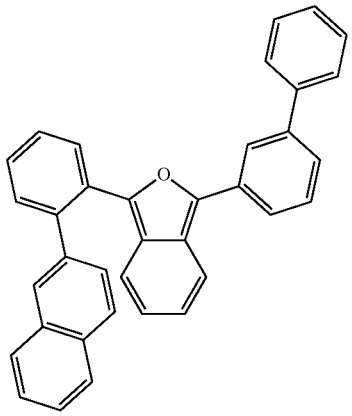
290
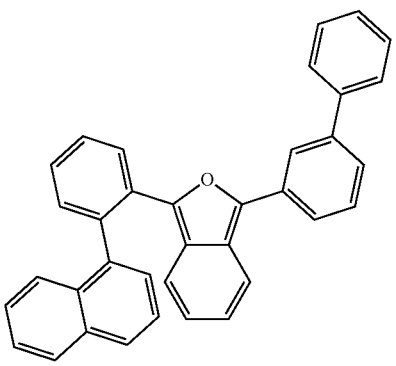
291
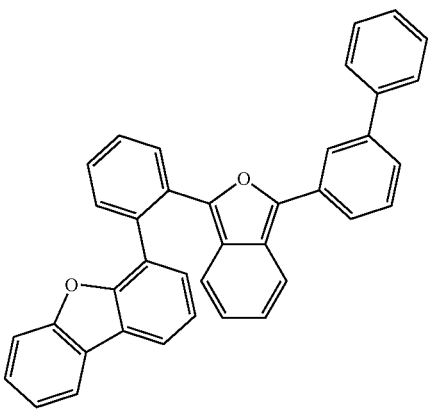
292
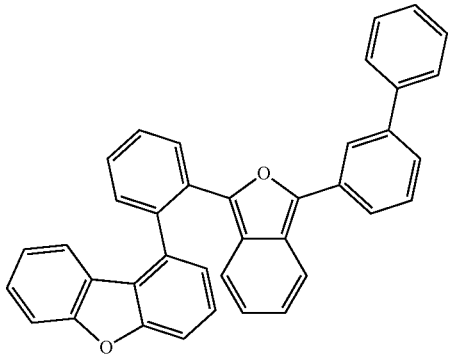

293
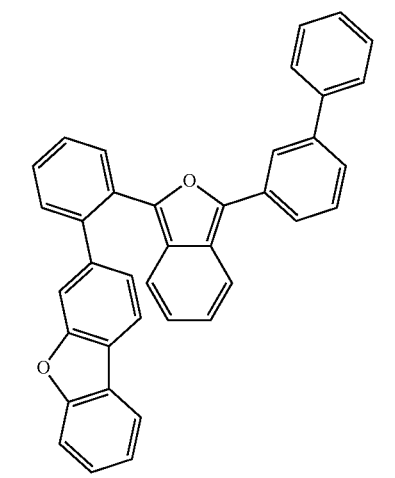
294
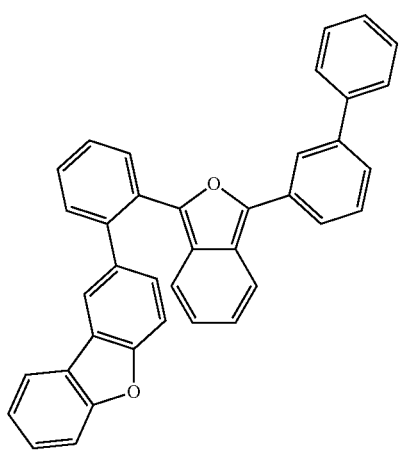
295
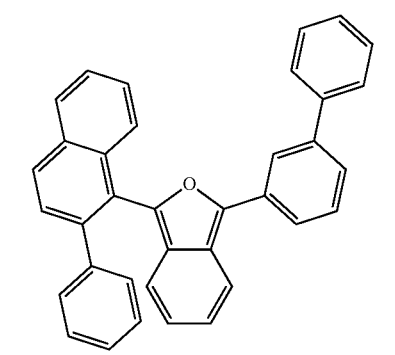
296
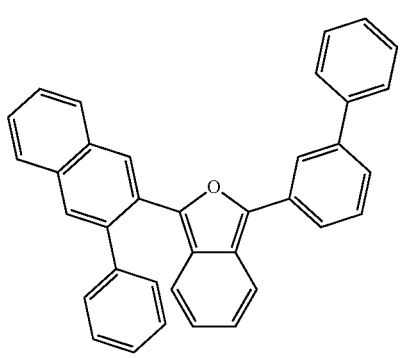
297
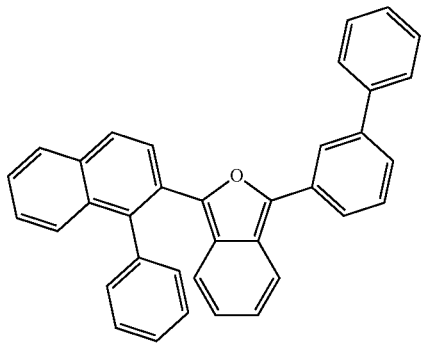
298
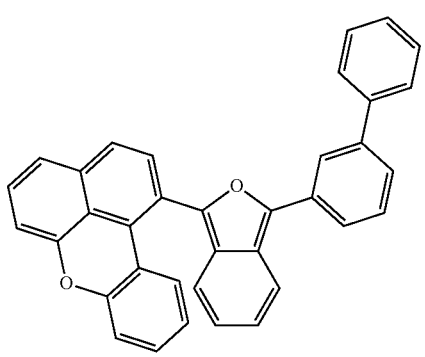
299
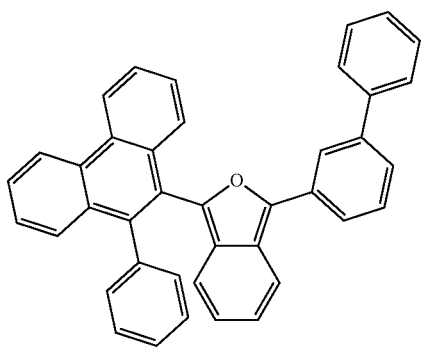
300
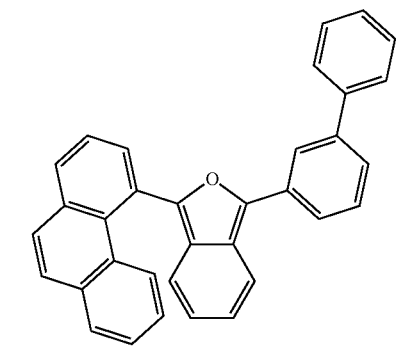

315
-continued
301
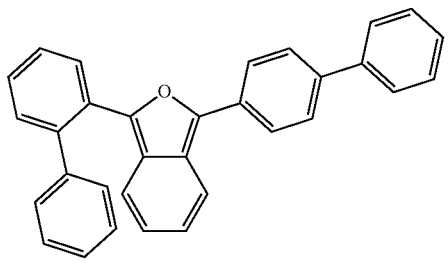
302
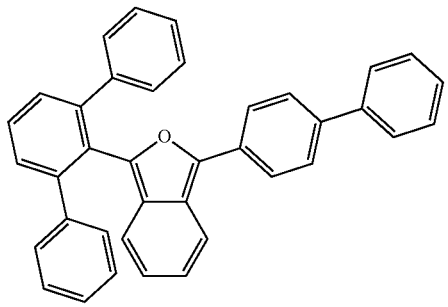
303
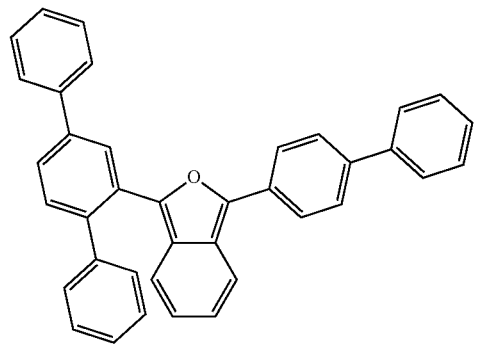
304
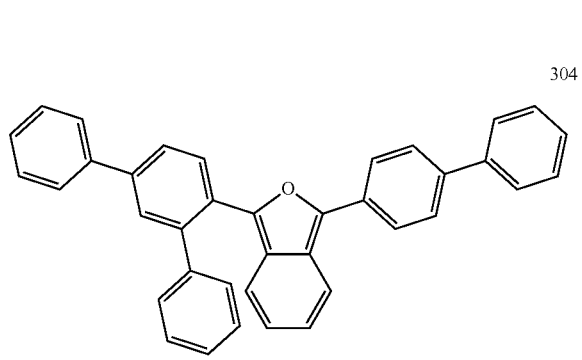
305
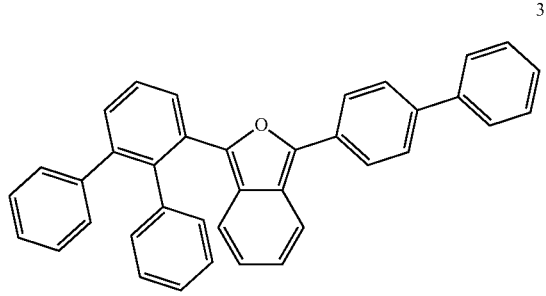
316
-continued
306
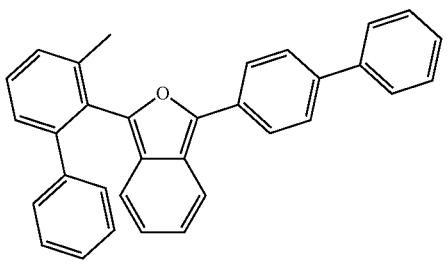
307
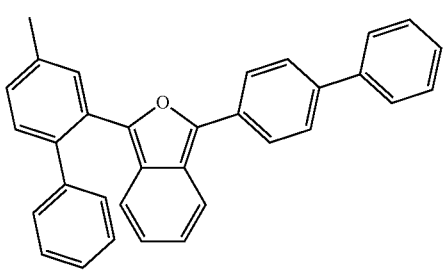
308
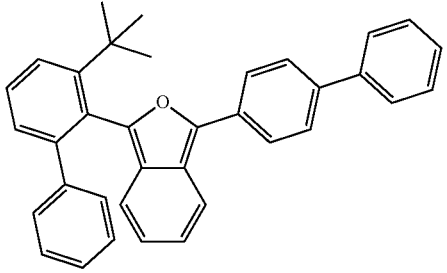
309
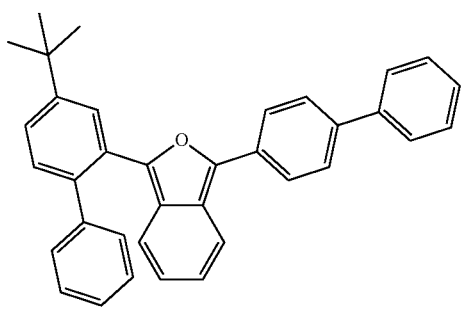
310
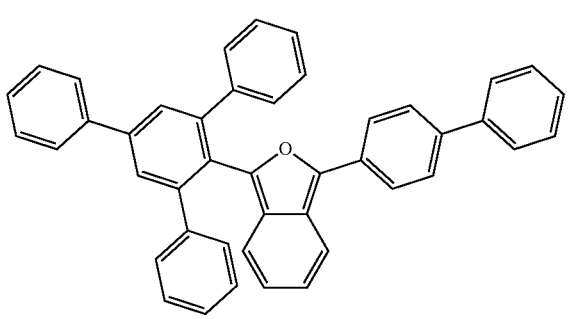

317
-continued
311
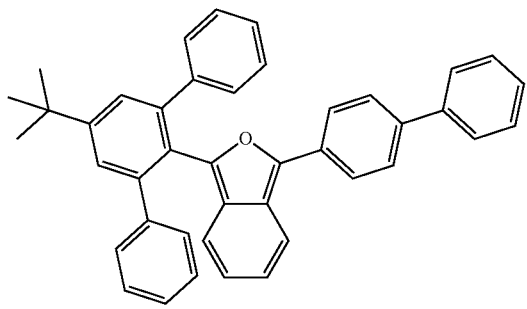
312
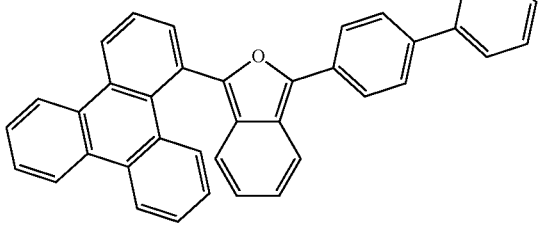
313
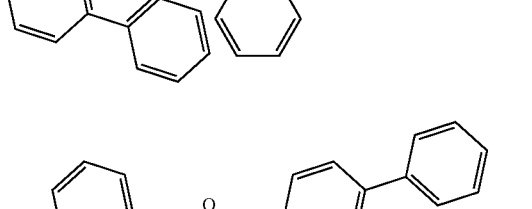
314
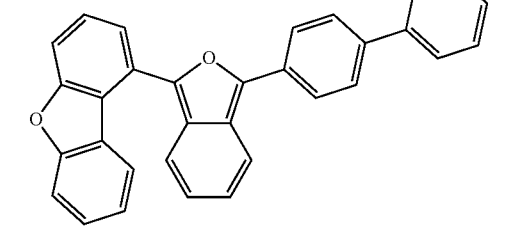
315
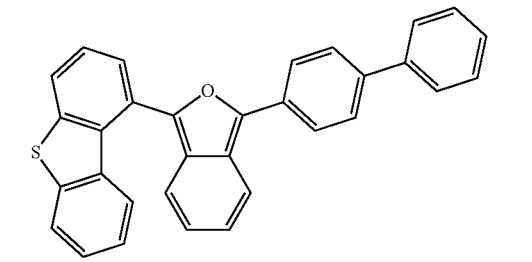
318
-continued
316
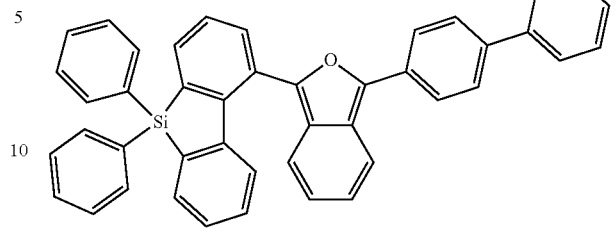
317
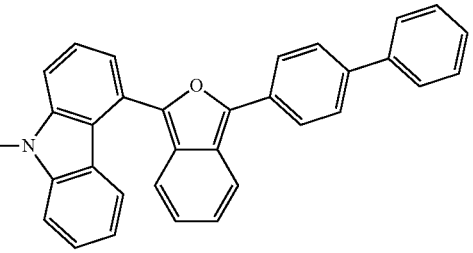
318
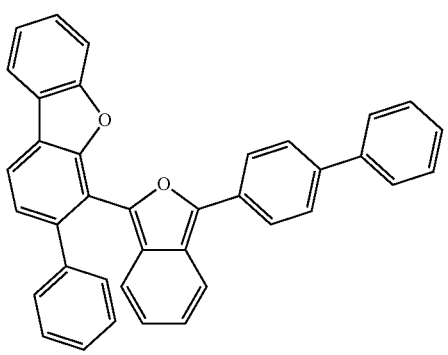
319
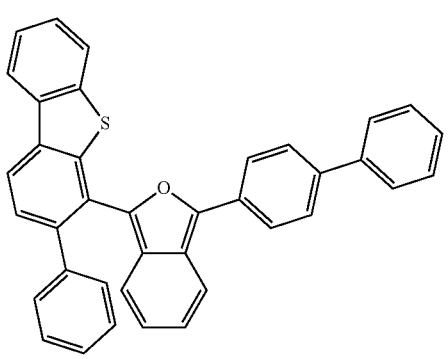
320
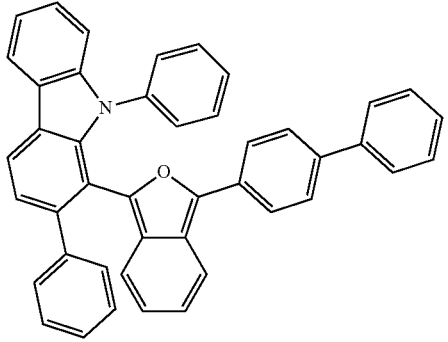

321
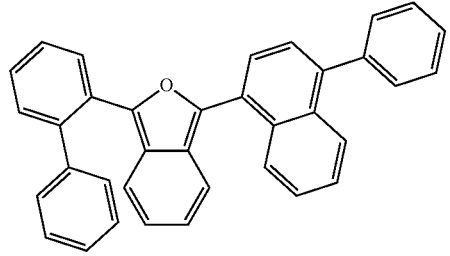
322
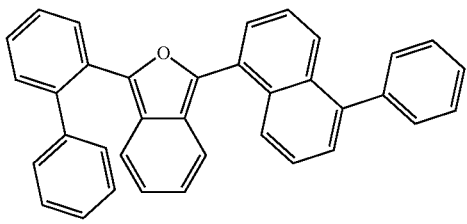
323
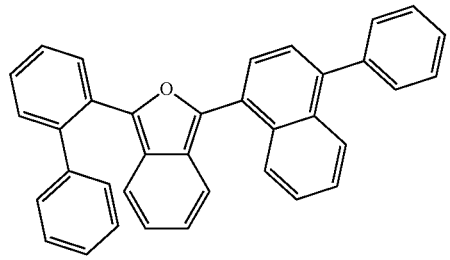
324
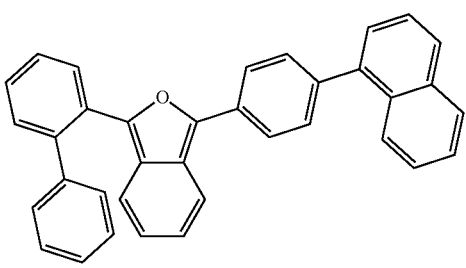
325
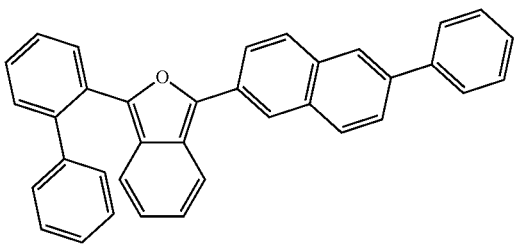
326
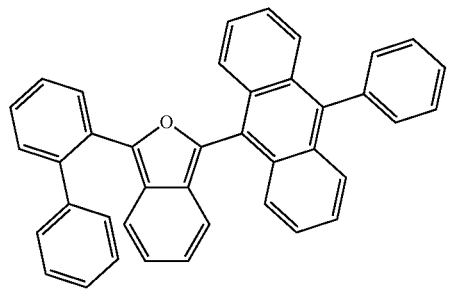
327
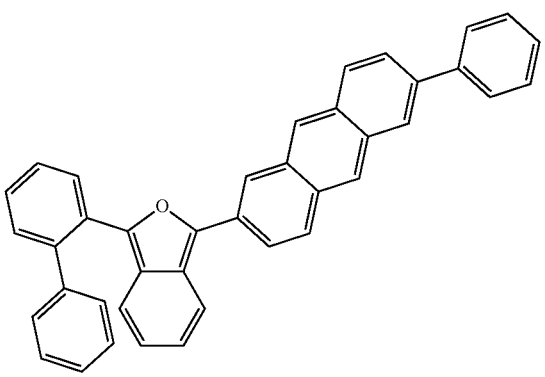
328
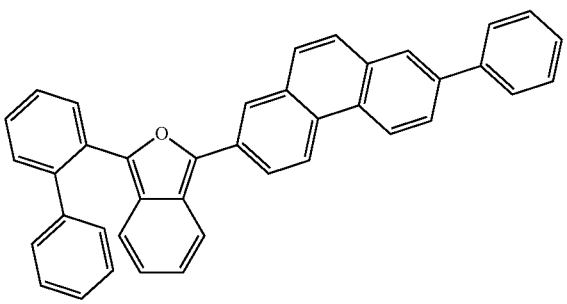
329
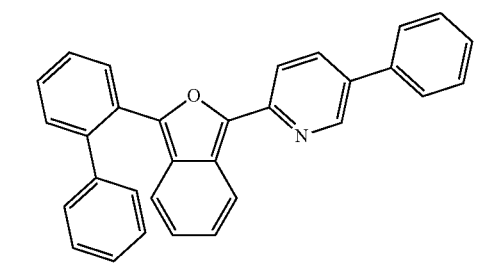
330
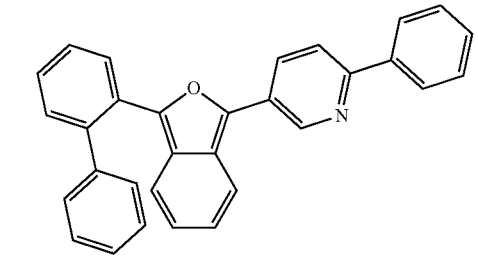
331
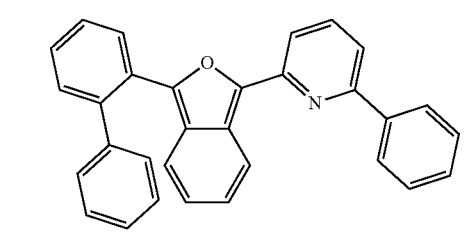

321
-continued
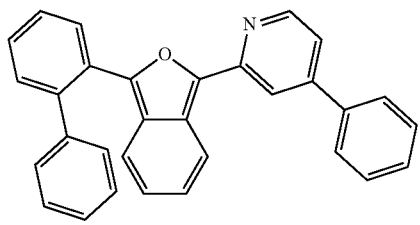  332
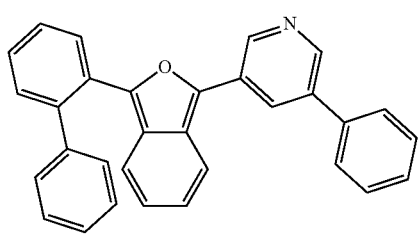  333
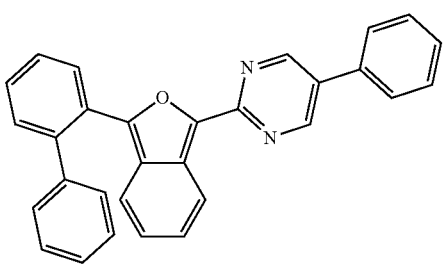  334
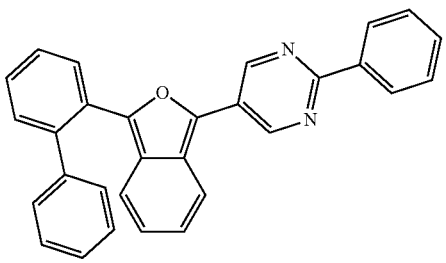  335
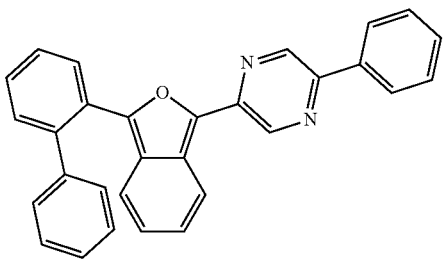  336
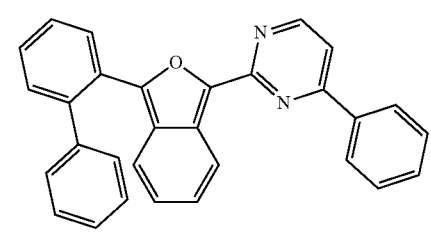  337
322
-continued
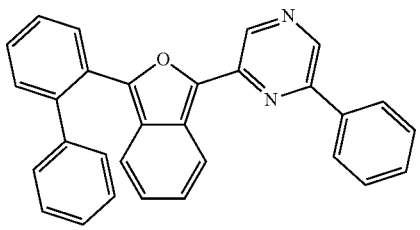  338
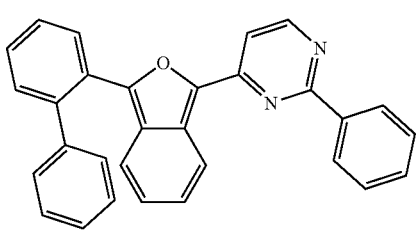  339
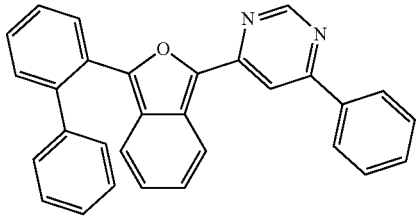  340
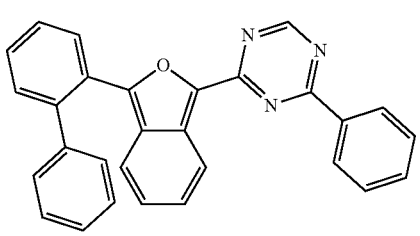  341
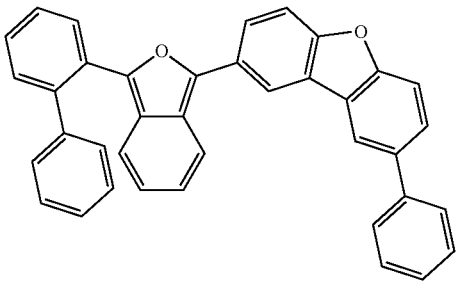  342
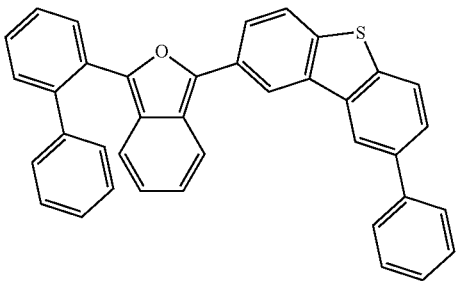  343

-continued
344
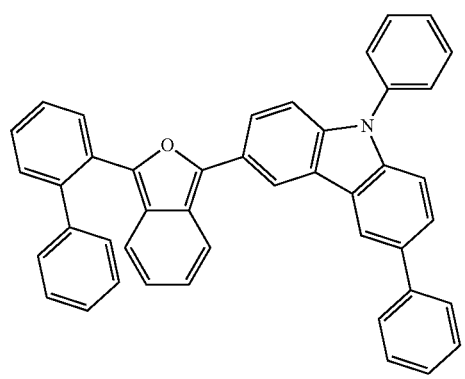
345
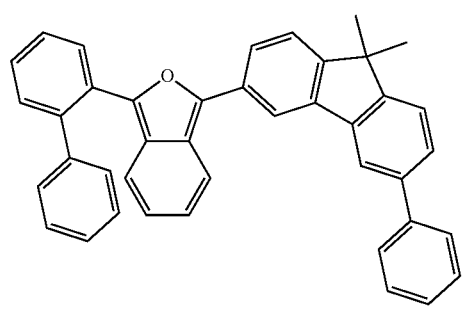
346
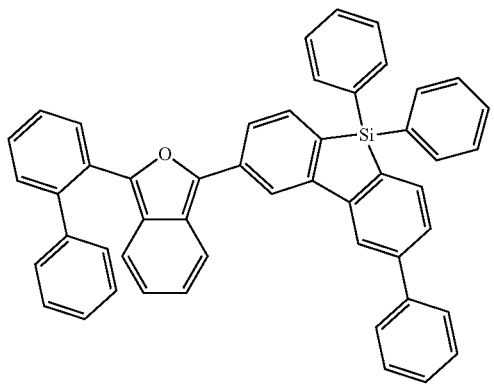
347
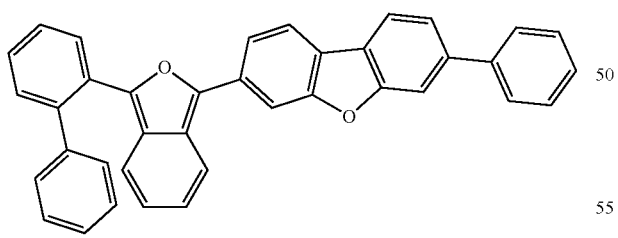
348
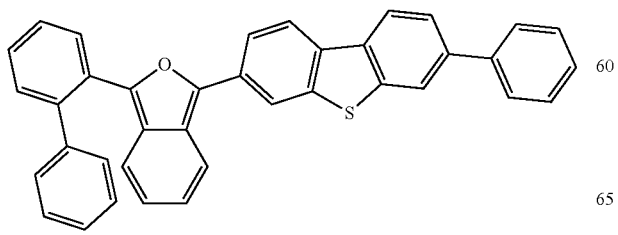
-continued
349
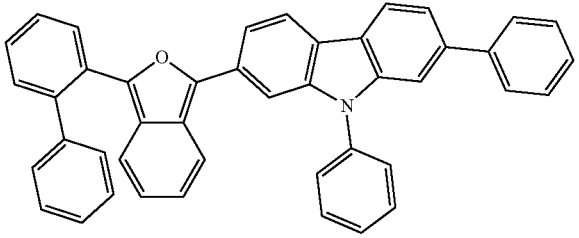
350
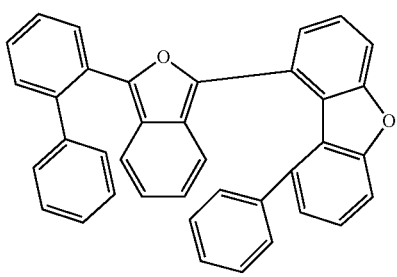
351
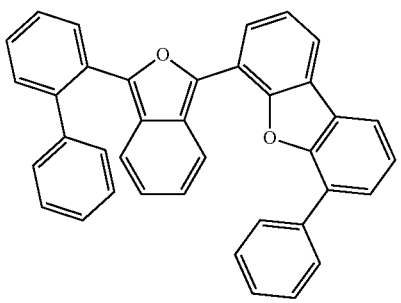
352
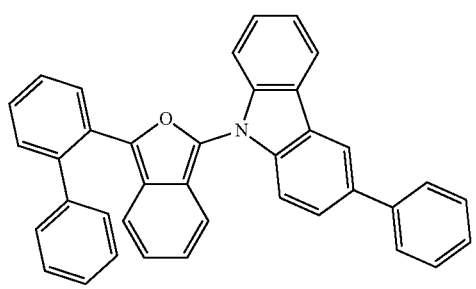
353
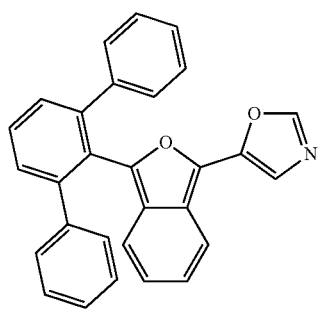

354
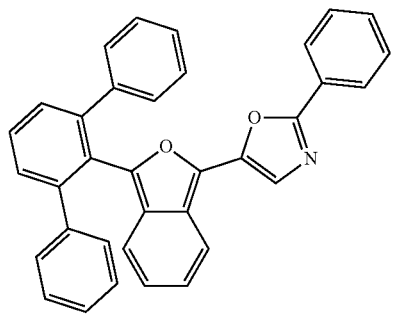
355
356
357
358
359
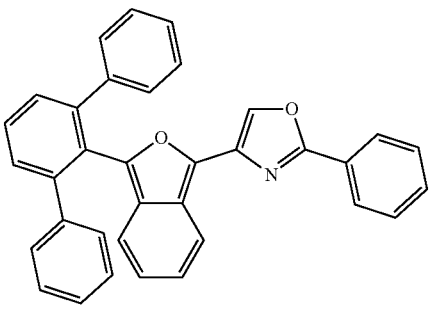
360
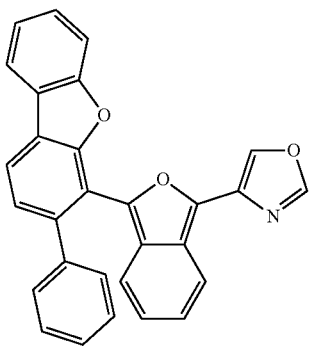
361
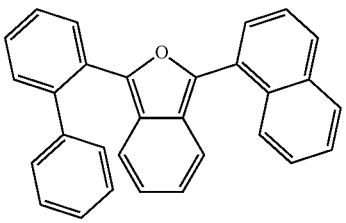
362
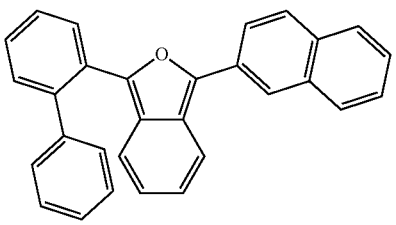
363
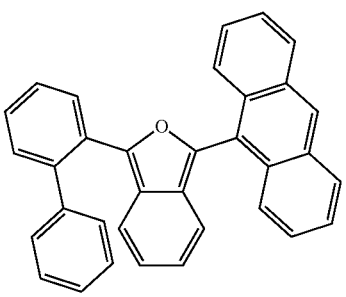

327
-continued
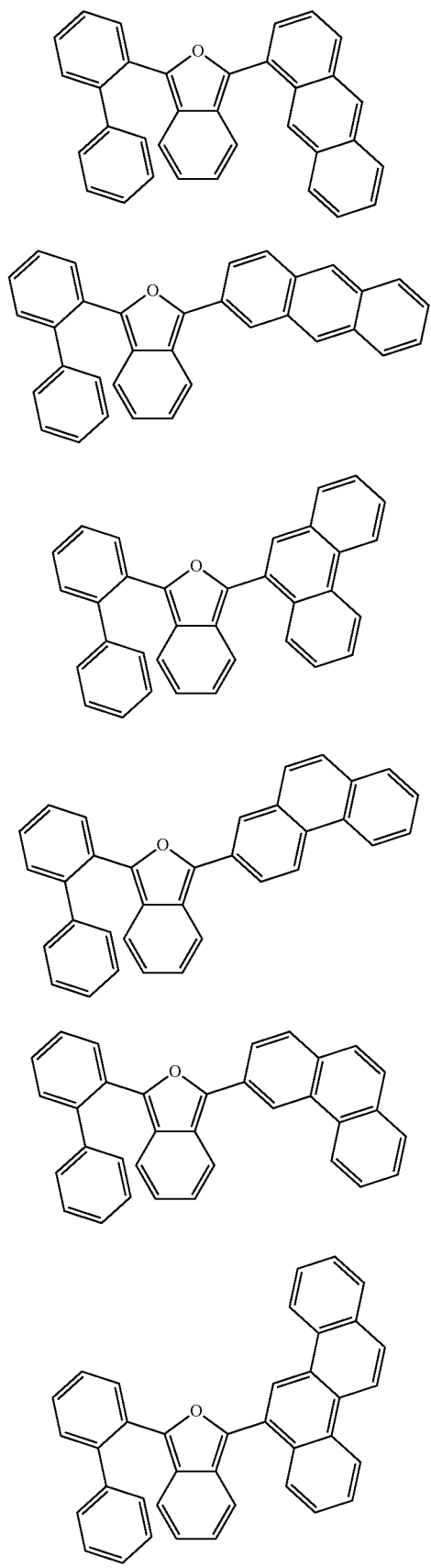
328
-continued
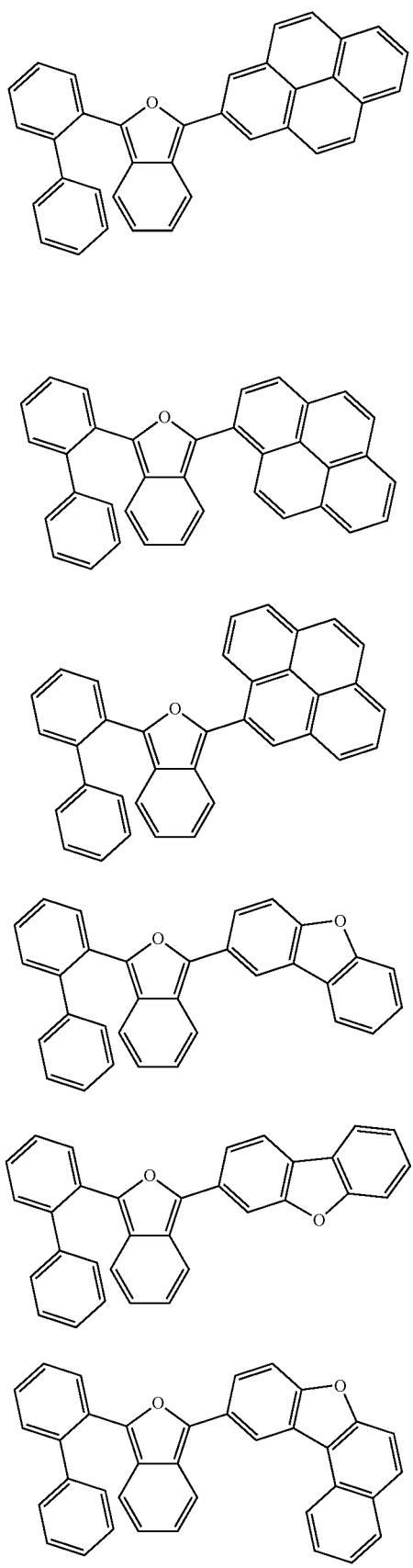

376 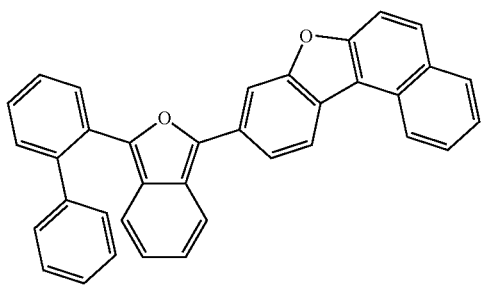
377 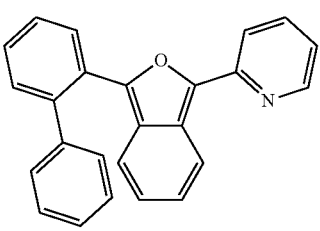
378 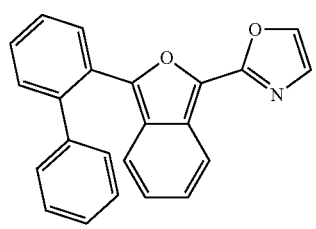
379 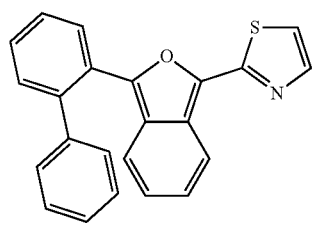
380 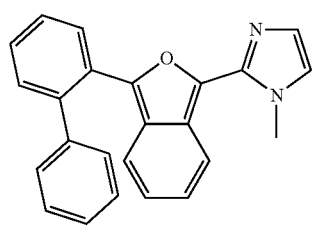
381 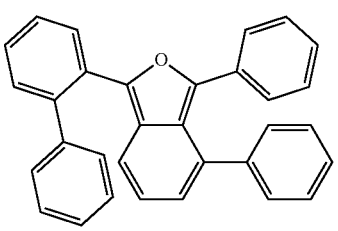
382 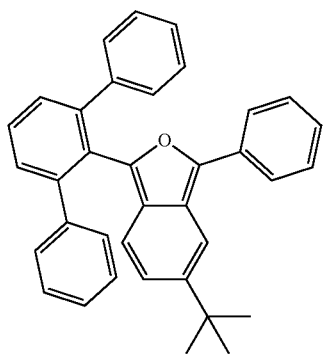
383 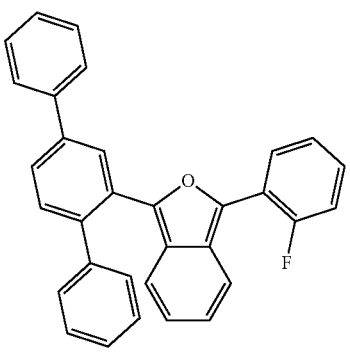
384 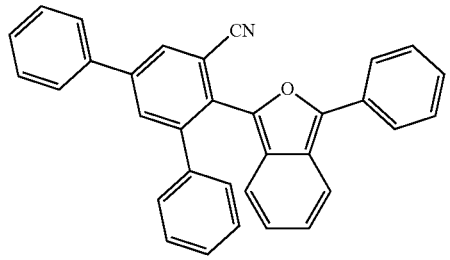
385 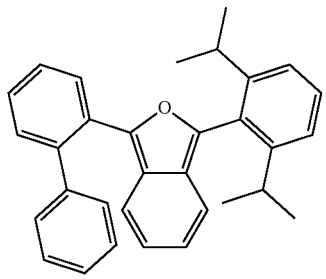
386 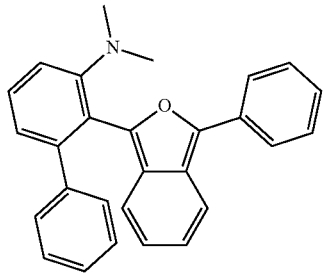

331 -continued
387
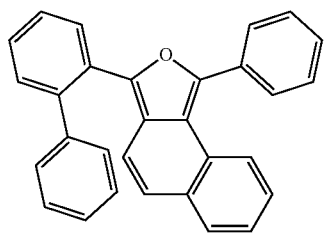
388
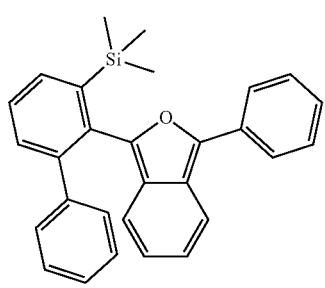
389
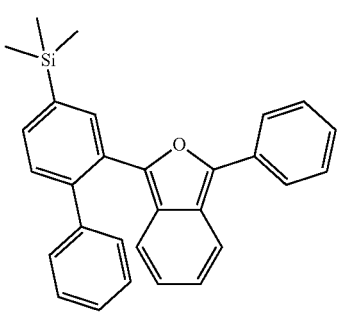
390
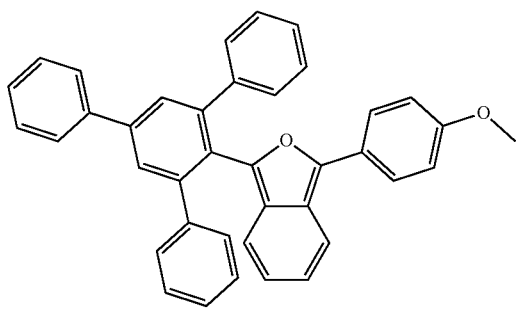
391
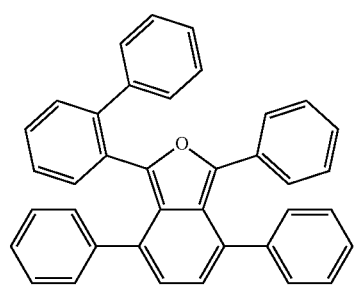
332 -continued
392
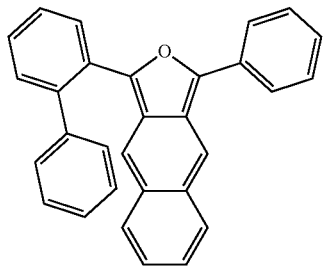
393
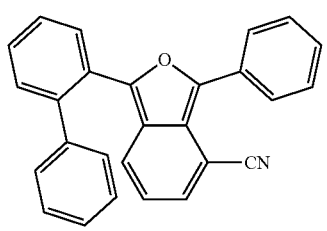
394
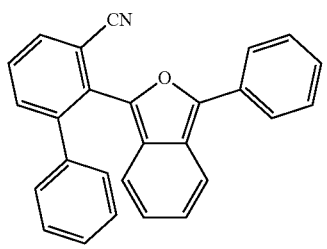
395
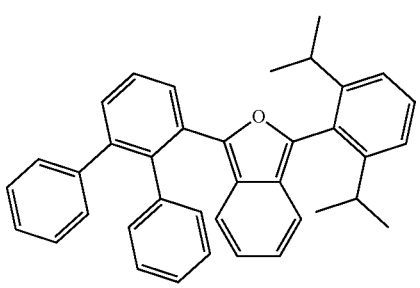
396
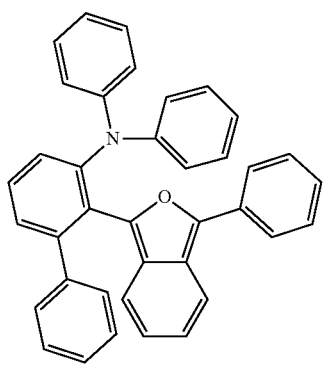

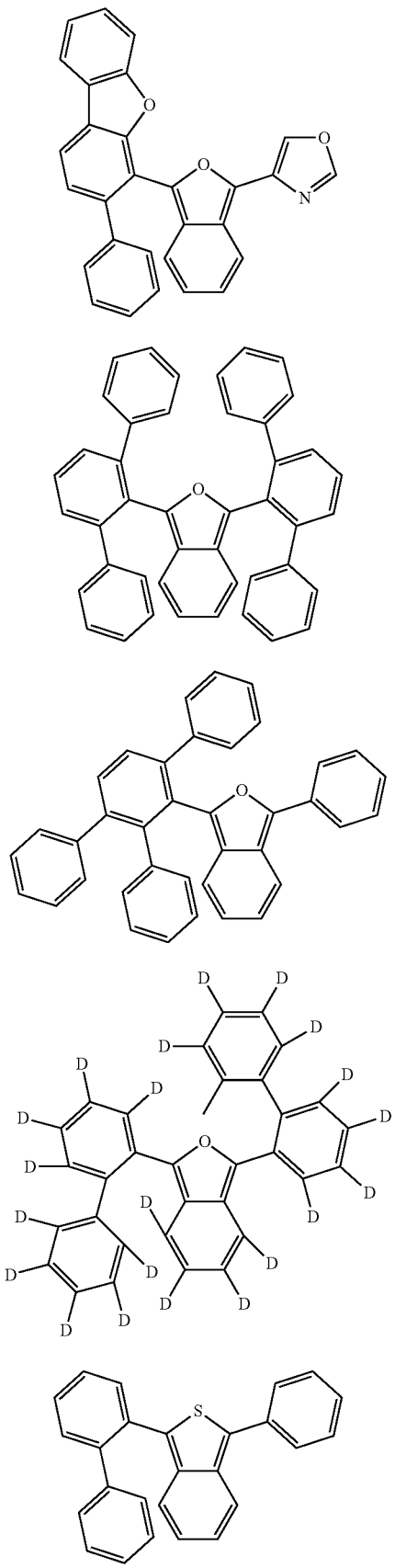

407 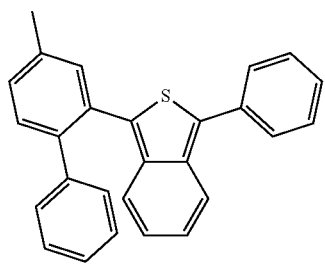
408 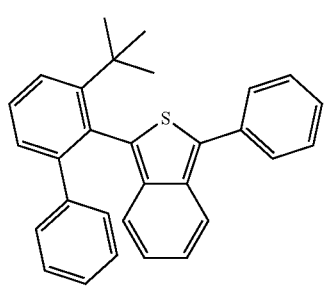
409 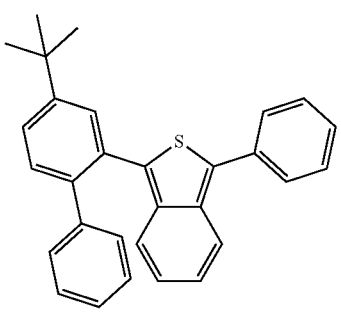
410 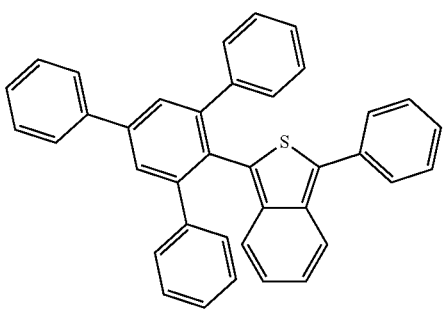
411 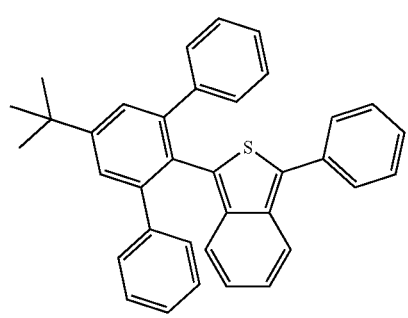
412 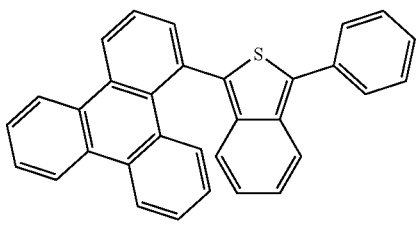
413 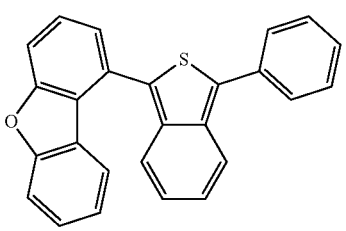
414 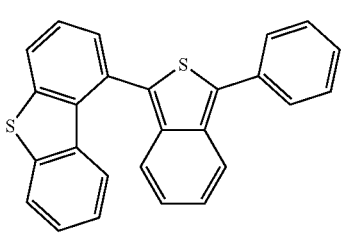
415 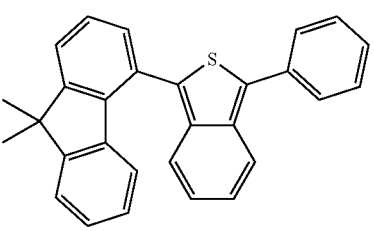
416 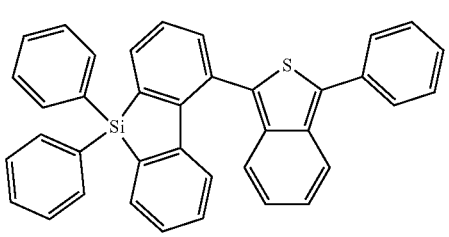
417 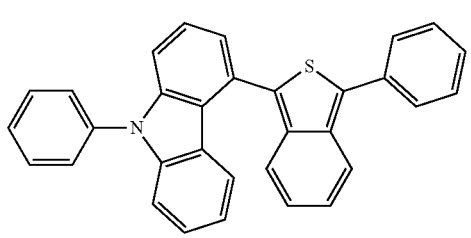

| 337 -continued | 338 -continued |
|---|---|
| 418 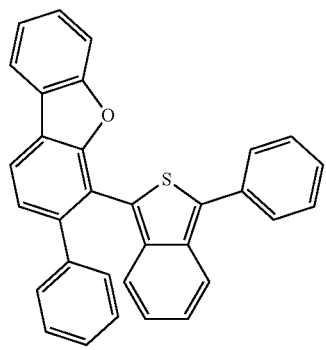 | 422 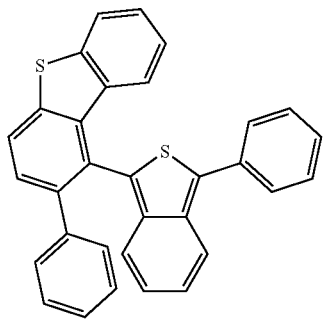 |
| 419 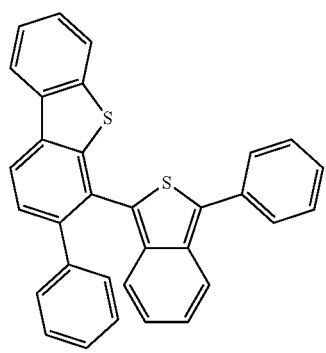 | 423 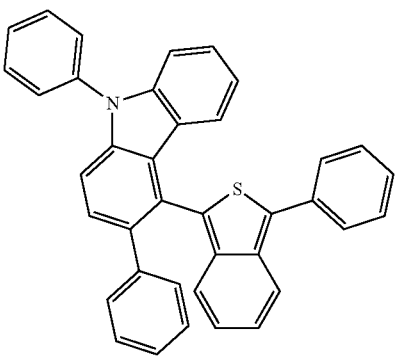 |
| 420 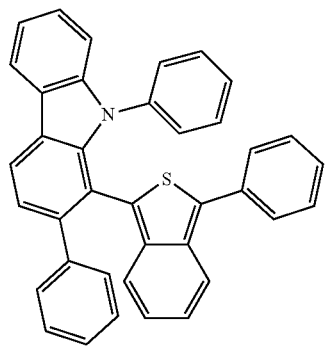 | 424 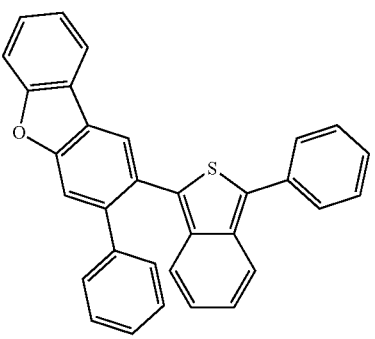 |
| 421 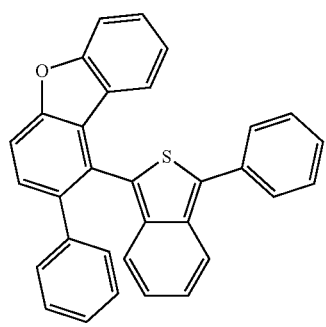 | 425 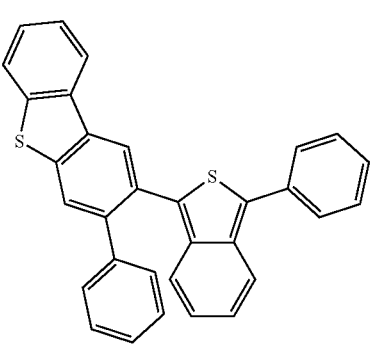 |

339
-continued
426
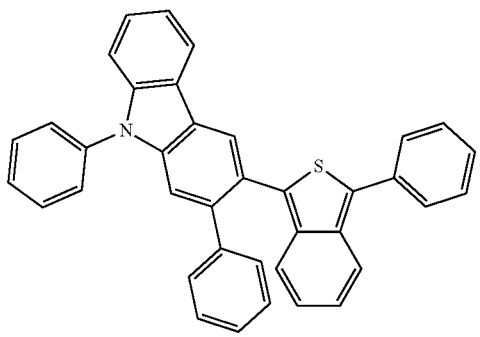
427
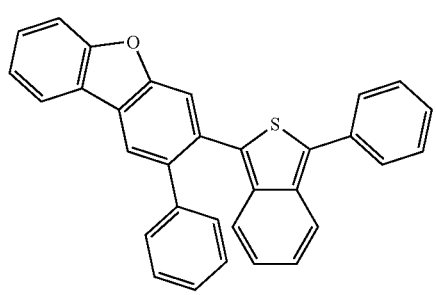
428
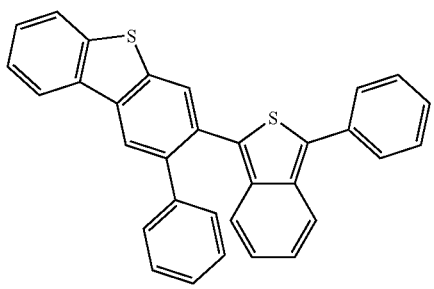
429
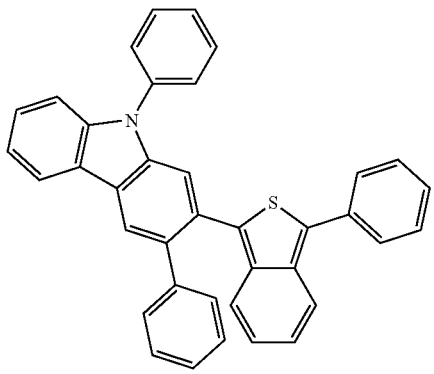
430
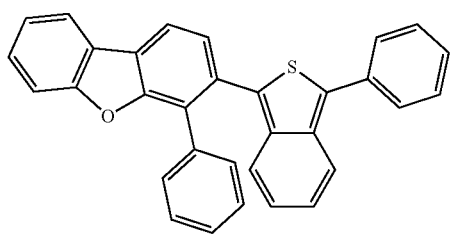
340
-continued
431
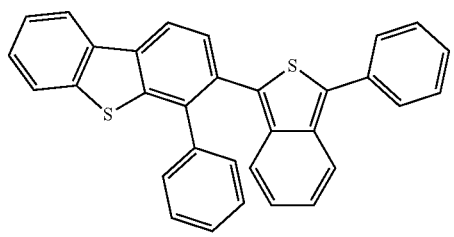
432
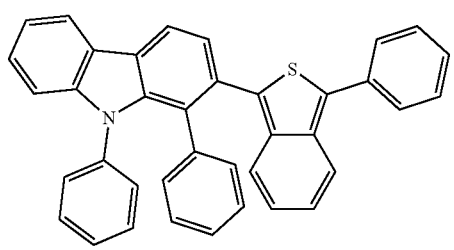
433
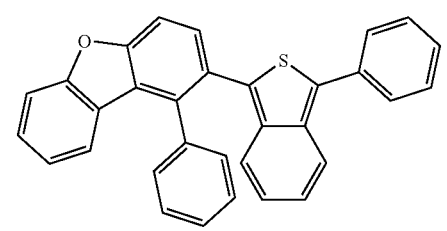
434
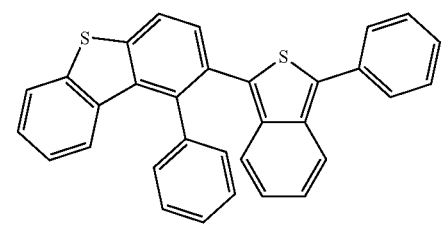
435
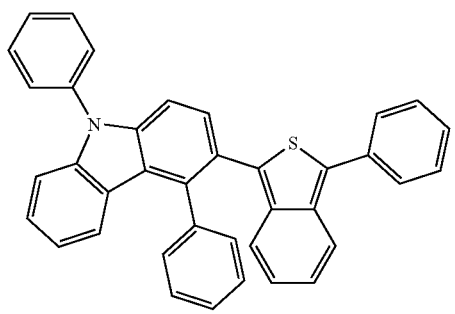
436
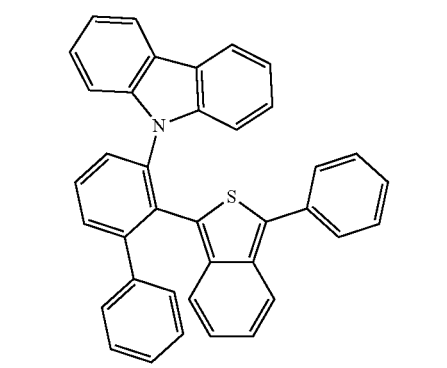

341
-continued
437
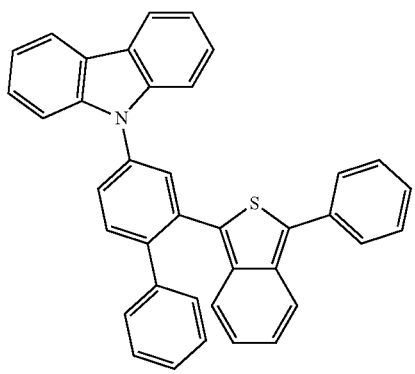
438
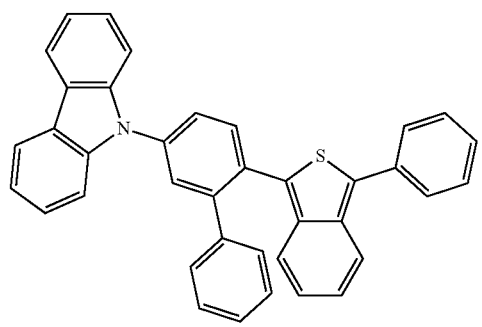
439
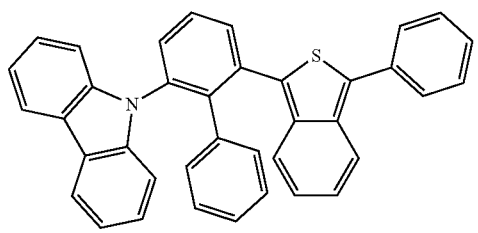
440
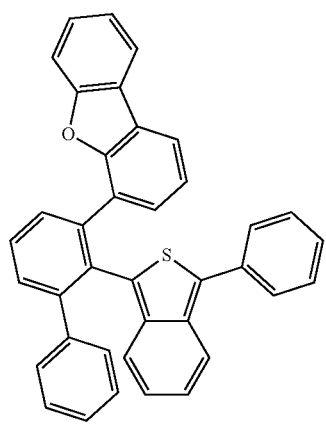
342
-continued
441
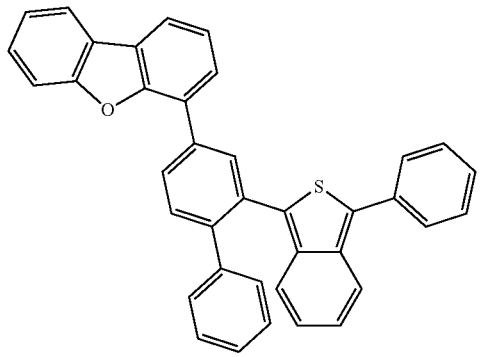
442
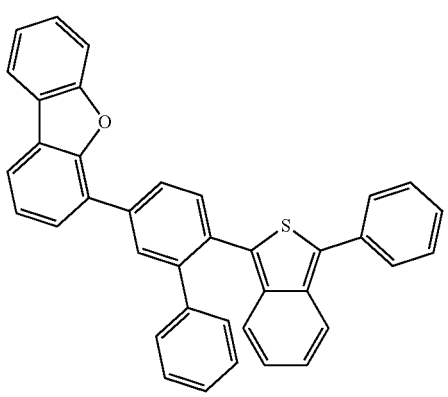
443
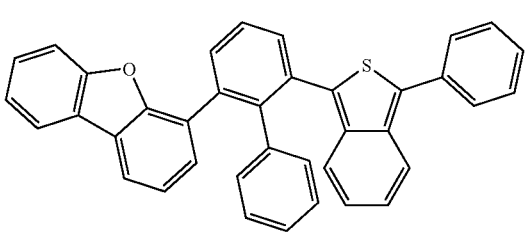
444
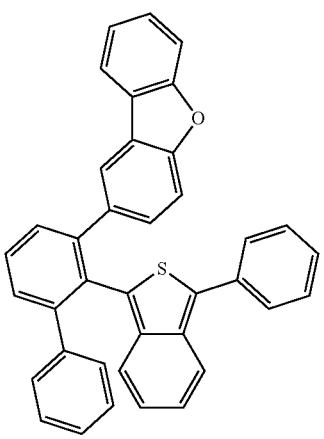

445
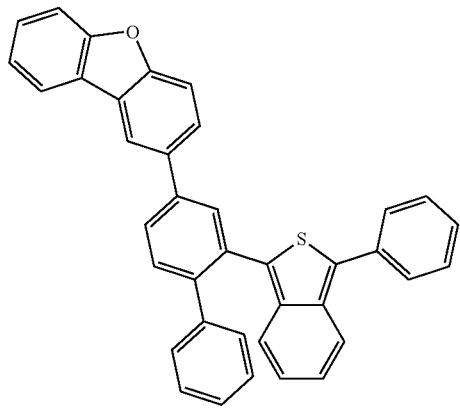
446
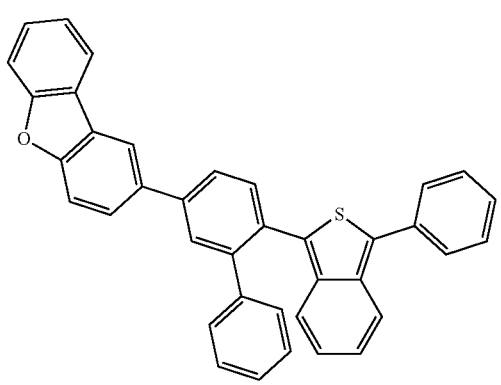
447
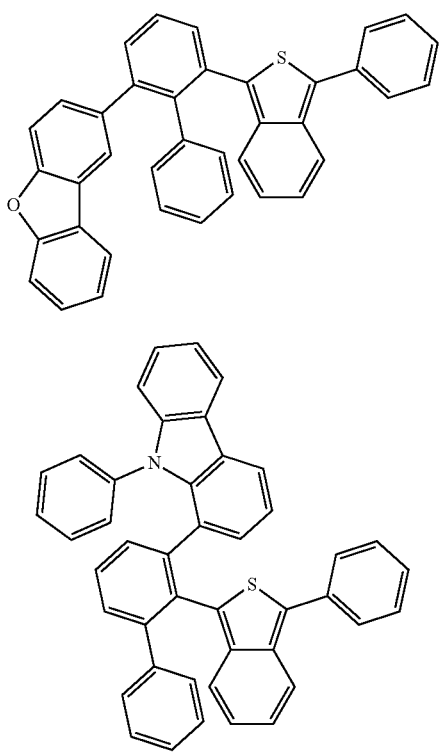
448
449
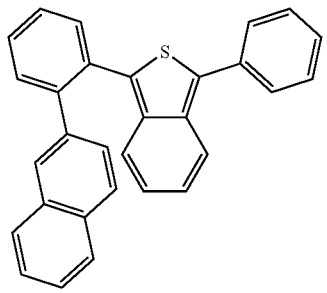
450
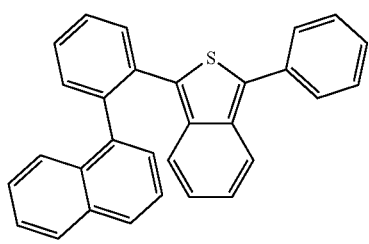
451
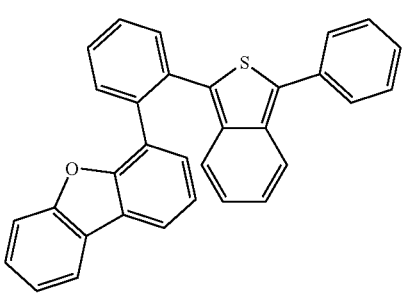
452
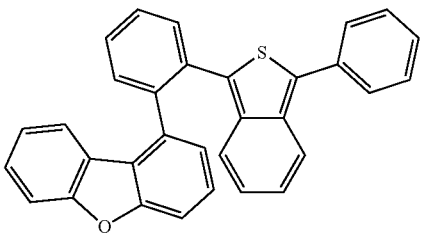
453
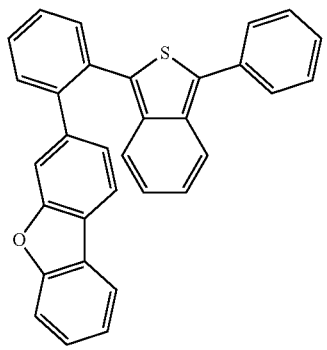

454 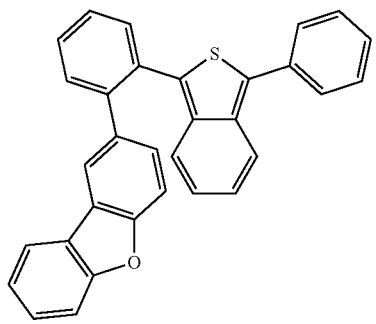
455 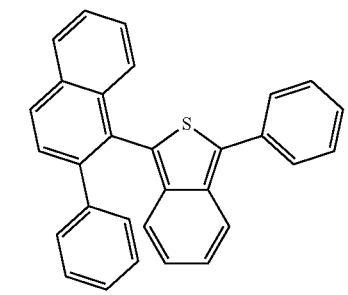
456 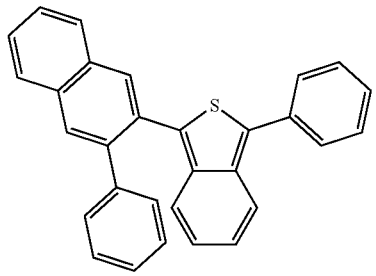
457
458 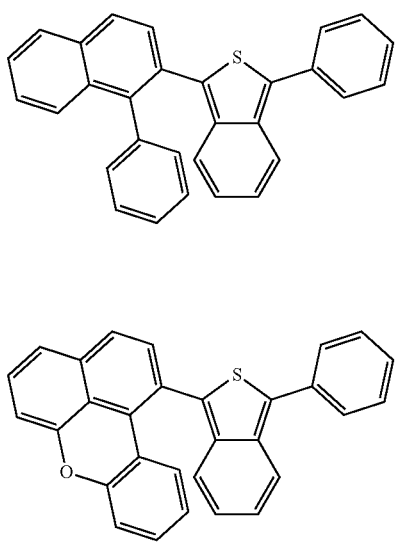
459 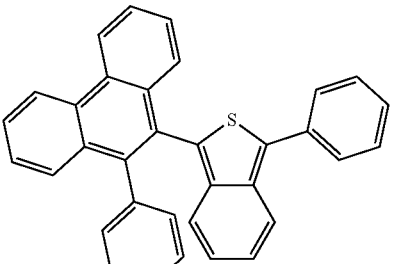
460 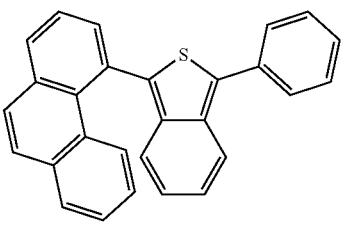
461 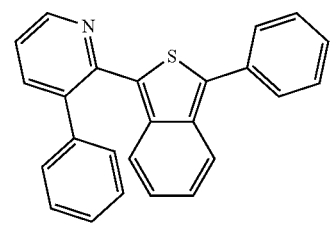
462 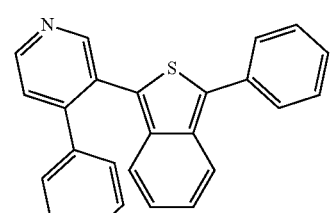
463 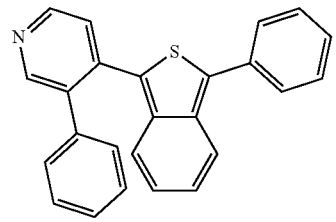
464 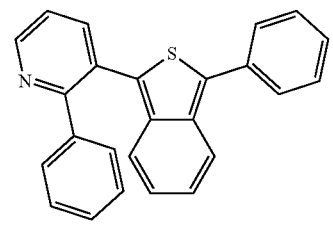

465 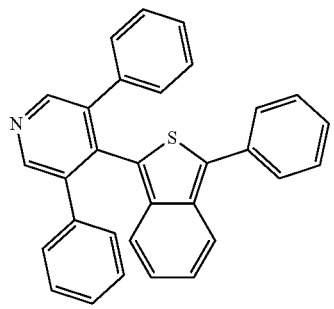
466 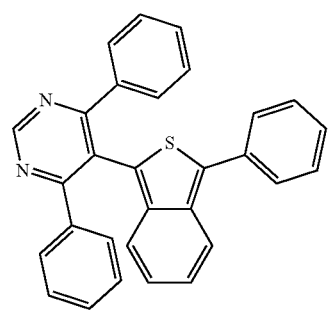
467 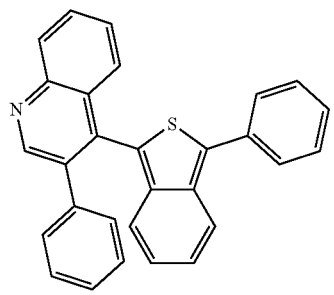
468 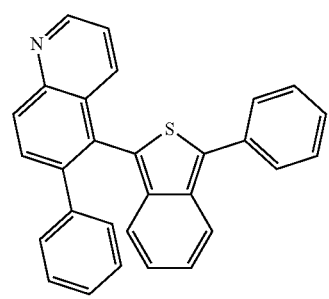
469 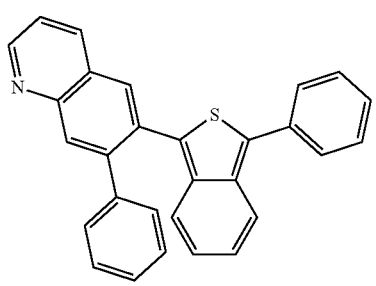
470 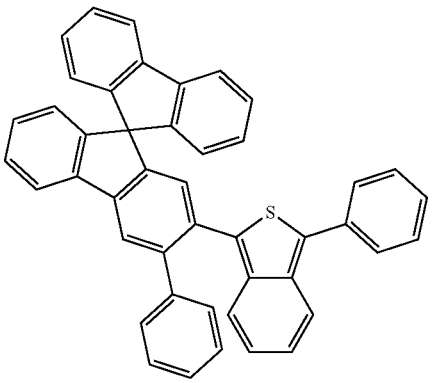
471 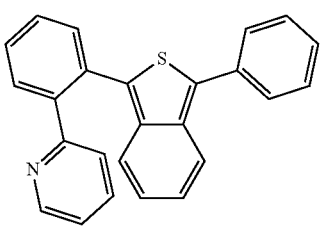
472 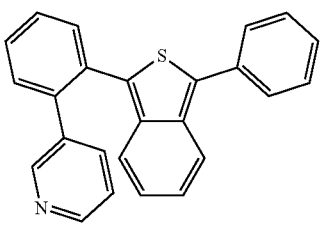
473 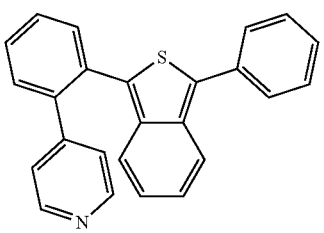
474 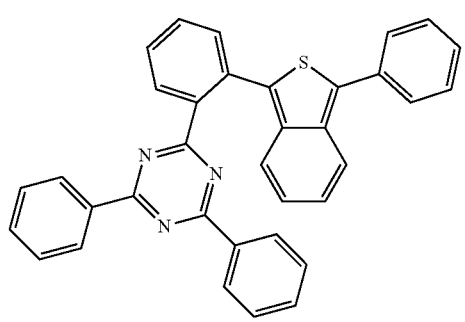

349
-continued
475
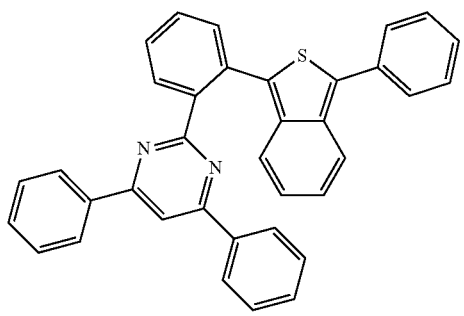
476
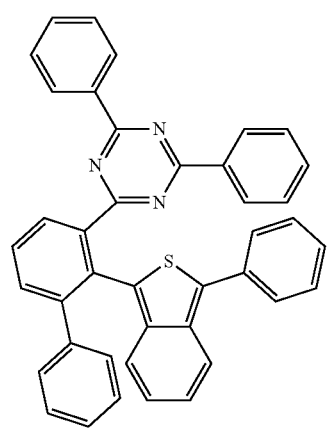
477
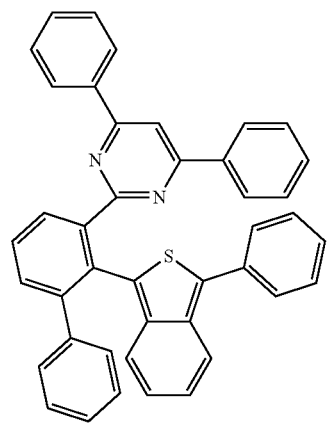
478
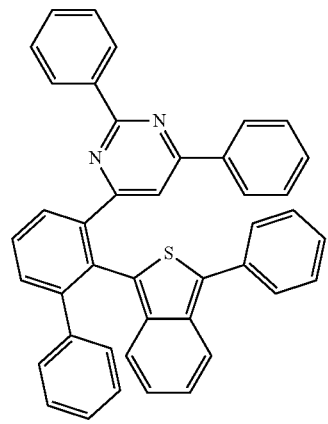
350
-continued
479
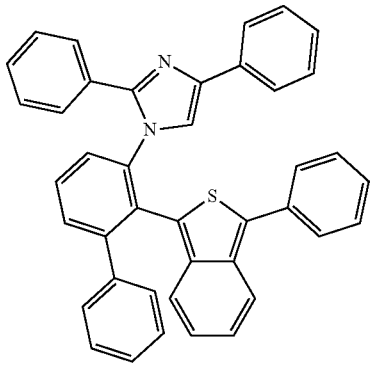
480
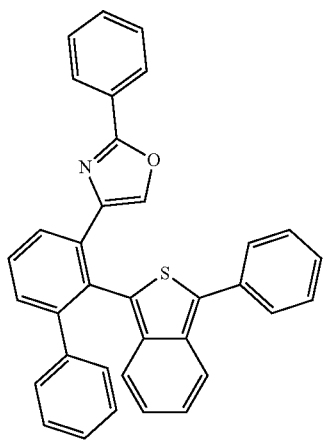
481
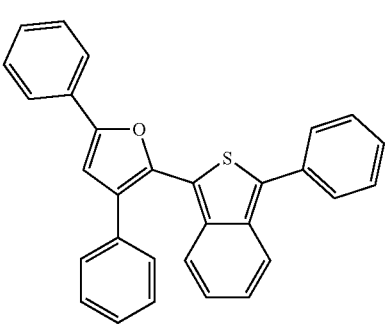
482
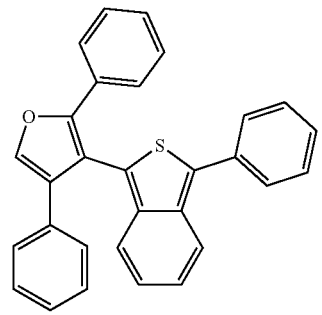

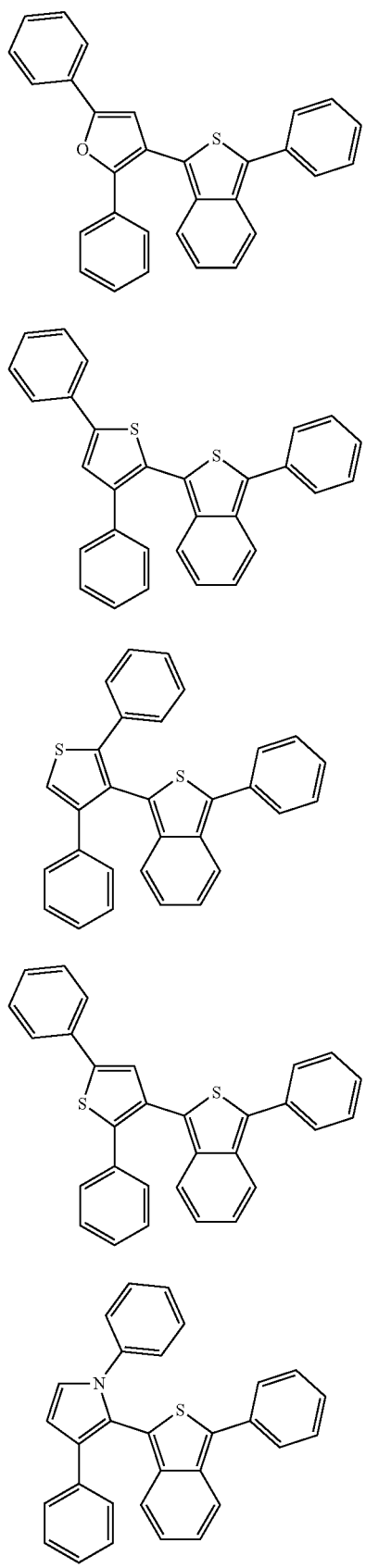
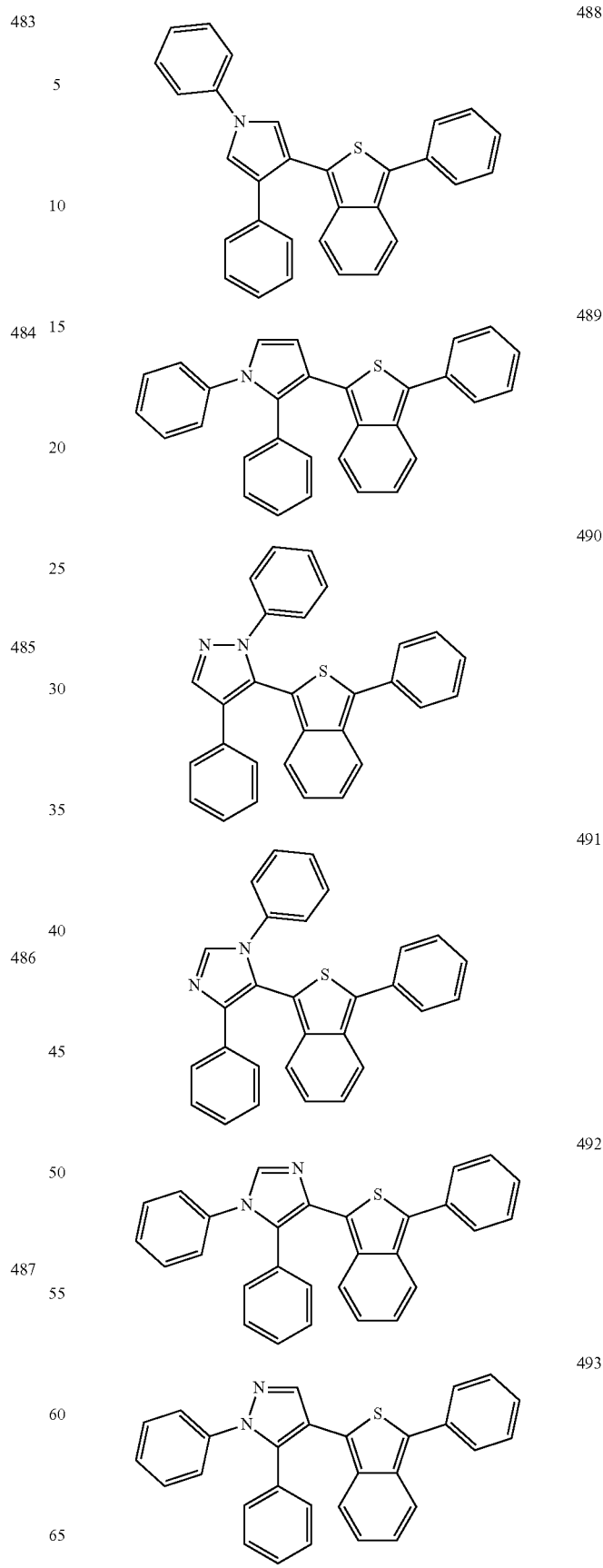

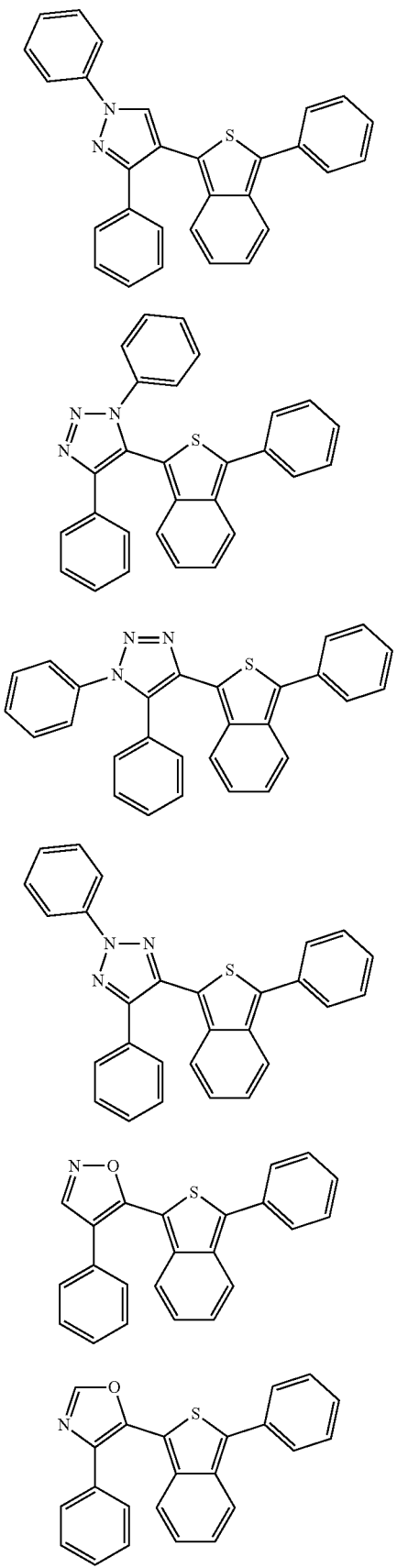
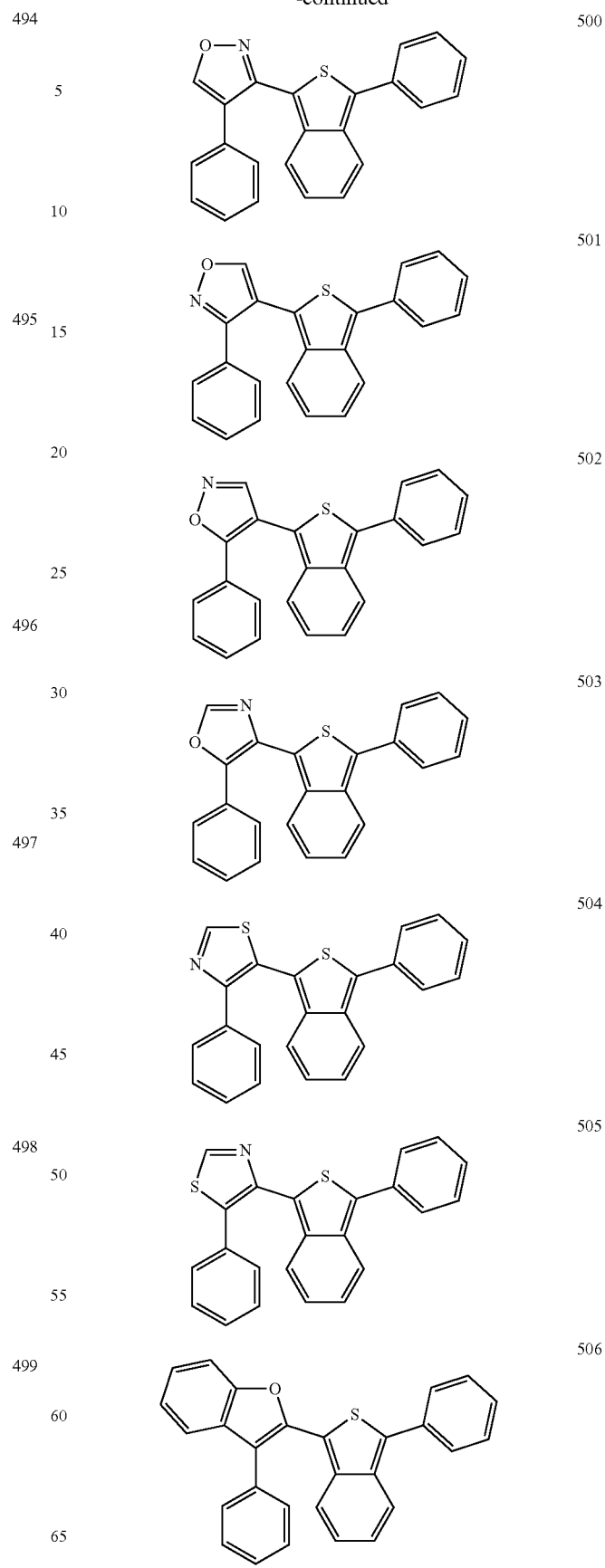

507 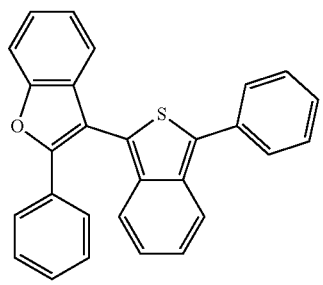
508 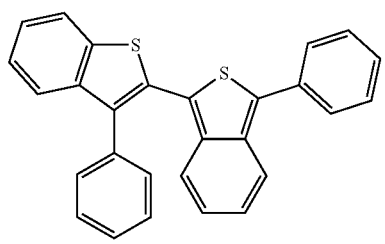
509 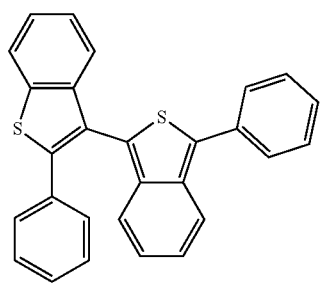
510 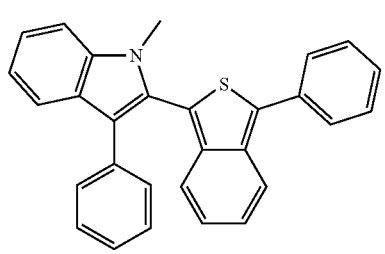
511 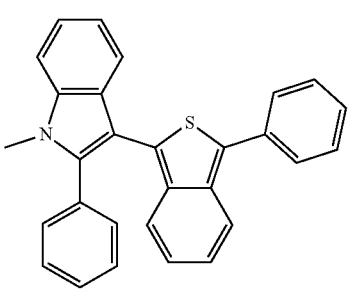
512 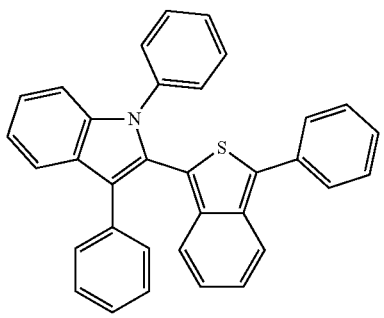
513 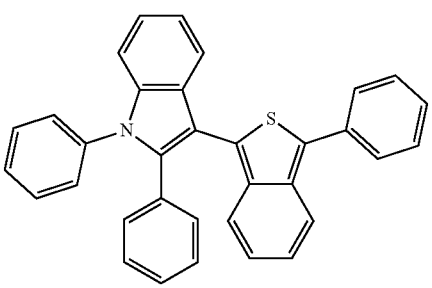
514 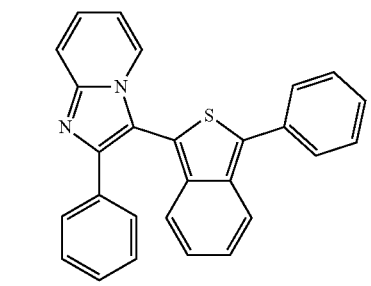
515 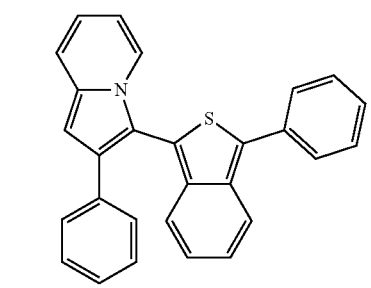
516 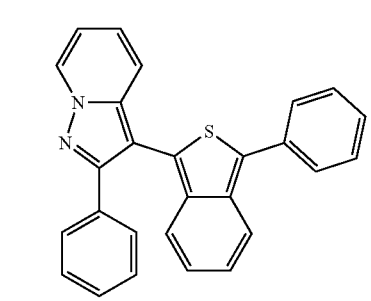

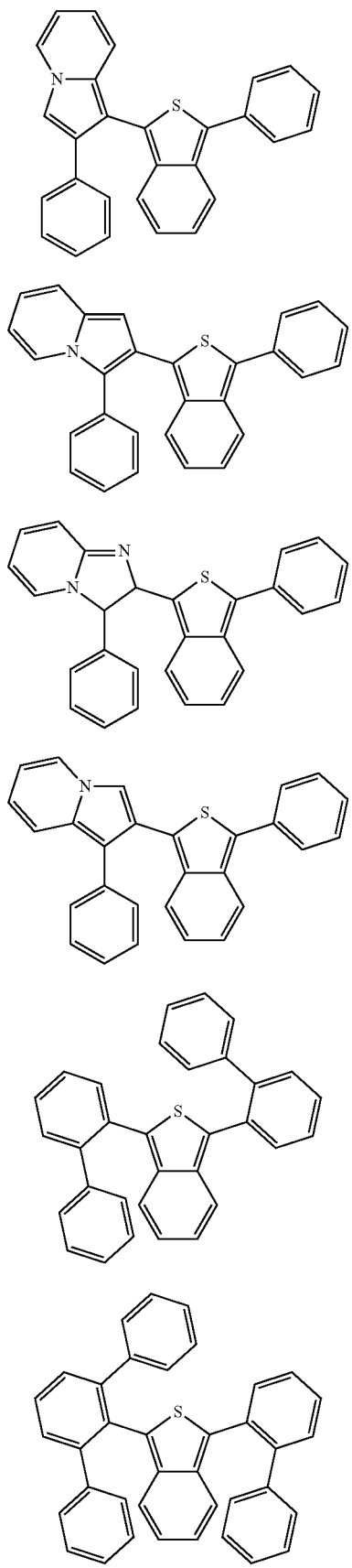
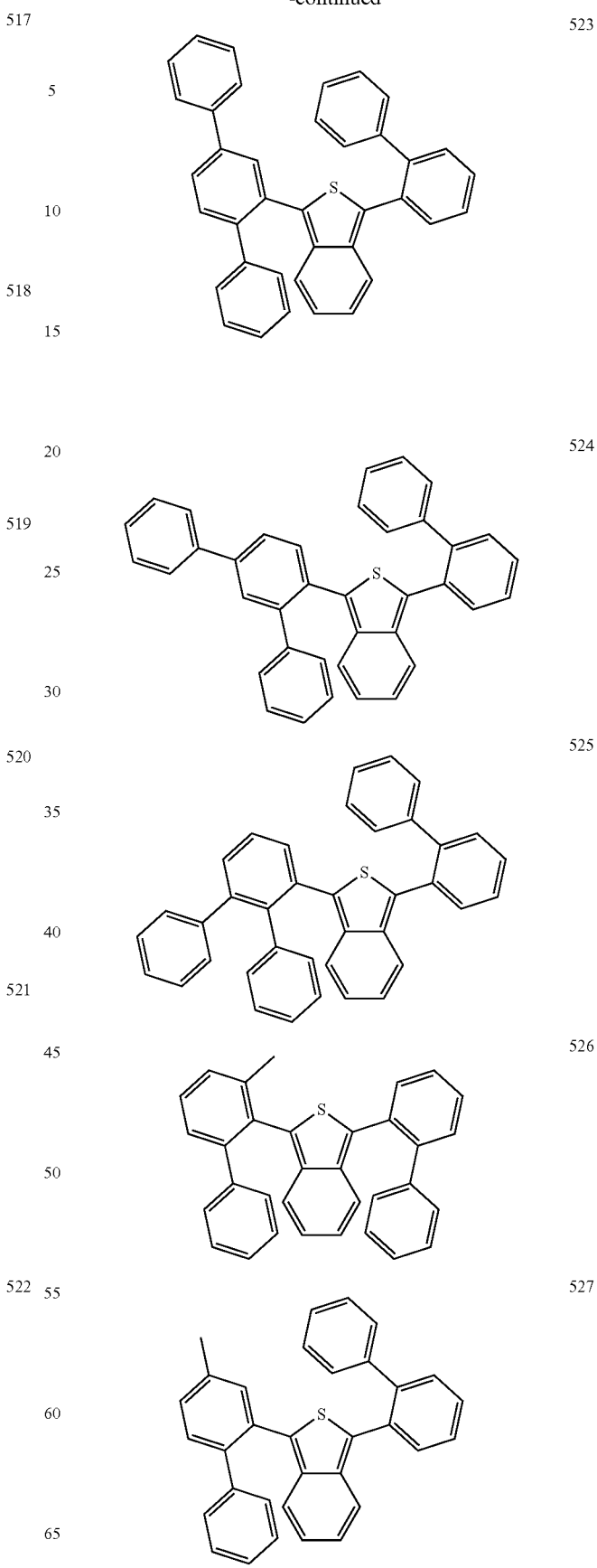

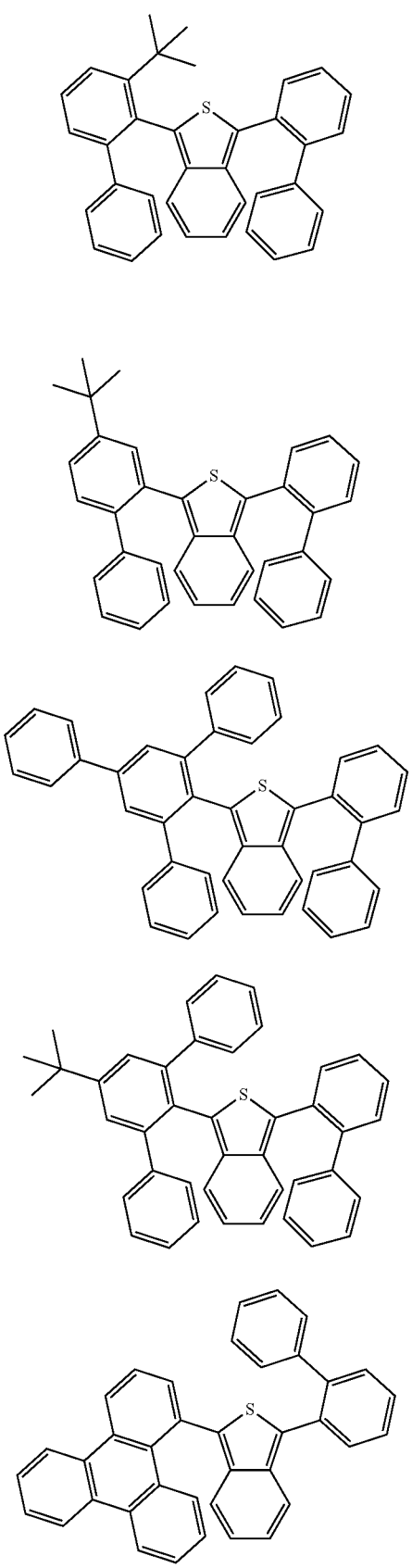
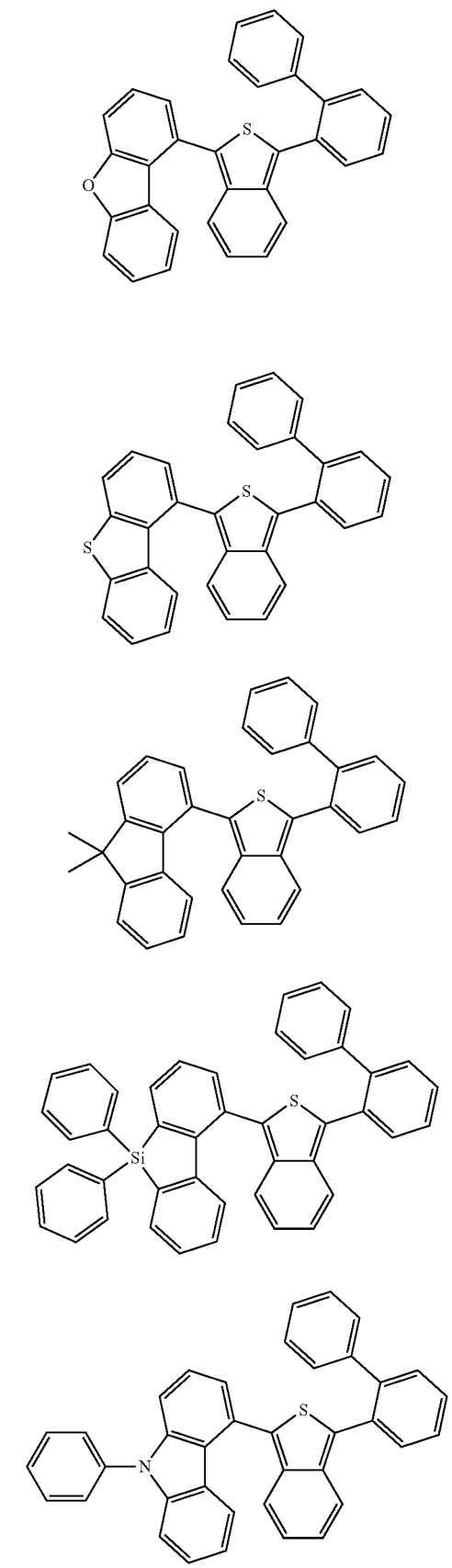

538
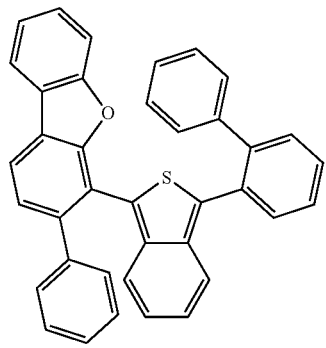
539
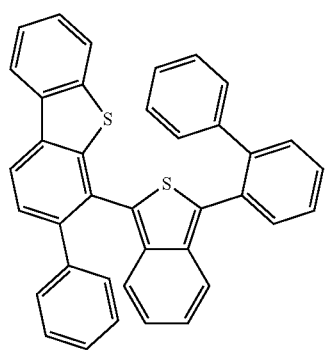
540
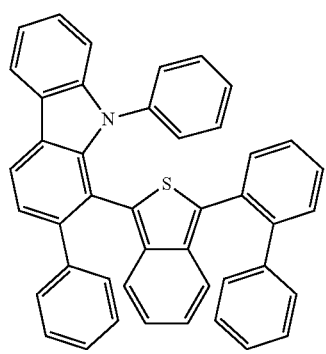
541
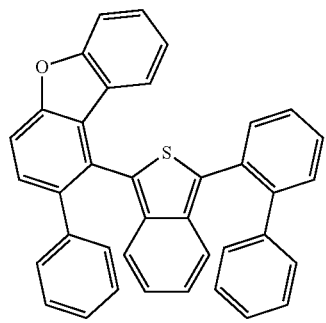
542
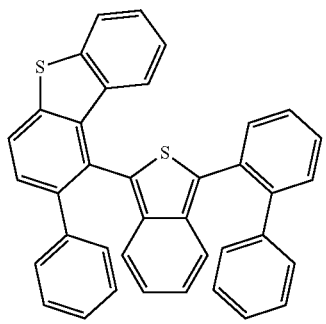
543
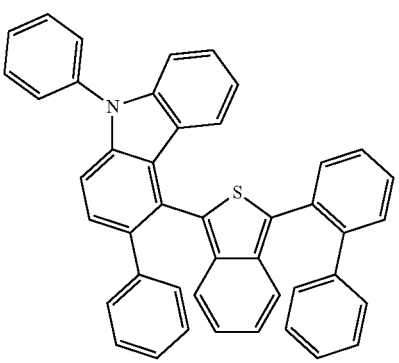
544
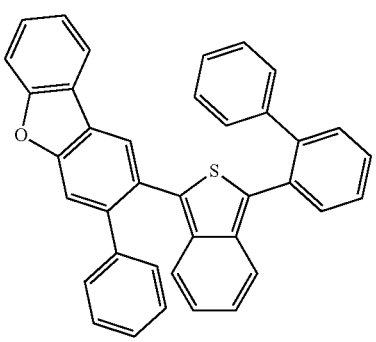
545
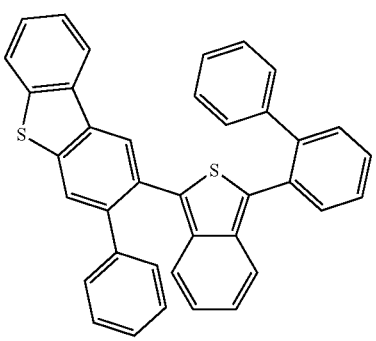

US 11,691,957 B2
546 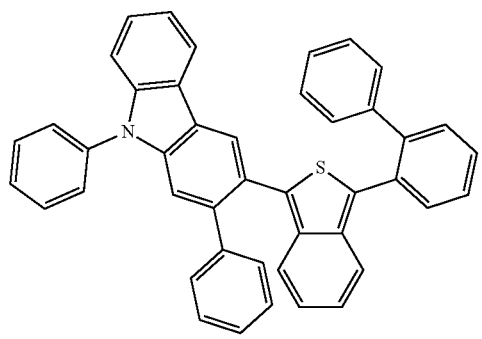
547 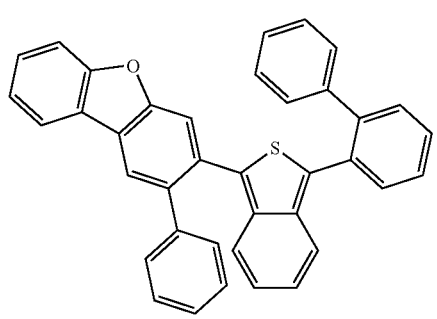
548 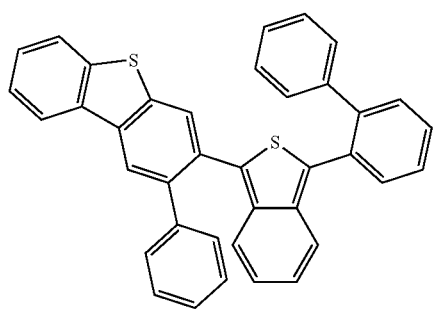
549 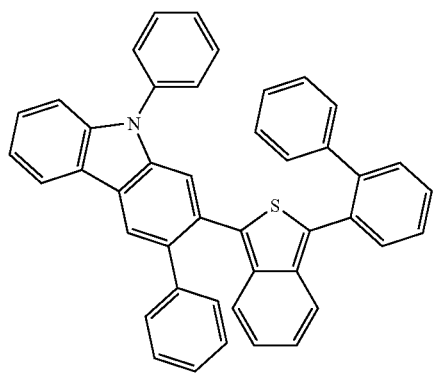
550 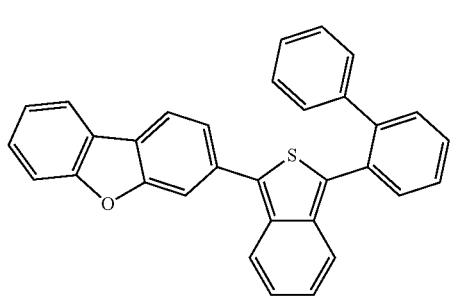
551 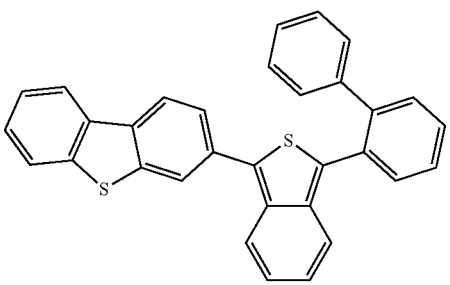
552 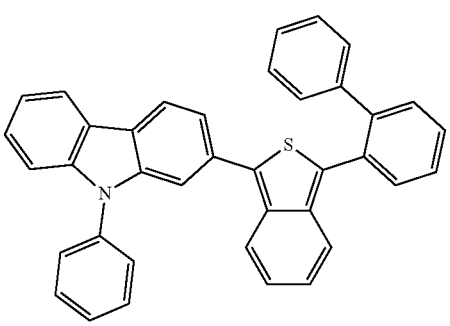
553 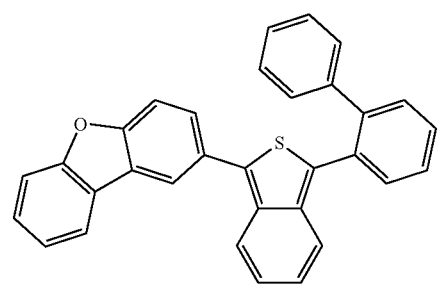
554 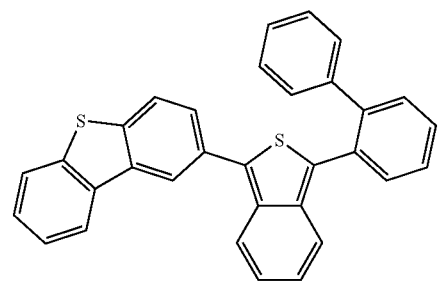
555 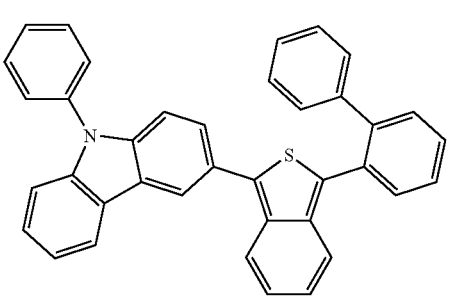

365
-continued
556
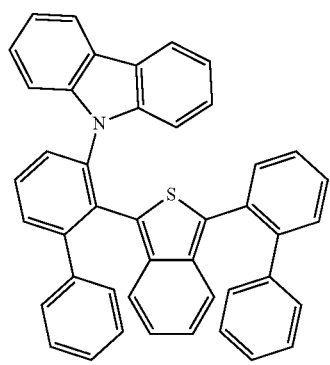
557
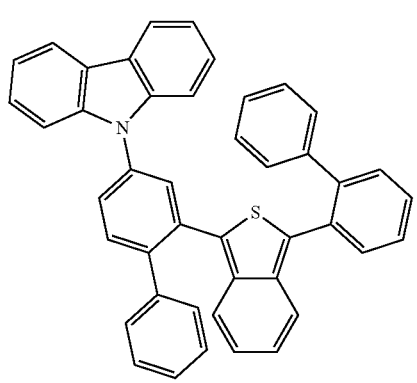
558
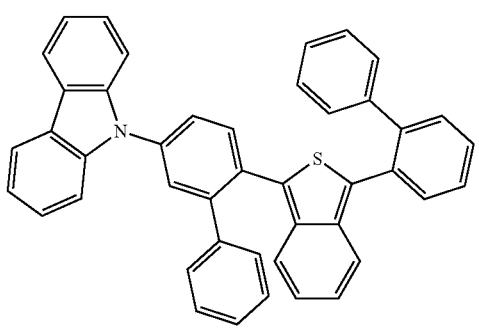
559
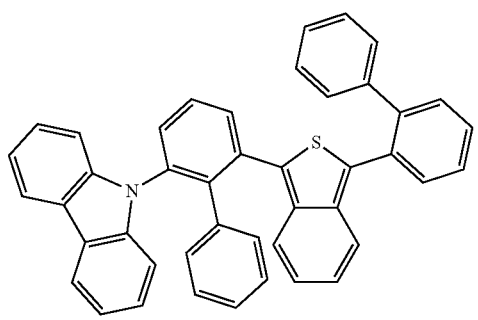
366
-continued
560
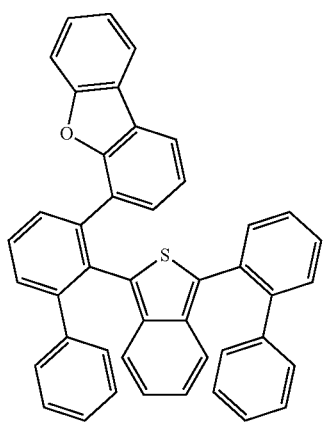
561
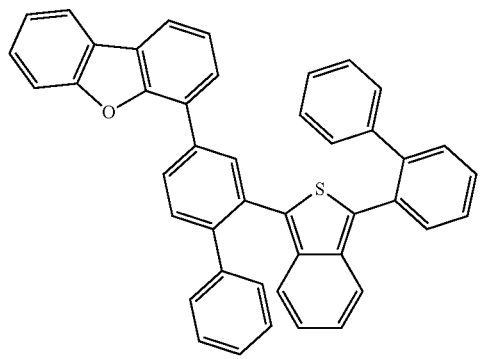
562
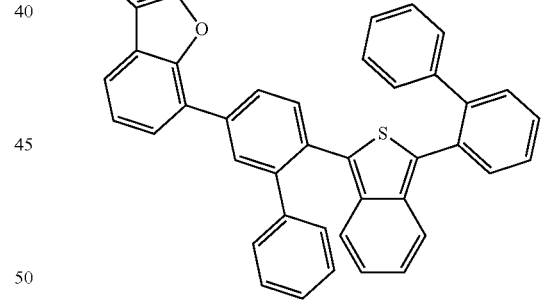
563
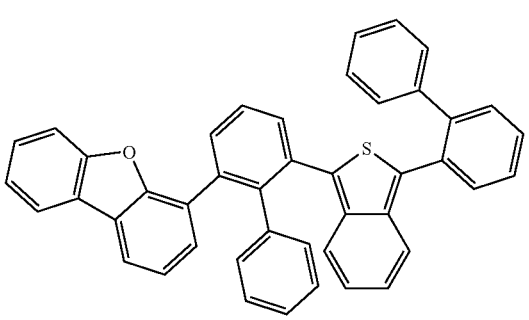

-continued
564
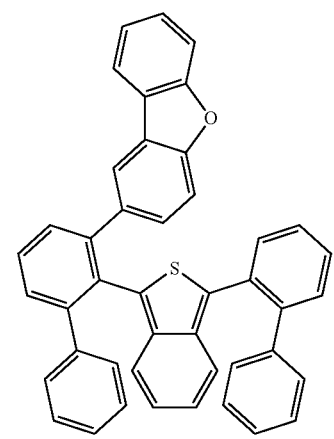
565
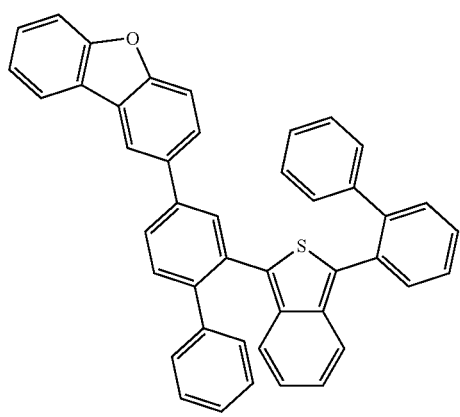
566
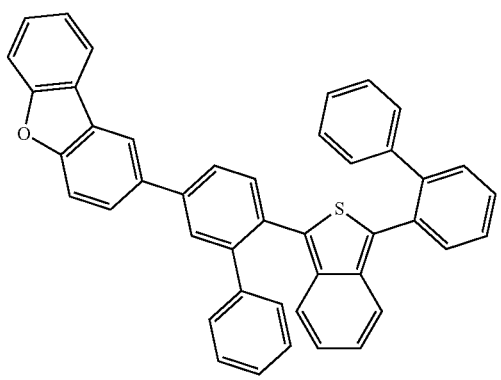
567
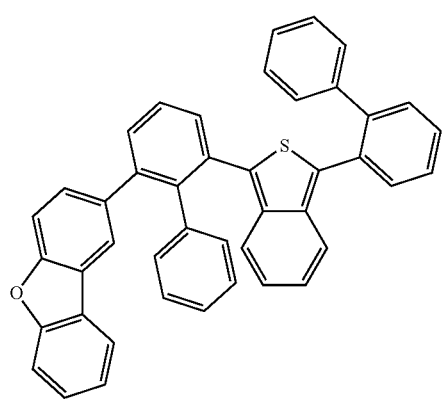
-continued
568
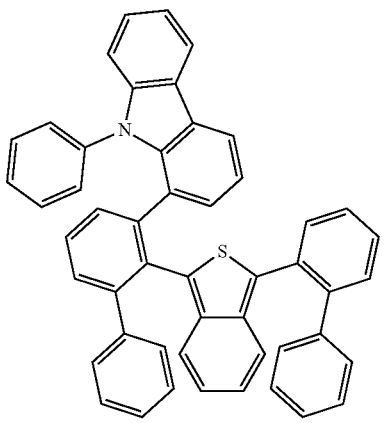
569
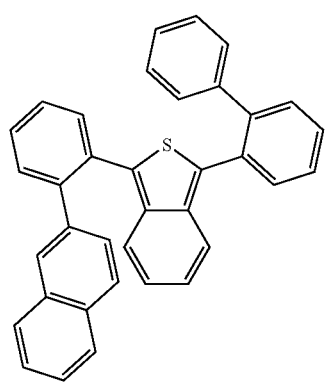
570
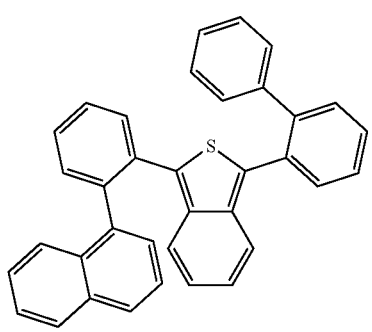
571
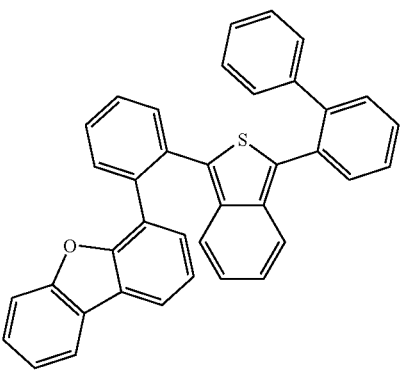

-continued
572
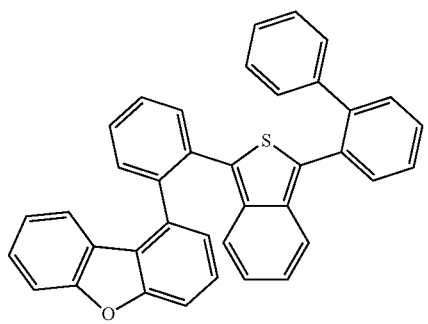
573
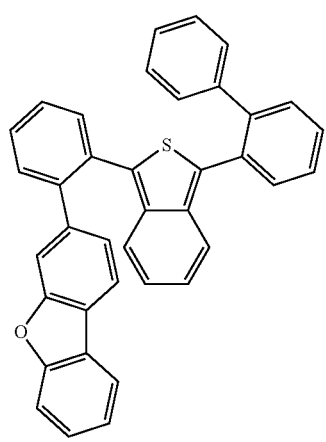
574
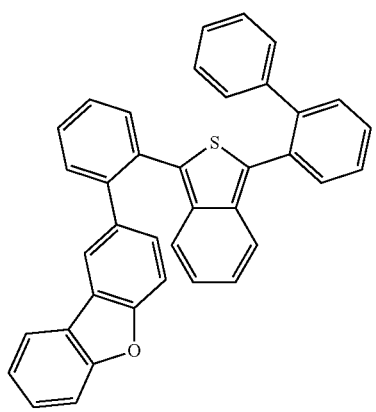
575
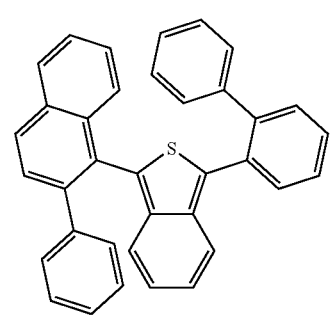
-continued
576
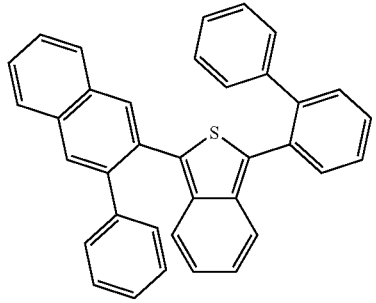
577
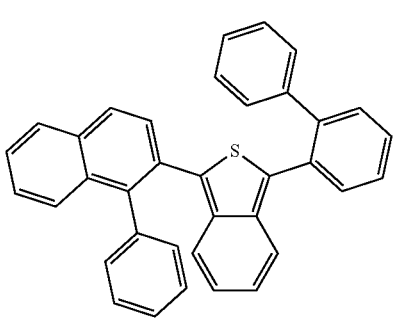
578
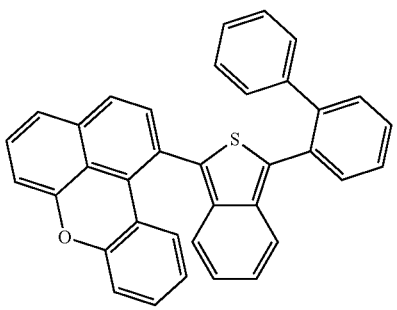
579
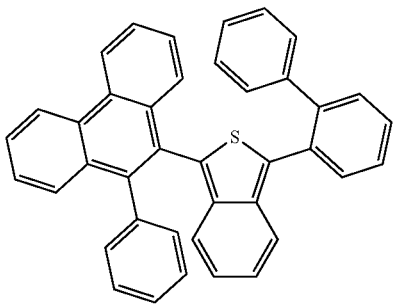
580
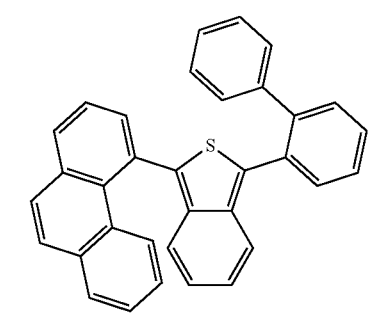

371
-continued
581
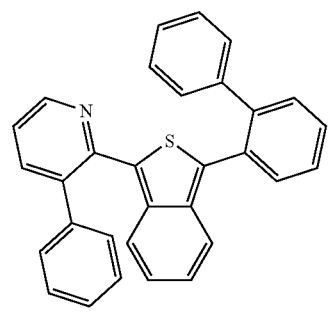
582
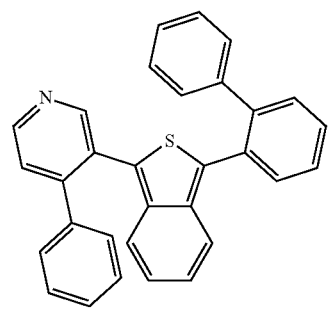
583
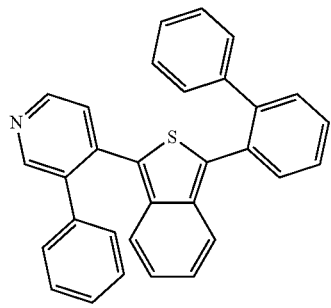
584
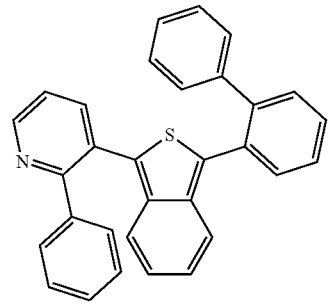
585
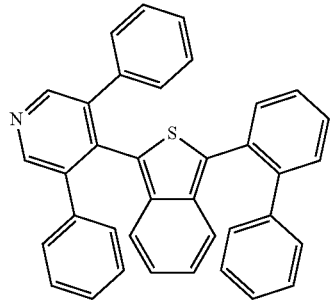
372
-continued
586
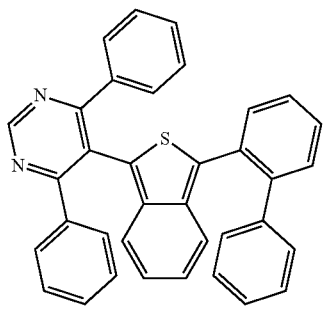
587
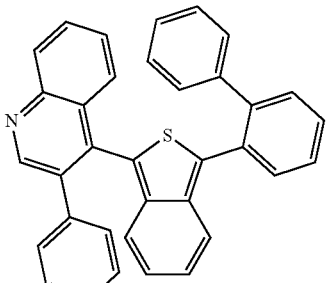
588
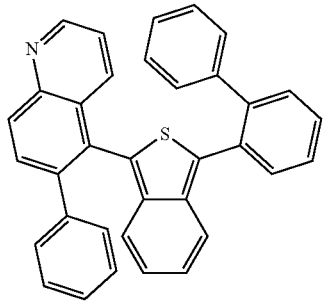
589
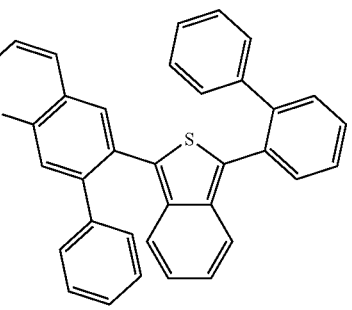
590
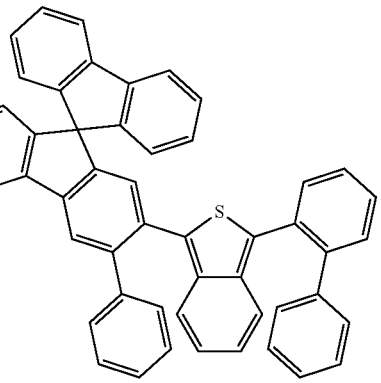

591 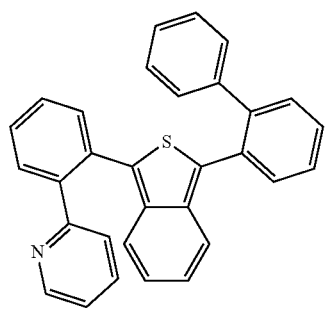
592 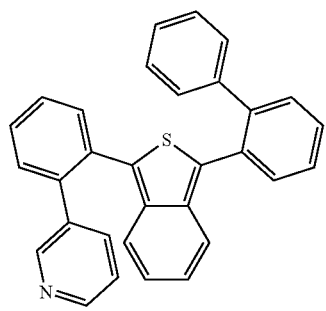
593 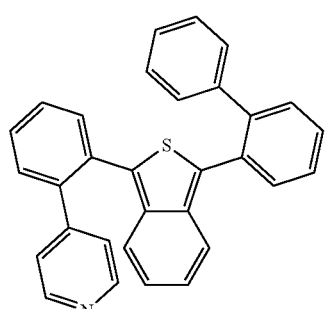
594 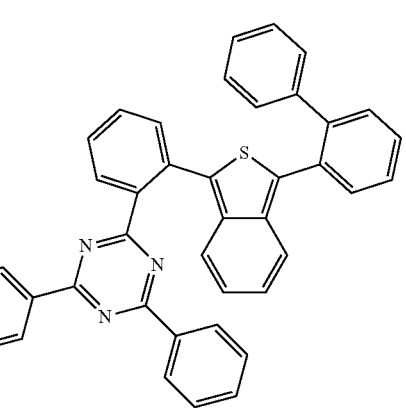
595 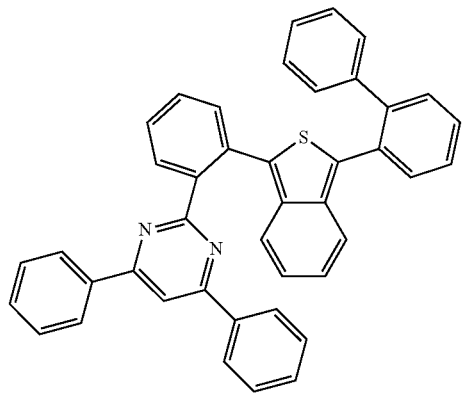
596 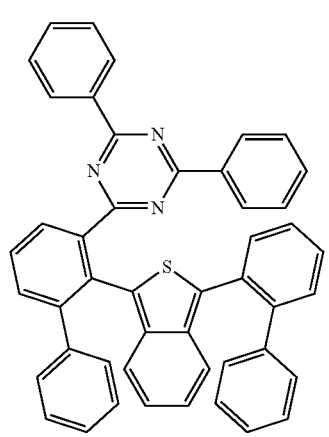
597 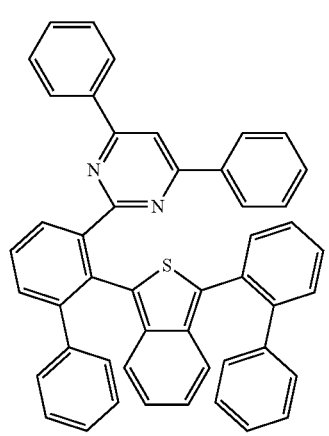

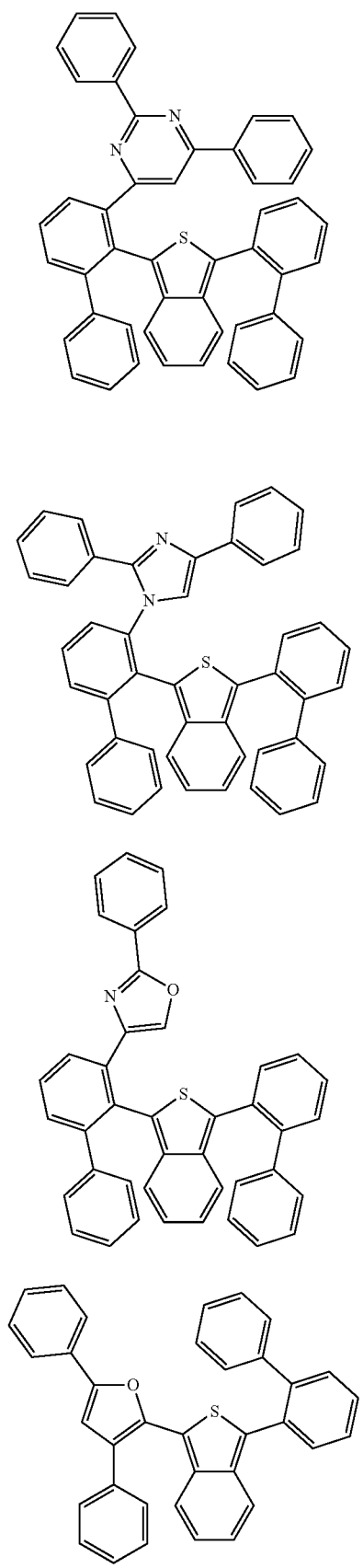
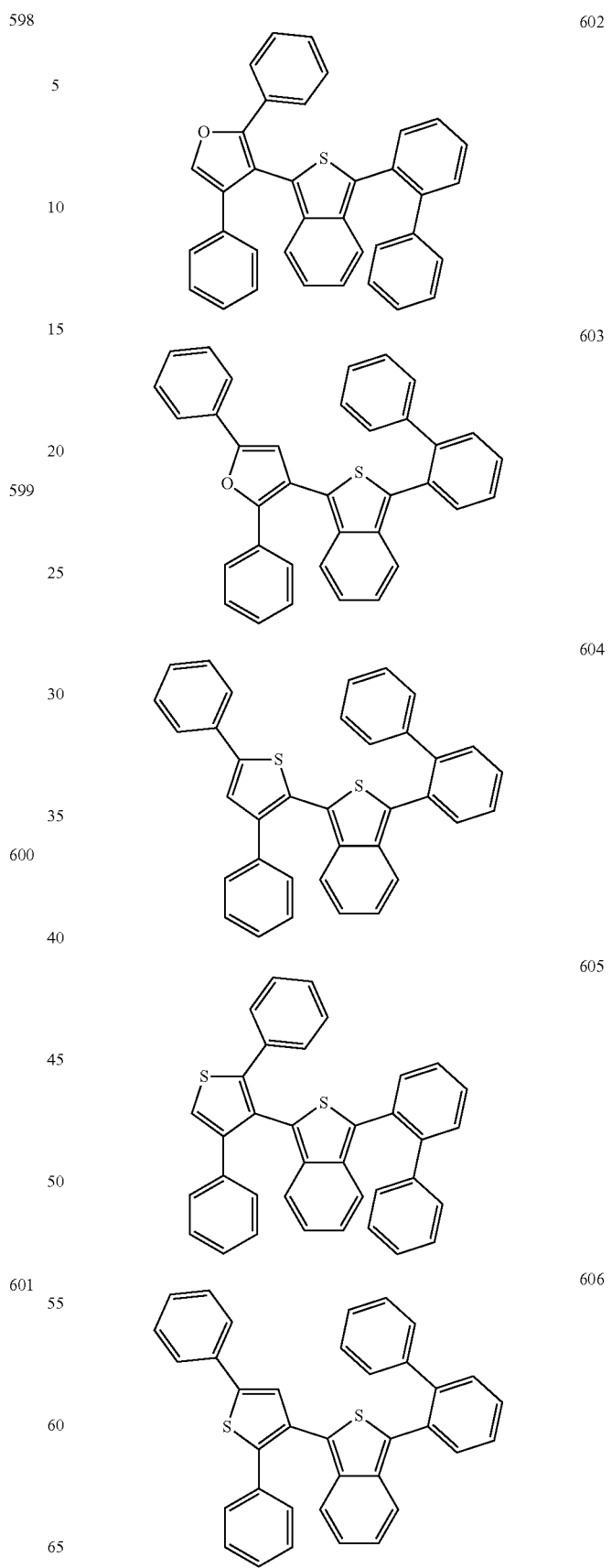

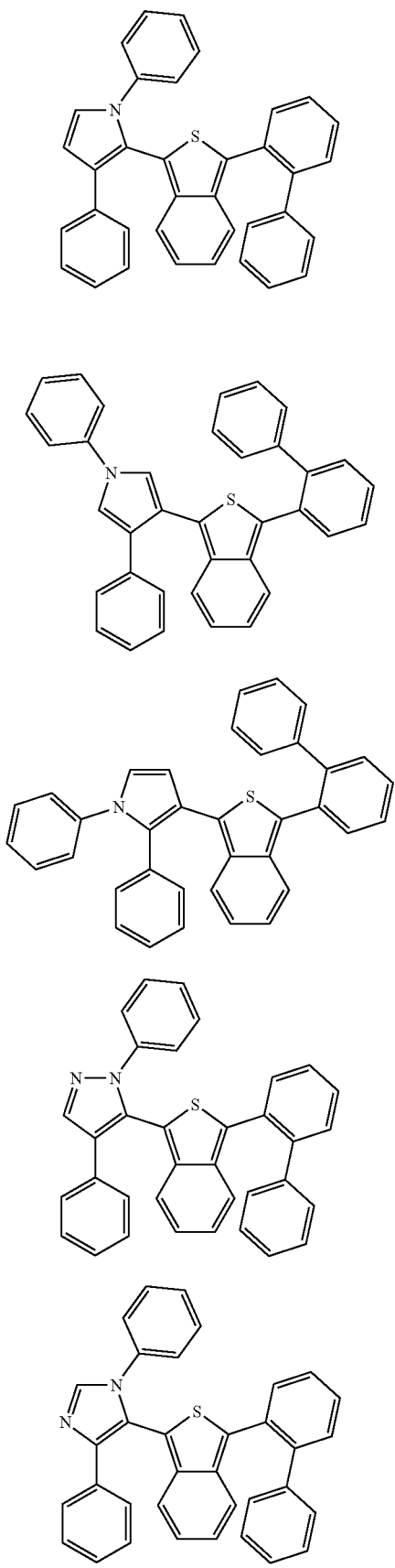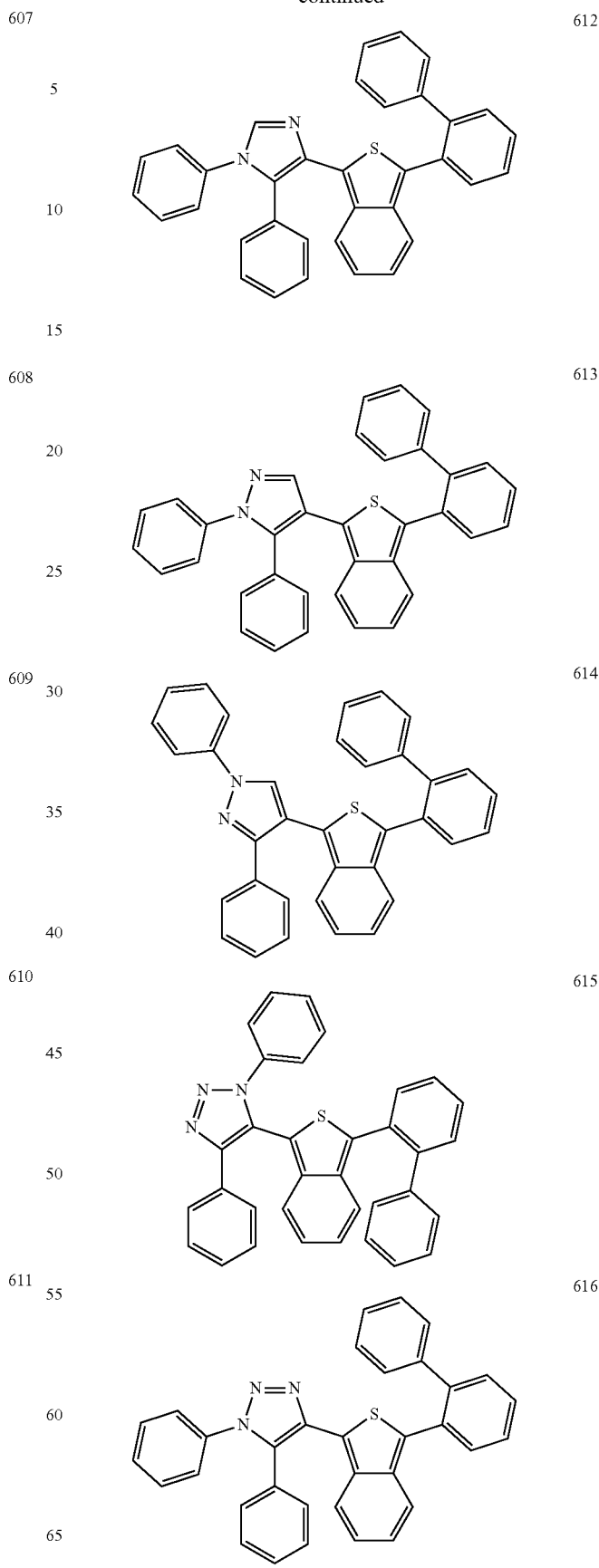

379
-continued
617
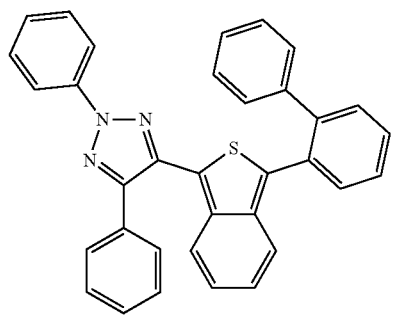
618
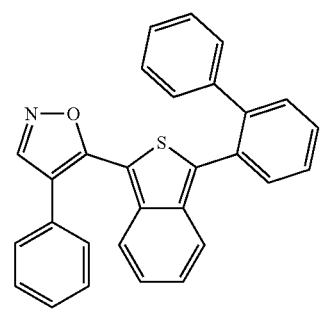
619
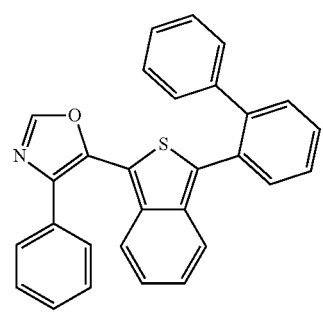
620
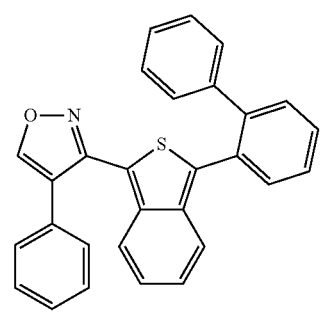
621
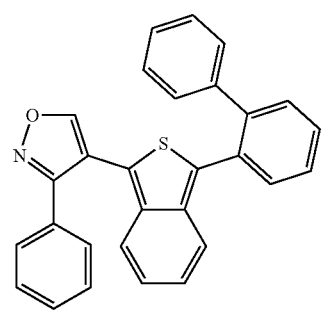
380
-continued
622
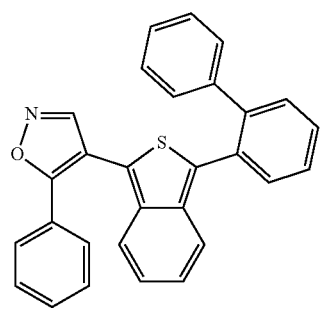
623
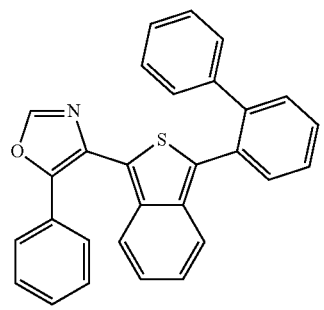
624
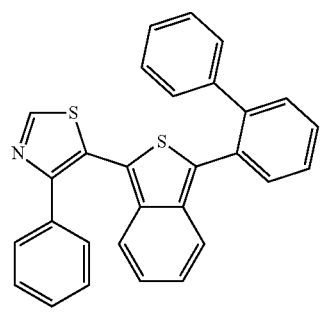
625
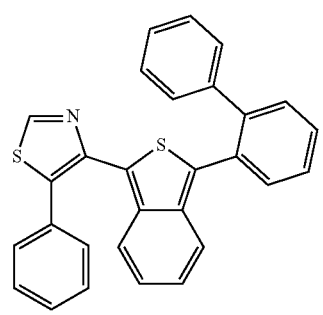
626
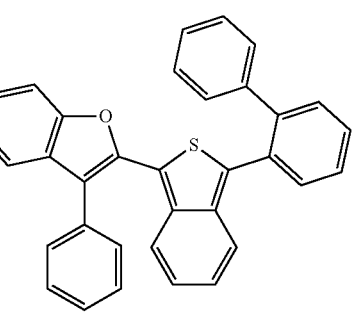

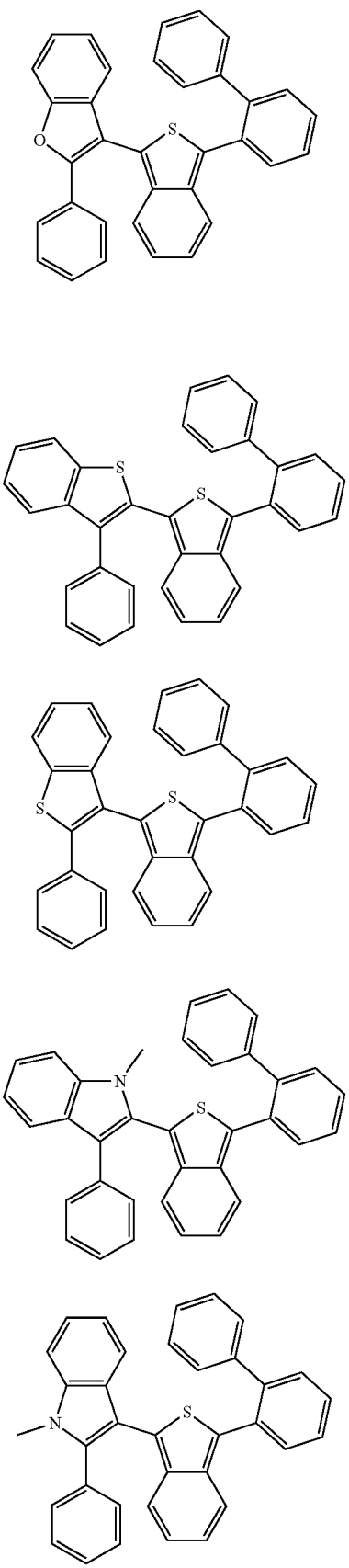
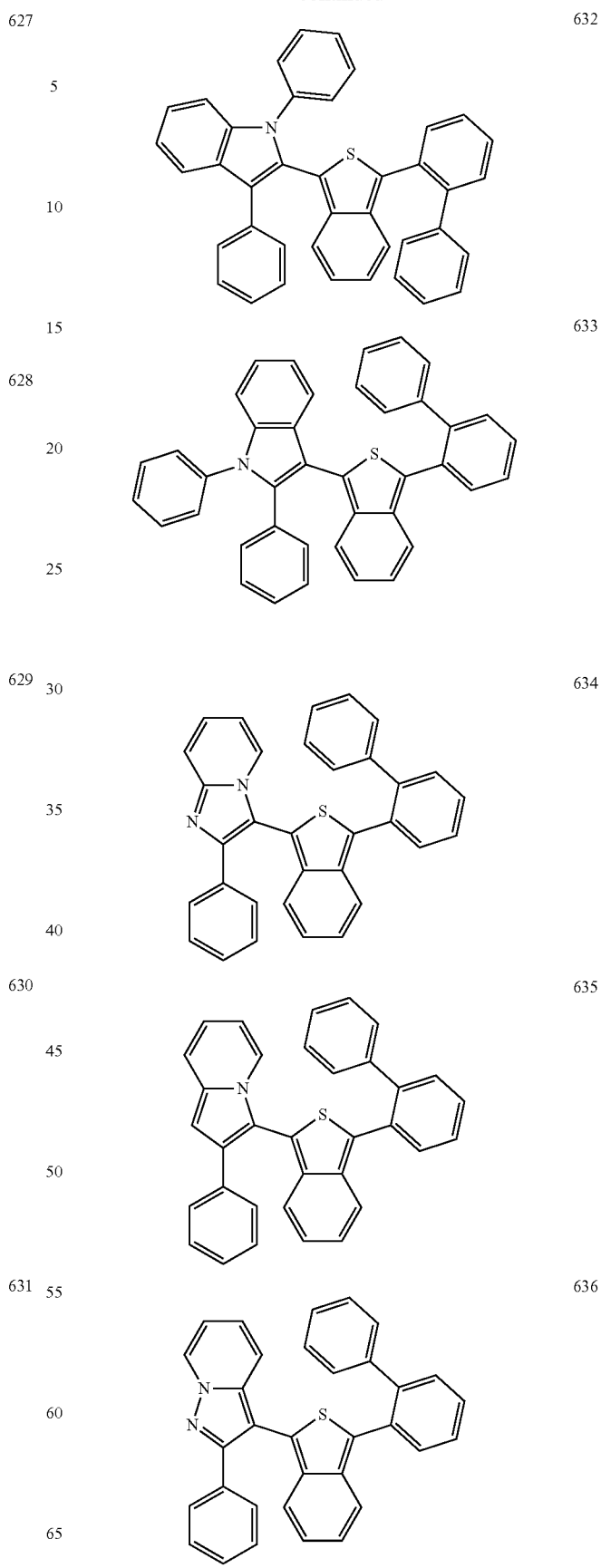

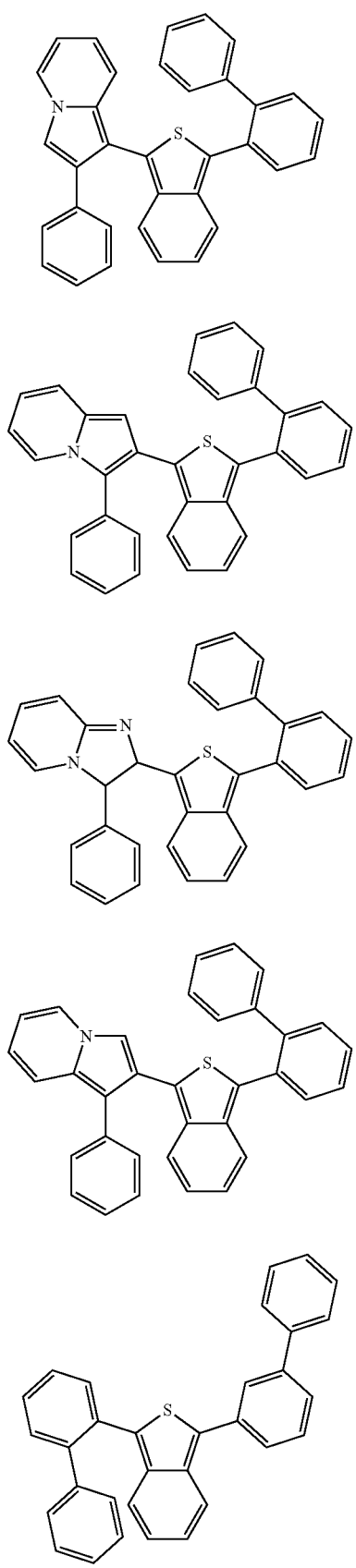
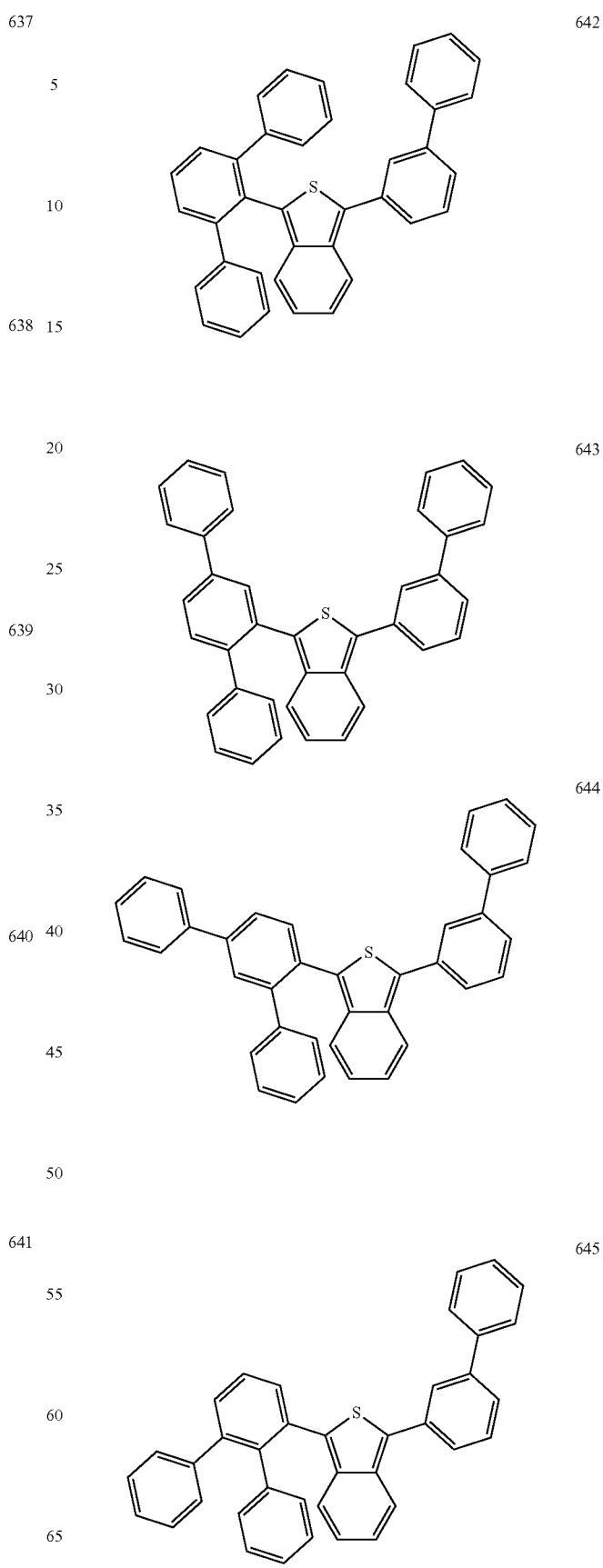

| | |
|---|---|
| 646 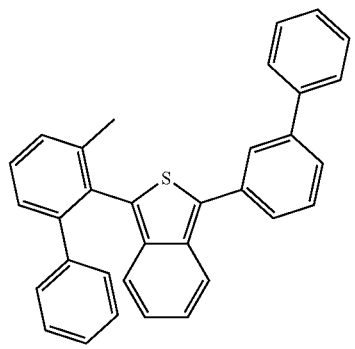 | 650 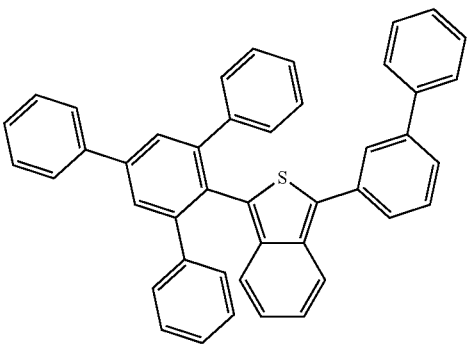 |
| 647 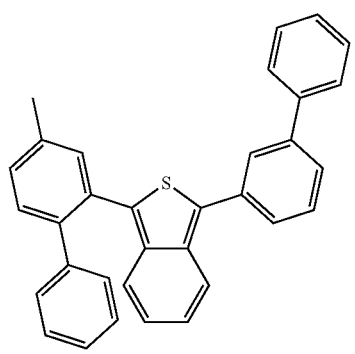 | 651 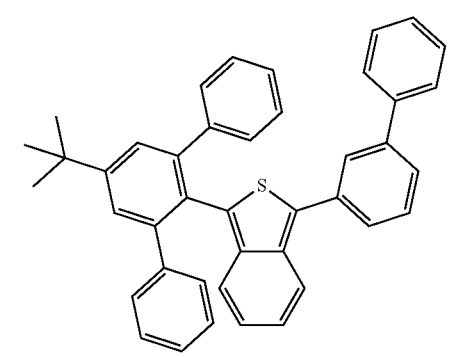 |
| 648 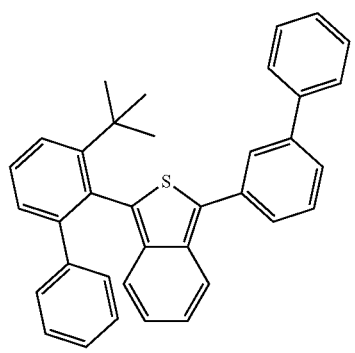 | 652 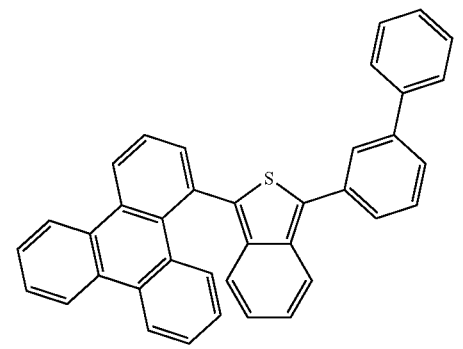 |
| 649 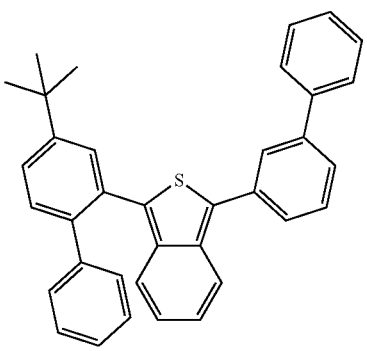 | 653 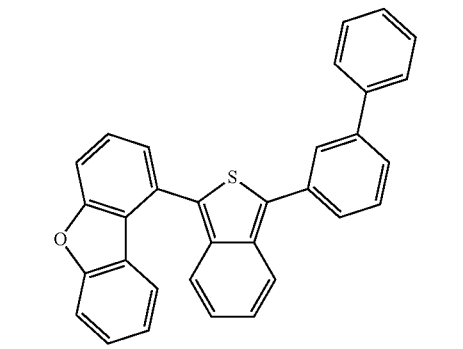 |

387
-continued
654
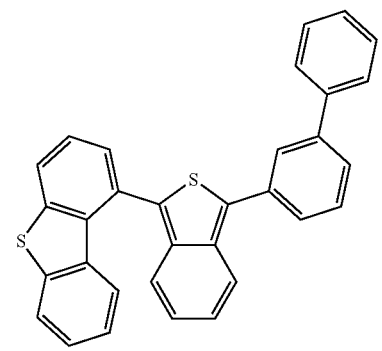
655
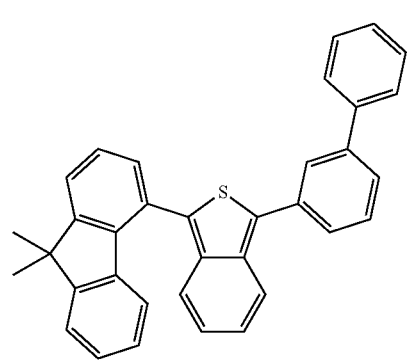
656
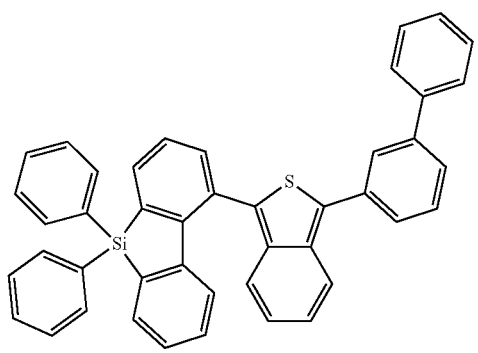
657
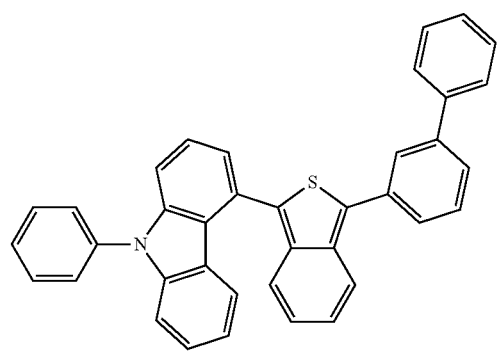
388
-continued
658
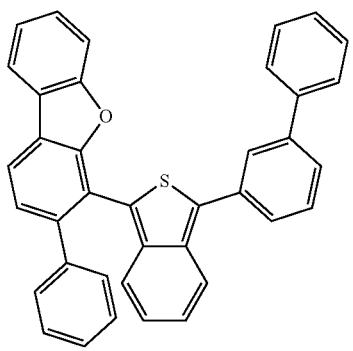
659
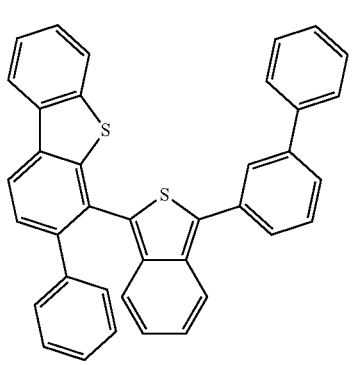
660
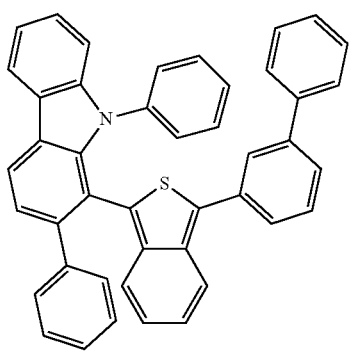
661
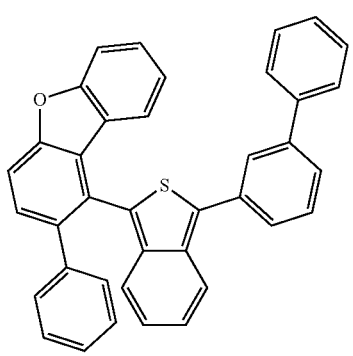

662
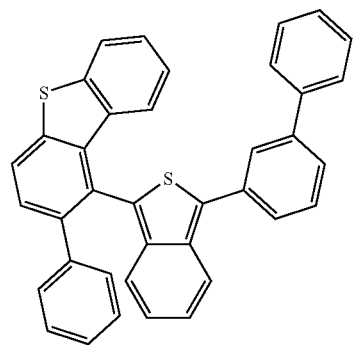
663
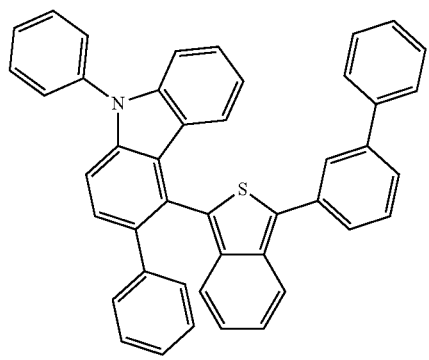
664
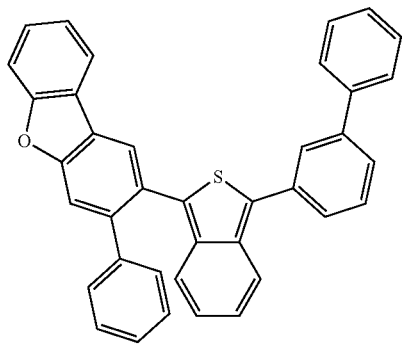
665
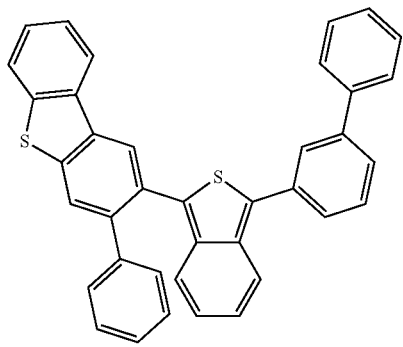
666
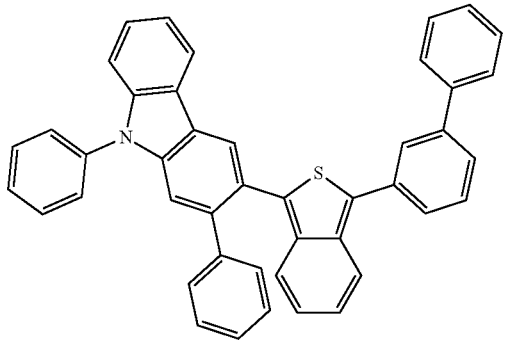
667
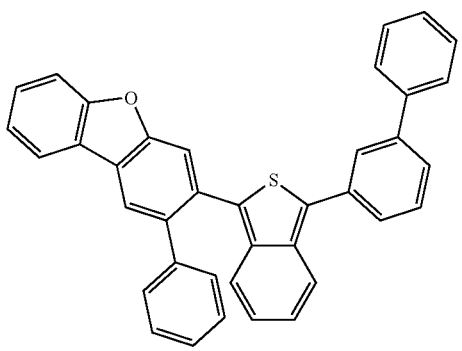
668
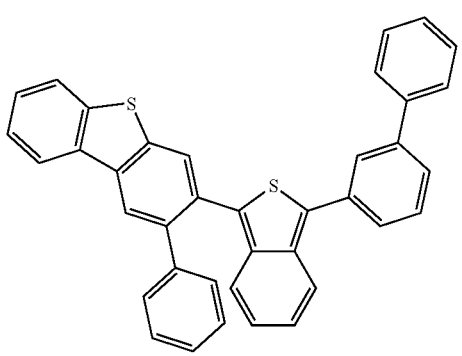
669
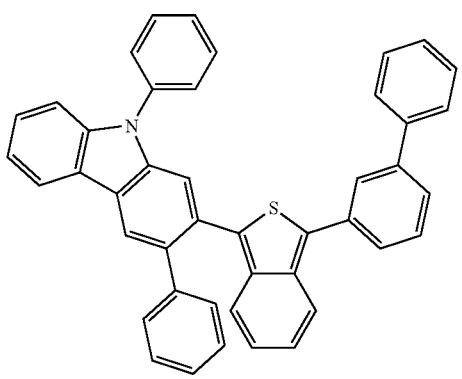

391
-continued
392
-continued
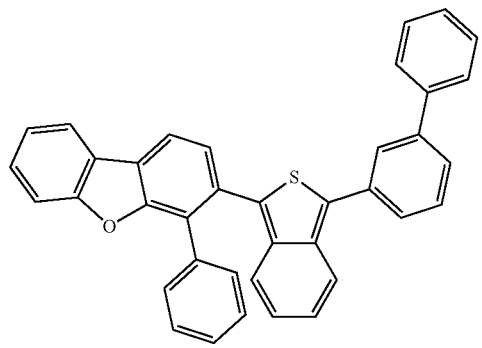
670
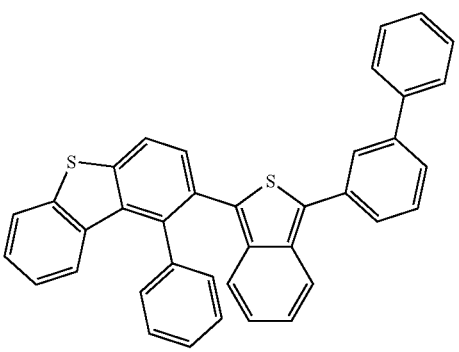
674
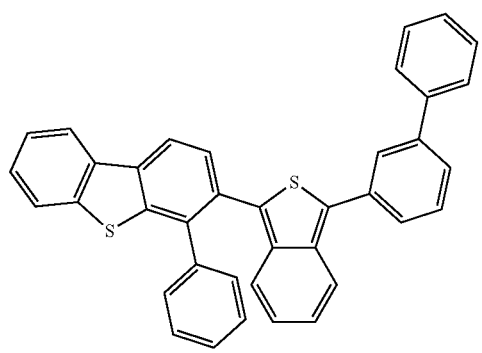
671
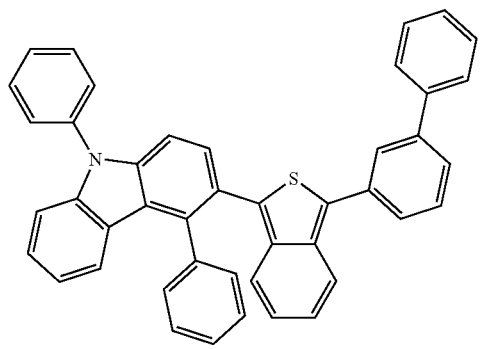
675
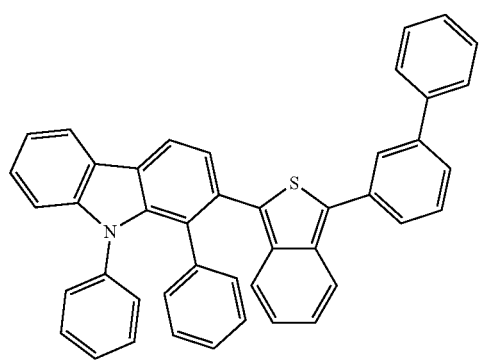
672
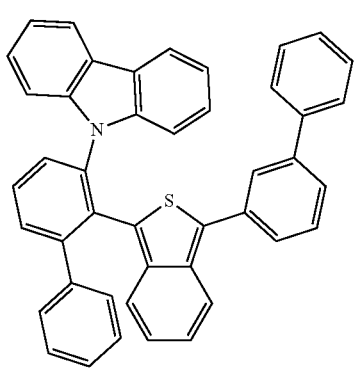
676
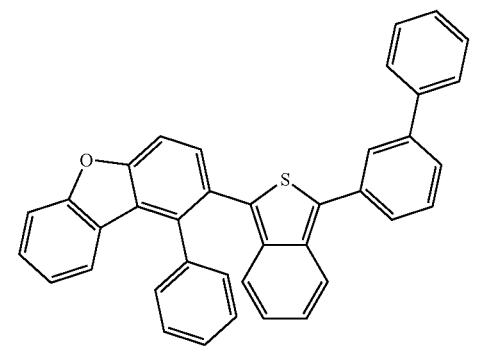
673
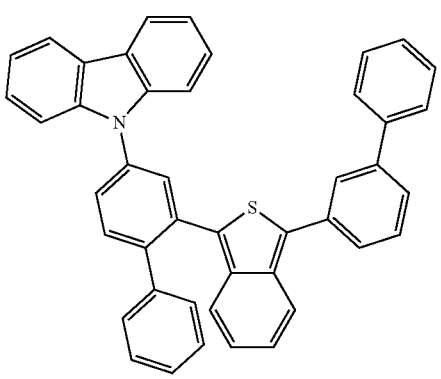
677

-continued
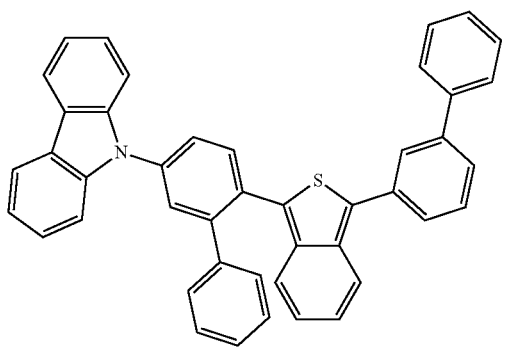
678
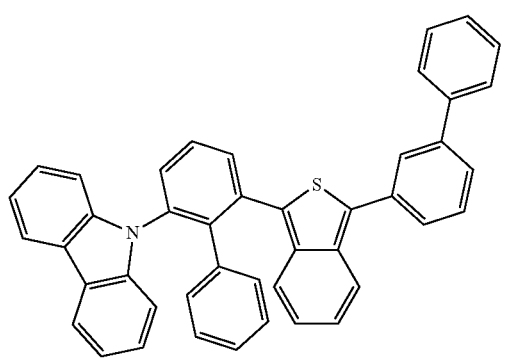
679
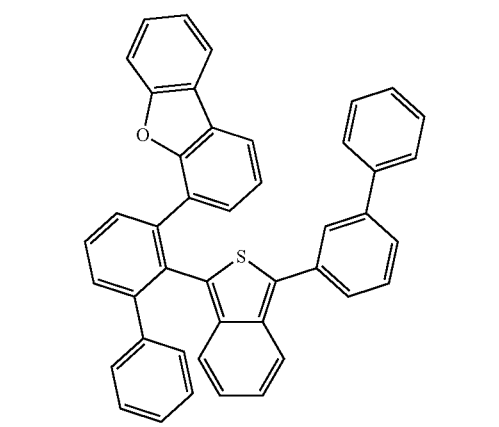
680
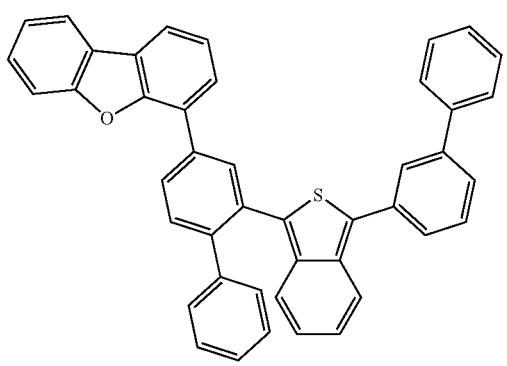
681
-continued
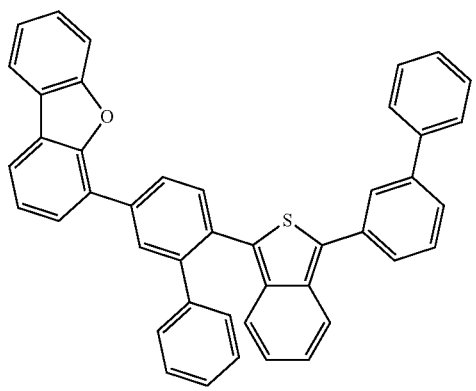
682
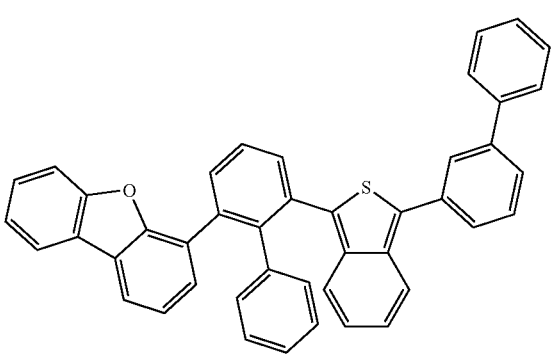
683
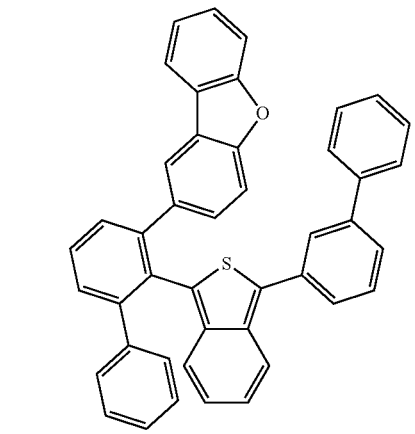
684
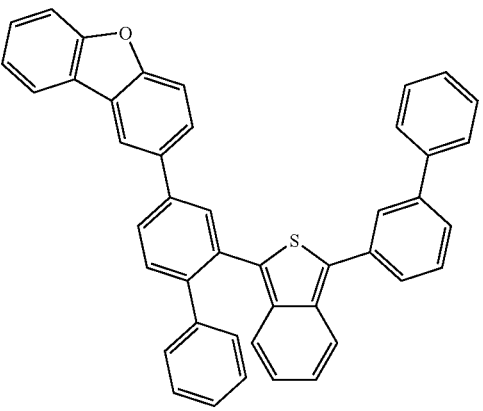
685

395
-continued
686
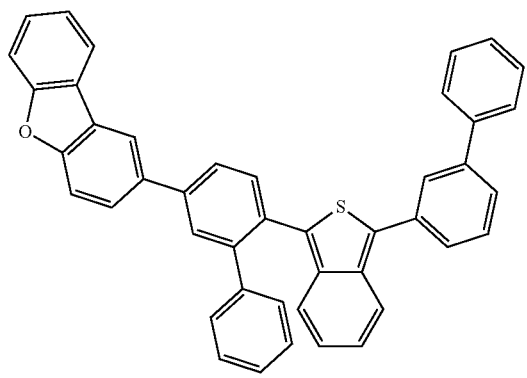
687
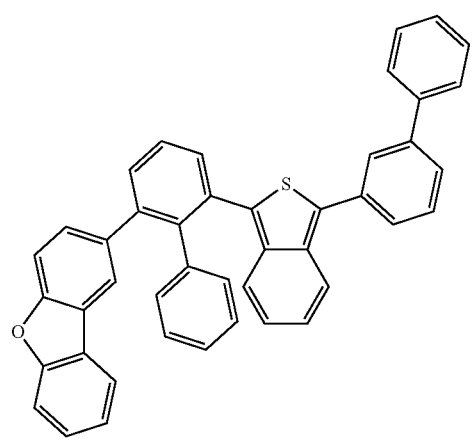
688
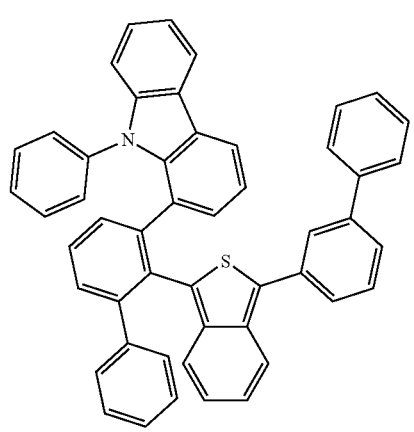
396
-continued
689
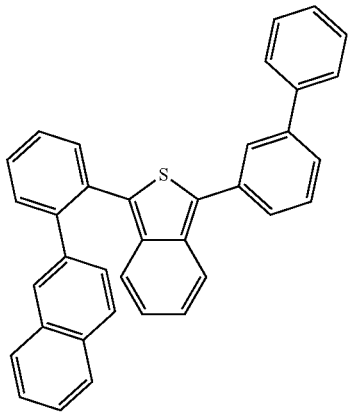
690
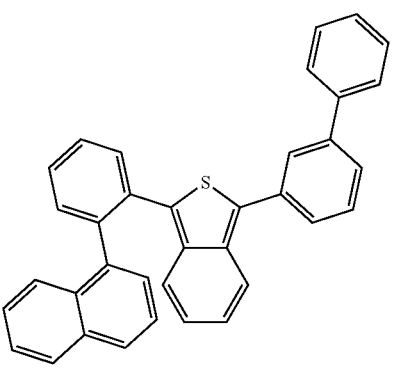
691
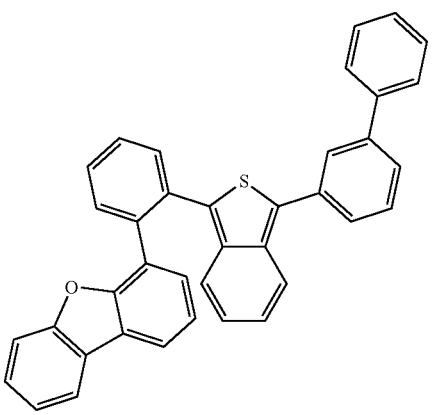
692
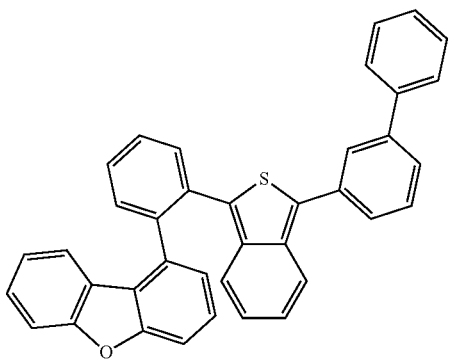

693
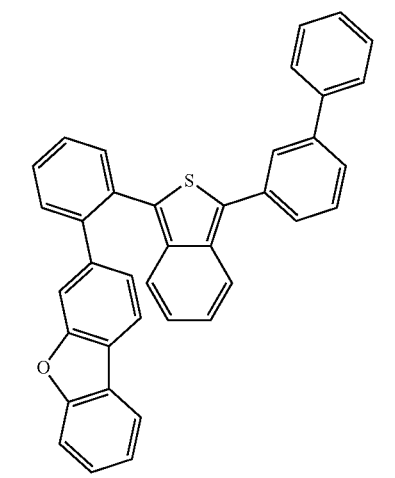
694
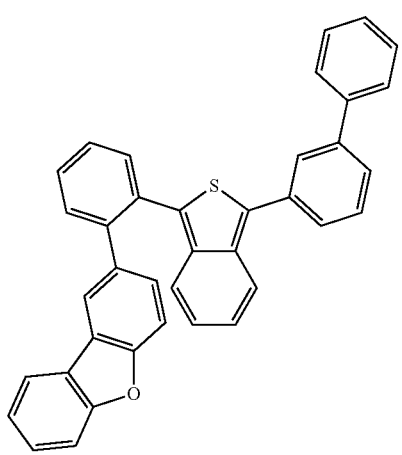
695
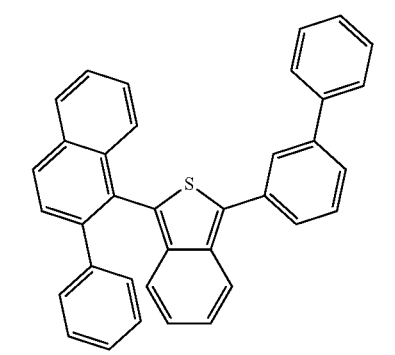
696
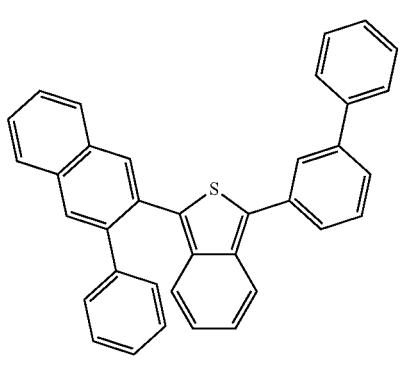
697
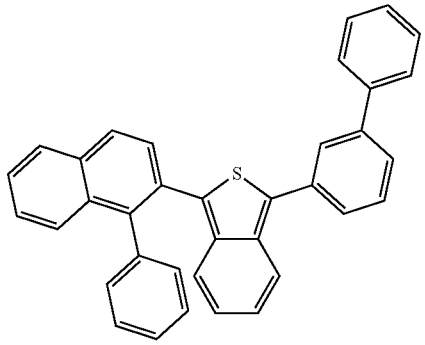
698
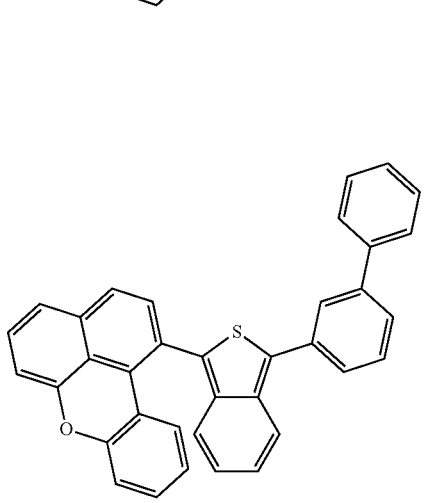
699
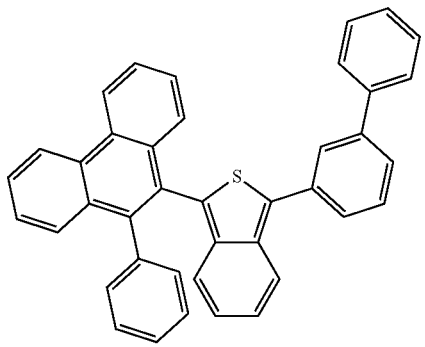
700
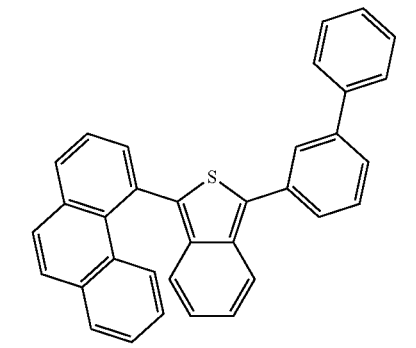

701 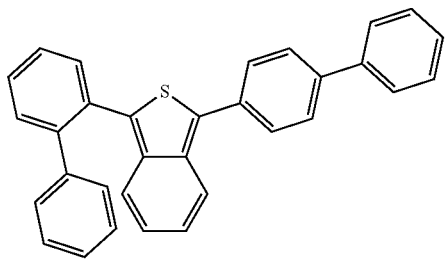
702 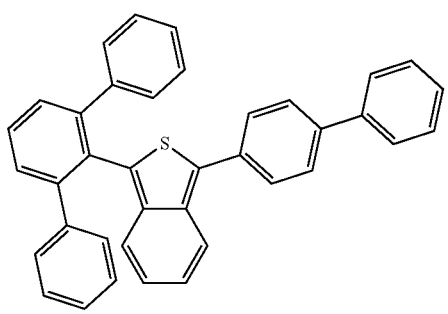
703 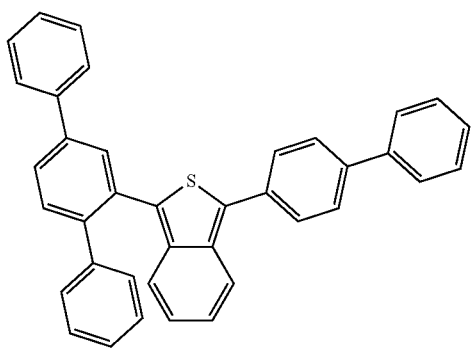
704 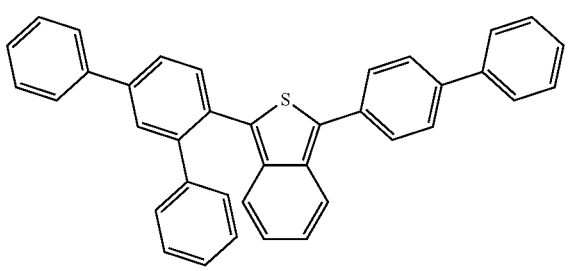
705 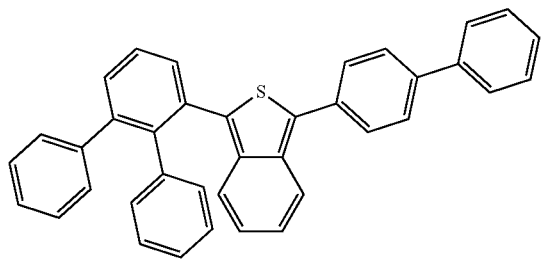
706 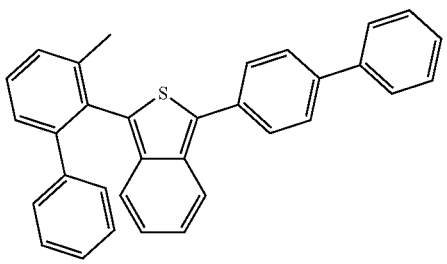
707 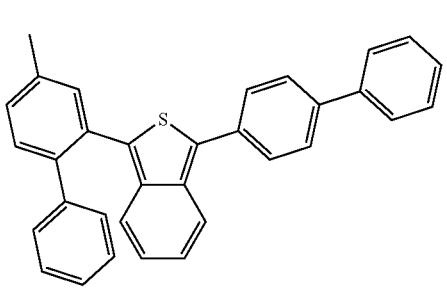
708 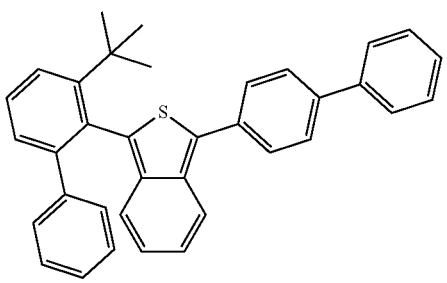
709 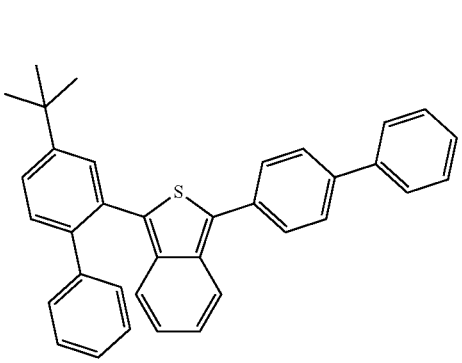
710 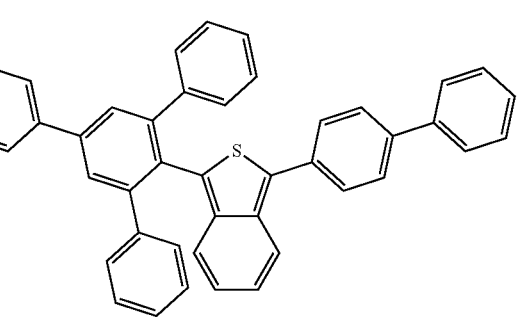

401
-continued
711
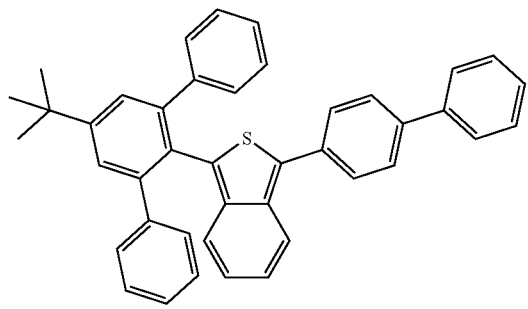
712
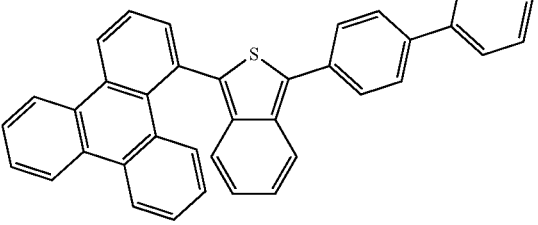
713
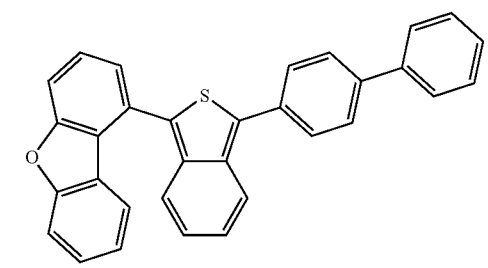
714
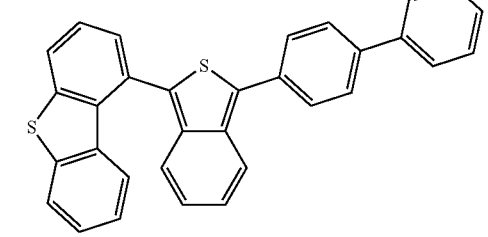
715
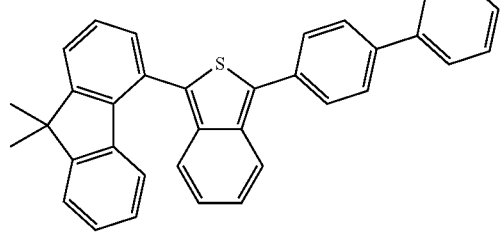
402
-continued
716
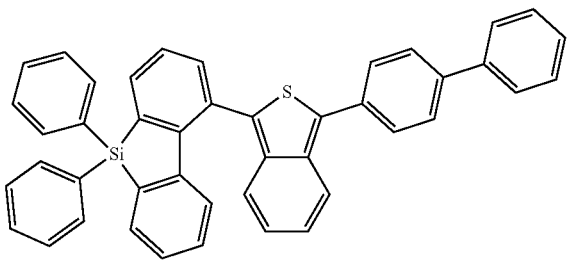
717
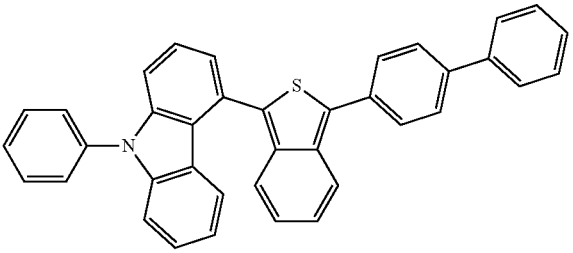
718
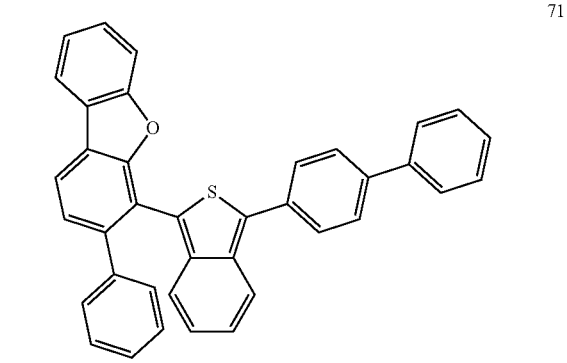
719
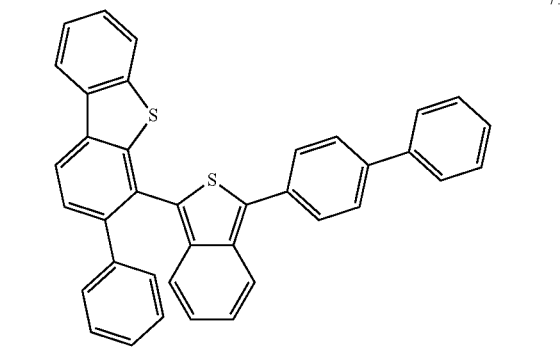
720
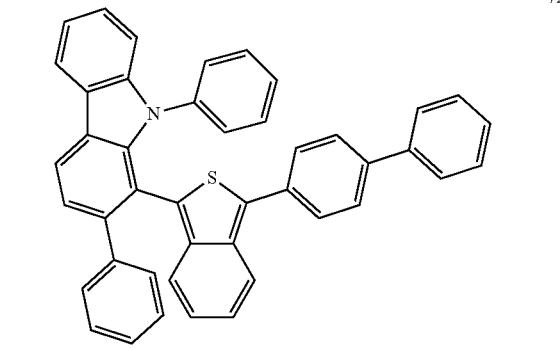

-continued
721
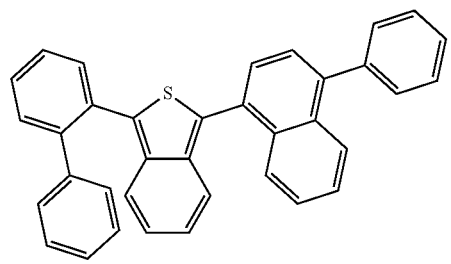
722
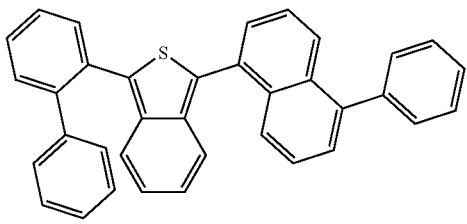
723
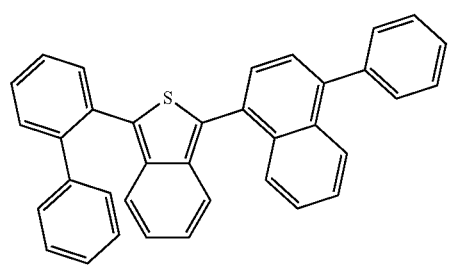
724
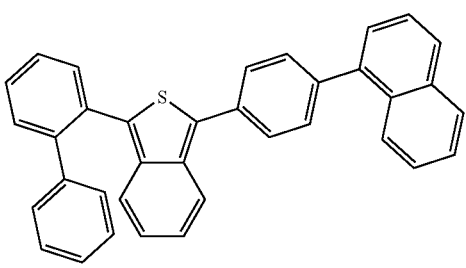
725
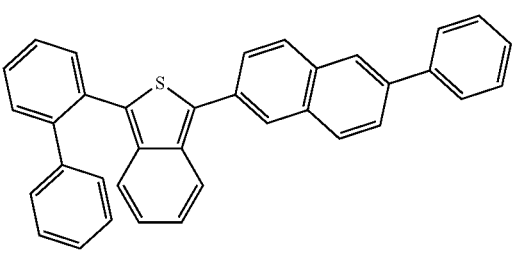
726
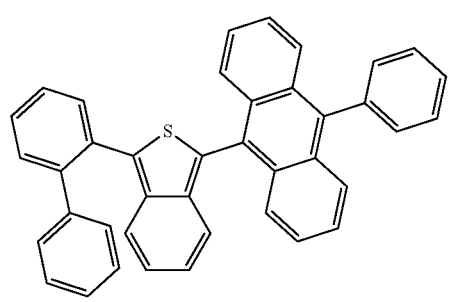
-continued
727
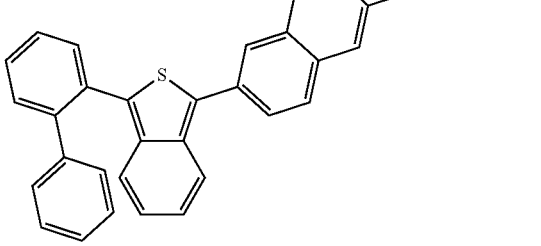
728
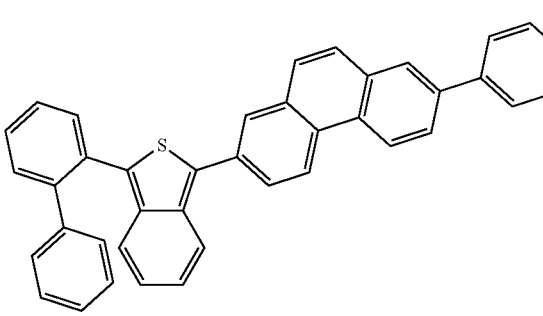
729
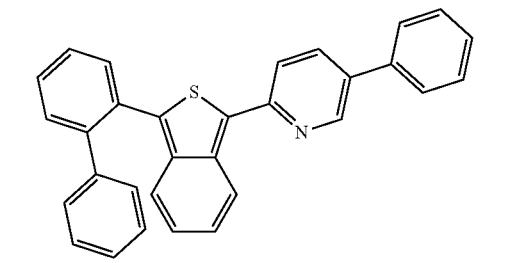
730
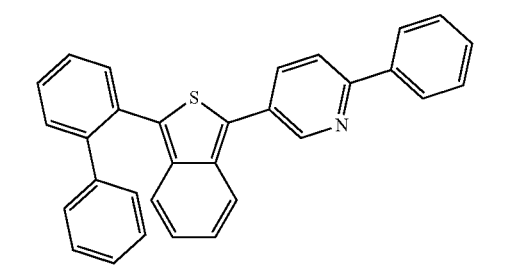
731
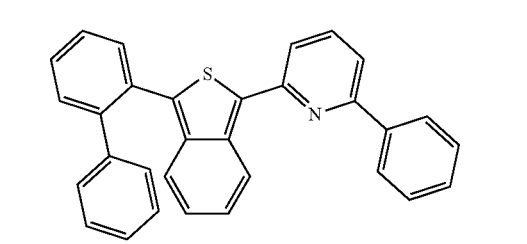

405
-continued
732
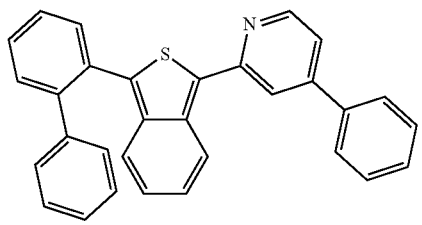
733
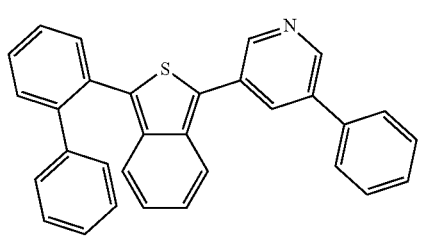
734
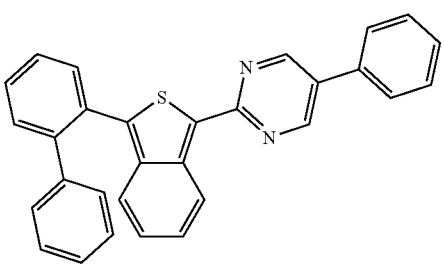
735
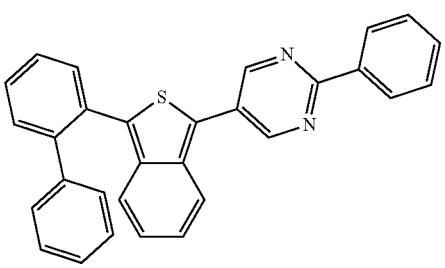
736
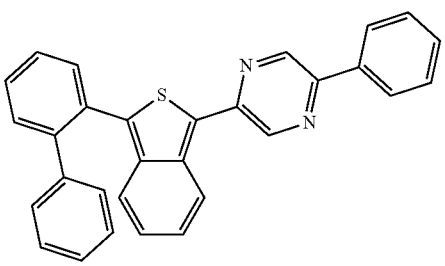
737
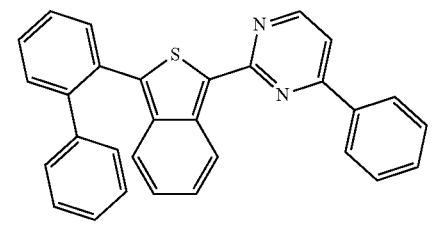
406
-continued
738
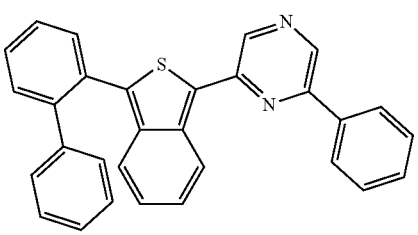
739
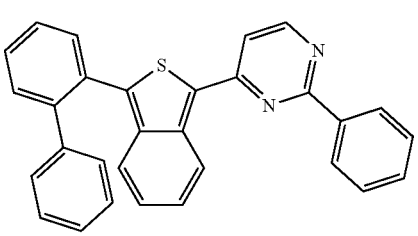
740
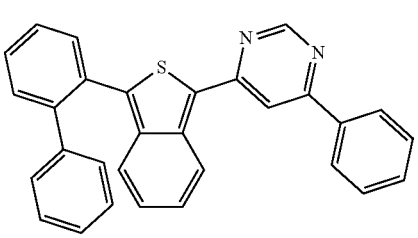
741
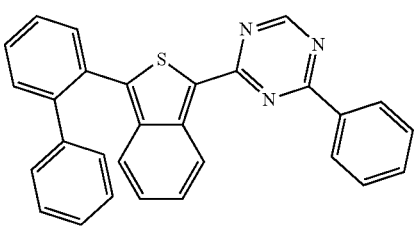
742
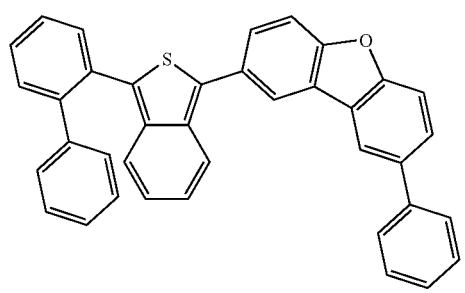
743
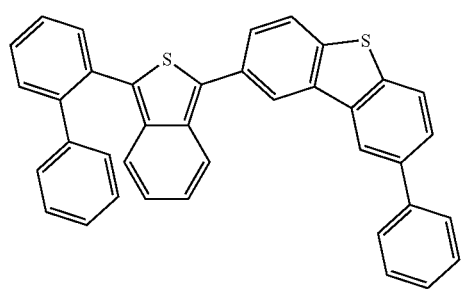

407
-continued
744
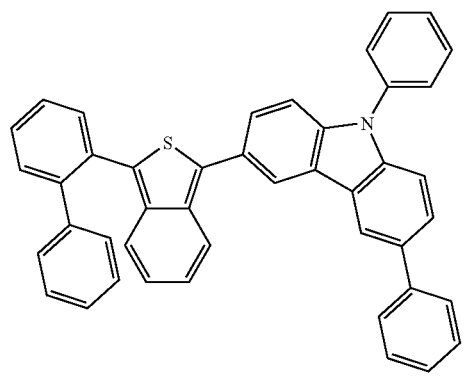
745
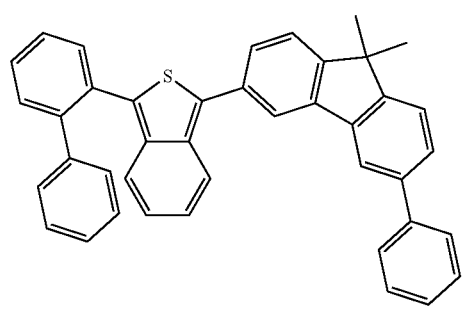
746
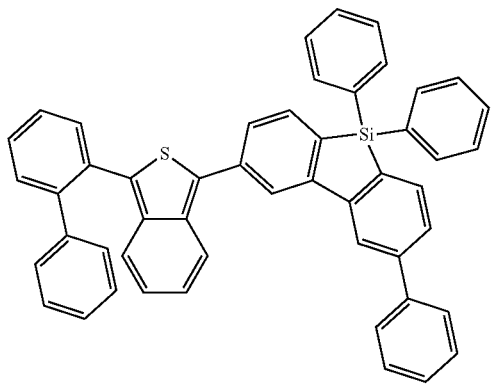
747
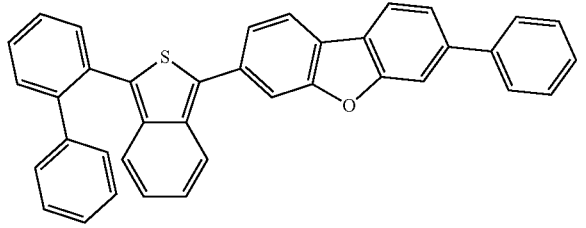
748
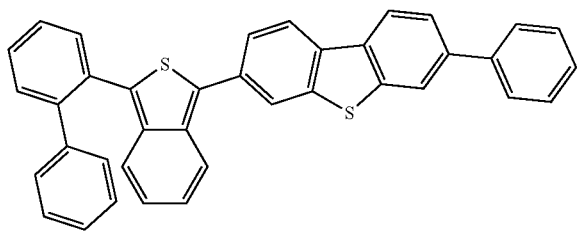
408
-continued
749
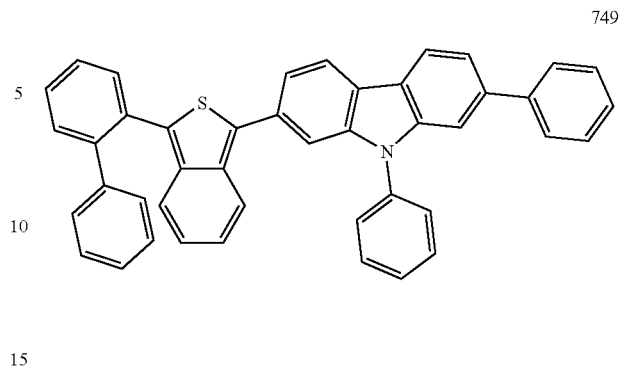
750
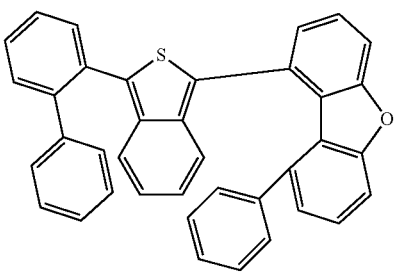
751
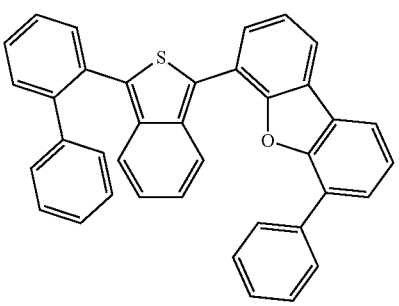
752
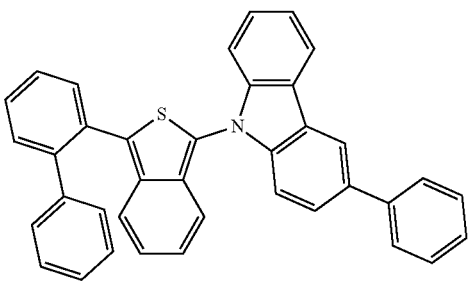
753
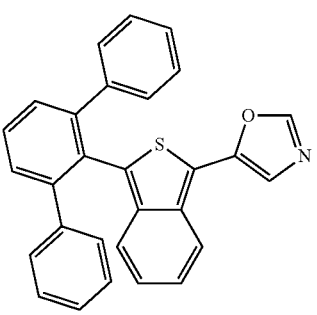

409
-continued
754
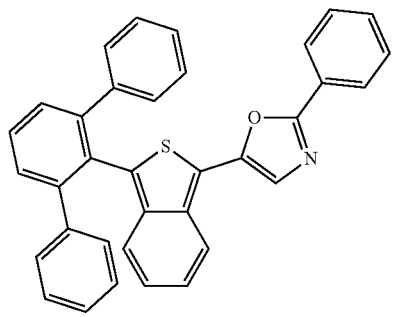
755
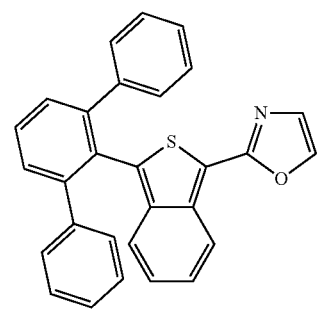
756
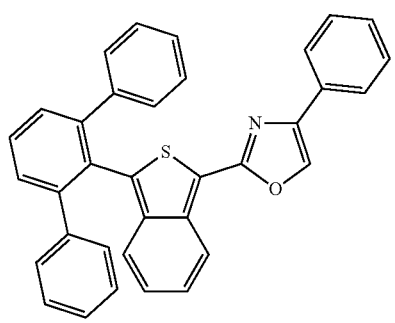
757
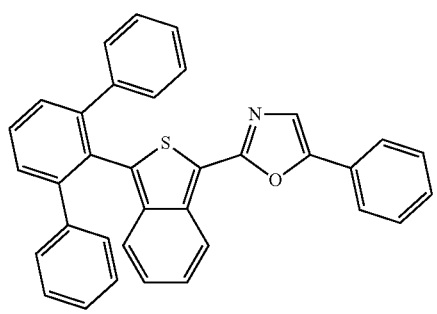
758
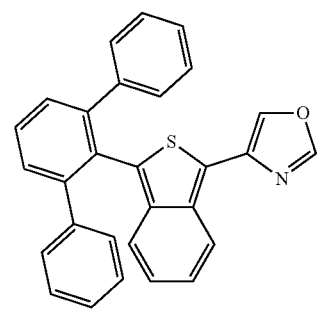
410
-continued
759
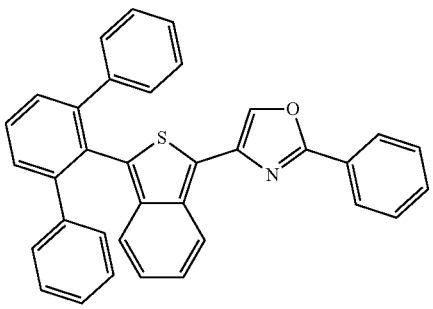
760
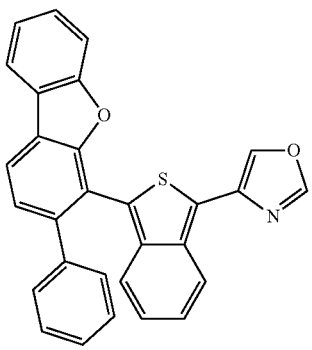
761
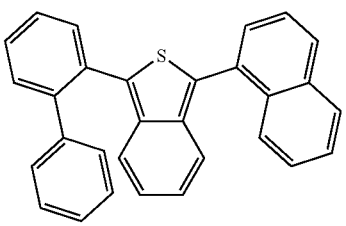
762
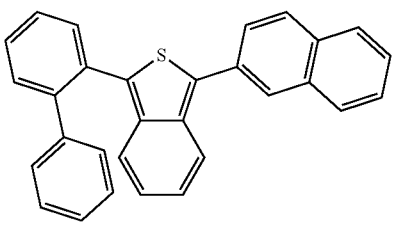
763
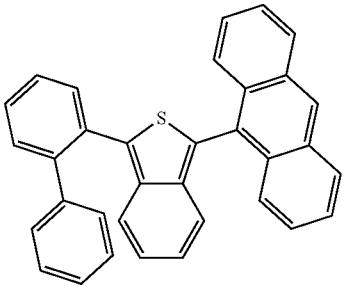

411
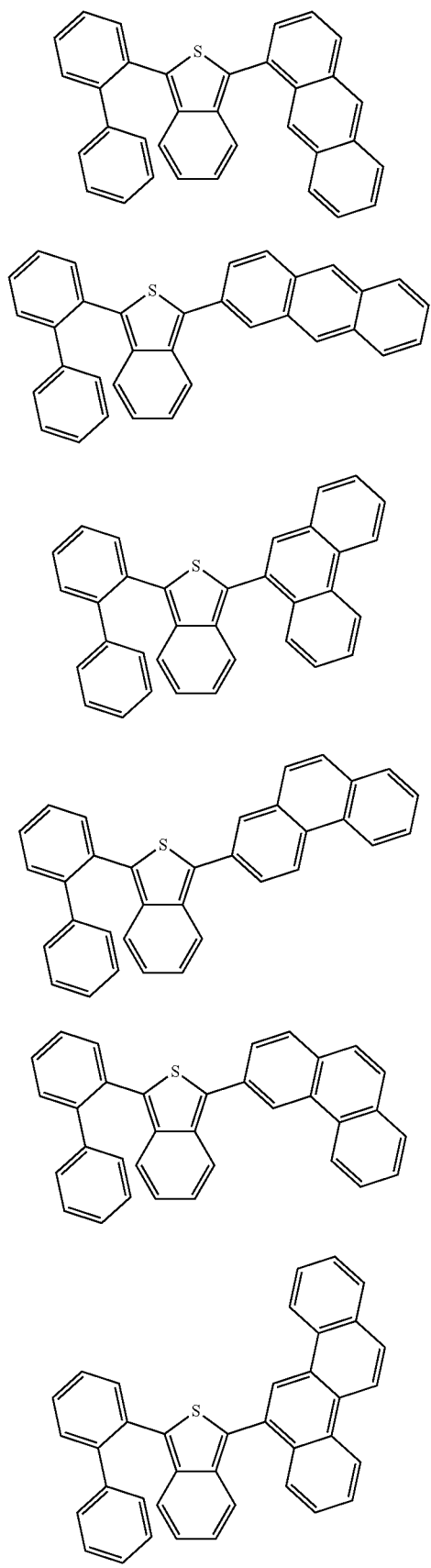
412
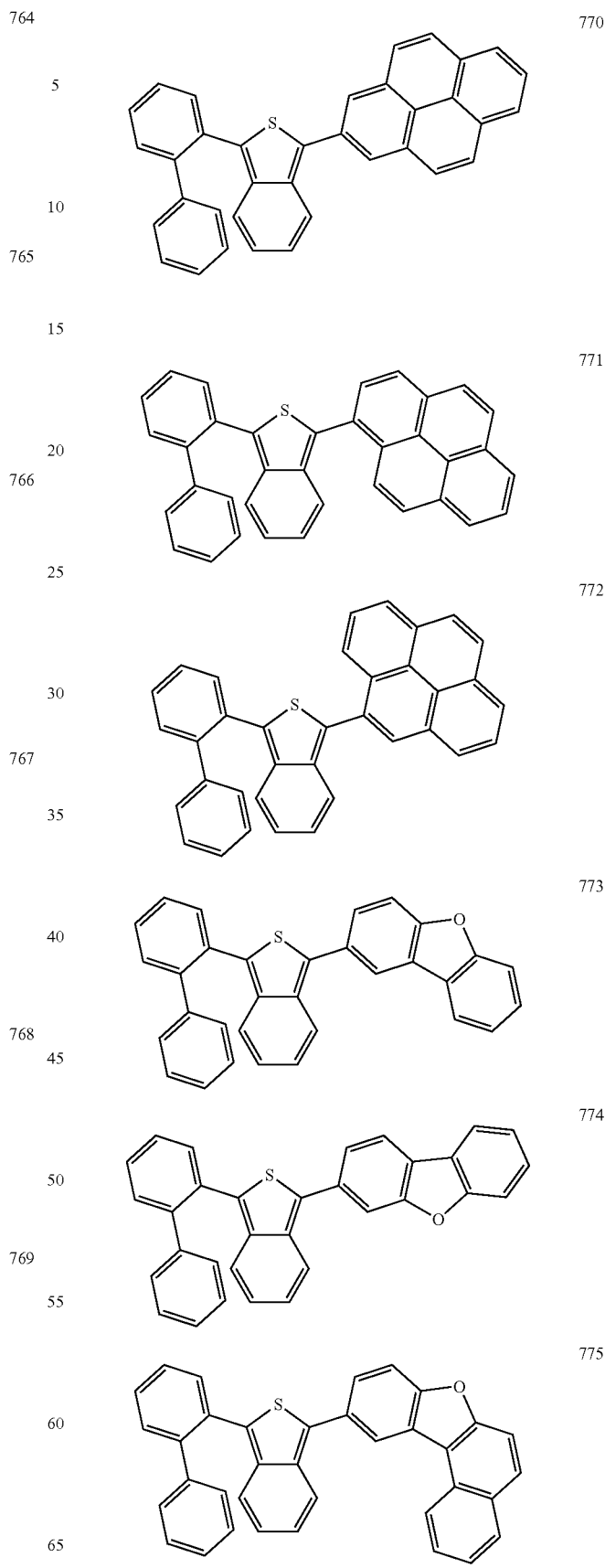

413
-continued
776
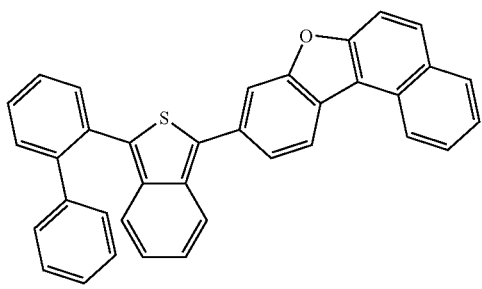
777
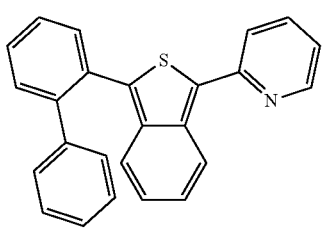
778
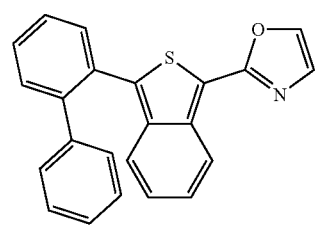
779
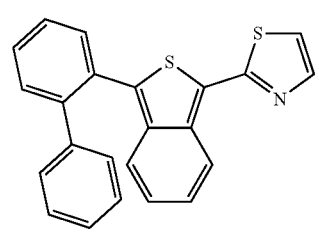
780
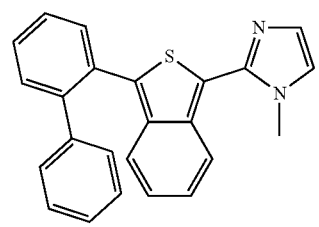
781
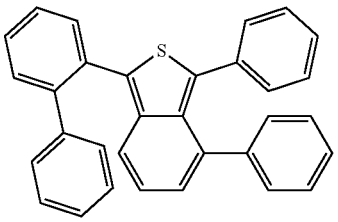
414
-continued
782
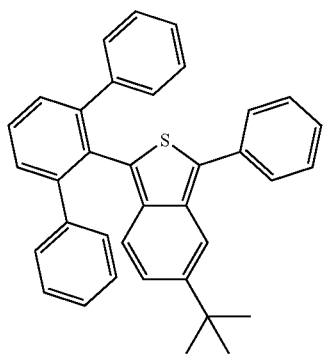
783
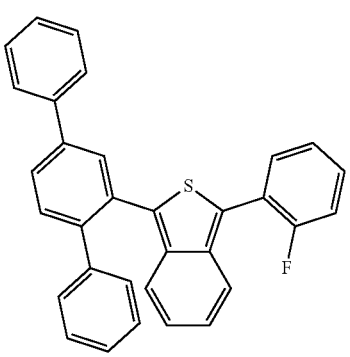
784
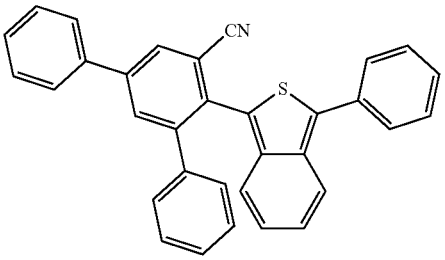
785
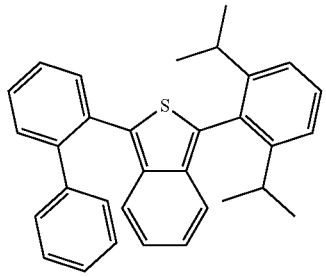
786
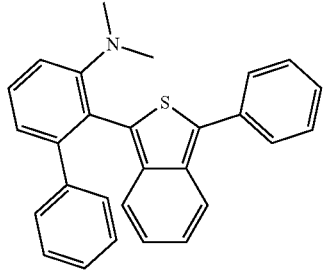

| 415 -continued | 416 -continued |
|---|---|
| 787 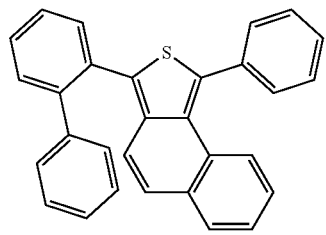 | 792 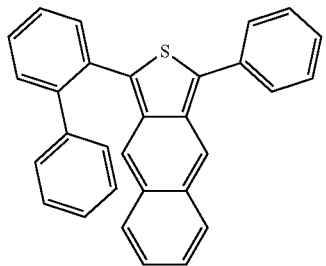 |
| 788 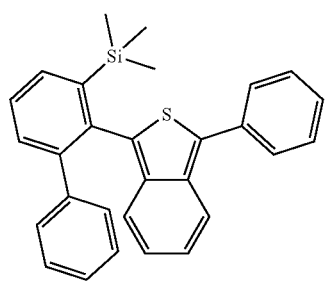 | 793 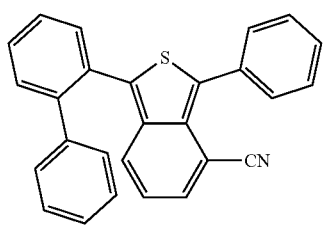 |
| 789 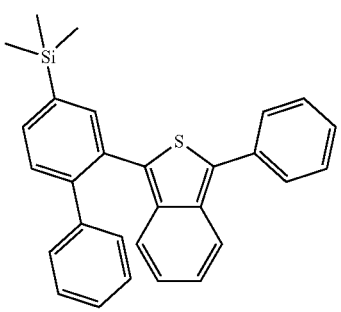 | 794 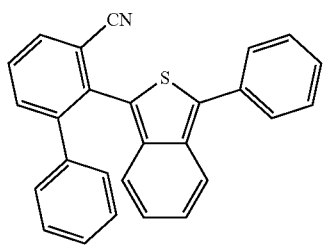 |
| 790 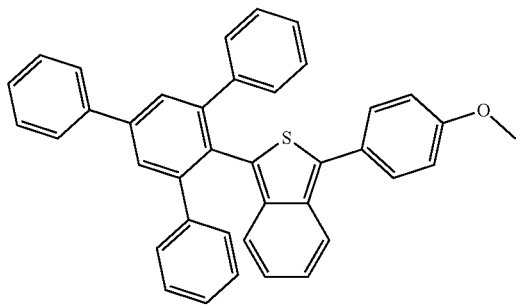 | 795 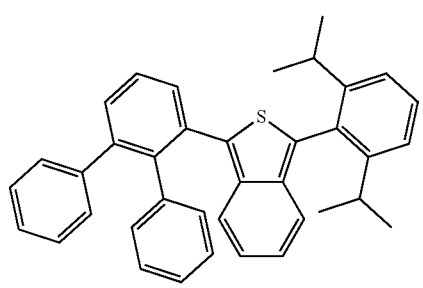 |
| 791 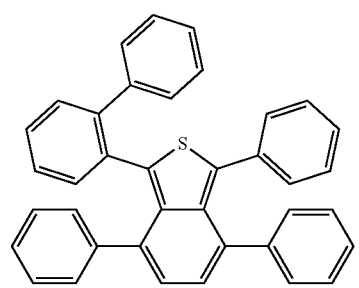 | 796 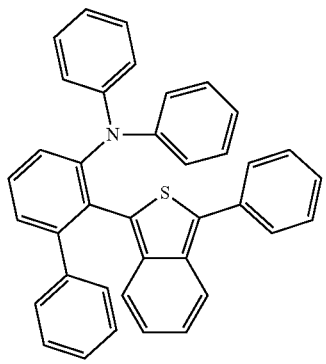 |

417
-continued

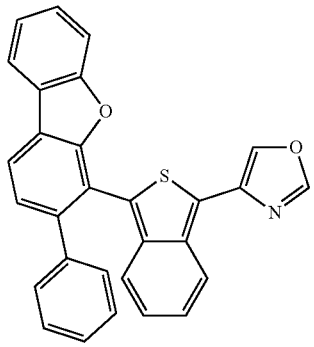
797

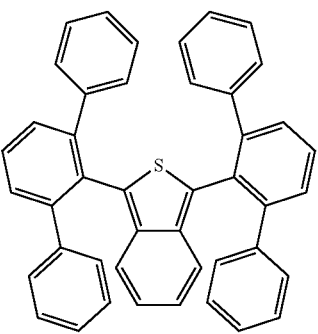
798

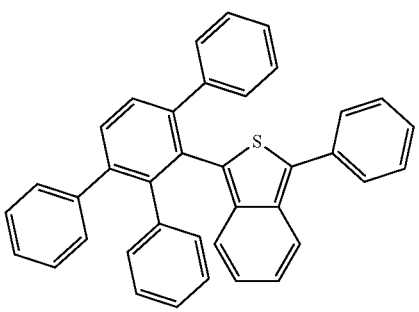
799

418
-continued

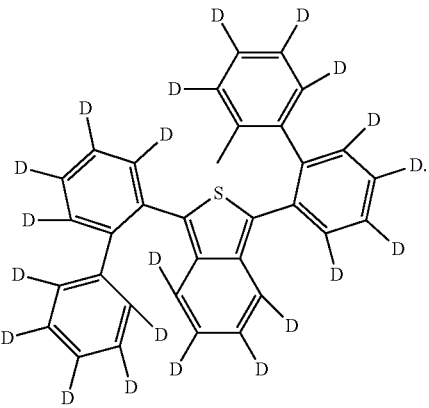
800

14. An organic light-emitting device comprising:
    a first electrode;
    a second electrode; and
    an organic layer disposed between the first electrode and the second electrode and comprising an emission layer,
    wherein the organic layer comprises at least one of the condensed cyclic compound of claim 1.

15. The organic light-emitting device of claim 14, wherein
    the first electrode is an anode,
    the second electrode is a cathode,
    the organic layer comprises a hole transport region disposed between the first electrode and the emission layer, and an electron transport region disposed between the emission layer and the second electrode,
    the hole transport region comprises a hole injection layer, a hole transport layer, an electron blocking layer, a buffer layer, or any combination thereof, and
    the electron transport region comprises a hole blocking layer, an electron transport layer, an electron injection layer, or any combination thereof.

16. The organic light-emitting device of claim 14, wherein the emission layer comprises the condensed cyclic compound.

17. The organic light-emitting device of claim 16, wherein the emission layer comprises a host and a dopant,
    the host comprises the condensed cyclic compound, and
    an amount of the host in the emission layer is larger than that of the dopant in the emission layer.

18. The organic light-emitting device of claim 17, wherein the dopant comprises a fluorescent dopant.

19. The organic light-emitting device of claim 16, wherein the emission layer emits blue light.

* * * * *